(12) United States Patent
Shachar et al.

(10) Patent No.: US 11,986,488 B2
(45) Date of Patent: May 21, 2024

(54) COMPOSITIONS AND METHODS FOR TREATING MALIGNANT, AUTOIMMUNE AND INFLAMMATORY DISEASES

(71) Applicant: Yeda Research and Development Co. Ltd., Rehovot (IL)

(72) Inventors: Idit Shachar, Ramat-Gan (IL); Hadas Lewinsky, Rehovot (IL); Lihi Radomir, Rehovot (IL); Anna Wiener, Rehovot (IL)

(73) Assignee: Yeda Research and Development Co. Ltd., Rehovot (IL)

( * ) Notice: Subject to any disclaimer, the term of this patent is extended or adjusted under 35 U.S.C. 154(b) by 181 days.

(21) Appl. No.: 17/089,769

(22) Filed: Nov. 5, 2020

(65) Prior Publication Data
US 2021/0052626 A1 Feb. 25, 2021

Related U.S. Application Data

(62) Division of application No. 16/068,172, filed as application No. PCT/IL2017/050019 on Jan. 5, 2017, now Pat. No. 10,828,318.

(60) Provisional application No. 62/275,378, filed on Jan. 6, 2016.

(51) Int. Cl.
| | |
|---|---|
| *A61K 31/713* | (2006.01) |
| *A61K 38/17* | (2006.01) |
| *A61P 29/00* | (2006.01) |
| *A61P 35/02* | (2006.01) |
| *A61P 37/06* | (2006.01) |
| *C07K 16/28* | (2006.01) |
| *A61K 39/00* | (2006.01) |

(52) U.S. Cl.
CPC ........ *A61K 31/713* (2013.01); *A61K 38/1774* (2013.01); *A61P 29/00* (2018.01); *A61P 35/02* (2018.01); *A61P 37/06* (2018.01); *C07K 16/2896* (2013.01); *A61K 2039/505* (2013.01); *C07K 2317/76* (2013.01)

(58) Field of Classification Search
CPC ... A61K 31/713; A61K 38/1774; A61P 29/00; A61P 35/02; A61P 37/06; C07K 16/2896
USPC .................................................. 424/133.1
See application file for complete search history.

(56) References Cited

U.S. PATENT DOCUMENTS

| | | | | |
|---|---|---|---|---|
| 9,109,029 | B2 * | 8/2015 | Shachar | ............ C12Q 1/6886 |
| 10,066,014 | B2 | 9/2018 | Shachar et al. | |
| 10,611,839 | B2 * | 4/2020 | Shachar | ............ C07K 16/3061 |
| 2005/0025789 | A1 | 2/2005 | Nieland et al. | |
| 2005/0027114 | A1 | 2/2005 | Kuo et al. | |
| 2019/0015441 | A1 | 1/2019 | Shachar et al. | |

FOREIGN PATENT DOCUMENTS

| | | | | |
|---|---|---|---|---|
| KR | 20030032940 | * | 4/2003 | ............ A61P 35/00 |
| WO | WO 2010/035259 | | 4/2010 | |
| WO | WO 2015/118538 | | 8/2015 | |
| WO | WO 2017/118985 | | 7/2017 | |

OTHER PUBLICATIONS

Communication Under Rule 164(2)(a) EPC dated Aug. 14, 2019 From the European Patent Office Re. Application No. 17704549.9. (8 Pages).
Final Official Action dated May 14, 2020 from the US Patent and Trademark Office Re. U.S. Appl. No. 16/068,172. (7 pages).
International Preliminary Report on Patentability dated Jul. 19, 2018 From the International Bureau of WIPO Re. Application No. PCT/IL2017/050019. (14 Pages).
International Search Report and the Written Opinion dated Jun. 12, 2017 From the International Searching Authority Re. Application No. PCT/IL2017/050019. (22 Pages).
Invitation to Pay Additional Fees and Communication Relating to the Results of the Partial International Search dated Apr. 11, 2017 From the International Searching Authority Re. Application No. PCT/IL2017/050019. (10 Pages).
Notification of Office Acton and Search Report dated Jul. 1, 2020 From the National Intellectual Property Administration of the People's Republic of China Re. Application No. 201780015429.X and Its Translation Into English. (24 Pages).
Official Action dated Jan. 3, 2020 From the US Patent and Trademark Office Re. U.S. Appl. No. 16/068,172. (14 pages).
Binsky-Ehrenreich et al. "CD84 Is A Survival Receptor for CLL Cells", Oncogene, XP055358089, 33(8): 1006-1016, Published Online Feb. 25, 2013.
Ding et al. "Decreased MicroRNA-142-3p/5p Expression Causes CD4+ T Cell Activation and B Cell Hyperstimulation in Systemic Lupus Erythematosus", Arthritis & Rheumatism, XP055137316, 64(9): 2953-2963, Sep. 1, 2012.
Grzywnowicz et al. "Programmed Death-1 and Its Ligand Are Novel Immunotolerant Molecules Expressed on Leukemia B Cells in Chronic Lymphocytic Leukemia", PLoS ONE, 7(4): e35178-1-e35178-8, Apr. 19, 2012.
Ito et al. "Clinical Development of Immune Checkpoint Inhibitors", BioMed Research International, 2015(Art.ID 605478): 1-12, 2015.
McClanahan et al. "PD-L1 Checkpoint Blockade Prevents Immune Dysfunction and Leukemia Development in A Mouse Model of Chronic Lymphocytic Leukemia", Blood, 126(2): 203-211, Published Online Mar. 23, 2015.

(Continued)

*Primary Examiner* — Yan Xiao

(57) ABSTRACT

A method of treating a malignant disease involving T cell exhaustion in a subject, with the proviso that said malignant disease is not a B cell malignancy, is disclosed. The method comprising administering to the subject a therapeutically effective amount of an agent capable of decreasing an activity or expression of CD84, thereby treating the malignant disease involving the T cell exhaustion. Also disclosed is a method of treating an autoimmune or inflammatory disease in a subject, the method comprising administering to a subject a therapeutically effective amount of an agent capable of decreasing an activity or expression of CD84. A method comprising administering to the subject a therapeutically effective amount of an agent capable of decreasing an activity or expression of SLAMF1, with the proviso that said agent is not an agent capable of decreasing an activity or expression of CD84, is also disclosed.

9 Claims, 80 Drawing Sheets

(56) References Cited

OTHER PUBLICATIONS

Oliver-Vila et al. "The Leukocyte Receptor CD84 Inhibits Fc[Epsilon]RI-Mediated Signaling Through Homophilic Interaction in Transfected RBL-2H3 Cells", Molecular Immunology, XP022513093, 45(8): 2138-2149, Feb. 19, 2008.

Schweighofer et al. "A Two-Gene Signature, SKI and SLAMF1, Predicts Time-to-Treatment in Previously Untreated Patients With Chronic Lymphocytic Leukemia", PLoS ONE, 6(12): e28277-1-e28277-11, Dec. 14, 2011.

Sierro et al. "The CD4-Like Molecule LAG-3, Biology and Therapeutic Applications", Expert Opinion on Therapeutic Targets, 15(1): 91-101, Published Online Dec. 11, 2010.

Woo et al. "Immune Inhibitory Molecules LAG-3 and PD-1 Synergistically Regulate T Cell Function to Promote Tumoral Immune Escape", Cancer Research, 72(4): 917-927, Published Online Dec. 20, 2011.

Xia et al. "Signaling Pathway and Dysregulation of PD1 and Its Ligand in Lymphoid Malignancies", Biochimica et Biophysica Acta, p. 1-14, Available Online Oct. 16, 2015.

Yurchenko et al. "CD150-Mediated Akt Signalling Pathway in Normal and Malignant B Cells", Experimental Oncology, 33(1): Mar. 9-18, 2011.

Notification of Office Acton dated Mar. 3, 2021 From the National Intellectual Property Administration of the People's Republic of China Re. Application No. 201780015429.X and Its Translation Into English. (11 Pages).

Notice of Reason(s) for Rejection dated Sep. 28, 2021 From the Japan Patent Office Re. Application No. 2018-534782 and Its Translation Into English. (5 Pages).

Requisition by the Examiner dated Dec. 27, 2023 From the Innovation, Science and Economic Development Canada, Canadian Intellectual Property Office Re. Application No. 3,009,127. (6 Pages).

* cited by examiner

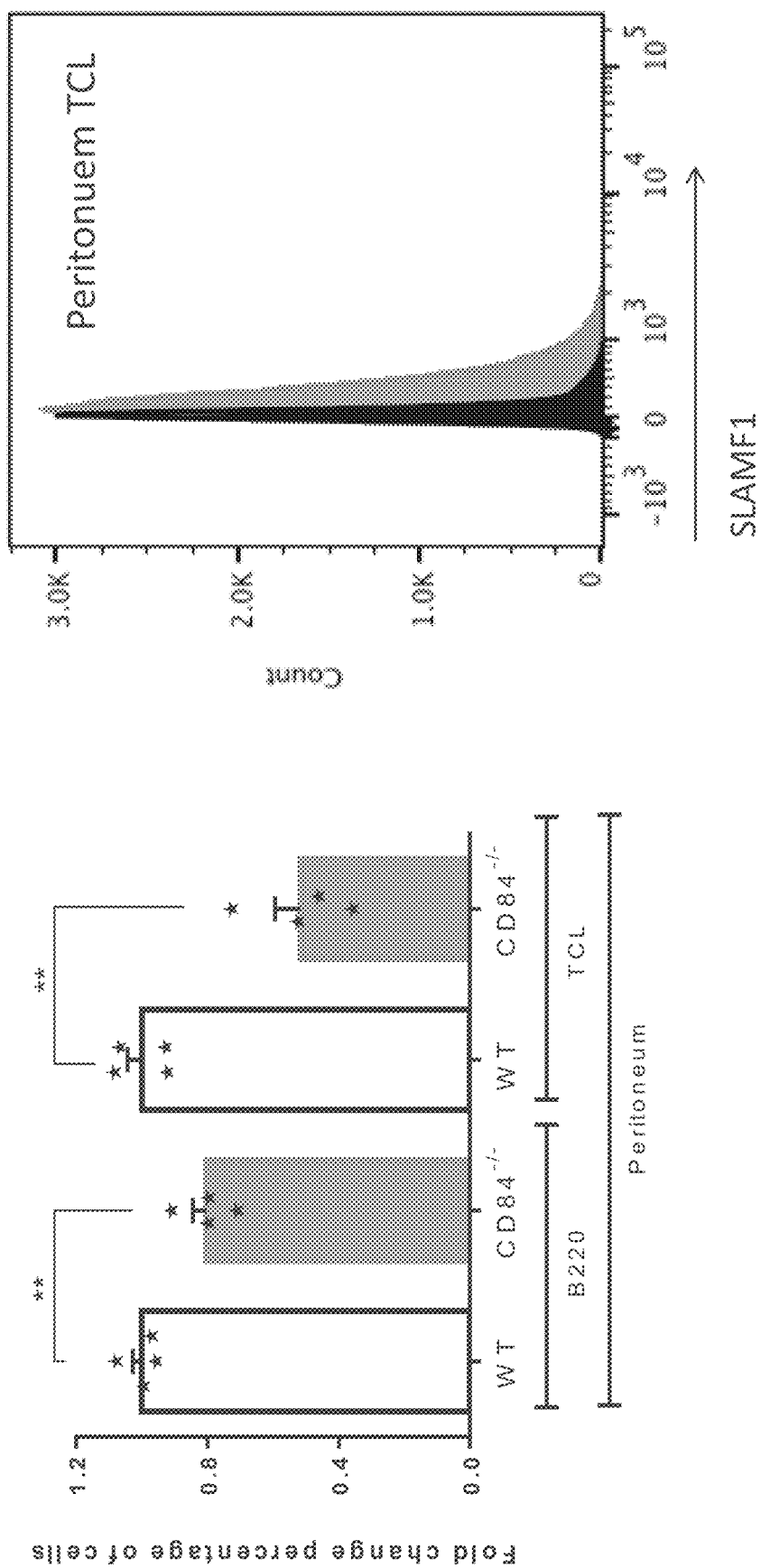

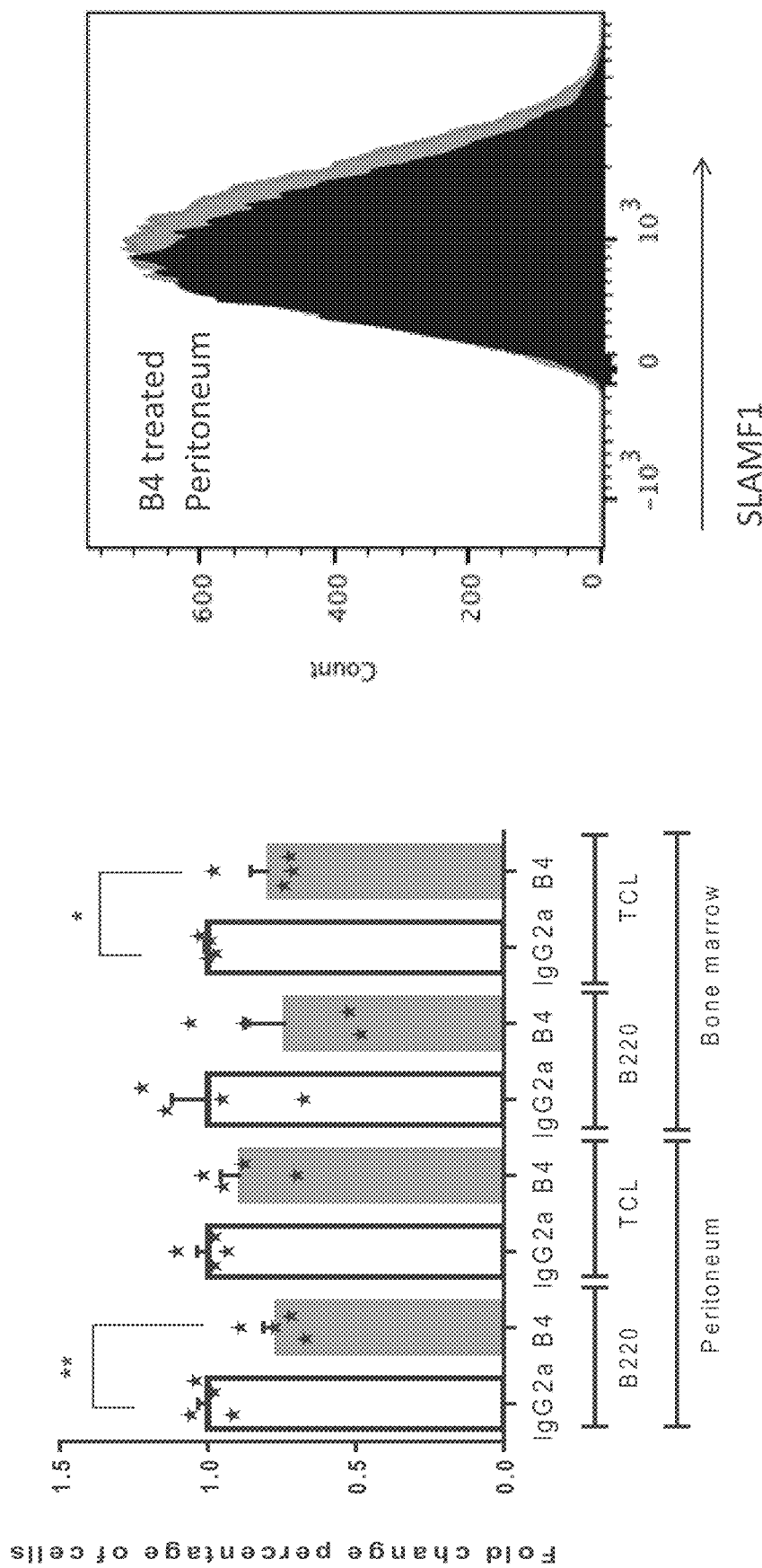

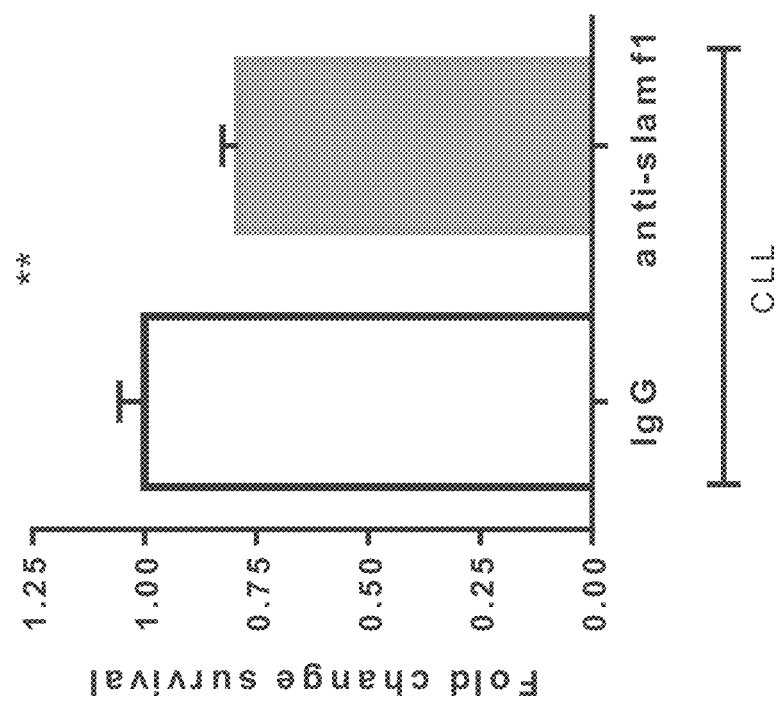

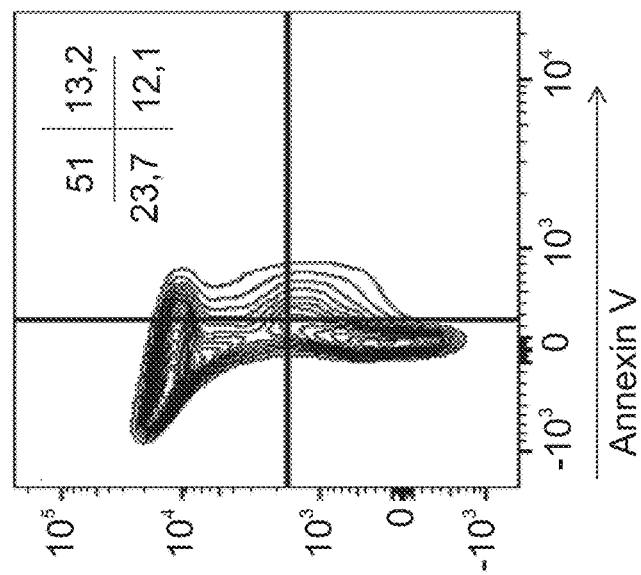
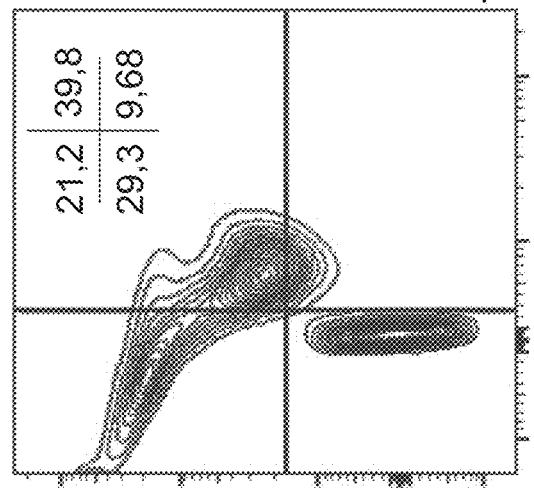
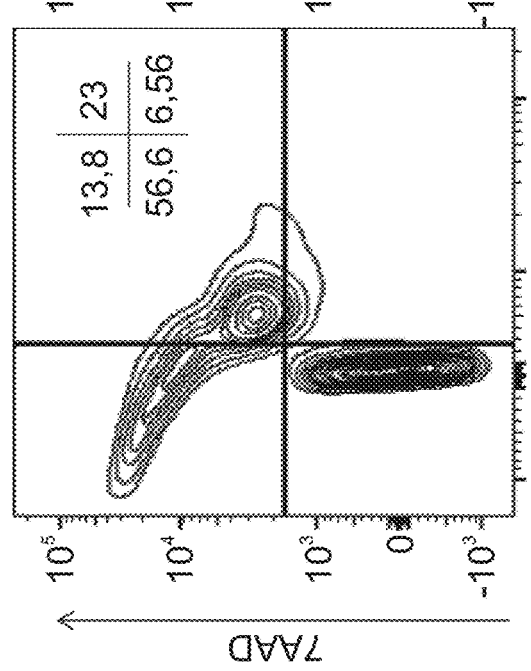

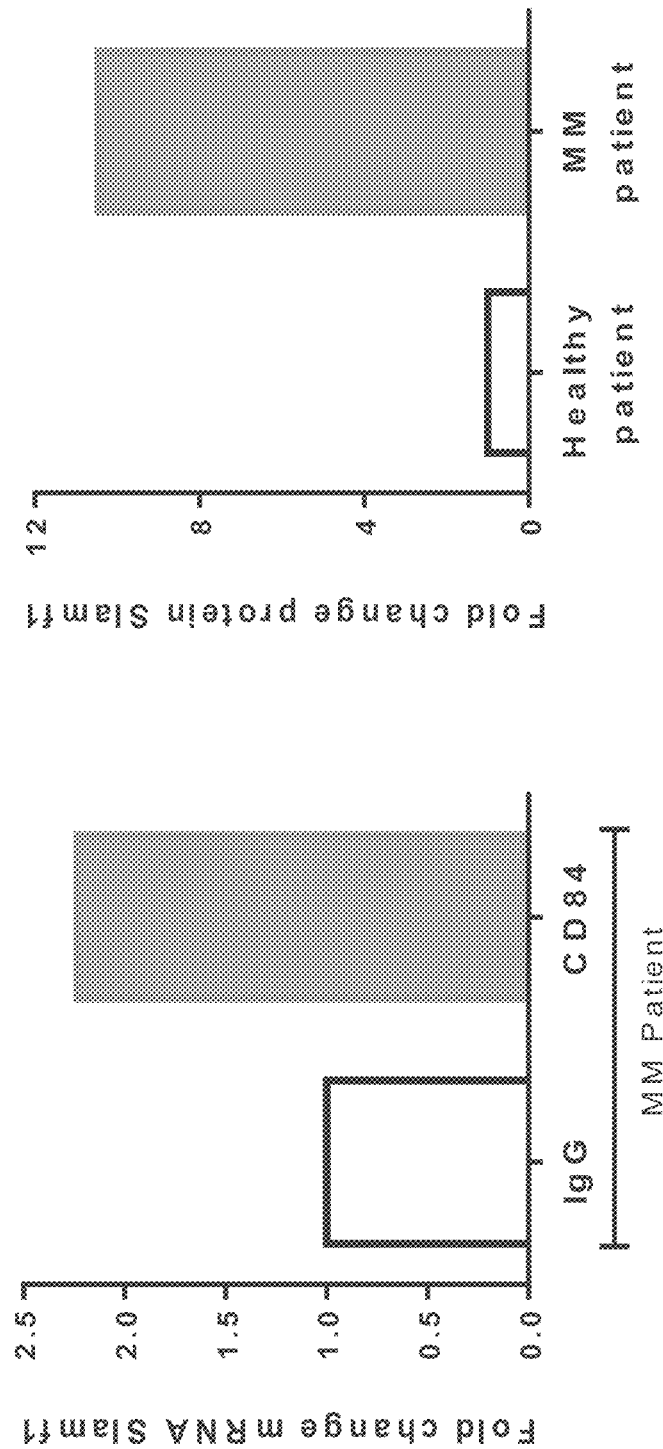

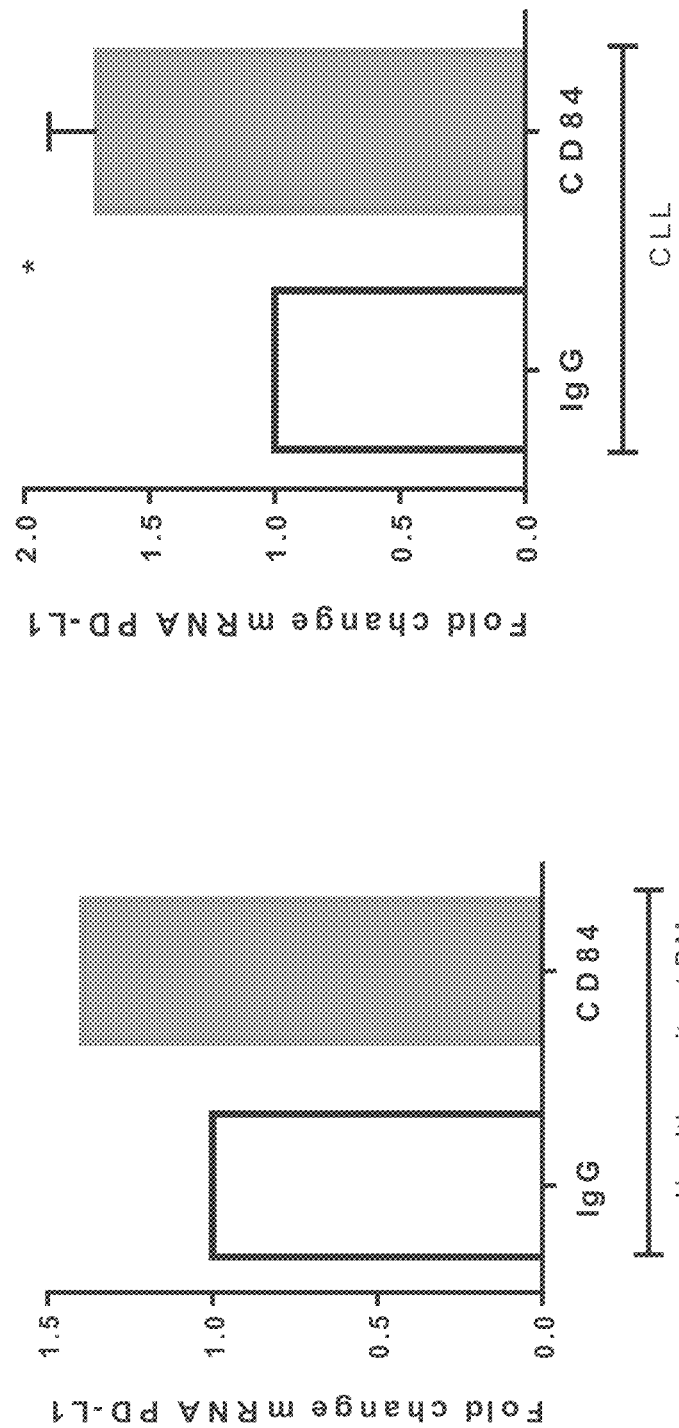

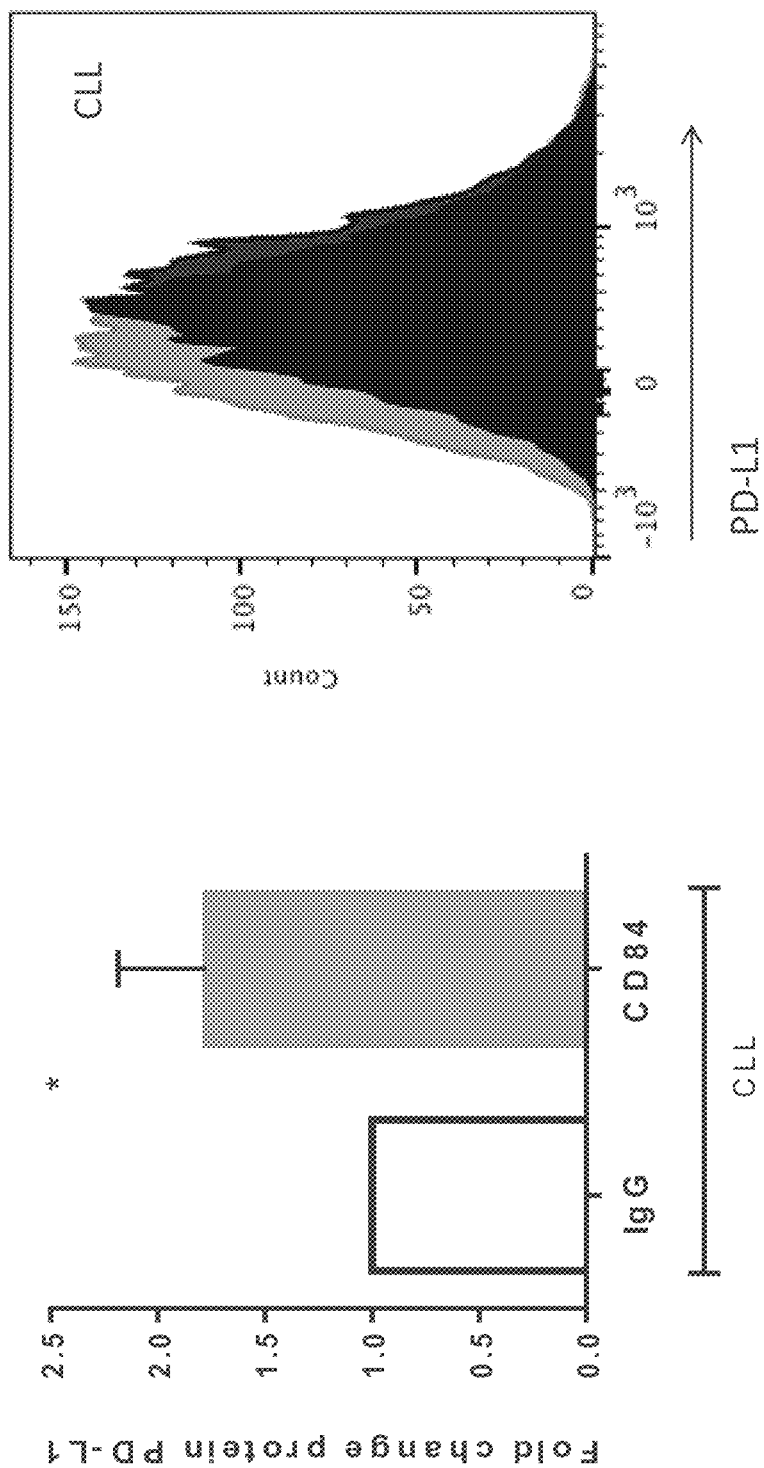

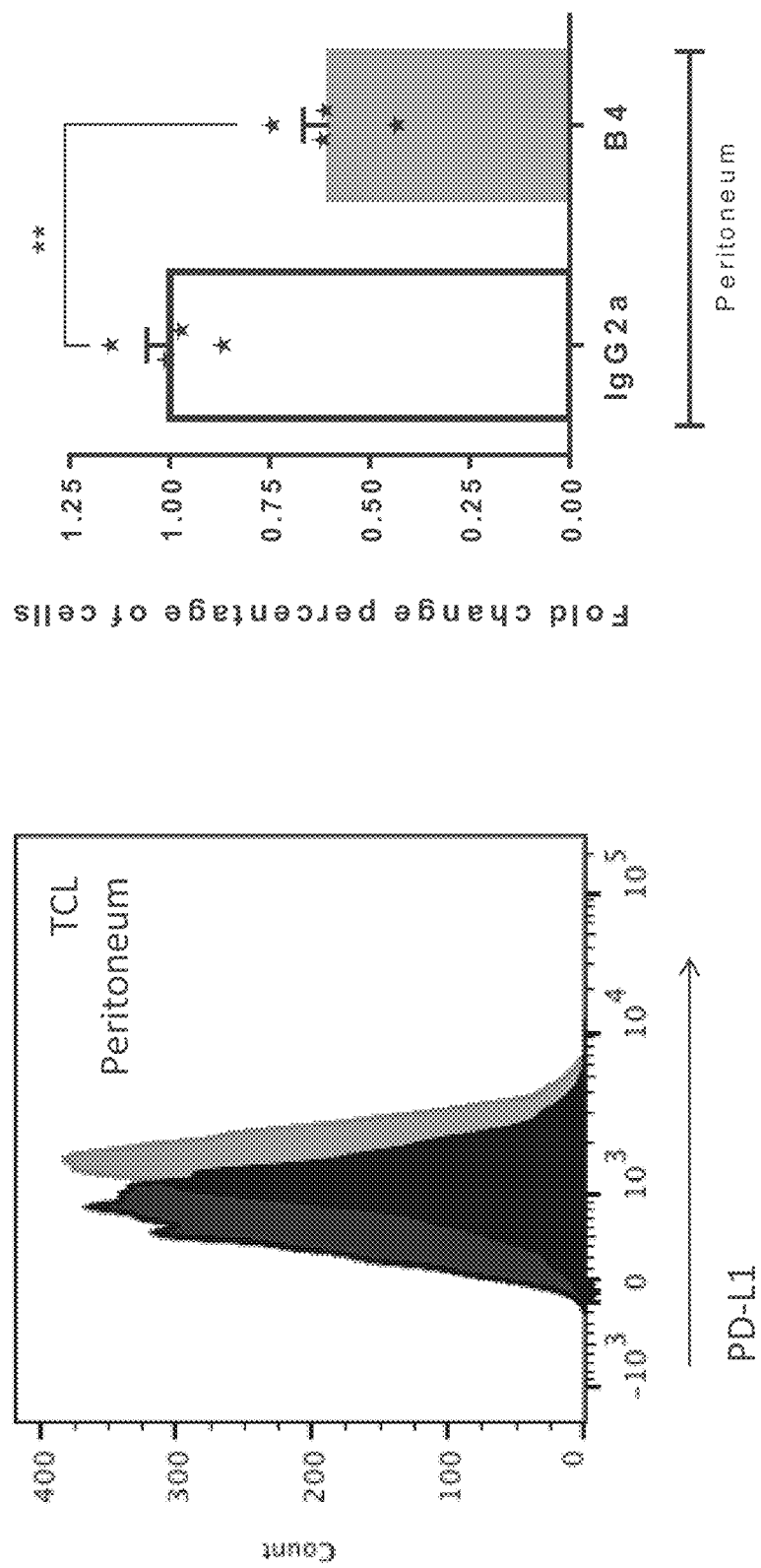

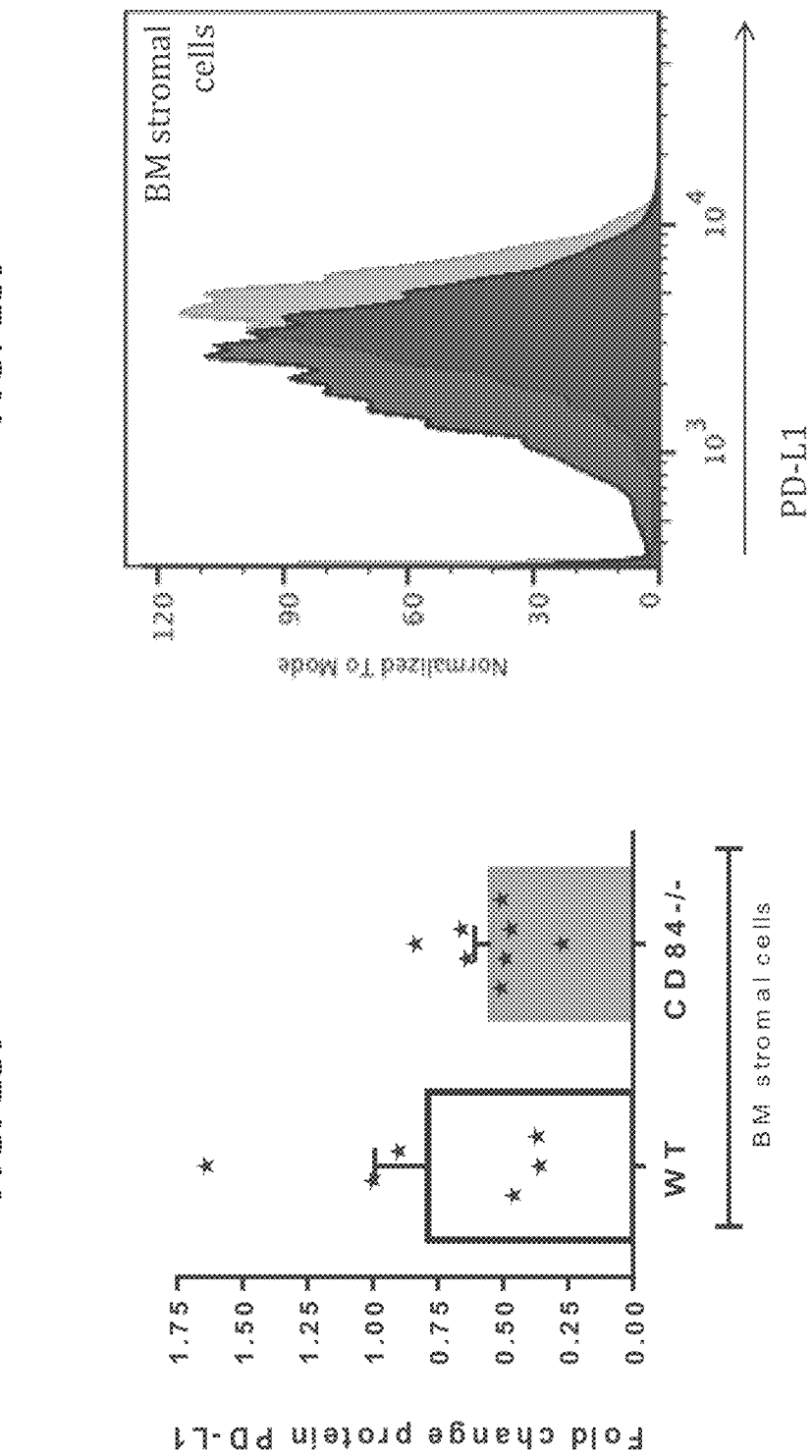

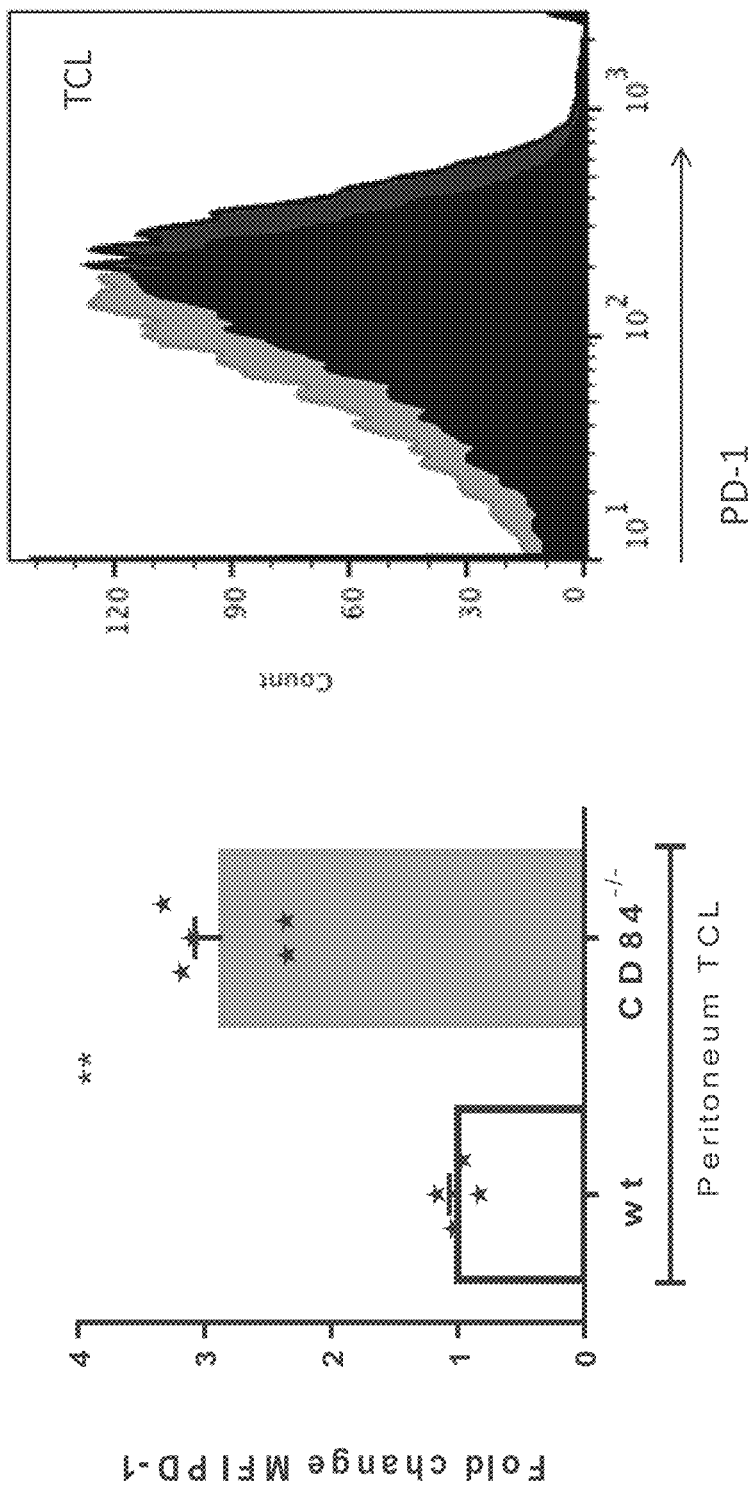

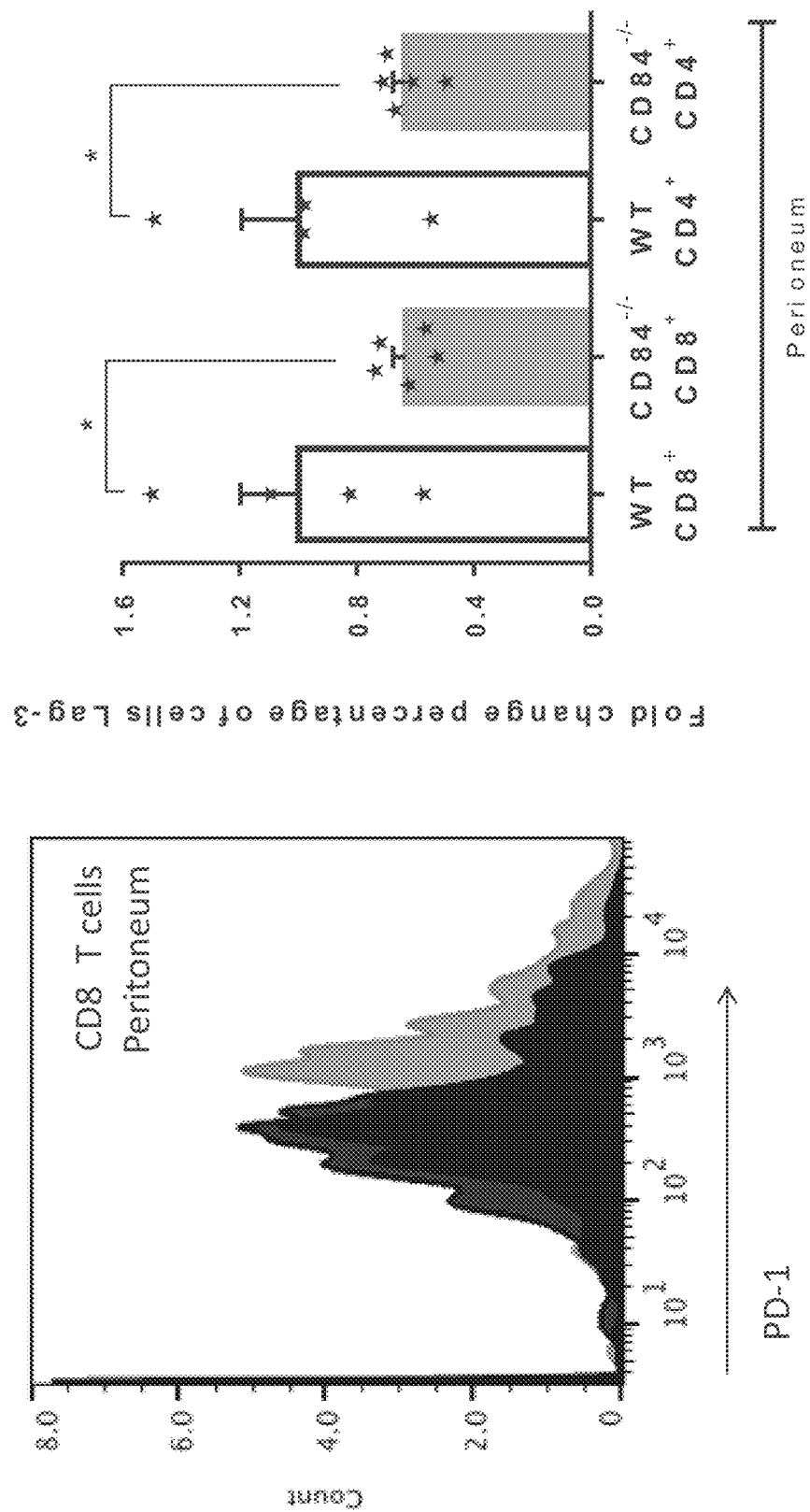

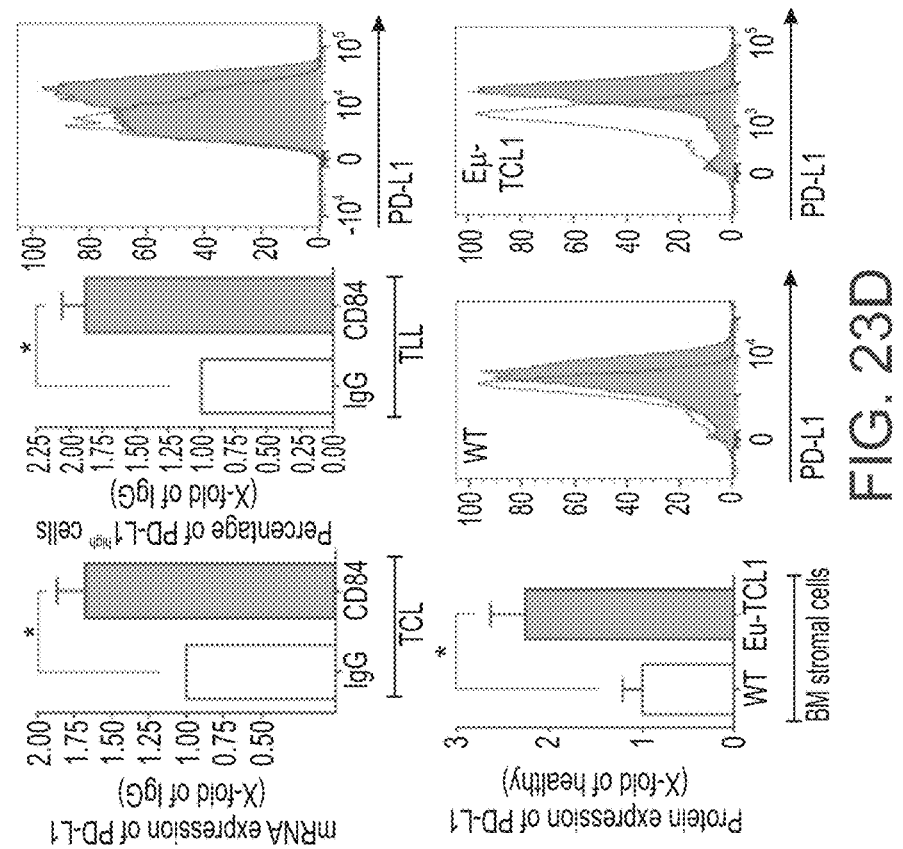
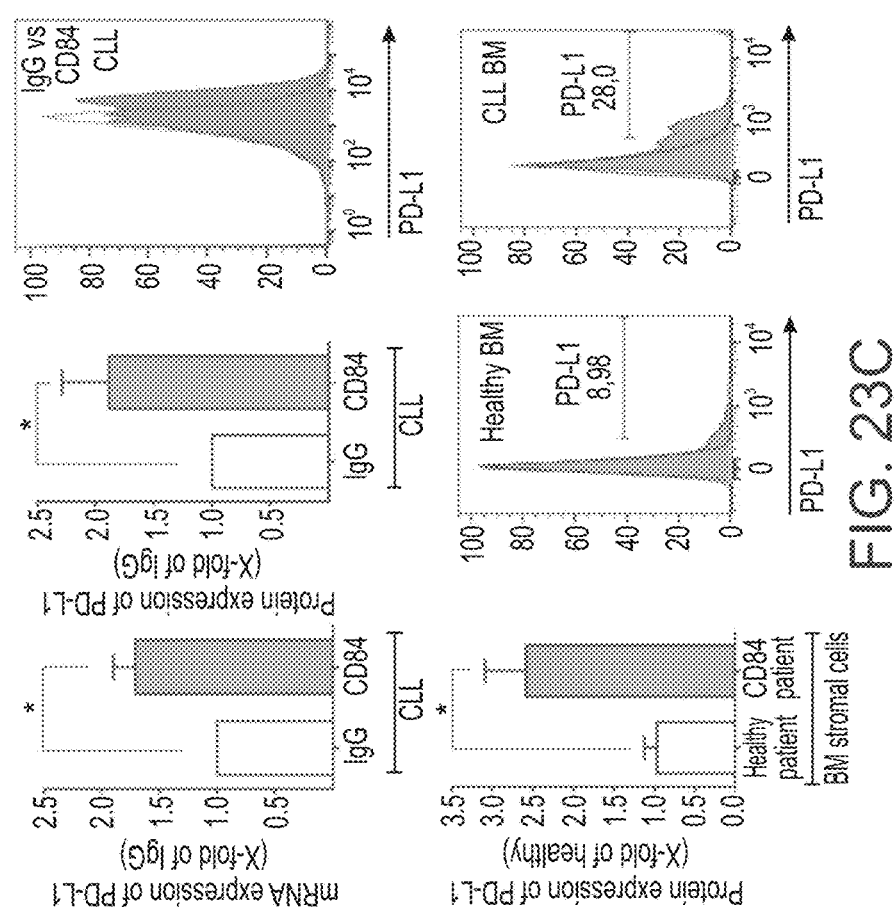
FIG. 23A  FIG. 23B  FIG. 23C  FIG. 23D

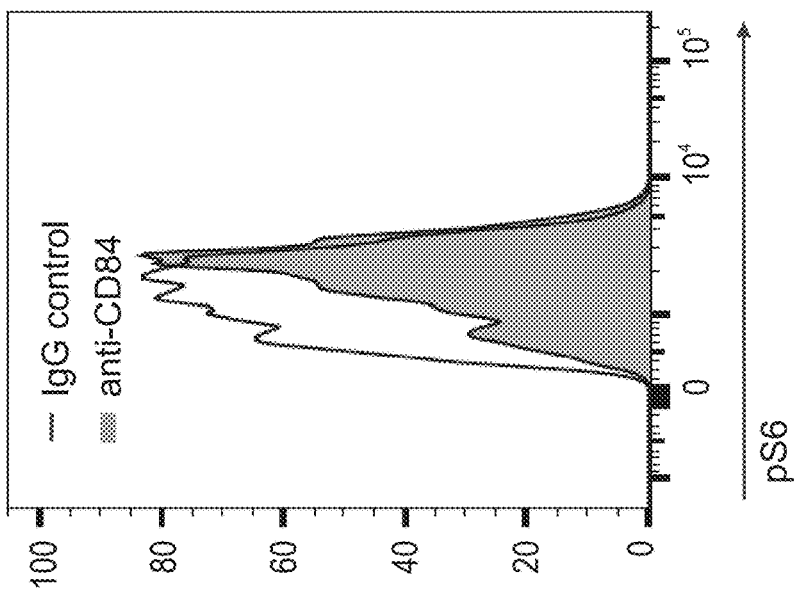
FIG. 24C
FIG. 24B
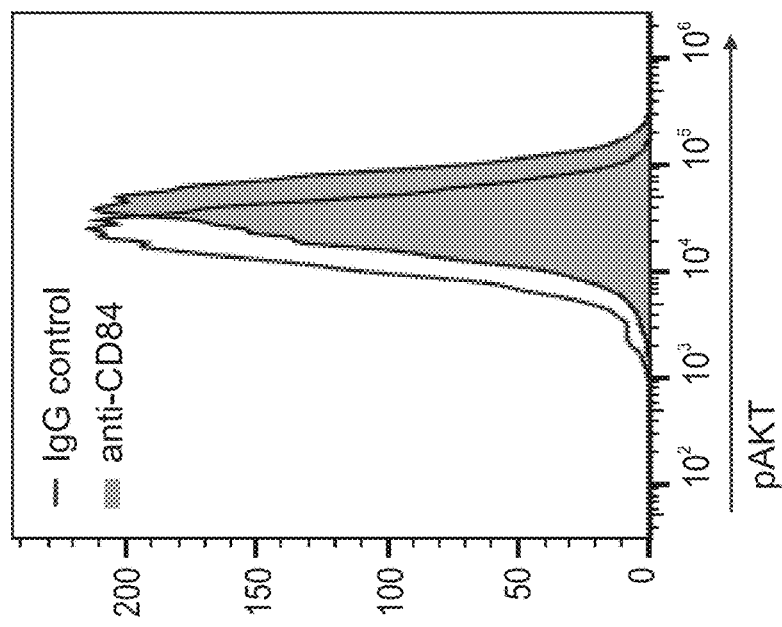
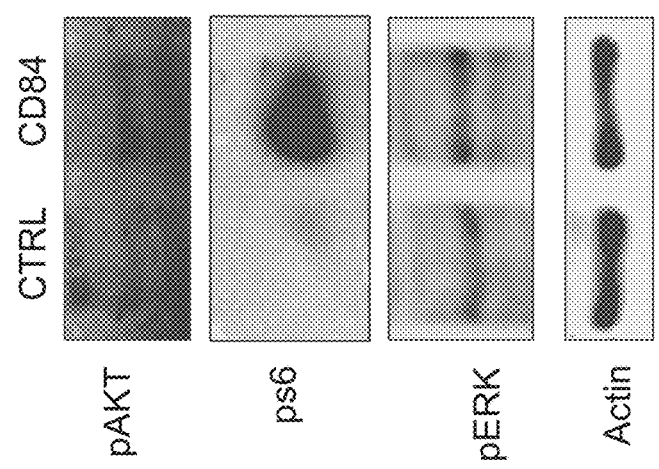
FIG. 24A

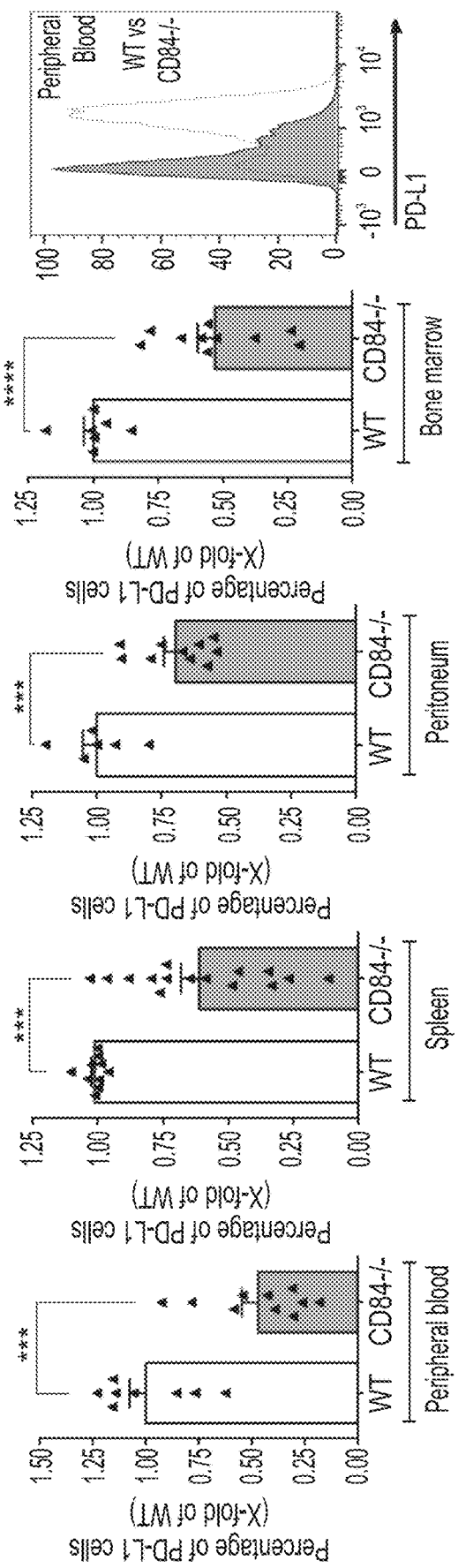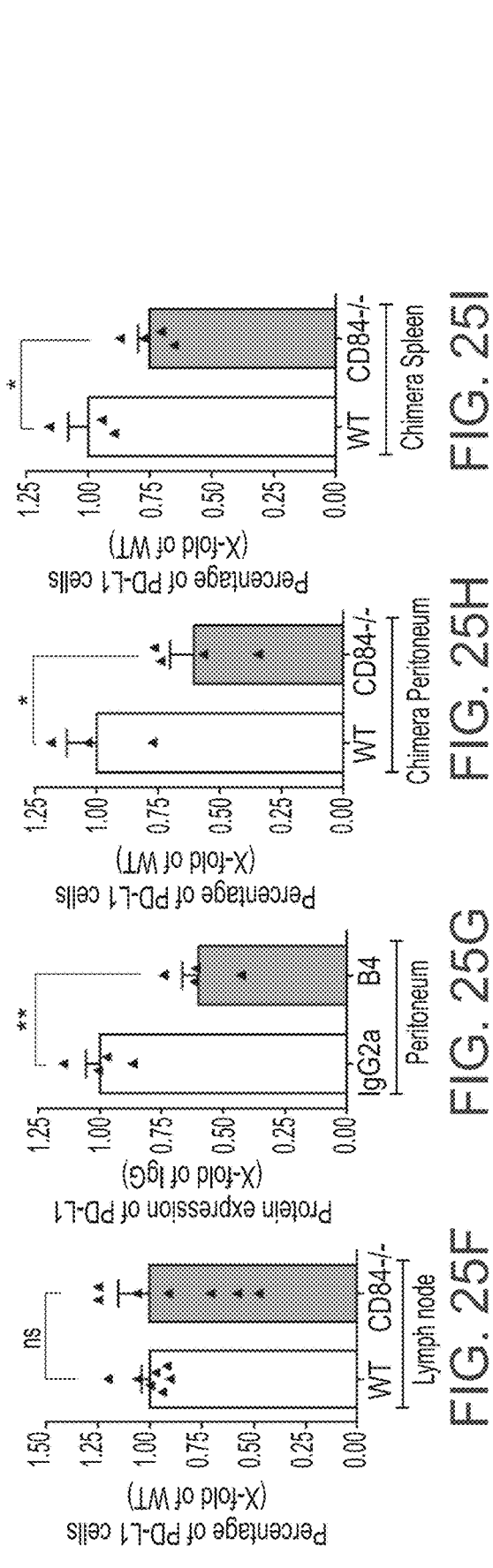

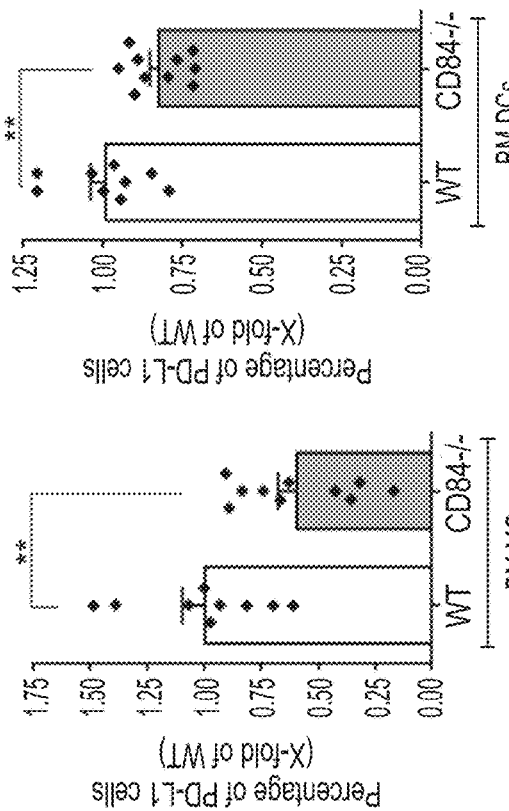
FIG. 26A
FIG. 26B
FIG. 26C
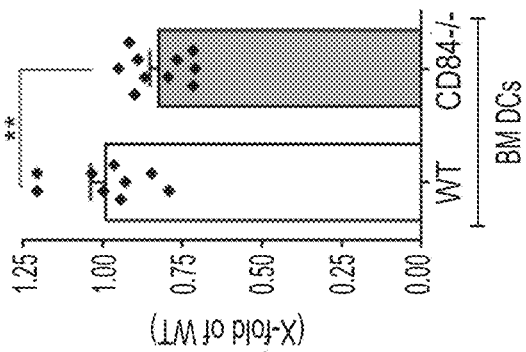
FIG. 26D
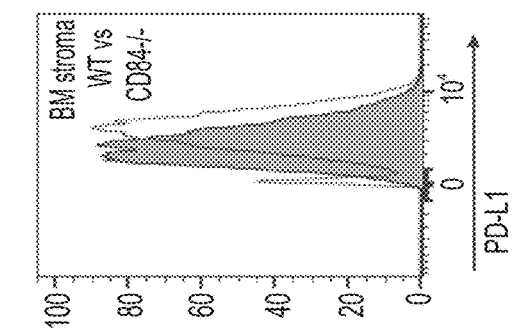
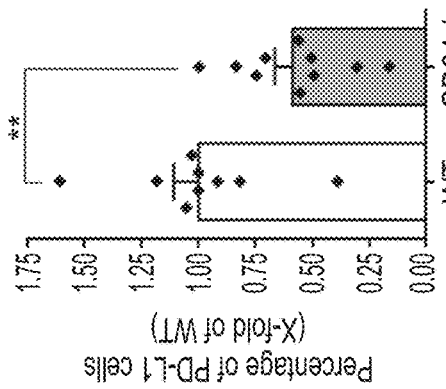
FIG. 26E
FIG. 26F
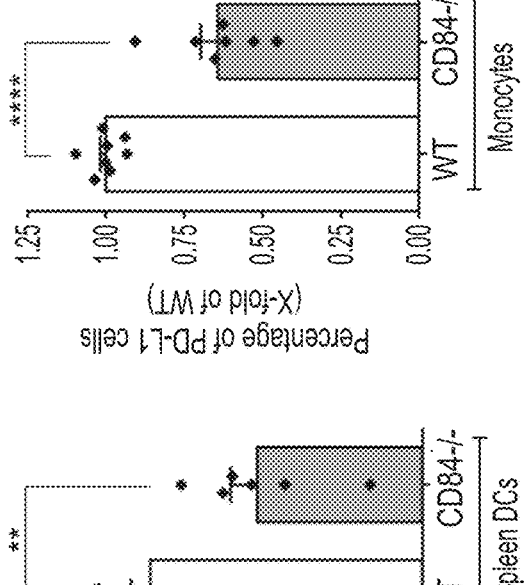
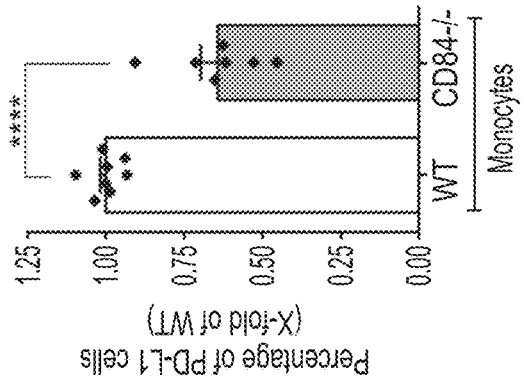
FIG. 26G
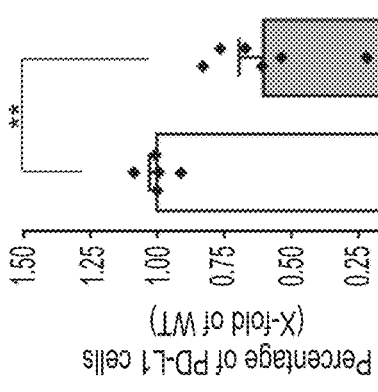

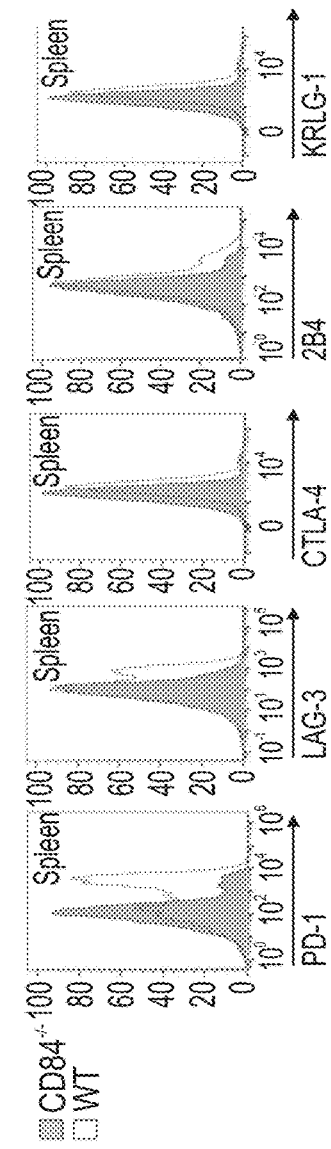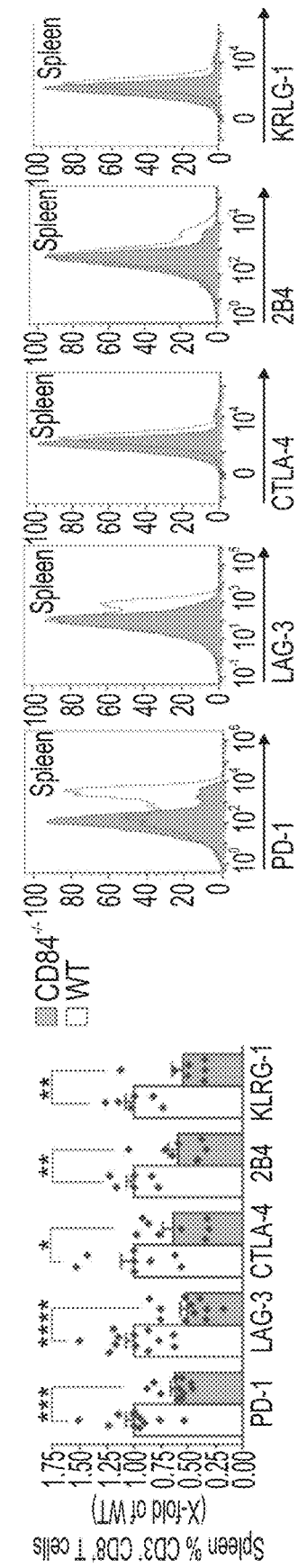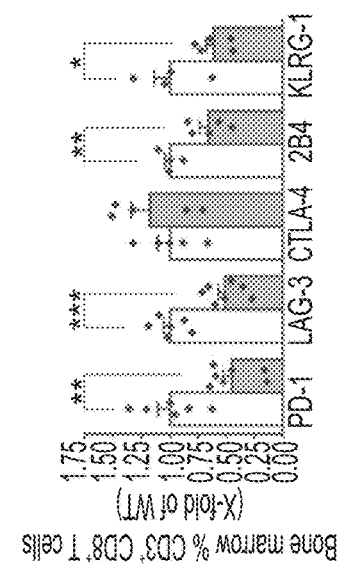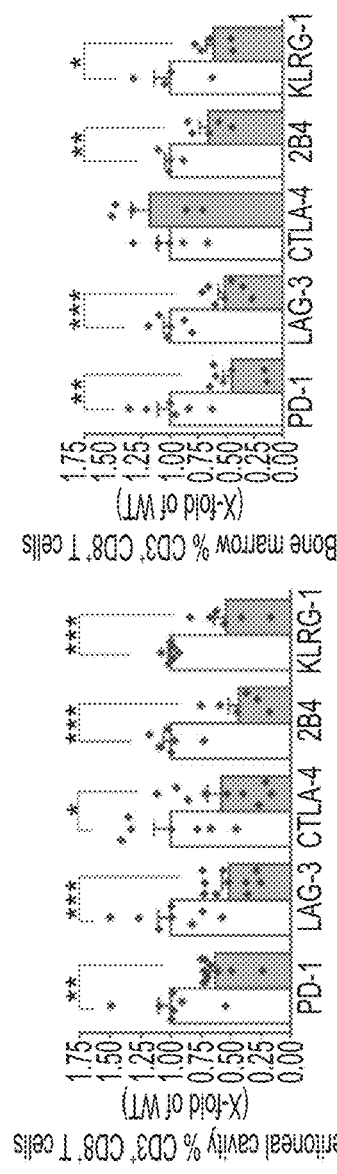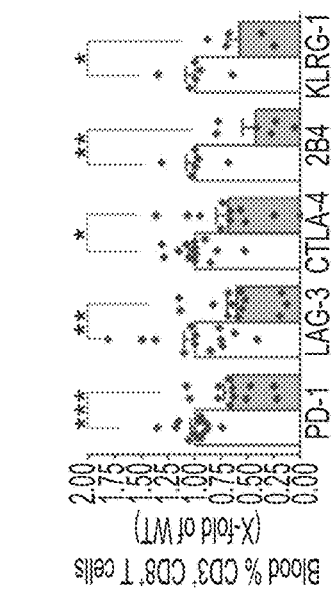

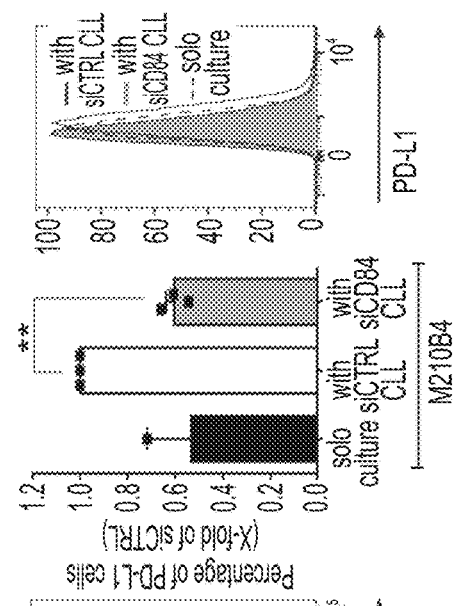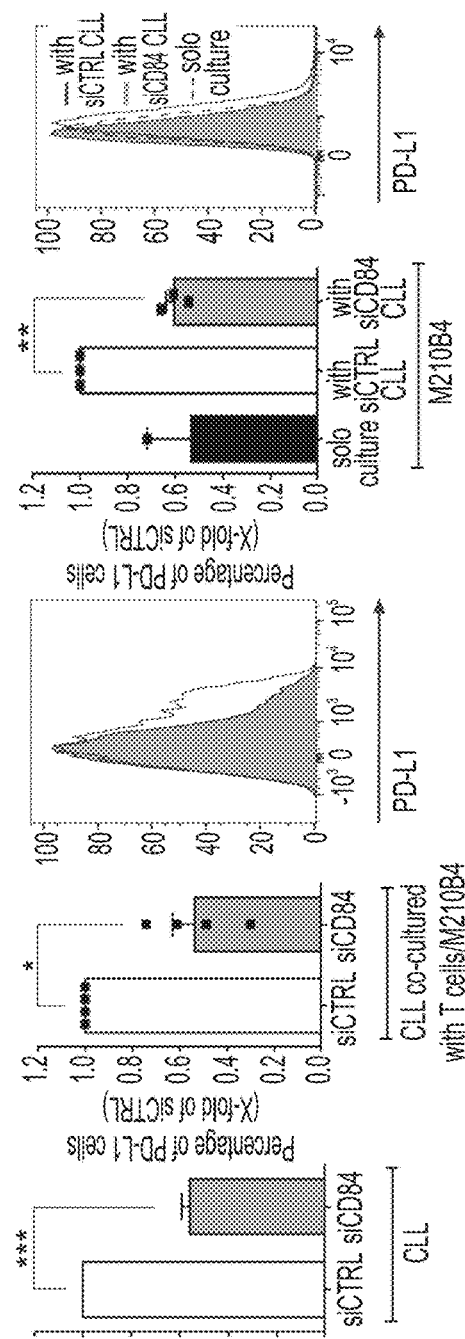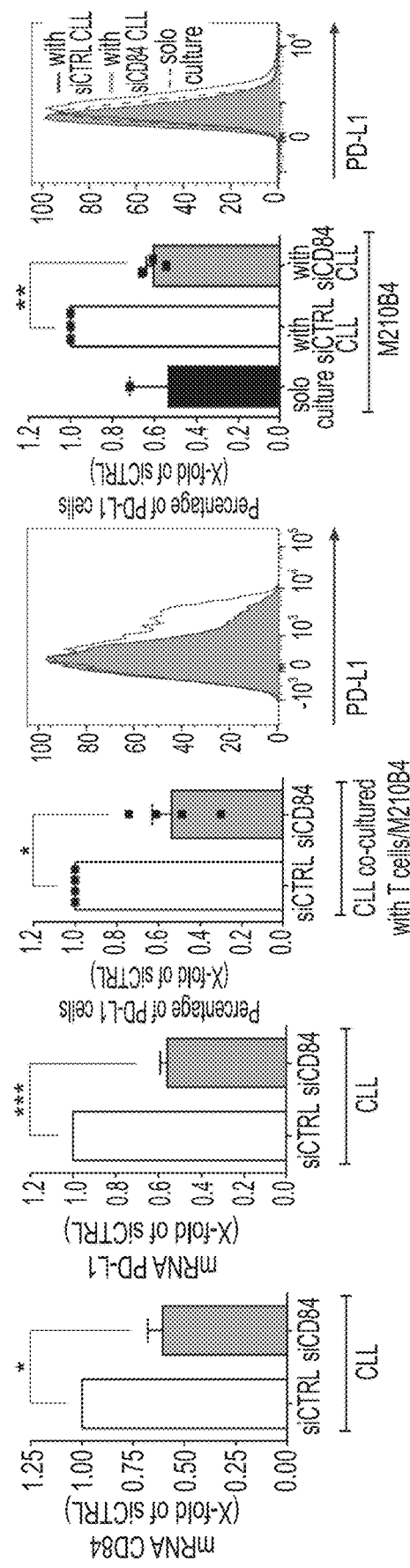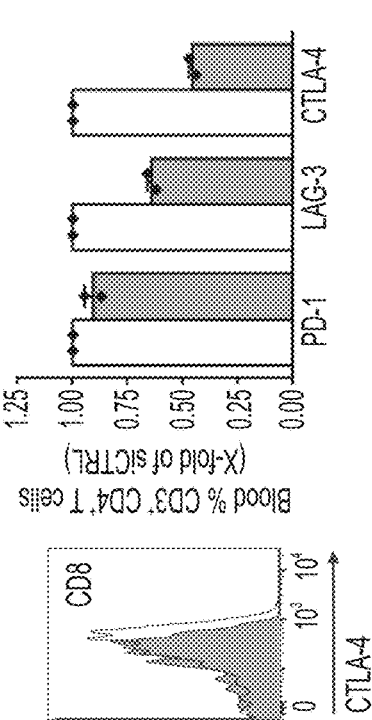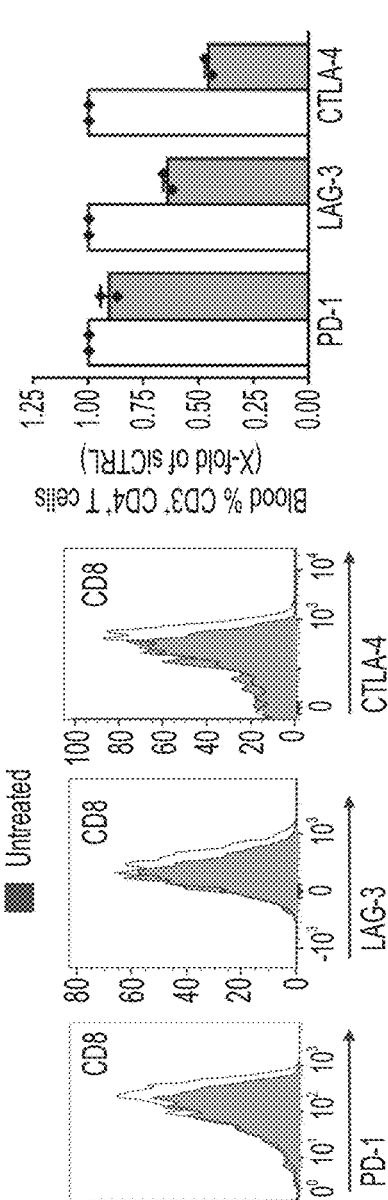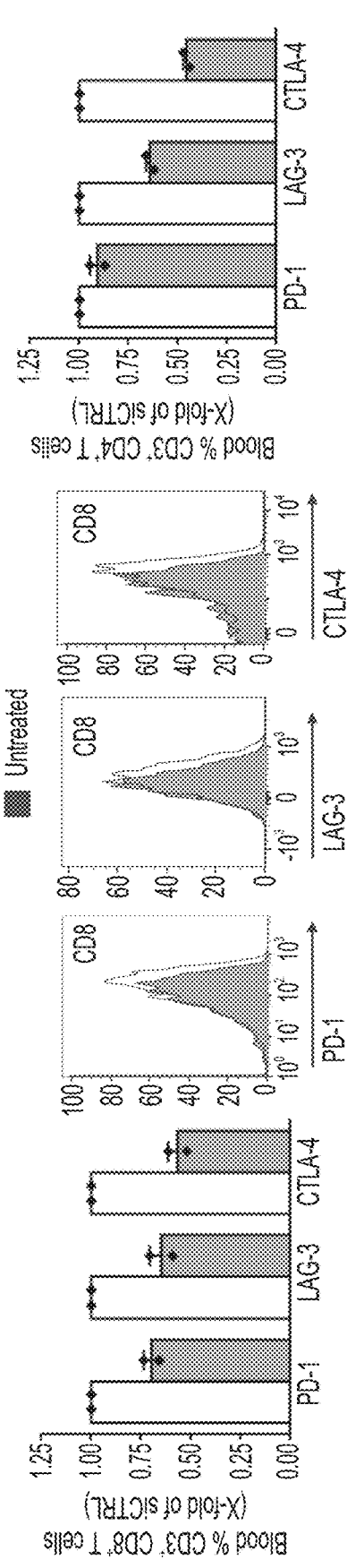

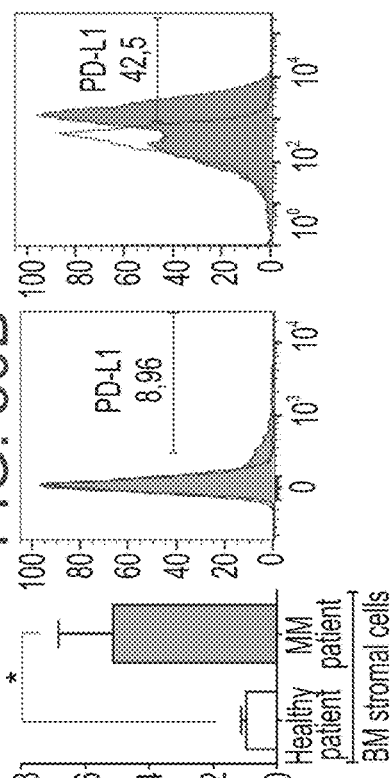
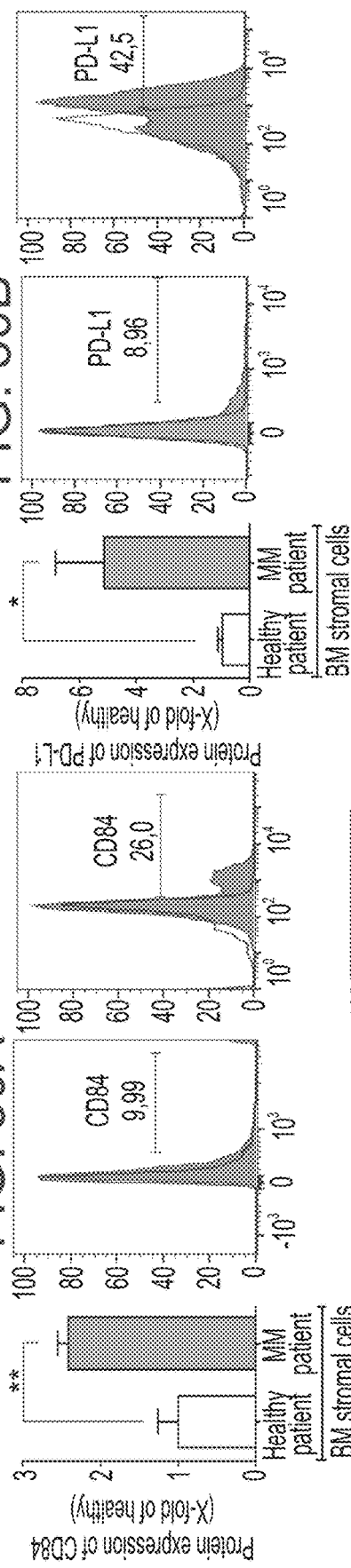
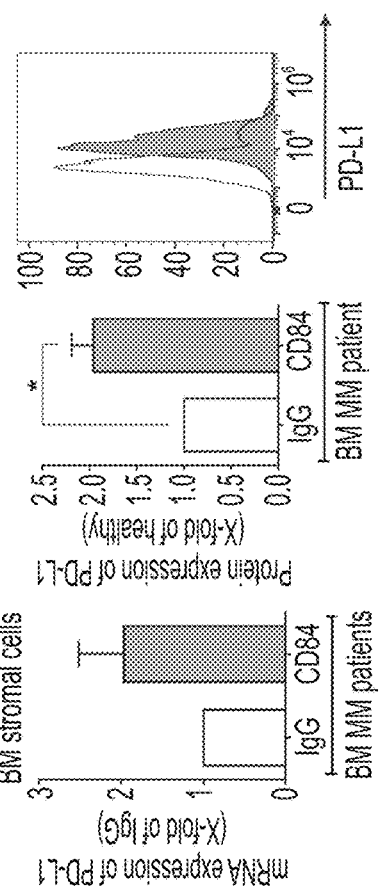
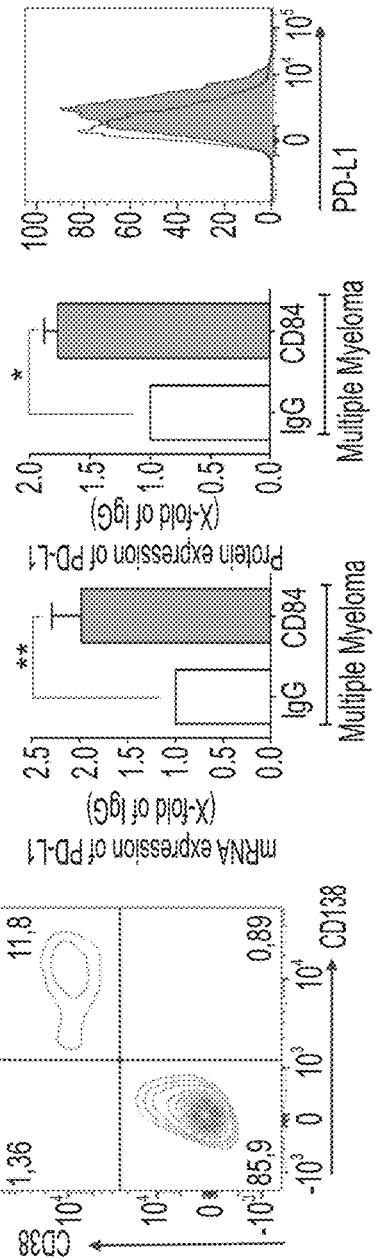
FIG. 30A
FIG. 30B
FIG. 30C
FIG. 30D

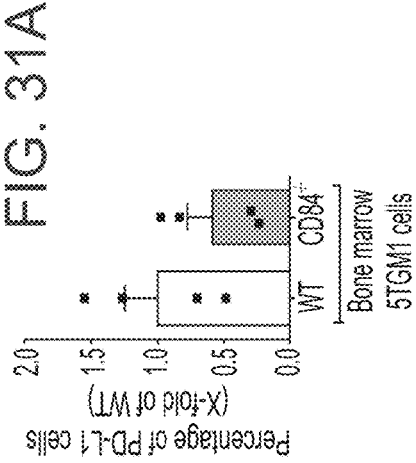
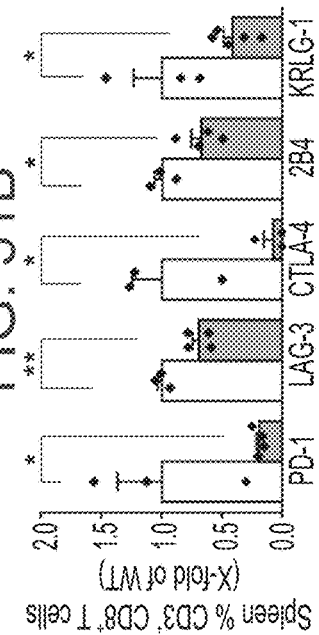
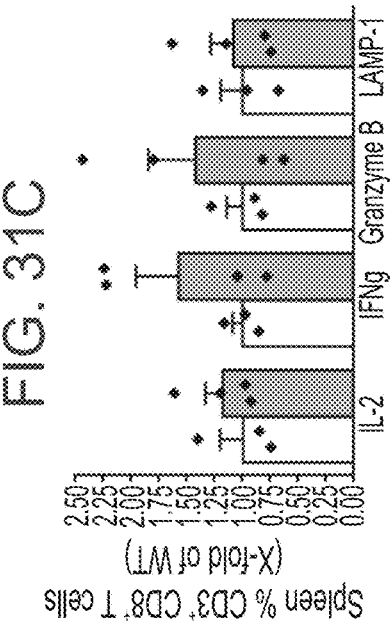
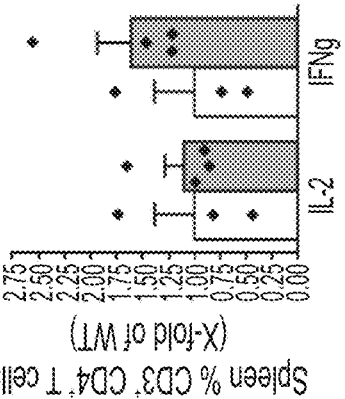
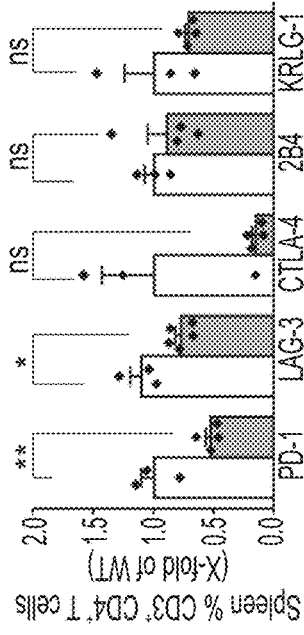

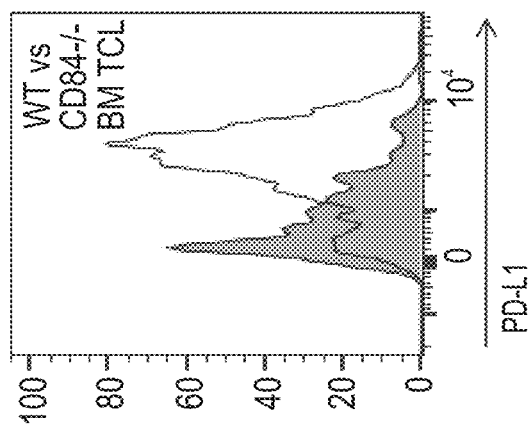
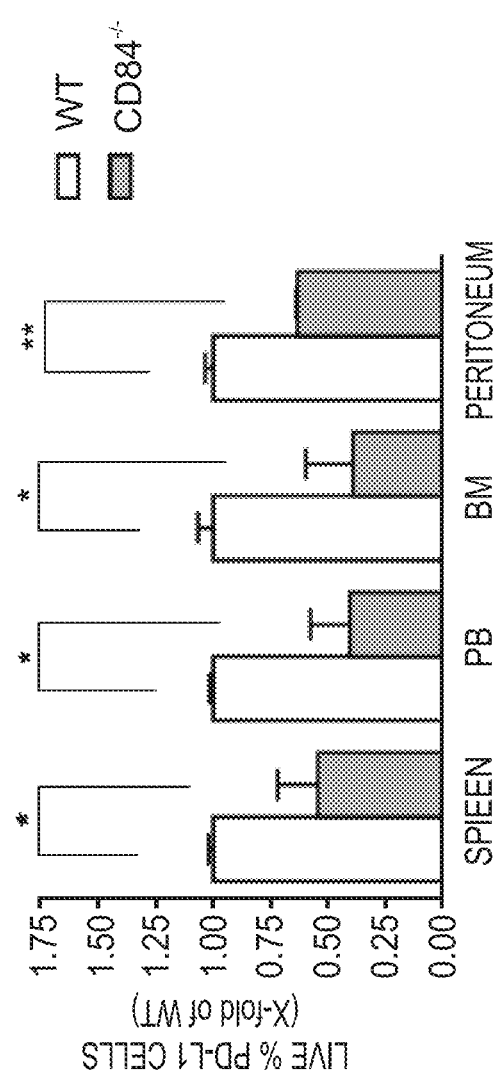

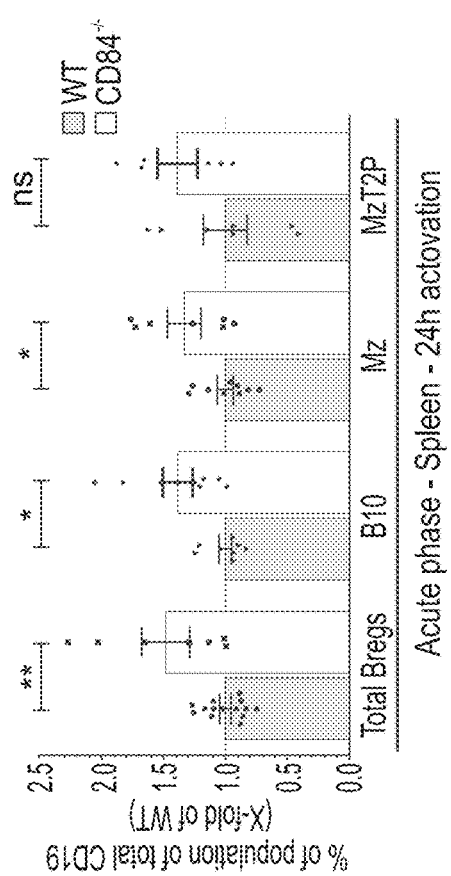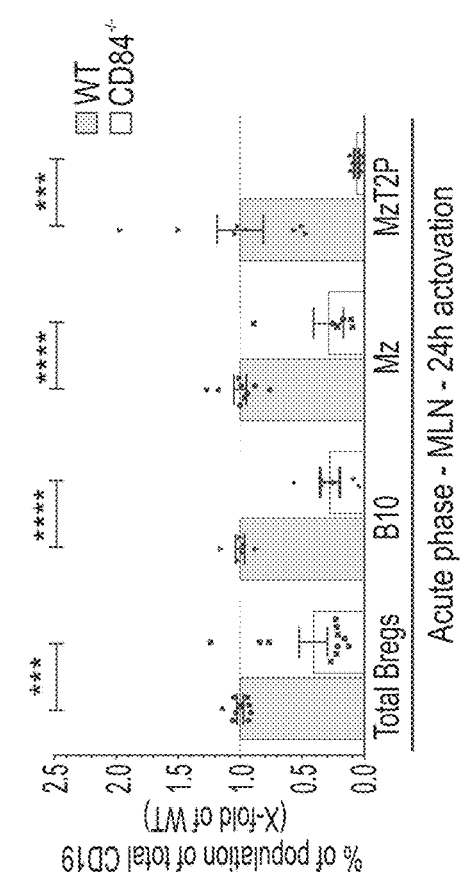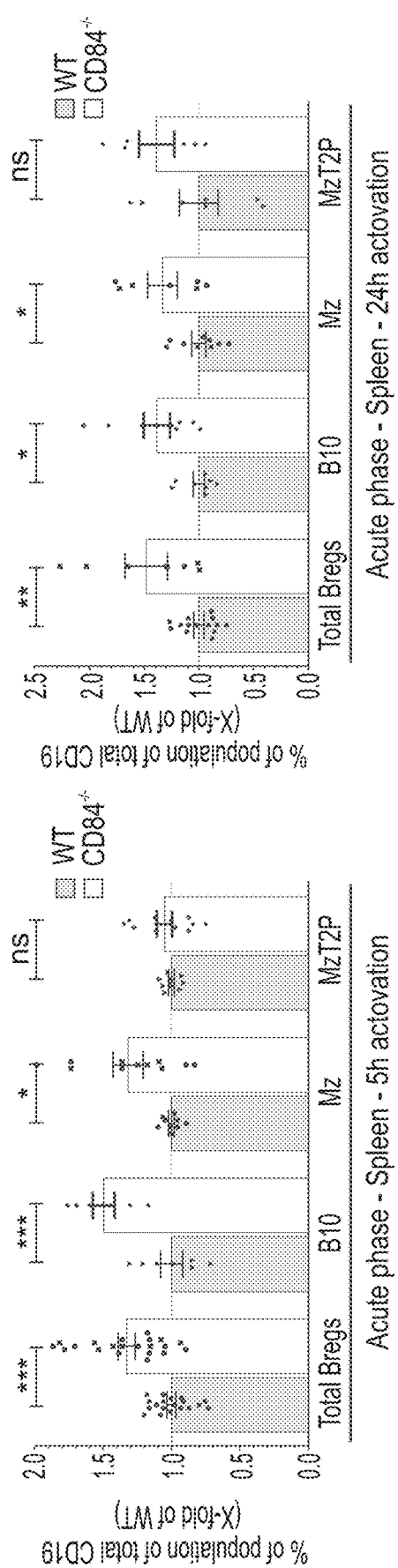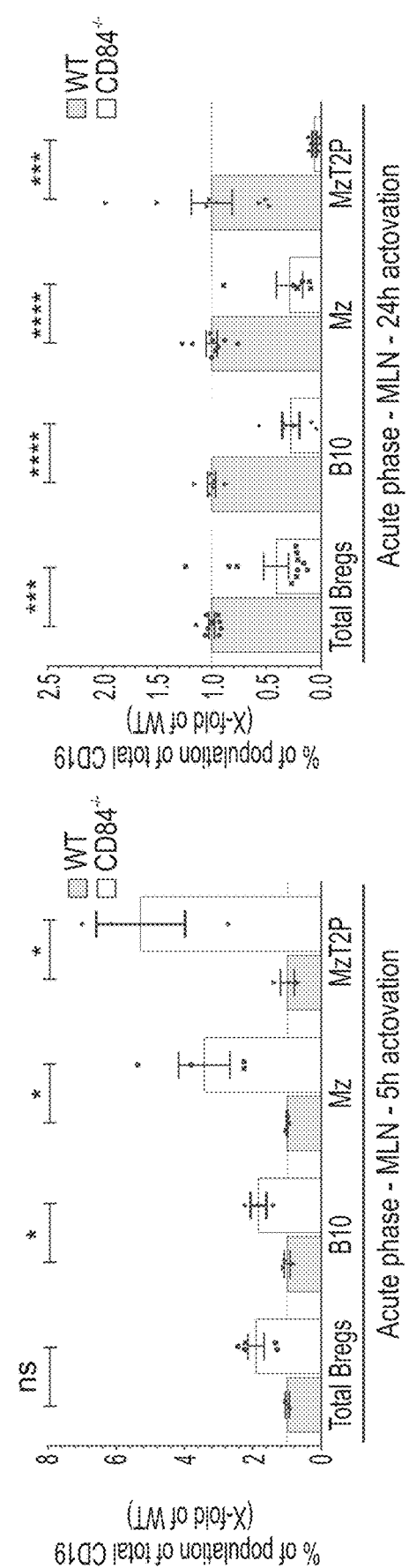

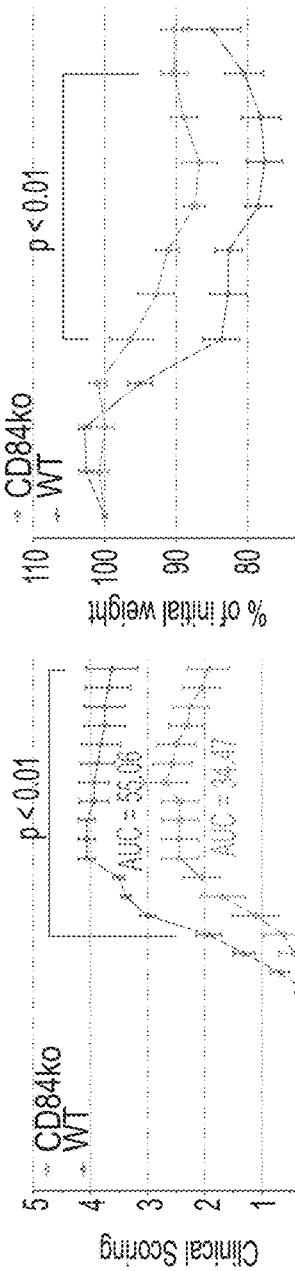
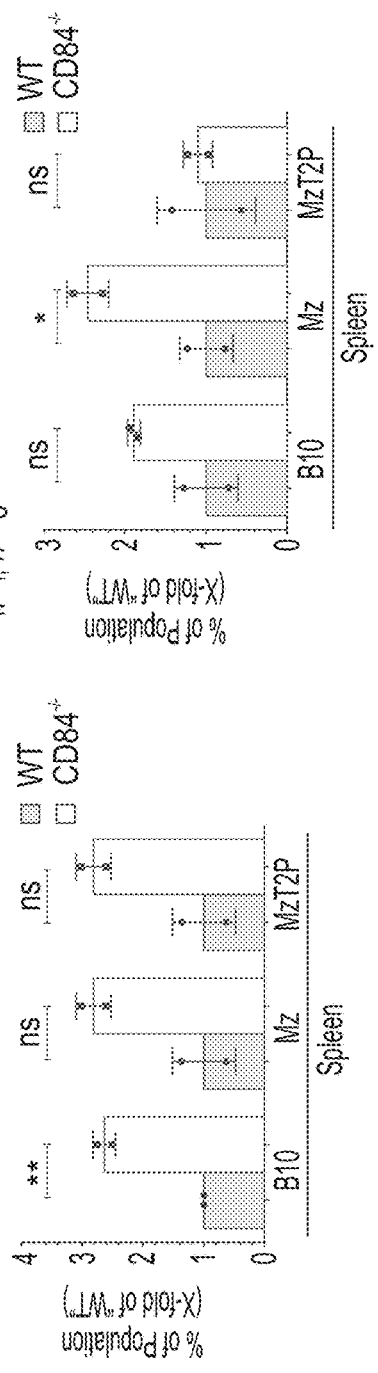
FIG. 41A
FIG. 41B
FIG. 41C
FIG. 41D
FIG. 41E
FIG. 41F

COMPOSITIONS AND METHODS FOR TREATING MALIGNANT, AUTOIMMUNE AND INFLAMMATORY DISEASES

RELATED APPLICATIONS

This application is a division of U.S. patent application Ser. No. 16/068,172 filed on Jul. 5, 2018, which is a National Phase of PCT Patent Application No. PCT/IL2017/050019 having International Filing Date of Jan. 5, 2017, which claims the benefit of priority under 35 USC § 119(e) of U.S. Provisional Patent Application No. 62/275,378 filed on Jan. 6, 2016. The contents of the above applications are all incorporated by reference as if fully set forth herein in their entirety.

FIELD AND BACKGROUND OF THE INVENTION

The present invention, in some embodiments thereof, relates to compositions and methods for preventing or reversing T cell exhaustion, and for enhancing an activity or level of B regulatory cells, for treating malignant, autoimmune and inflammatory diseases.

There are different types of B cell malignancies involving different stages of B cell differentiation. For example, multiple myeloma is a disease caused by malignant plasma cells while acute lymphoblastic leukemia (ALL) is a malignancy that arises from lymphoid precursor cells and Burkitt's lymphoma originates from germinal center B cells.

Chronic lymphocytic leukemia (CLL) is the most common leukemia in the western world. The disease is characterized by the progressive accumulation of B lymphocytes in peripheral blood, lymphoid organs and bone marrow. A major manifestation of the disease is immune dysregulation. CLL cells are small mature lymphocytes that are significantly impaired in their ability to undergo further maturation into immunoglobulin secreting cells. Despite possessing a B Cell Receptor and expressing MHC II molecules, they are very poor antigen presenting cells. The hallmark of the disease is decreased apoptosis, resulting in accumulation of malignant cells. In-vivo, CLL cells are dependent on their microenvironment for proliferation and survival.

The bone marrow (BM) stroma plays an essential role in B-lymphopoiesis, and can provide survival niches for both normal B cells and mature leukemic B cells. The adhesion of CLL cells to BM stromal cells or to the BM vasculature rescues these lymphocytes from apoptosis and extends their life span. For CLL, the complex cellular and molecular contexts created in the tissues, collectively referred to as the CLL microenvironment, provide signals for the expansion of the CLL clone, and enable primary drug resistance. In addition, in vitro and in vivo studies showed that CLL cells induce changes in their surroundings, e.g. an inflammatory cytokine milieu, an exhaustion phenotype in T cells, or the differentiation of myeloid cells with immunosuppressive activity. Some of these interactions are dependent on cell-cell contact, while others are mediated through chemokines, growth factors, and possibly through extracellular matrix components.

The SLAM family receptors consist of SLAMF1 (CD150), SLAMF2 (CD48), SLAMF3 (LY9), SLAMF4 (2B4), SLAMF5 (CD84), SLAMF6 (Ly108/NTBA), SLAMF7 (CRACC), SLAMF8 (BLAME) and SLAMF9 (CD84H), illustrated in FIG. 1. The receptors contain immunoreceptor tyrosine-based switch motif (ITSM) with the consensus sequence TxYxxI/V. The sequence has high affinity for SLAM-associated protein (SAP) and/or Ewing's sarcoma-associated transcript 2 (EAT-2) (in B cells and macrophages). Two of the members of the family, SLAMF8 and SLAMF9, have short intracellular tails that do not have tyrosine motifs. The receptors have no ligands, and in most of the cases homophilic interactions regulate their cellular induced cascade. SLAM family receptors are differently expressed during development of B cells.

CD84, a member of the SLAM family of receptors, is expressed on various cells including NK cells, NKT cells, B cells, T cells, monocytes, platelets, dendritic cells, eosinophils and neutrophils. The levels of CD84 were found to be up-regulated in CLL patients and activation of CD84 was shown to lead to a survival cascade, elevating the anti-apoptotic genes Bcl-2 and Mcl-1 [Binsky-Ehrenreich I. et al., Oncogene (2014) 33: 1006-1016]. Previous results show that CD84, expressed on CLL and their microenvironment, mediate an interaction that leads to an anti-apoptotic effect, supporting their survival [Marom et al. (2016) submitted]. The CD84 mediated cell to cell contact leads to elevated expression and secretion of CCL3 from CLL cells. Stromal cells, that highly express the receptors for CCL3, CCR1 and CCR5, bind the secreted chemokine. CCL3 induces upregulation of Bcl-2 expression in stromal cells, leading to their survival. Moreover, CLL3 induced cascade results in the secretion of the cytokines IL-6 and IL-8 (KC in mice), which are known to support CLL survival [Binsky-Ehrenreich, I. et al., Oncogene (2014) 33(8): 1006-1016]. In addition, CD84 expression in the microenvironment regulates CLL pathogenesis in vivo. Lack of CD84 expressed on cells in the microenvironment delays disease development and the accumulation of CLL cells in the BM compartment [Marom et al., supra].

SLAMF1, also called CD150, is expressed on hematopoietic stem cells, B cells, activated T cells, platelets and macrophages. It has 202 amino acids in its extracellular region, a hydrophobic membrane spanning region in the length of 22 amino acids and a 77 amino acid cytoplasmic region. There are at least two isoforms of SLAMF1, one is expressed on the cell surface and the other one is secreted and lacks the membrane spanning region. It has previously been found that adding secreted or transfected SLAMF1 to human B cells, up-regulates growth and differentiation of these cells. SLAMF1 was previously shown to have a role in autoimmunity. SLAMF1's expression is increased on T cells from multiple sclerosis patients compared to healthy controls, suggesting a role in autoimmunity.

SLAMF1 was also previously shown to have a role in tumors. Ligation of SLAMF1 receptors on Hodgkin's lymphoma cell lines leads to transportation of AKT from the cytoplasm to the nucleus, where the AKT pathway is known to promote cell survival [Yurchenko M. et al., Exp Oncol (2011) 33(1): 9-18]. In CLL, overexpression of SLAMF1 suggested a dysregulated signaling through SLAMF1 in CLL cells as compared to normal B cells [Schweighofer C. D. et al, PLoS One (2011)6(12): e28277]. In multiple myeloma patients, SLAMF1 was found to be a gene of high expression in multiple myeloma cells compared to healthy controls on RNA expression. Another interesting feature of SLAMF1 is its expression on tumors of the central nervous system and in carcinomas of uterine cervix, esophagus, rectum and oral cavity as well as in skin basiloma, where normal tissue counterparts of these tumors do not express the receptor.

Programmed cell death 1 (PD-1) and programmed cell death ligand 1 (PD-L1) are cell surface molecules shown to be involved in regulation of the immune response. PD-L1 is the ligand for the PD1 receptor. PD-L1 is expressed on T cells, B cells, monocytes, dendritic cells (DCs), epithelial cells, endothelial cells and macrophages. PD-L1 consists of 290 amino acids, with a transmembrane domain and a short intracellular domain. Functionally, PD-L1 has been described as immune co-inhibitor of T cells when binding PD-1 on the T cells (see FIG. 2). The membrane bound PD-1 is a protein consisting of 288 amino acids. Its structure consists of a transmembrane part, with an immunoglobulin domain and an intracellular part with an ITIM and ITSM. PD-L1/PD-1 induced pathway has a central role in regulation of T cell exhaustion. Exhausted T cells have been shown to overexpress PD-1, cytotoxic T lymphocyte antigen-4 (CTLA-4), lymphocyte-activation gene 3 (Lag-3), Tim-3, 2B4, CD160 and others.

It has previously been shown that PD-1 is up-regulated on CLL cells [Grzywnowicz, M. et al., PLoS One (2012) 7(4): e35178]. Overexpression of PD-1 on $CD8^+$ T cells was described in the Eμ-TCL1 CLL model mouse. The effector functions of these cells were affected, in that both IFNγ and CD107 were reduced on these T cells. Clinical trials using anti-PD-L1 or PD-1 antibodies have been tried in the following immunological cancers; advanced stage CLL, Multiple Myeloma, Non-Hodgkin's lymphoma, relapsed Hodgkin's lymphoma, Follicular lymphoma and Acute myeloid leukemia [Xia, Y. et al., Biochim Biophys Acta, Epub ahead of print Oct. 16, 2015]. Clinical trials have also been conducted with solid tumors for anti-PD-L1 or PD-1 antibodies in for example Melanoma, non-small cell lung cancer and advanced renal cell carcinoma [Xia, Y. et al., (2015) supra]. Anti-PD-L1 antibodies treatment has also been tried in the animal model of CLL (Eμ-TCL1 mouse model). There results showed increased function of T cells in the spleen, which displayed reduced expression of PD-1, Lag-3, KLRG-1 and 2B4, all described as exhaustion markers as well as an increase in the functionality of these T cells, displayed by an increase is IL-2, IL-4 and IFNγ as well as increase CD107 on CD8 T cells, a marker of effector cell cytotoxicity [McClanahan, F. et al, Blood (2015) 126(2): 203-211].

Lag-3 is found on activated T cells and NK cells. Lag-3 binds MHC-II (see FIG. 2) and has been shown to inhibit $CD4^+$ T cell proliferation and reduce IL-4, IL-2, IFNγ and TNFα production in T cells. Currently, the effect of antibody against Lag3 is in clinical trial for melanoma, renal cell carcinoma, breast cancer and pancreatic cancer, where in breast cancer and renal cancer there was some response and the rest are still ongoing (Sierro, Romero et al. 2011). The combined effect of blocking PD-1 and Lag-3 together has been shown in mouse models of cancer, where mice were injected with melanoma, colon adenocarcinoma and fibrosarcoma cell lines. The combined treatment in adenocarcinoma and fibrosarcoma injected mice were more effective compared to treatment with anti-PD-1 or anti-Lag-3 alone [Woo S. R. et al., Cancer Res (2012) 72(4): 917-927].

CTLA-4 is a transmembrane protein. It is strongly induced in activated T cells. Its ligand is the B7 protein. PD-1, Lag-3 and CTLA-4 have all been described as co-inhibitory molecules of T cells (see FIG. 2). Anti-CTL4 has been used in clinical trials for melanoma, prostate cancer, renal cell carcinoma and non-Hodgkin's lymphoma [Ito A. et al., Biomed Res Int (2015): 605478]. Combination therapies have also been tried. In melanoma combination of anti-CTLA-4 and PD-1 gave a more rapid and deeper clinical tumor response compared to treating patients with either one alone.

PCT publication no. WO2010/035259 teaches CD84 as a regulator protein that is essential for the survival of CLL cells. Based on this finding, the inventors of WO2010/035259 have suggested the use of CD84 as a target for B-CLL treatment and as a marker for the disease.

PCT Publication no. WO2015/118538 provides an isolated antibody comprising an antigen recognition domain which specifically binds CD84 and (i) down regulates the anti-apoptotic activity of stromal cells on chronic lymphocytic leukemia (CLL) cells; and/or (ii) induces mobilization of CLL cells from the bone marrow.

Additional related art:

U.S. Patent Application No. 20050027114 discloses methods of treating diseases such as chronic leukemia by agonizing or antagonizing an activity of a CD84-like polypeptide.

U.S. Patent Application No. 20050025789 discloses the treatment or prophylaxis of tumors in patients, using a co-stimulatory polypeptide (e.g., CD84)-expressing tumor cell for producing a vaccine for increasing the lytic activity of NK cells.

SUMMARY OF THE INVENTION

According to an aspect of some embodiments of the present invention there is provided a method of treating a malignant disease involving T cell exhaustion in a subject in need thereof, with the proviso that the malignant disease is not a B cell malignancy, the method comprising administering to the subject a therapeutically effective amount of an agent capable of decreasing an activity or expression of CD84, thereby treating the malignant disease involving the T cell exhaustion.

According to an aspect of some embodiments of the present invention there is provided a use of a therapeutically effective amount of an agent capable of decreasing an activity or expression of CD84 for treating a malignant disease involving T cell exhaustion in a subject in need thereof, with the proviso that the malignant disease is not a B cell malignancy.

According to an aspect of some embodiments of the present invention there is provided a method of preventing or reversing T cell exhaustion in a subject in need thereof, the method comprising administering to the subject a therapeutically effective amount of an agent capable of decreasing an activity or expression of CD84, with the proviso that the subject is not diagnosed with a B cell malignancy, thereby preventing or reversing the T cell exhaustion in the subject.

According to an aspect of some embodiments of the present invention there is provided a method of treating an autoimmune or inflammatory disease in a subject in need thereof, the method comprising administering to a subject a therapeutically effective amount of an agent capable of decreasing an activity or expression of CD84, thereby treating the autoimmune or inflammatory disease in the subject.

According to an aspect of some embodiments of the present invention there is provided a use of a therapeutically effective amount of an agent capable of decreasing an activity or expression of CD84 for treating an autoimmune or inflammatory disease in a subject in need thereof.

According to an aspect of some embodiments of the present invention there is provided a method of elevating an activity or level of B regulatory cells in a subject in need thereof, the method comprising administering to a subject a therapeutically effective amount of an agent capable of decreasing an activity or expression of CD84, thereby elevating the activity or level of the B regulatory cells in the subject.

According to an aspect of some embodiments of the present invention, there is provided a method of treating a malignant disease involving T cell exhaustion in a subject in need thereof, the method comprising administering to the subject a therapeutically effective amount of an agent capable of decreasing an activity or expression of SLAMF1, with the proviso that the agent is not an agent capable of decreasing an activity or expression of CD84, thereby treating the malignant disease involving the T cell exhaustion.

According to an aspect of some embodiments of the present invention, there is provided a use of a therapeutically effective amount of an agent capable of decreasing an activity or expression of SLAMF1, with the proviso that the agent is not an agent capable of decreasing an activity or expression of CD84, for treating a malignant disease involving T cell exhaustion in a subject in need thereof.

According to an aspect of some embodiments of the present invention, there is provided a method of preventing or reversing T cell exhaustion in a subject in need thereof, the method comprising administering to the subject a therapeutically effective amount of an agent capable of decreasing an activity or expression of SLAMF1, with the proviso that the agent is not an agent capable of decreasing an activity or expression of CD84, thereby preventing or reversing the T cell exhaustion in the subject.

According to some embodiments of the invention, the subject is diagnosed with a malignant disease.

According to some embodiments of the invention, the malignant disease is a solid tumor.

According to some embodiments of the invention, the solid tumor is selected from the group consisting of a melanoma, a lung cancer, a renal cell carcinoma, a prostate cancer, a breast cancer, an ovarian cancer, a head and neck cancer, a colon adenocarcinoma, a fibrosarcoma, a uterine cervix cancer, an esophagus cancer, a rectum cancer, an oral cavity cancer, a liver cancer and a pancreatic cancer.

According to some embodiments of the invention, the malignant disease comprises a T cell malignancy or a myeloid malignancy.

According to some embodiments of the invention, the malignant disease is a B cell malignancy.

According to some embodiments of the invention, the B cell malignancy is selected from the group consisting of a Hodgkin's Lymphoma, a non-Hodgkin's Lymphoma, a Diffuse large B-cell lymphoma, a B-cell chronic lymphocytic leukemia (B-CLL)/chronic lymphoid leukemia (CLL), a Chronic lymphocytic leukemia/small lymphocytic lymphoma, a chronic myelocytic leukemia (CML), an Extranodal marginal zone B-cell lymphoma-mucosa-associated lymphoid tissue lymphoma, a Follicular lymphoma, a Mantle cell lymphoma, a Nodal marginal zone B-cell lymphoma, a Burkitt's lymphoma, a Hairy cell leukemia, a Primary central nervous system lymphoma, a Splenic marginal zone B-cell lymphoma, a Lymphoplasmocytic lymphoma, a Primary mediastinal B-cell lymphoma, a multiple myeloma, an acute lymphocytic leukemia (ALL), an acute lymphoblastic pre-B cell leukemia, a plasma cell leukemia, a pre-B cell leukemia, an early pre-B cell leukemia and a pre-B acute lymphoblastoid leukemia.

According to some embodiments of the invention, elevating an activity or level of B regulatory cells is manifested by increased B regulatory cell levels in the spleen.

According to some embodiments of the invention, elevating an activity or level of B regulatory cells is manifested by an increase in production of anti-inflammatory cytokines by the B regulatory cells.

According to some embodiments of the invention, the anti-inflammatory cytokines are selected from the group consisting of IL-10, TGFβ-1 and IL-35.

According to some embodiments of the invention, elevating an activity or level of B regulatory cells is associated with an increase in expression of a Breg marker selected from the group consisting of CD19, IL-10 and CD1d by the B regulatory cells.

According to some embodiments of the invention, elevating an activity or level of B regulatory cells is associated with an increase in B10 B regulatory cells.

According to some embodiments of the invention, the subject is diagnosed with an autoimmune or inflammatory disease.

According to some embodiments of the invention, the autoimmune or inflammatory disease is selected from the group consisting of a multiple sclerosis, ulcerative colitis, Crohn's disease, arthritis and lupus.

According to some embodiments of the invention, the autoimmune or inflammatory disease is a chronic condition.

According to some embodiments of the invention, the autoimmune or inflammatory disease is an acute condition.

According to some embodiments of the invention, the agent capable of decreasing the activity or expression of the CD84 is a polynucleotide agent.

According to some embodiments of the invention, the polynucleotide agent is selected from the group consisting of an antisense, a siRNA, a microRNA, a Ribozyme and a DNAzyme.

According to some embodiments of the invention, the agent capable of decreasing the activity or expression of the CD84 is an antibody.

According to some embodiments of the invention, the antibody binds at least one epitope of an extracellular portion of CD84.

According to some embodiments of the invention, the antibody is a CD84 neutralizing antibody.

According to some embodiments of the invention, the agent capable of decreasing the activity or expression of the SLAMF1 is a polynucleotide agent.

According to some embodiments of the invention, the polynucleotide agent is selected from the group consisting of an antisense, a siRNA, a microRNA, a Ribozyme and a DNAzyme.

According to some embodiments of the invention, the agent capable of decreasing the activity or expression of the SLAMF1 is a SLAMF1 antibody.

According to some embodiments of the invention, the agent capable of decreasing the activity or expression of the CD84 downregulates an activity or expression of pro-grammed cell death ligand 1 (PD-L1), Programmed cell death 1 (PD-1), cytotoxic T lymphocyte antigen-4 (CTLA-4), lymphocyte-activation gene 3 (Lag-3), killer-cell lectin like receptor G1 (KLRG1) and/or 2B4 on the T cell.

According to some embodiments of the invention, the therapeutically effective amount of the agent capable of decreasing the activity or expression of CD84 causes reversal of the T cell exhaustion which is associated with an increase in production of IL-2, IL-4, IFNγ and/or expression of CD107 by the T cells.

According to some embodiments of the invention, the method further comprises administering to the subject a chemotherapeutic agent, an antibody immunotherapy and/or a radiation therapy.

According to some embodiments of the invention, the subject is a human subject.

Unless otherwise defined, all technical and/or scientific terms used herein have the same meaning as commonly understood by one of ordinary skill in the art to which the invention pertains. Although methods and materials similar or equivalent to those described herein can be used in the practice or testing of embodiments of the invention, exemplary methods and/or materials are described below. In case of conflict, the patent specification, including definitions, will control. In addition, the materials, methods, and examples are illustrative only and are not intended to be necessarily limiting.

BRIEF DESCRIPTION OF THE SEVERAL VIEWS OF THE DRAWINGS

Some embodiments of the invention are herein described, by way of example only, with reference to the accompanying drawings. With specific reference now to the drawings in detail, it is stressed that the particulars shown are by way of example and for purposes of illustrative discussion of embodiments of the invention. In this regard, the description taken with the drawings makes apparent to those skilled in the art how embodiments of the invention may be practiced.

In the drawings:

(FIGS. 3A-3C) $1\times10^5$ M210B4 cells were incubated with the agonistic anti-CD84 (4 μg/ml) or the IgG1 isotype control (4 μg/ml) antibodies. (FIG. 3A) After 24 hrs the cells were harvested. RNA was purified and SLAMF1 mRNA was determined by qRT-PCR (n=5, Two-tailed ratio paired T test, *P<0.05. (FIGS. 3B-3C) After 48 hrs protein levels of SLAMF1 were determined by flow cytometry (FIG. 3B) (n=6, Two-tailed ratio paired T test, *P<0.05). A representative histogram is shown in FIG. 3C, where CD84 stimulated sample is in black and control in light grey. (FIGS. 3D-3E) NLC (FIG. 3D) or BM stroma cells grown from BM aspirates (FIG. 3E) were incubated with the agonistic anti-CD84 (4 μg/ml) or the IgG1 isotype control (4 μg/ml) antibodies. After 24 hrs the cells were harvested, RNA was purified and SLAMF1 mRNA was determined with qRT-PCR (n=1). (FIGS. 3F-3H) $1\times10^7$ CLL cells were incubated with the agonistic anti-CD84 (4 μg/ml) or the IgG1 isotype control (4 μg/ml) antibodies. (FIG. 3F) After 24 hrs the cells were harvested, RNA was purified and mRNA levels were determined by qRT-PCR (n=5, Two-tailed ratio paired T test, *P<0.05 (FIGS. 3G-H) After 48 hrs protein levels of SLAMF1 were determined by flow cytometry (n=6, Two-tailed ratio paired T test, *P<0.05). A representative histogram is shown in FIG. 3H, where CD84 stimulated sample is in black and control in light grey.

(FIG. 4A) Bone marrow stromal cells were seeded from bone marrow aspirates from confirmed healthy bone marrow or bone marrow of CLL patients. After harvest, they were grown for three weeks and stained for SLAMF1 expression with a representative histogram for a healthy patient (showed in FIG. 4B) and for a CLL patient (in FIG. 4C), where the patients staining is shown as black and isotype control as light grey (n=3-6, Two-tailed T test, **p<0.01). (FIG. 4D) TCL cells and B cells were flushed out from the tibia and femur of sick Eμ-TCL1 transgenic mice and compared by staining for SLAMF1 expression, using flow cytometry, with a representative histogram (showed in FIG. 4E), where the TCL are shown in black and the B220 population in light grey (n=3, Twp-tailed T test, *p<0.05).

(FIG. 6A) At different days, blood from the tail vein was taken and stained for the CD5+B220+ population (n=6-10). (FIG. 6B) Animals were sacrificed at day 47 for an adoptive transfer experiment and the CD5+B220+ populations in spleen, BM and PB determined (n=6).

(FIGS. 7A-7D) After 14 days, the mice were sacrificed and number of malignant, CD5/B2220, cell populations in each compartment was measured by flow cytometry in (FIG. 7A) Peripheral blood (n=21, **p<0.0001), (FIG. 7B) spleen (n=14, p=0.0001), (FIG. 7C) peritoneum (n=16, p<0.0001) and (FIG. 7D) Bone marrow (n=14, **p<0.0001).

FIGS. 8A-8I are graphs illustrating that SLAMF1 expression is regulated by CD84 in vivo in the TCL1-Eμ CLL model mouse. (FIGS. 8A-8B) TCL-1 splenocytes ($4\times10^7$) were injected i.v. into the tail vein of C57BL/6 wt or CD84$^{-/-}$ mice. After 14 days, the mice were sacrificed and number of CD5/B220 SLAMF1 expressing TCL cells or B220 SLAMF1 expressing B cells were determined in BM and peritoneum were analyzed by flow cytometry. (FIG. 8A) Peritoneum (n=4, p<0.01) with a representative histogram in FIG. 8B, displaying the CD84$^{-/-}$ TCLs as the black curve and wt as the light grey, (FIG. 8C) Bone marrow (n=4, p=0.01), with a representative histogram in FIG. 8D, displaying the CD84$^{-/-}$ TCLs as the black curve and wt as the light grey. (FIG. 8E) Animals were injected with $4\times10^7$ TCL-1 splenocytes and treated i.v. starting from the second day with 1 mg/kg body weight with the B4 or isotype control antibody. After 14 days, the mice were sacrificed and number of CD5/B220 SLAMF1 expressing TCL cells or B220 SLAMF1 expressing B cells were determined in BM and peritoneum were analyzed by flow cytometry (n=4,

*p<0.05**p<0.01) with a representative histogram in (FIG. 8F) of the peritoneum and in (FIG. 8G) of the bone marrow, displaying the CD84$^{-/-}$ TCLs as the black curve and wt as the light grey. (FIG. 8H) Bone marrow stromal cells harvested from wt or CD84$^{-/-}$ animals, injected with 4×10$^7$ TCL-1 splenocytes, were grown for three weeks until confluence and measured for SLAMF1 expression with flow cytometry. A representative histogram is shown in FIG. 8I displaying the CD84$^{-/-}$ TCLs as the black curve and wt as the light grey (n=5-6).

FIGS. 9A-9J are graphs illustrating that downregulation of SLAMF1 induces CLL cell death. (FIGS. 9A-9C) 2×10$^6$ CLL cells were incubated with 10 μg/ml antagonistic anti-SLAMF1 for 24 hrs and stained with Annexin V and 7AAD, with representative diagrams in FIGS. 9B-9C (n=3, **p<0.01). (FIGS. 9D-9E) 0.625×10$^5$ or 0.5×10$^5$ M210B4 were seeded to 70% confluence, 24 hrs later siCTRL or siSLAMF1 was added and the cells were electroporated. After 24 hrs the cells were harvested, RNA was purified and mRNA levels of SLAMF1 were determined by qRT-PCR (FIG. 9D) (n=3, *p<0.05). After 48 hrs the cells were harvested and protein levels of SLAMF1 were determined by flow cytometry (FIG. 9E) (n=7, p<0.01). (FIGS. 9F-9J) 0.625×10$^5$ or 0.5×10$^5$ M210B4 were plated to 70% confluence, 24 hrs later siCTRL or siSLAMF1 was added and the cells were electroporated. After an additional 24 hrs 1.6×10$^6$ CLL cells were seeded on top of the electroporated layer. The cells were co-cultured for 48 hrs and thereafter cell survival of the CLL cells was determined by Annexin V and 7AAD staining on flowcytometry. Shown is cell survival in (FIG. 9F) and cell death (FIG. 9G) of the CLL cells. Representative plots are shown in FIGS. 9H-J (n=3-6, *p<0.001, *p<0.05).

FIGS. 11A-11B are graphs illustrating regulation of SLAMF1, by CD84, in Multiple myeloma. (FIG. 11A) Multiple myeloma cells from a bone marrow aspirate was incubated with the agonistic anti-CD84 antibody (4 μg/ml) or the IgG1, k isotype control (4 μg/ml). After 24 hrs the cells were harvested, RNA was purified and mRNA levels of SLAMF1 was determined with qRT-PCR (n=1). (FIG. 11B) Bone marrow stromal cells were seeded from bone marrow aspirates from confirmed healthy bone marrow or bone marrow of CLL patients. After harvest, they were grown for three weeks, until confluence, and stained for SLAMF1 expression (n=1).

(FIGS. 12A-12B) 1×10$^7$ 697 or REH cells, Acute lymphoblastic leukemia cell lines, were incubated with the agonistic anti-CD84 (4 μg/ml) or the IgG1 isotype control (4 μg/ml). After 24 hrs the cells were harvested, RNA was purified and mRNA levels of SLAMF1 was determined with qRT-PCR (n=2). (FIGS. 12C-D) 1×10$^7$ Ramos or Daudi cells, Burkitt's lymphoma cell lines, were incubated with the agonistic anti-CD84 antibody (4 μg/ml) or the IgG1, k isotype control (4 μg/ml). After 24 hrs the cells were harvested, RNA was purified and mRNA levels of SLAMF1 was determined with qRT-PCR (n=3).

FIGS. 13A-13H are graphs illustrating that PD-L1 is elevated on microenvironmental cells and CLL cells following CD84 activation. (FIGS. 13A-C) 1×10$^5$ M210B4 cells were incubated with the agonistic anti-CD84 (4 μg/ml) or the IgG1 isotype control (4 μg/ml) antibodies. (FIG. 13A) After 24 hrs the cells were harvested. RNA was purified and PD-L1 mRNA was determined by qRT-PCR (n=5, Two-tailed ratio paired T test, *P<0.05. (FIGS. 13B-13C) After 48 hrs protein levels of PD-L1 were determined by flow cytometry (FIG. 13B) (n=6, Two-tailed ratio paired T test, *P<0.05). A representative histogram is shown in FIG. 13C, where CD84 stimulated sample is in black and control in light grey. (FIGS. 13D-13E) NLC (FIG. 13D) or BM stromal cells grown from BM aspirates (FIG. 13E) were incubated with the agonistic anti-CD84 (4 μg/ml) or the IgG1 isotype control (4 μg/ml) antibodies. After 24 hrs the cells were harvested, RNA was purified and PD-L1 mRNA was determined with qRT-PCR (n=1). (FIGS. 13F-13H) 1×10$^7$ CLL cells were incubated with the agonistic anti-CD84 (4 μg/ml) or the IgG1 isotype control (4 μg/ml) antibodies. (FIG. 13F) After 24 hrs the cells were harvested, RNA was purified and mRNA levels were determined by qRT-PCR (n=3, Two-tailed ratio paired T test, *P<0.05 (FIGS. 13G-H). After 48 hrs protein levels of PD-L1 were determined by flow cytometry (n=4, Two-tailed ratio paired T test, *P<0.05). A representative histogram is shown in FIG. 13H, where CD84 stimulated sample is in black and control in light grey.

(FIGS. 14A-14B) Bone marrow stromal cells grown from bone marrow aspirates of confirmed healthy patients for approximately three weeks, until confluence, and incubated with the agonistic anti-CD84 antibody (4 μg/ml) or the IgG1 isotype control (4 μg/ml). After 24 hrs the cells were harvested, RNA was purified and mRNA levels of PD-1 was determined with qRT-PCR (n=1). After 48 hrs protein levels of PD-L1 were determined by flow cytometry (FIGS. 14A-14B) (n=3). (FIGS. 14C-14E) 1×10$^7$ CLL cells were incubated with the agonistic anti-CD84 antibody (5 μg/ml) or the IgG1, k isotype control (4 μg/ml). After 24 hrs the cells were harvested, RNA was purified and mRNA levels of PD-1 was determined with qRT-PCR (n=3, Two-tailed ratio paired T test, **P<0.01). After 48 hrs protein levels of PD-L1 were determined by flow cytometry (FIGS. 14D-14E) (n=2). A representative histogram is shown in FIG. 14E, where CD84 stimulated sample is in black and control in light grey.

FIGS. 15A-15J are graphs illustrating that PD-L1 expression is regulated by CD84 in vivo in the TCL1-Eμ CLL model mouse. (FIGS. 15A-15G) TCL-1 splenocytes (4×10$^7$) were injected i.v. into the tail vein of C57BL/6 wt or CD84$^{-/-}$ mice. After 14 days, the mice were sacrificed and numbers of CD5/B220 PD-L1 expressing TCL cells were determined in peripheral blood, spleen and peritoneum were analyzed by flow cytometry. (FIGS. 15A-15B) peripheral blood (n=6-7, Two-tailed T test, **p<0.01) (FIGS. 15C-15D) Spleen (n=6-7, Two-tailed T test, *p<0.05, p=0.01) (FIGS. 15E-15G) Peritoneum (n=3-5, Two-tailed T test, p<0.01) with a representative histogram in FIG. 15G of the peritoneum, displaying the CD84$^{-/-}$ TCLs as the black curve and wt as the light grey. (FIG. 15H) Animals were injected with 4×10$^7$ TCL-1 splenocytes and treated i.v. starting from the second day with 1 mg/kg body weight with the B4 or isotype control antibody. After 14 days, the mice were sacrificed and number of CD5/B220 PD-L1 expressing TCL cells were determined in the peritoneum and analyzed by flow cytometry (n=4, Two-tailed T test**p<0.01). (FIGS. 15I-15J) Bone marrow stromal cells harvested from either wt or CD84$^{-/-}$ animals, injected with 4×10$^7$ TCL-1 splenocytes, were grown for three weeks until confluence and measured for PD-L1 expression with flow cytometry (n=6-8) with a representative histogram in FIG. 15J of the BM stromal cells, displaying the ones harvested from CD84$^{-/-}$ as the black curve and wt as the light grey.

FIGS. 16A-16B are graphs illustrating that PD-1 expression is regulated by CD84 in vivo. (FIGS. 16A-16B) TCL-1 splenocytes (4×10$^7$) were injected i.v. into the tail vein of C57BL/6 wt or CD84$^{-/-}$ mice. After 28 days, the mice were sacrificed and numbers of CD5/B220 PD-L1 expressing TCL cells were determined in peritoneal cavity by flow cytometry (n=4-5, Two-tailed T test, **p<0.01) with a representative histogram in FIG. 16B of the peritoneum, displaying the CD84$^{-/-}$ TCLs as the black curve and wt as the light grey.

FIGS. 17A-17K are graphs illustrating a decrease in exhaustive markers on T cells following a decrease of PD-L1 on TCLs. (FIGS. 17A-C) TCL-1 splenocytes (4×10$^7$) were injected i.v. into the tail vein of C57BL/6 wt or CD84$^{-/-}$ mice. After 14 days, the mice were sacrificed, spleens were harvested and numbers of CD3$^+$CD8$^+$ T cells expressing PD-1 (FIG. 17A) and Lag-3 (FIG. 17B) were determined by flow cytometry (n=2). The numbers of CTLA-4 (FIG. 17C) were determined in peripheral blood, as no staining was seen in the spleen in two independent experiments (n=6-7, One-tailed T test*p<0.05). (FIGS. 17D-F) TCL-1 splenocytes (4×10$^7$) were injected i.v. into the tail vein of C57BL/6 wt or CD84$^{-/-}$ mice. After 14 days, the mice were sacrificed, cell from the peritoneal cavity were harvested and numbers of CD3$^+$CD8$^+$ T cells expressing PD-1 (FIG. 17D), Lag-3 (FIG. 17F) and CTLA-4 (FIG. 17H) were determined by flow cytometry (n=4-5, One-tailed T test*p<0.05) with representative histograms of CD3$^+$CD8$^+$ T cells PD-1 (in FIG. 17E), Lag-3 (in FIG. 17G) and CTLA-4 (in FIG. 17I) displaying the CD84$^{-/-}$ T cells as the black curve and wt as the light grey. (FIGS. 17J-K) TCL-1 splenocytes (4×10$^7$) were injected i.v. into the tail vein of C57BL/6 wt or CD84$^{-/-}$ mice. After 14 days, the mice were sacrificed and numbers of CD5/B220 PD-L1 expressing TCL cells were determined in lymph node by flow cytometry (FIG. 17J) (n=4-5). Conversely, the expression of the CTLA-4, Lag-3 and PD-1 on CD3$^+$CD4$^+$ and CD3$^+$CD8$^+$ T cells was determined in the same organ by flow cytometry (FIG. 17K) (n=4-5).

(FIGS. 18A-18D) BM cells (5×10$^6$) derived from 8 week old TCL-1 mice or negative control littermates (wt) were injected into lethally irradiated C57BL/6 (wt) or CD84 deficient (CD84$^{-/-}$) mice. (FIGS. 18A, 18C) After 6 months, mice were sacrificed, cells from the spleen and peritoneal cavity were harvested and the malignant CD5+B220 cells were analyzed for PD-L1 expression in peritoneum (FIG. 18A) and spleen (FIG. 18C) (n=3-4, Two-tailed T test, *p<0.05). (FIGS. 18B, 18D) BM cells (5×10$^6$) derived from 8 week old TCL-1 mice or negative control littermates (wt) were injected into lethally irradiated C57BL/6 (wt) or CD84 deficient (CD84$^{-/-}$) mice. After 6 months, mice were sacrificed, cells from the spleen and peritoneal cavity were harvested and the CD3$^+$CD4$^+$ or CD3$^+$CD8$^+$ T cells were analyzed for PD-1 expression in peritoneum (FIG. 18A) and spleen (FIG. 18C) (n=3-4, Two-tailed T test, *p<0.05). (FIGS. 18E-F) Non injected mice harvested for CD3$^+$CD4$^+$ or CD3$^+$CD8$^+$ T cells in peritoneal cavity (FIG. 18E) and spleen (FIG. 18F) expression of CTLA-4, Lag-3 and PD-1 to see basal state in expression.

(FIGS. 19A-B) TCL-1 splenocytes (4×10$^7$) were injected i.v. into the tail vein of C57BL/6 wt or CD84$^{-/-}$ mice. After 14 days, the mice were sacrificed, spleens were harvested, and T cells were recovered by using B220 beads to filter out B cells. To activate the T cells, they were further incubated for 24 hrs on CD3 and CD28 coated plates. RNA was purified and mRNA levels of IL-4 (FIG. 19A) and IFNγ (FIG. 19B) was determined with qRT-PCR (n=3-4, p=0.15).

(FIGS. 20A-20F) Bone marrow stromal cells were seeded from bone marrow aspirates from confirmed healthy bone marrow, bone marrow of CLL patients or multiple myeloma patients. After harvest, they were grown for three weeks and stained for PD-L1 expression (FIG. 20A) or CD84 expression statistics (FIG. 20D). Representative histograms for PD-L1 for a healthy patient (showed in FIG. 20B) and for a CLL patient (in FIG. 20C) and representative histograms for CD84 for a healthy patient (showed in FIG. 20E) and for a CLL patient (in FIG. 20F) where the patients staining is shown as black and isotype control as light grey (n=3-6, Two-tailed T test, **p<0.01).

(FIGS. 21A-B) Multiple myeloma cells from a bone marrow aspirate was incubated with the agonistic anti-CD84 antibody (4 μg/ml) or the IgG1 isotype control (4 μg/ml). After 24 hrs the cells were harvested, RNA was purified and mRNA levels of PD-L1 (FIG. 21A) or PD-1 (FIG. 21B) was determined with qRT-PCR (n=1).

(FIGS. 22A-22D) 1×10$^7$ Ramos or Daudi cells, Burkitt's lymphoma cell lines, were incubated with the agonistic anti-CD84 (4 μg/ml) or the IgG1 isotype control antibodies (4 μg/ml). After 24 hrs the cells were harvested, RNA was purified and mRNA levels of PD-L1 for Ramos (FIG. 22A) and Daudi (FIG. 22C) or PD-1 for Ramos (FIG. 22B) and Daudi (FIG. 22D), was determined with qRT-PCR (n=2-4). (FIGS. 22E-22F) 1×10$^7$ 697 or REH cells, Acute lymphoblastic leukemia cell lines, were incubated with the agonistic anti-CD84 antibody (4 μg/ml) or the IgG1, k isotype control (4 μg/ml). After 24 hrs the cells were harvested, RNA was purified and mRNA levels of PD-L1 was determined with qRT-PCR (n=2).

FIGS. 23A-23G are graphs illustrating that activation of CD84 leads to elevated expression of PD-L1. CLL cells derived from either patients or the CLL model mouse Eμ-TCL1 were stimulated with 5 μg/ml CD84, and PD-L1 levels were examined on mRNA after purification by RT-PCR using primers for PD-L1 and PSMB (n=3) (*p<0.05) (FIG. 23A) and protein levels by flow cytometry (n=4) (*p<0.05) (FIGS. 23A-B). Bone marrow stromal cells derived from human CLL (n=4) and healthy patients (n=4) (*p<0.05) (FIG. 23C) or Eμ-TCL1 (n=5) and healthy (n=5) mice (*p<0.05) (FIG. 23D) were harvested and grown until confluent and examined for their basal levels of PD-L1. M210B4 were stimulated with 4 μg/ml CD84 and analyzed on mRNA level by RT-PCR using primers for PD-L1 and L32 (n=5) (*p<0.05) (FIG. 23E) or analyzed on protein level by flow cytometry (n=6) (**p<0.01) (FIG. 23E). Bone marrow stromal cells derived from either healthy or CLL patients (FIG. 23F) or monocytes derived from CLL patients (FIG. 23G) were stimulated by 4 µg/ml CD84, purified and analyzed on mRNA by RT-PCR using PSMB as housekeeping gene (n=3) (*p<0.05).

FIGS. 24A-24C are graphs illustrating that activation of cell surface CD84 elevates PD-L1 levels through pAKT and mTOR. (FIG. 24A) $1\times10^5$ cells were stimulated with CD84 (4 µg/ml, SCBT) in 24 well plates for 30 minutes, followed by anti-FAB crosslinking for 5 minutes. Thereafter lysed, separated on 12% wt/vol SDS-polyacrylamide gel electrophoresis and blotted with anti-phosphoS6, anti-phospho-AKTt, anti-phosphoERK and actin as housekeeping gene. Blots shown are representative of three experiments. (FIGS. 24B-C) $1\times10^5$ cells were stimulated with CD84 (4 µg/ml, SCBT) in 24 well plates for 20 minutes, followed by anti-FAB crosslinking for 5 minutes. Thereafter fixed and permeabilized with BD bioscience kit, stained for anti-pAKT (cell-signaling) and anti-rabbit secondary APC antibody.

FIGS. 25A-25I are graphs illustrating decreased PD-L1 expression in vivo on TCL-1 cells derived from $CD84^{-/-}$ mice. TCL-1 splenocytes ($4\times10^7$) were injected i.v. into the tail vein of C57BL/6 wt or $CD84^{-/-}$ mice. After 14-21 days, the mice were sacrificed and expression of PD-L1 was determined on CD5/CD19 TCL cells in peripheral blood (n=8-10, *p<0.001) (FIGS. 25A, 25E), spleens (n=12-14, p<0.001) (FIG. 25B), peritoneum (n=6-10, p<0.001) (FIG. 25C), BM (n=7-10, p<0.0001) (FIG. 25D) and lymph node (n=7-8, ns p=0.9893) (FIG. 25F) by flow cytometry. Representative histogram is shown from peripheral blood. (FIG. 25G) Animals were injected with $4\times10^7$ TCL-1 splenocytes and treated i.v. starting from the second day with 1 mg/kg body weight with the B4 or isotype control antibody. After 14 days, mice were sacrificed and PD-L1 expression was determined on TCL1 cells from the peritoneum (n=4, p<0.01). (FIGS. 25H-I) BM cells ($5\times10^6$) derived from 8-week-old TCL-1 mice or negative control littermates (wt) were injected into lethally irradiated C57BL/6 (wt) or CD84-deficient ($CD84^{-/-}$) mice. After 6 months, mice were killed and the expression of PD-L1 was determined on TCL1 cells in the peritoneum (FIG. 25H) and spleen (FIG. 25I) (n=3-4, *p<0.05).

FIGS. 26A-26G are graphs illustrating decreased PD-L1 expression in vivo on the microenvironment in the $CD84^{-/-}$ mice injected with murine CLLs. TCL-1 splenocytes ($4\times10^7$) were injected i.v. into the tail vein of C57BL/6 wt or $CD84^{-/-}$ mice. After 14-21 days, the mice were sacrificed and expression of PD-L1 was determined on bone marrow stromal cells (n=9-10, p<0.01) (FIG. 26A) with a representative histogram (FIG. 26B), macrophages (n=9-10, n=5-6, p<0.01) (FIGS. 26C, 26E) and dendritic cells (n=9-10, n=6, p<0.01) (FIGS. 26D, 26F) in the bone marrow and spleen and monocytes in the peripheral blood (n=7-9, **p<0.001) (FIG. 26G).

FIGS. 27A-27H are graphs illustrating that $CD84^{-/-}$ mice injected with murine CLLs exhibit less exhausted CD8 T cells. TCL-1 splenocytes ($4\times10^7$) were injected i.v. into the tail vein of C57BL/6 wt or $CD84^{-/-}$ mice. After 14-21 days, the mice were sacrificed and expression of the exhaustive marker PD-1, Lag-3, CTLA-4, 2B4 and KLRG1 was determined on CD4 (s4) and CD8 on spleen (n=6-11, *p<0.05, p<0.01, *p<0.001, ****p<0.001) (FIGS. 27A-27B), peripheral blood (n=5-11, *p<0.05, p<0.01, *p<0.001) (FIG. 27C), peritoneal cavity (n=6-10, *p<0.05, p<0.01, *p<0.001) (FIG. 27D) and bone marrow (n=4-7, *p<0.05, p<0.01, *p<0.001) (FIG. 27E). From the spleen cells were as well collected and cultured for 24 hours with anti-CD3 (Biolegend) and the last two hours of culture with brefeldin-A. These cells were then harvested and CD4 T cells were examined for expression of IFNγ and IL-2 (s4) and CD8 T cells were examined for expression of IFNγ, IL-2 Granzyme B and LAMP-1 (n=7-8, *p<0.05, **p<0.01, ns p=0.3172) (FIG. 27F-27G). BM cells ($5\times10^6$) derived from 8-week-old TCL-1 mice or negative control littermates (wt) were injected into lethally irradiated C57BL/6 (wt) or CD84-deficient ($CD84^{-/-}$) mice. After 6 months, mice were killed and the expression of PD-1 was determined on CD8 (FIG. 27H) and CD4 (s4) T cells in the peritoneum and spleen (n=3-4, *p<0.05).

FIGS. 29A-29F are graphs illustrating that disruption of CD84 in human CLL reduces PD-L1 on CLLs and stroma as well as induces less exhausted T cells. CLL cells were treated with siCD84 (Dharmacon) for 24 hours and the amount of CD84 (n=4, *p<0.05) (FIG. 29A) and PD-L1 (n=4, *p<0.001) (FIG. 29B) was examined. Thereafter, these cells were incubated with either M210B4 or T cells derived from the same patient. The M210B4 cells were stained for their amount of PD-L1 (n=3, p<0.01) (FIG. 29C). The T cells were stained for CD4 and CD8 as well as the exhaustion markers PD-1, LAG-3 and CTLA-4 (n=2) (FIGS. 29D-F).

FIGS. 30A-30D are graphs illustrating that activation of CD84 induces PD-L1 expression in Multiple myeloma (MM). (FIGS. 30A-B) Bone marrow stromal cells derived from human MM (n=3) and healthy patients (n=4) (**p<0.01, *p<0.5) were harvested and grown until confluent and examined for their basal levels of CD84 and PD-L1. (FIG. 30C) Bone marrow stromal cells derived from human MM were harvested and grown until confluent and thereafter were stimulated with 4 µg/ml CD84 and analyzed on mRNA level by RT-PCR using primers for PD-L1 and PSMB as housekeeping gene (n=3) (*p<0.05) or analyzed on protein level by flow cytometry (n=3) (*p<0.05). (FIG. 30D) Bone marrow aspirates derived human MM ($CD138^+$, $CD38^+$) were stimulated with 5 µg/ml CD84 and analyzed on mRNA level by RT-PCR using primers for PD-L1 and PSMB as housekeeping gene (n=5) (**p<0.01) (24 hours) or analyzed on protein level by flow cytometry (n=3) (*p<0.05) (48 hours).

FIGS. 31A-31E are graphs illustrating that MM chimeric $CD84^{-/-}$ show reduced expression of PD-L1 and exhibit less exhausted T cells. $CD84^{-/-}$ or wt mice were lethally irradiated and their bone marrow was reconstituted with C57BL/Kalwrij bone marrow and thereafter injected with the 5TGM1 MM cell line. (FIG. 31A) MM cells in the bone marrow showed reduced PD-L1 expression in CD84 lacking microenvironment (n=4). (FIG. 31B-31C) $CD8^+$ T cells display significantly reduced PD-1, Lag-3, CTLA-4, 2B4 and KLRG-1 (n=3-4, **p=0.01, *p<0.05) (FIG. 31B) as well as increased cytokines and cytotoxic factors (FIG. 31C) (n=3-4). (FIGS. 31D-E) $CD4^+$ T cells display reduced PD-1, Lag-3, CTLA-4, 2B4 and KLRG-1 (n=3-4, **p=0.01, *p<0.05) (FIG. 31D) as well as increased cytokines and cytotoxic factors (FIG. 31E) (n=3-4).

FIGS. 34A-34B are graphs illustrating TCL (CD19, CD5 positive) cells gated on Annexin-V and 7AAD negative cells and the solely live cells expression of PD-L1 (n=2-4, **p<0.01, *p<0.05).

FIGS. 40A-40D are graphs illustrating that CD84 affects regulatory B cell populations in colitis. wt and CD84$^{-/-}$ mice were treated with 2% DSS for 5 days via their drinking water followed by normal water until the end of the experiment. On day 10 mice were sacrificed and their spleens and mesenteric lymph nodes (MLN) were harvested. B cells were enriched using b220$^+$ beads and activated with LPS$^+$ PIM (PMA, Ionomycin and Monensin) for 5 or 24 hours. FACS analysis was carried out for Breg subsets. Total Bregs: CD19$^+$, IL-10$^+$; B10: CD19$^+$, IL-10$^+$, CD1d$^{hi}$, CD5$^+$; Mz: CD19$^+$, IL-10$^+$, CD24$^+$, CD21$^+$, CD23$^-$; T2-MzP: CD19$^+$, IL-10$^+$, CD24$^+$, CD21$^+$, CD23$^+$. (FIG. 40A) Spleen populations, activated for 5 hours. (FIG. 40B) MLN populations, activated for 5 hours. (FIG. 40C) Spleen populations, activated for 24 hours. (FIG. 40D) MLN populations, activated for 24 hours. Each dot represents a biological repeat, bars indicate SEM. Ns p>0.01, p<0.01, *p<0.001, *p<0.001, **p<0.0001.

FIGS. 41A-41F are graphs illustrating the role of CD84 in EAE. Mice were injected with MOG peptide in Fruend's full adjuvant S.C. near the tail bone, followed by I.P. injection of pertussis toxin on days 0 and 2. Mice were scored daily (FIG. 41A) and weighted every two days (FIG. 41B). On day 27, two mice from each group were sacrificed and analyzed for their Breg populations in the spleen following a 5 hour (FIG. 41C) or 24 hour (FIG. 41D) activation. (FIG. 41E) Splenocytes were activated with CD3+Ab for 24 hours. Th1 (INFγ and T-Bet) and Th17 (IL-17 and RORγT) markers were analyzed by FACS. (FIG. 41F) Splenocytes analyzed for Treg (CD4+, CD25+, FOXP3+) and Th17 (CD4+, RoRγT+) population. Each dot represents a biological repeat, bars indicate SEM. Ns p>0.01, *p<0.01, **p<0.001.

DESCRIPTION OF SPECIFIC EMBODIMENTS OF THE INVENTION

The present invention, in some embodiments thereof, relates to compositions and methods for preventing or reversing T cell exhaustion, and for enhancing an activity or level of B regulatory cells, for treating malignant, autoimmune and inflammatory diseases.

The principles and operation of the present invention may be better understood with reference to the drawings and accompanying descriptions.

Before explaining at least one embodiment of the invention in detail, it is to be understood that the invention is not necessarily limited in its application to the details set forth in the following description or exemplified by the Examples. The invention is capable of other embodiments or of being practiced or carried out in various ways. Also, it is to be understood that the phraseology and terminology employed herein is for the purpose of description and should not be regarded as limiting.

Figure 1:
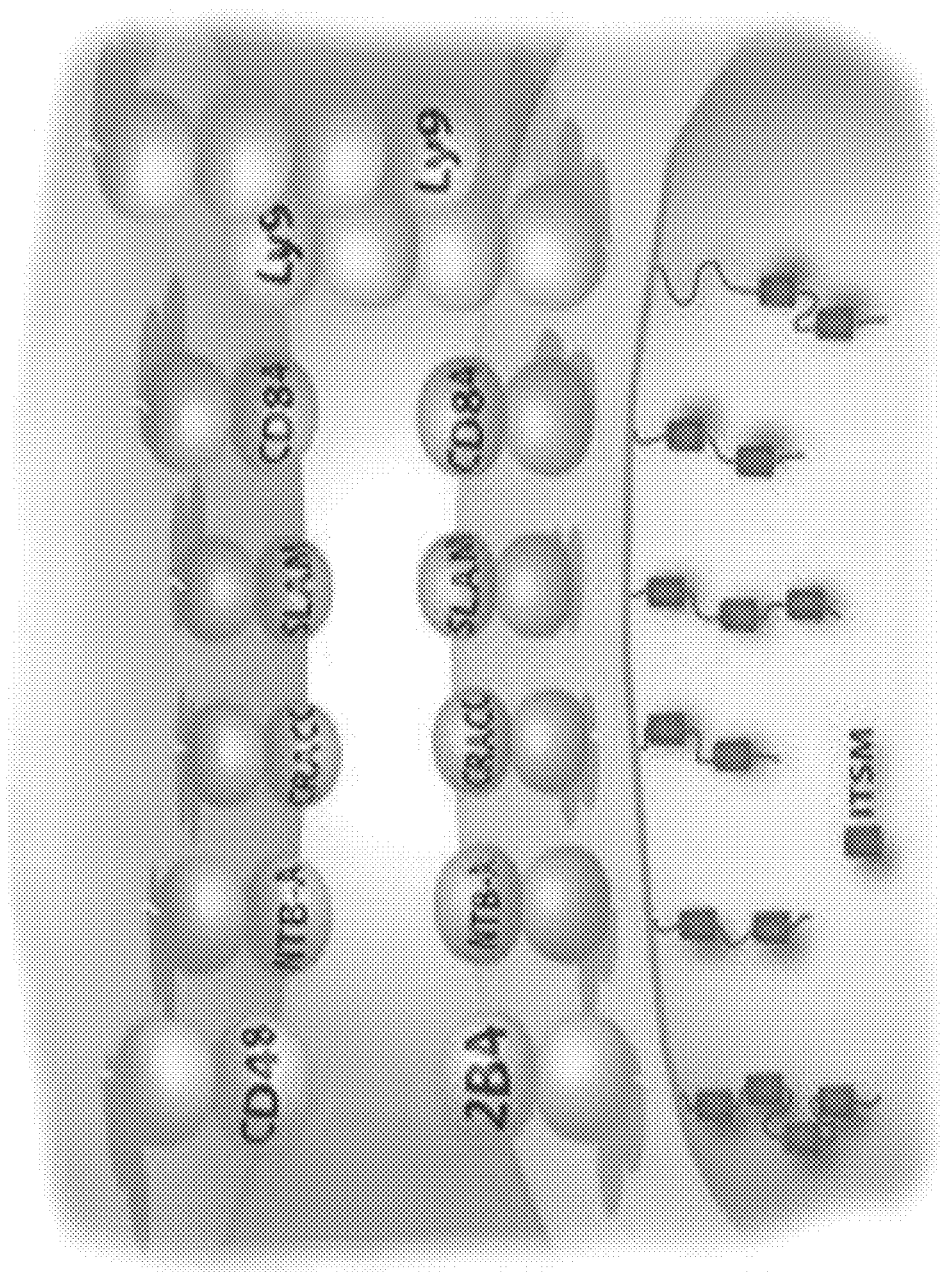
FIG. 1 is a schematic illustration of SLAM family receptors and their ligands. Displayed are all the SLAM family receptor on two cells, except SLAMF8 and SLAMF9. SLAM family receptors all bind each other on a different cell except for SLAMF2 (CD48) and SLAMF4 (2B4), who bind each other. Furthermore, their intracellular ITSMs are displayed in the figure, which SLAMF8 and SLAMF9 lack (incorporated from Cannons, Tangye et al. 2011).
Figure 2:
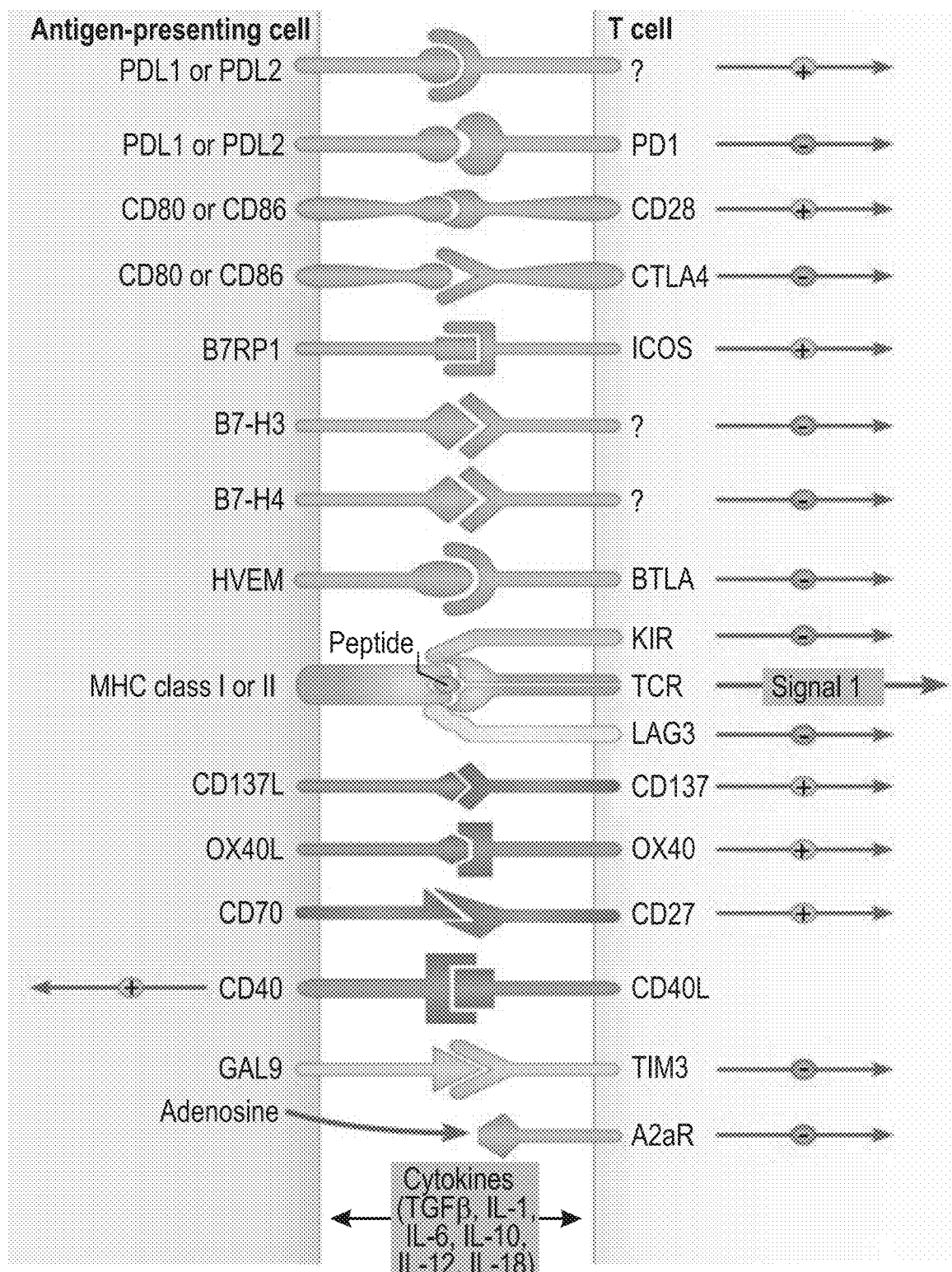
FIG. 2 is a schematic illustration of co-stimulation/inhibition of T cells. Antigen presenting cells affect T cells by expressing many ligands that are either co-stimulatory (plus dot on arrow) or co-inhibitory (minus dot on arrow) upon binding their receptor on the T cells. Amongst these, PD-1, Lag-3 and CTLA-4, are all co-inhibitory (minus dot on arrow).

Balance of the immune system is crucial in order to achieve an effective response (e.g. to eliminate pathogens and tumors) while maintaining tolerance to prevent the occurrence of tissue damage and autoimmune diseases. T cells are central to preserving this balance and are regulated by a balance between co-stimulatory and inhibitory signals (i.e. immune checkpoints) many of which are initiated by ligand-receptor interactions. Various immune checkpoints exist (see e.g. FIG. 2), among them are the two immune-checkpoint inhibitory receptors cytotoxic T-lymphocyte-associated antigen 4 (CTLA4) and programmed cell death protein 1 (PD-1). CTLA-4 and PD-1 regulate immune responses at different levels and by different mechanisms and have been most actively studied in the context of clinical cancer immunotherapy [Pardoll, Nature Reviews Cancer (2012) 12: 252-264].

It is known that tumors co-opt certain immune-checkpoint pathways as a major mechanism of immune resistance, particularly against T cells that are specific for tumor antigens. In addition, chronic antigen exposure, such as occurs with chronic viral infection and cancer, can lead to persistent immune check-point expression, which induces a state of exhaustion among cognate antigen-specific T cells[Pardoll, (2012) supra].

While reducing the present invention to practice, the present inventors have now uncovered that stimulation of CD84 upregulates the expression of another SLAM family member, SLAMF1 (see Examples 2-3 of the Examples section which follows). Downregulation of SLAMF1, such as in stromal cell of the microenvironment, induces apoptosis of CLL cells (see Example 4 of the Examples section which follows). CD84 was shown to regulate SLAMF1 expression in various B cell malignancies including in multiple myeloma, Burkitt's lymphoma and acute lymphocytic leukemia (ALL) (see Example 6 of the Examples section which follows).

Importantly, the present inventors uncovered that CD84 controls the expression levels of PD-L1, possibly via SLAMF1 (see Examples 5 and 7 of the Examples section which follows). PD-L1 levels were upregulated following CD84 activation (see Example 7 of the Examples section which follows) and were significantly reduced in CD84 knockout mice (see Example 9 of the Examples section which follows). PD-L1 binds to its receptor, PD-1, that is a known co-inhibitor of T cells in vitro and in vivo. PD-1 is typically co-expressed on T cells with Lag-3 and CTLA-4, all of which are regarded as markers of exhaustive T cells. The present inventors have further illustrated that the levels of PD-1, Lag-3 and CTLA-4 are significantly reduced in CLL model mice deficient in CD84 (see Example 9 of the Examples section which follows). Furthermore, T cells harvested from CLL model mice deficient in CD84 showed increased functionality compared to T cells from normal CLL mice as illustrated by elevated levels of IL-4 and IFN-γ (see Example 9 of the Examples section which follows). CD84 was shown to regulate PD-L1 expression in various B cell malignancies including in CLL, multiple myeloma, Burkitt's lymphoma and ALL (see Examples 10-11 of the Examples section which follows).

Thus, CD84 has a major role in enhancing malignant cell survival by both inhibiting the activity of T cells (e.g. by enhancing exhaustion phenotype on T cells, e.g. expression of PD-L1/PD-1, thereby rendering the T cells less capable of attacking and killing malignant cells) and reducing apoptosis of malignant cells (e.g. by expression of SLAMF1). Taken together, downregulation of the activity or expression of CD84 can be used as a therapeutic modality to interrupt the CD84-induced survival pathway and to enhance malignant cell apoptosis and killing.

The present inventors have further illustrated in vivo that CD84 plays a role in Bregs activity. That is, CD84 expression causes Breg anergy thereby mediating autoimmunity and inflammation. Specifically, the present inventors illustrated that in CD84 knock out mice, less severe colitis is presented (see Examples 12-14 of the Examples section which follows). These results were comparable for both acute colitis and chronic colitis (see Examples 12-13 of the Examples section which follows) Similarly, milder EAE is presented in CD84 knock out mice (see Example 15 of the Examples section which follows). The milder disease symptoms were accompanied by higher B regulatory cell levels in spleen of CD84 knock out animals (see Examples 14 and 15 of the Examples section which follows). Together, these results suggest a new role for CD84 in regulatory B cell anergy. Accordingly, downregulation of the activity or expression of CD84 can be further used as a therapeutic modality to increase the regulatory activity of Bregs and to thereby enhance treatment of autoimmune and inflammatory conditions.

Thus, according to one aspect of the present invention there is provided a method of preventing or reversing T cell exhaustion in a subject in need thereof, the method comprising administering to the subject a therapeutically effective amount of an agent capable of decreasing an activity or expression of CD84, with the proviso that the subject is not diagnosed with a B cell malignancy, thereby preventing or reversing the T cell exhaustion in the subject.

According to another aspect of the present invention there is provided a method of preventing or reversing T cell exhaustion in a subject in need thereof, the method comprising administering to the subject a therapeutically effective amount of an agent capable of decreasing an activity or expression of SLAMF1, with the proviso that the agent is not an agent capable of decreasing an activity or expression of CD84, thereby preventing or reversing the T cell exhaustion in the subject.

As used herein, the term "subject" or "subject in need thereof" refers to a mammalian e.g., human subject, male or female at any age, who has a disease or condition involving T cell exhaustion.

As used herein, the phrase "T cell exhaustion" or "exhausted T cell" refers to a state of T cell dysfunction that arises from sustained T cell receptor (TCR) signaling which typically occurs during chronic infections or cancer. T cell exhaustion is distinguished from anergy in that it arises from sustained signaling and not through incomplete or deficient signaling. It is defined by poor effector function of the T cell and sustained expression of inhibitory receptors (also referred to as "exhausted T cell phenotype"). Exhaustion can result from both extrinsic negative regulatory pathways (e.g., immunoregulatory cytokines, such as, IL-10 and transforming growth factor-β (TGF-β), IL-35) as well as cell intrinsic negative regulatory (co-stimulatory) pathways (e.g. PD-1, B7-H3, B7-H4, Lag-3, CTLA-4, Tim-3). Accordingly, T cell exhaustion prevents optimal control of infections and tumors by the T cell.

The term dysfunctional when relating to T cells typically refers to unresponsiveness to antigen recognition, specifically, impaired capacity to translate antigen recognition into down-stream T-cell effector functions, such as proliferation, cytokine production (e.g., IL-2, IL-4, IFNγ) and/or target cell killing.

As used herein, the term "preventing" refers to a postponement of development of T cell exhaustion and/or a reduction in the number of exhausted T cells which are expected to develop in response to a disease or condition (e.g. malignant disease).

As used herein, the term "reversing" refers to renewing, reactivating, restoring or enhancing T cell function of exhausted T-cells.

Examples of enhancing T-cell function include, but are not limited to, increased (antigen-dependent or antigen-independent) secretion of IFNγ and/or IL-4 from CD8+ T-cells, increased proliferation, increased antigen responsiveness (e.g., viral, pathogen, or tumor clearance) relative to such levels before the intervention.

According to one embodiment, T cell function is enhanced by at least about 10%, 20%, 30%, 40%, 50%, 60%, 70%, 80%, 90%, 100%, 120%, 150% or 200%. Measuring enhancement of T cell function is known to one of ordinary skill in the art and include, for example, flow cytometric assay (FACS), ELISA, mixed lymphocyte reaction (MLR), ELISpot, intracellular cytokine staining (ICS), Viral Suppression Assay (VSA), Cytotoxicity Assay and Proliferation Assay.

According to one embodiment, preventing or reversing T cell exhaustion is effected by administering to the subject a therapeutically effective amount of an agent capable of decreasing an activity or expression of CD84.

As used herein, the term "CD84", also known as LY9B or SLAMF5, refers to an expressed isoform of the CD84 gene. Examples include but are not limited to Q9UIB8-1, Q9UIB8-2, Q9UIB8-3, Q9UIB8-4, Q9UIB8-5, Q9UIB8-6 and Q9UIB8-7. According to an embodiment, the CD84 is human CD84. According to one embodiment, CD84 is set forth in Accession Numbers NP_001171808.1, NP_001171810.1, NP_001171811.1 or NP_003865.1.

According to a specific embodiment of this aspect of the present invention, decreasing an activity or expression of CD84 relates to all CD84 isoforms. To this end, agents which recognize all the isoforms of CD84 (i.e., pan CD84) are used.

According to another embodiment, preventing or reversing T cell exhaustion is effected by administering to the subject a therapeutically effective amount of an agent capable of decreasing an activity or expression of SLAMF1.

As used herein, the term "SLAMF1", also known as SLAM, CD150, or CDw150, refers to an expressed isoform of the SLAMF1 gene. Examples include but are not limited to Q13291. According to one embodiment, SLAMF1 is set forth in Accession Number NP_003028.1.

Downregulation of CD84 or SLAMF1 can be effected on the genomic (e.g., using DNA editing tools) and/or the transcript level using a variety of molecules which interfere with transcription and/or translation [e.g., RNA silencing agents (e.g., antisense, siRNA, shRNA, micro-RNA), Ribozyme and DNAzyme], or on the protein level using e.g., antagonists, enzymes that cleave the polypeptide and the like.

Following is a list of agents capable of downregulating expression level and/or activity of CD84 or SLAMF1.

One example, of an agent capable of downregulating CD84 or SLAMF1 is a CDR-containing polypeptide such as an antibody or antibody fragment capable of specifically binding CD84 or SLAMF1. According to a specific embodiment, the antibody specifically binds at least one epitope of an extracellular portion of CD84 or SLAMF1 and neutralizes/blocks its activity such as by interfering with its homophilic interactions.

As used herein, the term "epitope" refers to any antigenic determinant on an antigen to which the paratope of an antibody binds.

Epitopic determinants usually consist of chemically active surface groupings of molecules such as amino acids or carbohydrate side chains and usually have specific three dimensional structural characteristics, as well as specific charge characteristics.

The term "antibody" as used in this invention includes intact molecules as well as functional fragments thereof, such as Fab, F(ab')2, and Fv that are capable of binding to macrophages. These functional antibody fragments are defined as follows: (1) Fab, the fragment which contains a monovalent antigen-binding fragment of an antibody molecule, can be produced by digestion of whole antibody with the enzyme papain to yield an intact light chain and a portion of one heavy chain; (2) Fab', the fragment of an antibody molecule that can be obtained by treating whole antibody with pepsin, followed by reduction, to yield an intact light chain and a portion of the heavy chain; two Fab' fragments are obtained per antibody molecule; (3) (Fab')2, the fragment of the antibody that can be obtained by treating whole antibody with the enzyme pepsin without subsequent reduction; F(ab')2 is a dimer of two Fab' fragments held together by two disulfide bonds; (4) Fv, defined as a genetically engineered fragment containing the variable region of the light chain and the variable region of the heavy chain expressed as two chains; and (5) Single chain antibody ("SCA"), a genetically engineered molecule containing the variable region of the light chain and the variable region of the heavy chain, linked by a suitable polypeptide linker as a genetically fused single chain molecule.

Methods of producing polyclonal and monoclonal antibodies as well as fragments thereof are well known in the art (See for example, Harlow and Lane, Antibodies: A Laboratory Manual, Cold Spring Harbor Laboratory, New York, 1988, incorporated herein by reference).

Antibody fragments according to some embodiments of the invention can be prepared by proteolytic hydrolysis of the antibody or by expression in E. coli or mammalian cells (e.g. Chinese hamster ovary cell culture or other protein expression systems) of DNA encoding the fragment. Antibody fragments can be obtained by pepsin or papain digestion of whole antibodies by conventional methods. For example, antibody fragments can be produced by enzymatic cleavage of antibodies with pepsin to provide a 5S fragment denoted F(ab')2. This fragment can be further cleaved using a thiol reducing agent, and optionally a blocking group for the sulfhydryl groups resulting from cleavage of disulfide linkages, to produce 3.5S Fab' monovalent fragments. Alternatively, an enzymatic cleavage using pepsin produces two monovalent Fab' fragments and an Fc fragment directly. These methods are described, for example, by Goldenberg, U.S. Pat. Nos. 4,036,945 and 4,331,647, and references contained therein, which patents are hereby incorporated by reference in their entirety. See also Porter, R. R. [Biochem. J. 73: 119-126 (1959)]. Other methods of cleaving antibodies, such as separation of heavy chains to form monovalent light-heavy chain fragments, further cleavage of fragments, or other enzymatic, chemical, or genetic techniques may also be used, so long as the fragments bind to the antigen that is recognized by the intact antibody.

Fv fragments comprise an association of VH and VL chains. This association may be noncovalent, as described in Inbar et al. [Proc. Nat'l Acad. Sci. USA 69:2659-62 (19720]. Alternatively, the variable chains can be linked by an intermolecular disulfide bond or cross-linked by chemicals such as glutaraldehyde. Preferably, the Fv fragments comprise VH and VL chains connected by a peptide linker. These single-chain antigen binding proteins (sFv) are prepared by constructing a structural gene comprising DNA sequences encoding the VH and VL domains connected by an oligonucleotide. The structural gene is inserted into an expression vector, which is subsequently introduced into a host cell such as E. coli. The recombinant host cells synthesize a single polypeptide chain with a linker peptide bridging the two V domains. Methods for producing sFvs are described, for example, by [Whitlow and Filpula, Methods 2: 97-105 (1991); Bird et al., Science 242:423-426 (1988); Pack et al., Bio/Technology 11:1271-77 (1993); and U.S. Pat. No. 4,946,778, which is hereby incorporated by reference in its entirety.

Another form of an antibody fragment is a peptide coding for a single complementarity-determining region (CDR). CDR peptides ("minimal recognition units") can be obtained by constructing genes encoding the CDR of an antibody of interest. Such genes are prepared, for example, by using the polymerase chain reaction to synthesize the variable region from RNA of antibody-producing cells. See, for example, Larrick and Fry [Methods, 2: 106-10 (1991)].

Humanized forms of non-human (e.g., murine) antibodies are chimeric molecules of immunoglobulins, immunoglobulin chains or fragments thereof (such as Fv, Fab, Fab', F(ab').sub.2 or other antigen-binding subsequences of antibodies) which contain minimal sequence derived from non-human immunoglobulin. Humanized antibodies include human immunoglobulins (recipient antibody) in which residues form a complementary determining region (CDR) of the recipient are replaced by residues from a CDR of a non-human species (donor antibody) such as mouse, rat or rabbit having the desired specificity, affinity and capacity. In some instances, Fv framework residues of the human immunoglobulin are replaced by corresponding non-human residues. Humanized antibodies may also comprise residues which are found neither in the recipient antibody nor in the imported CDR or framework sequences. In general, the humanized antibody will comprise substantially all of at least one, and typically two, variable domains, in which all or substantially all of the CDR regions correspond to those of a non-human immunoglobulin and all or substantially all of the FR regions are those of a human immunoglobulin consensus sequence. The humanized antibody optimally also will comprise at least a portion of an immunoglobulin constant region (Fc), typically that of a human immunoglobulin [Jones et al., Nature, 321:522-525 (1986); Riechmann et al., Nature, 332:323-329 (1988); and Presta, Curr. Op. Struct. Biol., 2:593-596 (1992)].

Methods for humanizing non-human antibodies are well known in the art. Generally, a humanized antibody has one or more amino acid residues introduced into it from a source which is non-human. These non-human amino acid residues are often referred to as import residues, which are typically taken from an import variable domain. Humanization can be essentially performed following the method of Winter and co-workers [Jones et al., Nature, 321:522-525 (1986); Riechmann et al., Nature 332:323-327 (1988); Verhoeyen et al., Science, 239:1534-1536 (1988)], by substituting rodent CDRs or CDR sequences for the corresponding sequences of a human antibody. Accordingly, such humanized antibodies are chimeric antibodies (U.S. Pat. No. 4,816,567), wherein substantially less than an intact human variable domain has been substituted by the corresponding sequence from a non-human species. In practice, humanized antibodies are typically human antibodies in which some CDR residues and possibly some FR residues are substituted by residues from analogous sites in rodent antibodies.

Human antibodies can also be produced using various techniques known in the art, including phage display libraries [Hoogenboom and Winter, J. Mol. Biol., 227:381 (1991); Marks et al., J. Mol. Biol., 222:581 (1991)]. The techniques of Cole et al. and Boerner et al. are also available for the preparation of human monoclonal antibodies (Cole et al., Monoclonal Antibodies and Cancer Therapy, Alan R. Liss, p. 77 (1985) and Boerner et al., J. Immunol., 147(1):86-95 (1991)]. Similarly, human antibodies can be made by introduction of human immunoglobulin loci into transgenic animals, e.g., mice in which the endogenous immunoglobulin genes have been partially or completely inactivated. Upon challenge, human antibody production is observed, which closely resembles that seen in humans in all respects, including gene rearrangement, assembly, and antibody repertoire. This approach is described, for example, in U.S. Pat. Nos. 5,545,807; 5,545,806; 5,569,825; 5,625,126; 5,633,425; 5,661,016, and in the following scientific publications: Marks et al., Bio/Technology 10: 779-783 (1992); Lonberg et al., Nature 368: 856-859 (1994); Morrison, Nature 368 812-13 (1994); Fishwild et al., Nature Biotechnology 14, 845-51 (1996); Neuberger, Nature Biotechnology 14: 826 (1996); and Lonberg and Huszar, Intern. Rev. Immunol. 13, 65-93 (1995).

According to one embodiment, the antibody specifically binds at least one epitope of an extracellular portion of CD84 and neutralizes/blocks its activity such as by interfering with its homophilic interactions.

According to one embodiment, a CDR-containing polypeptide (e.g., antibody) capable of specifically binding CD84 can be produced from the hyridoma that has been deposited at the CNCN Pasteur Institut on Sep. 23, 2009 under the deposit number CNCM 1-4228 (F8). Additional anti-CD84 antibodies which can be used in accordance with the present teachings are taught in PCT publication numbers WO2010/035259 and WO2015/118538, both of which are incorporated herein by reference.

Additionally or alternatively, a CDR-containing polypeptide (e.g., antibody) capable of specifically binding CD84 is commercially available from e.g. Santa Cruz Biotechnology, OriGene, Abcam, etc.

According to one embodiment, a CDR-containing polypeptide (e.g., antibody) capable of specifically binding SLAMF1 is commercially available from e.g. Abcam, Biolegend, Santa Cruz Biotechnology, etc.

Another molecule which can be used to downregulate CD84 or SLAMF1 activity is a non-functional form of CD84 or SLAMF1 which binds CD84 or SLAMF1, respectively, but inhibits its signaling activity such as by inhibiting its homophilic interactions.

Thus, the present teachings further provide for an isolated polypeptide which comprises an amino acid sequence of a soluble CD84 or SLAMF1 (i.e., non-membrane bound), wherein the soluble CD84 or SLAMF1 binds CD84 or SLAMF1, respectively, expressed on cells (e.g., B cells, T cells, stroma cells, e.g. with a binding affinity of at least $10^{-5}$ nM) and inhibits its homophilic interactions (i.e. the binding of a molecule on the surface of one cell to the same molecule on the surface of another cell.

According to a specific embodiment, the soluble CD84 or SLAMF1 comprises an extracellular domain of CD84 or SLAMF1 and is devoid of a transmembrane domain. Exemplary soluble CD84 polypeptides which can be used in accordance with the present teachings are taught in PCT publication number WO2010/035259, which is incorporated herein by reference.

According to a specific embodiment, the soluble CD84 or SLAMF1 is fused to a moiety for increasing solubility of the soluble CD84 or SLAMF1.

According to a specific embodiment, the moiety for increasing solubility of the soluble CD84 or SLAMF1 is a heterologous amino acid sequence or a chemical moiety such as PEG and the like.

As used herein the phrase "heterologous amino acid sequence" refers to an amino acid sequence which does not endogenously form a part of the CD84 or SLAMF1 amino acid sequence. Preferably, the heterologous amino acid sequence does not down-regulate the biological activity of the soluble CD84 or SLAMF1 polypeptide.

Downregulation of CD84 or SLAMF1 can be also achieved by RNA silencing. As used herein, the phrase "RNA silencing" refers to a group of regulatory mechanisms [e.g. RNA interference (RNAi), transcriptional gene silencing (TGS), post-transcriptional gene silencing (PTGS), quelling, co-suppression, and translational repression] mediated by RNA molecules which result in the inhibition or "silencing" of the expression of a corresponding protein-coding gene. RNA silencing has been observed in many types of organisms, including plants, animals, and fungi.

As used herein, the term "RNA silencing agent" refers to an RNA which is capable of specifically inhibiting or "silencing" the expression of a target gene. In certain embodiments, the RNA silencing agent is capable of preventing complete processing (e.g., the full translation and/or expression) of an mRNA molecule through a post-transcriptional silencing mechanism. RNA silencing agents include noncoding RNA molecules, for example RNA duplexes comprising paired strands, as well as precursor RNAs from which such small non-coding RNAs can be generated. Exemplary RNA silencing agents include dsRNAs such as siRNAs, miRNAs and shRNAs. In one embodiment, the RNA silencing agent is capable of inducing RNA interference. In another embodiment, the RNA silencing agent is capable of mediating translational repression.

According to an embodiment of the invention, the RNA silencing agent is specific to the target RNA (e.g., CD84 or SLAMF1) and does not cross inhibit or silence a gene or a splice variant which exhibits 99% or less global homology to the target gene, e.g., less than 98%, 97%, 96%, 95%, 94%, 93%, 92%, 91%, 90%, 89%, 88%, 87%, 86%, 85%, 84%, 83%, 82%, 81% global homology to the target gene.

RNA interference refers to the process of sequence-specific post-transcriptional gene silencing in animals mediated by short interfering RNAs (siRNAs). The corresponding process in plants is commonly referred to as post-transcriptional gene silencing or RNA silencing and is also referred to as quelling in fungi. The process of post-transcriptional gene silencing is thought to be an evolutionarily-conserved cellular defense mechanism used to prevent the expression of foreign genes and is commonly shared by diverse flora and phyla. Such protection from foreign gene expression may have evolved in response to the production of double-stranded RNAs (dsRNAs) derived from viral infection or from the random integration of transposon elements into a host genome via a cellular response that specifically destroys homologous single-stranded RNA or viral genomic RNA.

The presence of long dsRNAs in cells stimulates the activity of a ribonuclease III enzyme referred to as dicer. Dicer is involved in the processing of the dsRNA into short pieces of dsRNA known as short interfering RNAs (siRNAs). Short interfering RNAs derived from dicer activity are typically about 21 to about 23 nucleotides in length and comprise about 19 base pair duplexes. The RNAi response also features an endonuclease complex, commonly referred to as an RNA-induced silencing complex (RISC), which mediates cleavage of single-stranded RNA having sequence complementary to the antisense strand of the siRNA duplex. Cleavage of the target RNA takes place in the middle of the region complementary to the antisense strand of the siRNA duplex.

Accordingly, some embodiments of the invention contemplate use of dsRNA to downregulate protein expression from mRNA.

According to one embodiment, the dsRNA is greater than 30 bp. The use of long dsRNAs (i.e. dsRNA greater than 30 bp) has been very limited owing to the belief that these longer regions of double stranded RNA will result in the induction of the interferon and PKR response. However, the use of long dsRNAs can provide numerous advantages in that the cell can select the optimal silencing sequence alleviating the need to test numerous siRNAs; long dsRNAs will allow for silencing libraries to have less complexity than would be necessary for siRNAs; and, perhaps most importantly, long dsRNA could prevent viral escape mutations when used as therapeutics.

Various studies demonstrate that long dsRNAs can be used to silence gene expression without inducing the stress response or causing significant off-target effects—see for example [Strat et al., Nucleic Acids Research, 2006, Vol. 34, No. 13 3803-3810; Bhargava A et al. Brain Res. Protoc. 2004; 13:115-125; Diallo M., et al., Oligonucleotides. 2003; 13:381-392; Paddison P. J., et al., Proc. Natl Acad. Sci. USA. 2002; 99:1443-1448; Tran N., et al., FEBS Lett. 2004; 573:127-134].

In particular, the invention according to some embodiments thereof contemplates introduction of long dsRNA (over 30 base transcripts) for gene silencing in cells where the interferon pathway is not activated (e.g. embryonic cells and oocytes) see for example Billy et al., PNAS 2001, Vol 98, pages 14428-14433. and Diallo et al, Oligonucleotides, Oct. 1, 2003, 13(5): 381-392. doi:10.1089/154545703322617069.

The invention according to some embodiments thereof also contemplates introduction of long dsRNA specifically designed not to induce the interferon and PKR pathways for down-regulating gene expression. For example, Shinagwa and Ishii [Genes & Dev. 17 (11): 1340-1345, 2003] have developed a vector, named pDECAP, to express long double-strand RNA from an RNA polymerase II (Pol II)promoter. Because the transcripts from pDECAP lack both the 5'-cap structure and the 3'-poly(A) tail that facilitate ds-RNA export to the cytoplasm, long ds-RNA from pDECAP does not induce the interferon response.

Another method of evading the interferon and PKR pathways in mammalian systems is by introduction of small inhibitory RNAs (siRNAs) either via transfection or endogenous expression.

The term "siRNA" refers to small inhibitory RNA duplexes (generally between 18-30 base pairs) that induce the RNA interference (RNAi) pathway. Typically, siRNAs are chemically synthesized as 21mers with a central 19 bp duplex region and symmetric 2-base 3'-overhangs on the termini, although it has been recently described that chemically synthesized RNA duplexes of 25-30 base length can have as much as a 100-fold increase in potency compared with 21mers at the same location. The observed increased potency obtained using longer RNAs in triggering RNAi is theorized to result from providing Dicer with a substrate (27mer) instead of a product (21mer) and that this improves the rate or efficiency of entry of the siRNA duplex into RISC.

It has been found that position of the 3'-overhang influences potency of a siRNA and asymmetric duplexes having a 3'-overhang on the antisense strand are generally more potent than those with the 3'-overhang on the sense strand (Rose et al., 2005). This can be attributed to asymmetrical strand loading into RISC, as the opposite efficacy patterns are observed when targeting the antisense transcript.

The strands of a double-stranded interfering RNA (e.g., a siRNA) may be connected to form a hairpin or stem-loop structure (e.g., a shRNA). Thus, as mentioned the RNA silencing agent of some embodiments of the invention may also be a short hairpin RNA (shRNA).

The term "shRNA", as used herein, refers to an RNA agent having a stem-loop structure, comprising a first and second region of complementary sequence, the degree of complementarity and orientation of the regions being sufficient such that base pairing occurs between the regions, the first and second regions being joined by a loop region, the loop resulting from a lack of base pairing between nucleotides (or nucleotide analogs) within the loop region. The number of nucleotides in the loop is a number between and including 3 to 23, or 5 to 15, or 7 to 13, or 4 to 9, or 9 to 11. Some of the nucleotides in the loop can be involved in base-pair interactions with other nucleotides in the loop. Examples of oligonucleotide sequences that can be used to form the loop include 5'-UUCAAGAGA-3' (Brummelkamp, T. R. et al. (2002) Science 296: 550) and 5'-UUUGUGUAG-3' (Castanotto, D. et al. (2002) RNA 8:1454). It will be recognized by one of skill in the art that the resulting single chain oligonucleotide forms a stem-loop or hairpin structure comprising a double-stranded region capable of interacting with the RNAi machinery.

Synthesis of RNA silencing agents suitable for use with some embodiments of the invention can be effected as follows. First, the CD84 or SLAMF1 mRNA sequence is scanned downstream of the AUG start codon for AA dinucleotide sequences. Occurrence of each AA and the 3' adjacent 19 nucleotides is recorded as potential siRNA target sites. Preferably, siRNA target sites are selected from the open reading frame, as untranslated regions (UTRs) are richer in regulatory protein binding sites. UTR-binding proteins and/or translation initiation complexes may interfere with binding of the siRNA endonuclease complex [TuschlChemBiochem. 2:239-245]. It will be appreciated though, that siRNAs directed at untranslated regions may also be effective, as demonstrated for GAPDH wherein siRNA directed at the 5' UTR mediated about 90% decrease in cellular GAPDH mRNA and completely abolished protein level (www(dot)ambion(dot)com/techlib/tn/91/912(dot)html).

Second, potential target sites are compared to an appropriate genomic database (e.g., human, mouse, rat etc.) using any sequence alignment software, such as the BLAST software available from the NCBI server (www(dot)ncbi(dot)nlm(dot)nih(dot)gov/BLAST/). Putative target sites which exhibit significant homology to other coding sequences are filtered out.

Qualifying target sequences are selected as template for siRNA synthesis. Preferred sequences are those including low G/C content as these have proven to be more effective in mediating gene silencing as compared to those with G/C content higher than 55%. Several target sites are preferably selected along the length of the target gene for evaluation. For better evaluation of the selected siRNAs, a negative control is preferably used in conjunction. Negative control siRNA preferably include the same nucleotide composition as the siRNAs but lack significant homology to the genome. Thus, a scrambled nucleotide sequence of the siRNA is preferably used, provided it does not display any significant homology to any other gene.

For example, a suitable CD84 siRNA can be commercially obtained from e.g. Santa Cruz Biotechnology, Qiagen or OriGene. A suitable SLAMF1 siRNA can be commercially obtained from e.g. GE Lifescience, Qiagenor, OriGene.

It will be appreciated that the RNA silencing agent of some embodiments of the invention need not be limited to those molecules containing only RNA, but further encompasses chemically-modified nucleotides and non-nucleotides.

In some embodiments, the RNA silencing agent provided herein can be functionally associated with a cell-penetrating peptide." As used herein, a "cell-penetrating peptide" is a peptide that comprises a short (about 12-30 residues) amino acid sequence or functional motif that confers the energy-independent (i.e., non-endocytotic) translocation properties associated with transport of the membrane-permeable complex across the plasma and/or nuclear membranes of a cell. The cell-penetrating peptide used in the membrane-permeable complex of some embodiments of the invention preferably comprises at least one non-functional cysteine residue, which is either free or derivatized to form a disulfide link with a double-stranded ribonucleic acid that has been modified for such linkage. Representative amino acid motifs conferring such properties are listed in U.S. Pat. No. 6,348,185, the contents of which are expressly incorporated herein by reference. The cell-penetrating peptides of some embodiments of the invention preferably include, but are not limited to, penetratin, transportan, pIsl, TAT(48-60), pVEC, MTS, and MAP.

mRNAs to be targeted using RNA silencing agents include, but are not limited to, those whose expression is correlated with an undesired phenotypic trait. Exemplary mRNAs that may be targeted are those that encode truncated proteins i.e. comprise deletions. Accordingly, the RNA silencing agent of some embodiments of the invention may be targeted to a bridging region on either side of the deletion. Introduction of such RNA silencing agents into a cell would cause a down-regulation of the mutated protein while leaving the non-mutated protein unaffected.

According to another embodiment the RNA silencing agent may be a miRNA. The term "microRNA", "miRNA", and "miR" are synonymous and refer to a collection of non-coding single-stranded RNA molecules of about 19-28 nucleotides in length, which regulate gene expression. miRNAs are found in a wide range of organisms (viruses.fw-darw.humans) and have been shown to play a role in development, homeostasis, and disease etiology.

Below is a brief description of the mechanism of miRNA activity.

Genes coding for miRNAs are transcribed leading to production of an miRNA precursor known as the pri-miRNA. The pri-miRNA is typically part of a polycistronic RNA comprising multiple pri-miRNAs. The pri-miRNA may form a hairpin with a stem and loop. The stem may comprise mismatched bases.

The hairpin structure of the pri-miRNA is recognized by Drosha, which is an RNase III endonuclease. Drosha typically recognizes terminal loops in the pri-miRNA and cleaves approximately two helical turns into the stem to produce a 60-70 nucleotide precursor known as the pre-miRNA. Drosha cleaves the pri-miRNA with a staggered cut typical of RNase III endonucleases yielding a pre-miRNA stem loop with a 5' phosphate and ~2 nucleotide 3' overhang. It is estimated that approximately one helical turn of stem (~10 nucleotides) extending beyond the Drosha cleavage site is essential for efficient processing. The pre-miRNA is then actively transported from the nucleus to the cytoplasm by Ran-GTP and the export receptor Ex-portin-5.

The double-stranded stem of the pre-miRNA is then recognized by Dicer, which is also an RNase III endonuclease. Dicer may also recognize the 5' phosphate and 3' overhang at the base of the stem loop. Dicer then cleaves off the terminal loop two helical turns away from the base of the stem loop leaving an additional 5' phosphate and ~2 nucleotide 3' overhang. The resulting siRNA-like duplex, which may comprise mismatches, comprises the mature miRNA and a similar-sized fragment known as the miRNA*. The miRNA and miRNA* may be derived from opposing arms of the pri-miRNA and pre-miRNA. MiRNA* sequences may be found in libraries of cloned miRNAs but typically at lower frequency than the miRNAs.

Although initially present as a double-stranded species with miRNA*, the miRNA eventually become incorporated as a single-stranded RNA into a ribonucleoprotein complex known as the RNA-induced silencing complex (RISC). Various proteins can form the RISC, which can lead to variability in specifity for miRNA/miRNA* duplexes, binding site of the target gene, activity of miRNA (repress or activate), and which strand of the miRNA/miRNA* duplex is loaded in to the RISC.

When the miRNA strand of the miRNA:miRNA* duplex is loaded into the RISC, the miRNA* is removed and degraded. The strand of the miRNA:miRNA* duplex that is loaded into the RISC is the strand whose 5' end is less tightly paired. In cases where both ends of the miRNA:miRNA* have roughly equivalent 5' pairing, both miRNA and miRNA* may have gene silencing activity.

The RISC identifies target nucleic acids based on high levels of complementarity between the miRNA and the mRNA, especially by nucleotides 2-7 of the miRNA.

A number of studies have looked at the base-pairing requirement between miRNA and its mRNA target for achieving efficient inhibition of translation (reviewed by Bartel 2004, Cell 116-281). In mammalian cells, the first 8 nucleotides of the miRNA may be important (Doench & Sharp 2004 GenesDev 2004-504). However, other parts of the microRNA may also participate in mRNA binding. Moreover, sufficient base pairing at the 3' can compensate for insufficient pairing at the 5' (Brennecke et al, 2005 PLoS 3-e85). Computation studies, analyzing miRNA binding on whole genomes have suggested a specific role for bases 2-7 at the 5' of the miRNA in target binding but the role of the first nucleotide, found usually to be "A" was also recognized (Lewis et at 2005 Cell 120-15). Similarly, nucleotides 1-7 or 2-8 were used to identify and validate targets by Krek et al (2005, Nat Genet 37-495).

The target sites in the mRNA may be in the 5' UTR, the 3' UTR or in the coding region. Interestingly, multiple miRNAs may regulate the same mRNA target by recognizing the same or multiple sites. The presence of multiple miRNA binding sites in most genetically identified targets may indicate that the cooperative action of multiple RISCs provides the most efficient translational inhibition.

miRNAs may direct the RISC to downregulate gene expression by either of two mechanisms: mRNA cleavage or translational repression. The miRNA may specify cleavage of the mRNA if the mRNA has a certain degree of complementarity to the miRNA. When a miRNA guides cleavage, the cut is typically between the nucleotides pairing to residues 10 and 11 of the miRNA. Alternatively, the miRNA may repress translation if the miRNA does not have the requisite degree of complementarity to the miRNA. Translational repression may be more prevalent in animals since animals may have a lower degree of complementarity between the miRNA and binding site.

It should be noted that there may be variability in the 5' and 3' ends of any pair of miRNA and miRNA*. This variability may be due to variability in the enzymatic processing of Drosha and Dicer with respect to the site of cleavage. Variability at the 5' and 3' ends of miRNA and miRNA* may also be due to mismatches in the stem structures of the pri-miRNA and pre-miRNA. The mismatches of the stem strands may lead to a population of different hairpin structures. Variability in the stem structures may also lead to variability in the products of cleavage by Drosha and Dicer.

The term "microRNA mimic" refers to synthetic non-coding RNAs that are capable of entering the RNAi pathway and regulating gene expression. miRNA mimics imitate the function of endogenous microRNAs (miRNAs) and can be designed as mature, double stranded molecules or mimic precursors (e.g., or pre-miRNAs). miRNA mimics can be comprised of modified or unmodified RNA, DNA, RNA-DNA hybrids, or alternative nucleic acid chemistries (e.g., LNAs or 2'-0,4'-C-ethylene-bridged nucleic acids (ENA)). For mature, double stranded miRNA mimics, the length of the duplex region can vary between 13-33, 18-24 or 21-23 nucleotides. The miRNA may also comprise a total of at least 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39 or 40 nucleotides. The sequence of the miRNA may be the first 13-33 nucleotides of the pre-miRNA. The sequence of the miRNA may also be the last 13-33 nucleotides of the pre-miRNA.

It will be appreciated from the description provided herein above, that contacting CD84 or SLAMF1 expressing cells with a miRNA may be affected in a number of ways:

1. Transiently transfecting the CD84 or SLAMF1 expressing cells with the mature double stranded miRNA.
2. Stably, or transiently transfecting the CD84 or SLAMF1 expressing cells with an expression vector which encodes the mature miRNA.
3. Stably, or transiently transfecting the CD84 or SLAMF1 expressing cells with an expression vector which encodes the pre-miRNA. The pre-miRNA sequence may comprise from 45-90, 60-80 or 60-70 nucleotides. The sequence of the pre-miRNA may comprise a miRNA and a miRNA* as set forth herein. The sequence of the pre-miRNA may also be that of a pri-miRNA excluding from 0-160 nucleotides from the 5' and 3' ends of the pri-miRNA.
4. Stably, or transiently transfecting the CD84 or SLAMF1 expressing cells with an expression vector which encodes the pri-miRNA Thepri-miRNA sequence may comprise from 45-30,000, 50-25,000, 100-20,000, 1,000-1,500 or 80-100 nucleotides. The sequence of the pri-miRNA may comprise a pre-miRNA, miRNA and miRNA*, as set forth herein, and variants thereof.

Preparation of miRNAs mimics can be effected by chemical synthesis methods or by recombinant methods.

Another agent capable of downregulating a CD84 or SLAMF1 is a DNAzyme molecule capable of specifically cleaving an mRNA transcript or DNA sequence of the CD84 or SLAMF1, respectively. DNAzymes are single-stranded polynucleotides which are capable of cleaving both single and double stranded target sequences (Breaker, R. R. and Joyce, G. Chemistry and Biology 1995; 2:655; Santoro, S. W. & Joyce, G. F. Proc. Natl, Acad. Sci. USA 1997; 943:4262) A general model (the "10-23" model) for the DNAzyme has been proposed. "10-23" DNAzymes have a catalytic domain of 15 deoxyribonucleotides, flanked by two substrate-recognition domains of seven to nine deoxyribonucleotides each. This type of DNAzyme can effectively cleave its substrate RNA at purine:pyrimidine junctions (Santoro, S. W. & Joyce, G. F. Proc. Natl, Acad. Sci. USA 199; for rev of DNAzymes see Khachigian, L M [CurrOpin-MolTher 4:119-21 (2002)].

Examples of construction and amplification of synthetic, engineered DNAzymes recognizing single and double-stranded target cleavage sites have been disclosed in U.S. Pat. No. 6,326,174 to Joyce et al. DNAzymes of similar design directed against the human Urokinase receptor were recently observed to inhibit Urokinase receptor expression, and successfully inhibit colon cancer cell metastasis in vivo (Itoh et al., 2002, Abstract 409, Ann Meeting Am. Soc. Gen. Ther. www(dot)asgt(dot)org). In another application, DNAzymes complementary to bcr-ab1 oncogenes were successful in inhibiting the oncogenes expression in leukemia cells, and lessening relapse rates in autologous bone marrow transplant in cases of CML and ALL.

Downregulation of a CD84 or SLAMF1 can also be effected by using an antisense polynucleotide capable of specifically hybridizing with an mRNA transcript encoding the CD84 or SLAMF1, respectively.

Design of antisense molecules which can be used to efficiently downregulate a CD84 or SLAMF1 must be effected while considering two aspects important to the antisense approach. The first aspect is delivery of the oligonucleotide into the cytoplasm of the appropriate cells, while the second aspect is design of an oligonucleotide which specifically binds the designated mRNA within cells in a way which inhibits translation thereof.

The prior art teaches of a number of delivery strategies which can be used to efficiently deliver oligonucleotides into a wide variety of cell types [see, for example, Luft J Mol Med 76: 75-6 (1998); Kronenwett et al. Blood 91: 852-62 (1998); Rajur et al. BioconjugChem 8: 935-40 (1997); Lavigne et al. BiochemBiophys Res Commun 237: 566-71 (1997) and Aoki et al. (1997) BiochemBiophys Res Commun 231: 540-5 (1997)].

In addition, algorithms for identifying those sequences with the highest predicted binding affinity for their target mRNA based on a thermodynamic cycle that accounts for the energetics of structural alterations in both the target mRNA and the oligonucleotide are also available [see, for example, Walton et al. BiotechnolBioeng 65: 1-9 (1999)].

Such algorithms have been successfully used to implement an antisense approach in cells. For example, the algorithm developed by Walton et al. enabled scientists to successfully design antisense oligonucleotides for rabbit beta-globin (RBG) and mouse tumor necrosis factor-alpha (TNF alpha) transcripts. The same research group has more recently reported that the antisense activity of rationally selected oligonucleotides against three model target mRNAs (human lactate dehydrogenase A and B and rat gp130) in cell culture as evaluated by a kinetic PCR technique proved effective in almost all cases, including tests against three different targets in two cell types with phosphodiester and phosphorothioate oligonucleotide chemistries.

In addition, several approaches for designing and predicting efficiency of specific oligonucleotides using an in vitro system were also published (Matveeva et al., Nature Biotechnology 16: 1374-1375 (1998)].

Several clinical trials have demonstrated safety, feasibility and activity of antisense oligonucleotides. For example, antisense oligonucleotides suitable for the treatment of cancer have been successfully used [Holmund et al., CurrOpinMolTher 1:372-85 (1999)], while treatment of hematological malignancies via antisense oligonucleotides targeting c-myb gene, p53 and Bcl-2 had entered clinical trials and had been shown to be tolerated by patients [GerwitzCurrOpinMolTher 1:297-306 (1999)].

More recently, antisense-mediated suppression of human heparanase gene expression has been reported to inhibit pleural dissemination of human cancer cells in a mouse model [Uno et al., Cancer Res 61:7855-60 (2001)].

Thus, the current consensus is that recent developments in the field of antisense technology which, as described above, have led to the generation of highly accurate antisense design algorithms and a wide variety of oligonucleotide delivery systems, enable an ordinarily skilled artisan to design and implement antisense approaches suitable for downregulating expression of known sequences without having to resort to undue trial and error experimentation.

Another agent capable of downregulating a CD84 or SLAMF1 is a ribozyme molecule capable of specifically cleaving an mRNA transcript encoding a CD84 or SLAMF1, respectively. Ribozymes are being increasingly used for the sequence-specific inhibition of gene expression by the cleavage of mRNAs encoding proteins of interest [Welch et al., CurrOpinBiotechnol. 9:486-96 (1998)]. The possibility of designing ribozymes to cleave any specific target RNA has rendered them valuable tools in both basic research and therapeutic applications. In the therapeutics area, ribozymes have been exploited to target viral RNAs in infectious diseases, dominant oncogenes in cancers and specific somatic mutations in genetic disorders [Welch et al., ClinDiagnVirol. 10:163-71 (1998)]. Most notably, several ribozyme gene therapy protocols for HIV patients are already in Phase 1 trials. More recently, ribozymes have been used for transgenic animal research, gene target validation and pathway elucidation. Several ribozymes are in various stages of clinical trials. ANGIOZYME was the first chemically synthesized ribozyme to be studied in human clinical trials. ANGIOZYME specifically inhibits formation of the VEGF-r (Vascular Endothelial Growth Factor receptor), a key component in the angiogenesis pathway. Ribozyme Pharmaceuticals, Inc., as well as other firms have demonstrated the importance of anti-angiogenesis therapeutics in animal models. HEPTAZYME, a ribozyme designed to selectively destroy Hepatitis C Virus (HCV) RNA, was found effective in decreasing Hepatitis C viral RNA in cell culture assays (Ribozyme Pharmaceuticals, Incorporated—WEB home page).

An additional method of regulating the expression of a CD84 or SLAMF1 gene in cells is via triplex forming oligonuclotides (TFOs). Recent studies have shown that TFOs can be designed which can recognize and bind to polypurine/polypirimidine regions in double-stranded helical DNA in a sequence-specific manner. These recognition rules are outlined by Maher III, L. J., et al., Science, 1989; 245:725-730; Moser, H. E., et al., Science, 1987; 238:645-630; Beal, P. A., et al, Science, 1992; 251:1360-1363; Cooney, M., et al., Science, 1988; 241:456-459; and Hogan, M. E., et al., EP Publication 375408. Modification of the oligonuclotides, such as the introduction of intercalators and backbone substitutions, and optimization of binding conditions (pH and cation concentration) have aided in overcoming inherent obstacles to TFO activity such as charge repulsion and instability, and it was recently shown that synthetic oligonucleotides can be targeted to specific sequences (for a recent review see Seidman and Glazer, J Clin Invest 2003; 112:487-94).

In general, the triplex-forming oligonucleotide has the sequence correspondence:

| oligo  | 3'--A | G | G | T |
| duplex | 5'--A | G | C | T |
| duplex | 3'--T | C | G | A |

However, it has been shown that the A-AT and G-GC triplets have the greatest triple helical stability (Reither and Jeltsch, BMC Biochem, 2002, Sep. 12, Epub). The same authors have demonstrated that TFOs designed according to the A-AT and G-GC rule do not form non-specific triplexes, indicating that the triplex formation is indeed sequence specific.

Thus for any given sequence in the CD84 or SLAMF1 regulatory region a triplex forming sequence may be devised. Triplex-forming oligonucleotides preferably are at least 15, more preferably 25, still more preferably 30 or more nucleotides in length, up to 50 or 100 bp.

Transfection of cells (for example, via cationic liposomes) with TFOs, and formation of the triple helical structure with the target DNA induces steric and functional changes, blocking transcription initiation and elongation, allowing the introduction of desired sequence changes in the endogenous DNA and resulting in the specific downregulation of gene expression. Examples of such suppression of gene expression in cells treated with TFOs include knockout of episomal supFG1 and endogenous HPRT genes in mammalian cells (Vasquez et al., Nucl Acids Res. 1999; 27:1176-81, and Puri, et al, J BiolChem, 2001; 276:28991-98), and the sequence- and target specific downregulation of expression of the Ets2 transcription factor, important in prostate cancer etiology (Carbone, et al, Nucl Acid Res. 2003; 31:833-43), and the pro-inflammatory ICAM-1 gene (Besch et al, JBiolChem, 2002; 277:32473-79). In addition, Vuyisich and Beal have recently shown that sequence specific TFOs can bind to dsRNA, inhibiting activity of dsRNA-dependent enzymes such as RNA-dependent kinases (Vuyisich and Beal, Nuc. Acids Res 2000; 28:2369-74).

Additionally, TFOs designed according to the abovementioned principles can induce directed mutagenesis capable of effecting DNA repair, thus providing both downregulation and upregulation of expression of endogenous genes (Seidman and Glazer, J Clin Invest 2003; 112:487-94). Detailed description of the design, synthesis and administration of effective TFOs can be found in U.S. Patent Application Nos. 2003 017068 and 2003 0096980 to Froehler et al, and 2002 0128218 and 2002 0123476 to Emanuele et al, and U.S. Pat. No. 5,721,138 to Lawn.

Downregulation of CD84 or SLAMF1 can also be achieved by inactivating the gene (e.g., CD84 or SLAMF1 gene, respectively) via introducing targeted mutations involving loss-of function alterations (e.g. point mutations, deletions and insertions) in the gene structure.

As used herein, the phrase "loss-of-function alterations" refers to any mutation in the DNA sequence of a gene (e.g., CD84 or SLAMF1) which results in downregulation of the expression level and/or activity of the expressed product, i.e., the mRNA transcript and/or the translated protein. Non-limiting examples of such loss-of-function alterations include a missense mutation, i.e., a mutation which changes an amino acid residue in the protein with another amino acid residue and thereby abolishes the enzymatic activity of the protein; a nonsense mutation, i.e., a mutation which introduces a stop codon in a protein, e.g., an early stop codon which results in a shorter protein devoid of the enzymatic activity; a frame-shift mutation, i.e., a mutation, usually, deletion or insertion of nucleic acid(s) which changes the reading frame of the protein, and may result in an early termination by introducing a stop codon into a reading frame (e.g., a truncated protein, devoid of the enzymatic activity), or in a longer amino acid sequence (e.g., a read-through protein) which affects the secondary or tertiary structure of the protein and results in a non-functional protein, devoid of the enzymatic activity of the non-mutated polypeptide; a read-through mutation due to a frame-shift mutation or a modified stop codon mutation (i.e., when the stop codon is mutated into an amino acid codon), with an abolished enzymatic activity; a promoter mutation, i.e., a mutation in a promoter sequence, usually 5' to the transcription start site of a gene, which results in down-regulation of a specific gene product; a regulatory mutation, i.e., a mutation in a region upstream or downstream, or within a gene, which affects the expression of the gene product; a deletion mutation, i.e., a mutation which deletes coding nucleic acids in a gene sequence and which may result in a frame-shift mutation or an in-frame mutation (within the coding sequence, deletion of one or more amino acid codons); an insertion mutation, i.e., a mutation which inserts coding or non-coding nucleic acids into a gene sequence, and which may result in a frame-shift mutation or an in-frame insertion of one or more amino acid codons; an inversion, i.e., a mutation which results in an inverted coding or non-coding sequence; a splice mutation i.e., a mutation which results in abnormal splicing or poor splicing; and a duplication mutation, i.e., a mutation which results in a duplicated coding or non-coding sequence, which can be in-frame or can cause a frame-shift.

According to specific embodiments loss-of-function alteration of a gene may comprise at least one allele of the gene.

The term "allele" as used herein, refers to any of one or more alternative forms of a gene locus, all of which alleles relate to a trait or characteristic. In a diploid cell or organism, the two alleles of a given gene occupy corresponding loci on a pair of homologous chromosomes.

According to other specific embodiments loss-of-function alteration of a gene comprises both alleles of the gene. In such instances the e.g. CD84 or SLAMF1 may be in a homozygous form or in a heterozygous form. According to this embodiment, homozygosity is a condition where both alleles at the e.g. CD84 or SLAMF1 locus are characterized by the same nucleotide sequence. Heterozygosity refers to different conditions of the gene at the e.g. CD84 or SLAMF1 locus.

Methods of introducing nucleic acid alterations to a gene of interest are well known in the art [see for example Menke D. Genesis (2013) 51:—618; Capecchi, Science (1989) 244:1288-1292; Santiago et al. Proc Natl AcadSci USA (2008) 105:5809-5814; International Patent Application Nos. WO 2014085593, WO 2009071334 and WO 2011146121; U.S. Pat. Nos. 8,771,945, 8,586,526, 6,774,279 and UP Patent Application Publication Nos. 20030232410, 20050026157, US20060014264; the contents of which are incorporated by reference in their entireties] and include targeted homologous recombination, site specific recombinases, PB transposases and genome editing by engineered nucleases. Agents for introducing nucleic acid alterations to a gene of interest can be designed publically available sources or obtained commercially from Transposagen, Addgene and Sangamo Biosciences.

Following is a description of various exemplary methods used to introduce nucleic acid alterations to a gene of interest and agents for implementing same that can be used according to specific embodiments of the present invention.

Genome Editing using engineered endonucleases—this approach refers to a reverse genetics method using artificially engineered nucleases to cut and create specific double-stranded breaks at a desired location(s) in the genome, which are then repaired by cellular endogenous processes such as, homology directed repair (HDS) and non-homologous end-joining (NFfEJ). NFfEJ directly joins the DNA ends in a double-stranded break, while HDR utilizes a homologous sequence as a template for regenerating the missing DNA sequence at the break point. In order to introduce specific nucleotide modifications to the genomic DNA, a DNA repair template containing the desired sequence must be present during HDR. Genome editing cannot be performed using traditional restriction endonucleases since most restriction enzymes recognize a few base pairs on the DNA as their target and the probability is very high that the recognized base pair combination will be found in many locations across the genome resulting in multiple cuts not limited to a desired location. To overcome this challenge and create site-specific single- or double-stranded breaks, several distinct classes of nucleases have been discovered and bioengineered to date. These include the meganucleases, Zinc finger nucleases (ZFNs), transcription-activator like effector nucleases (TALENs) and CRISPR/Cas system.

Meganucleases—Meganucleases are commonly grouped into four families: the LAGLIDADG family, the GIY-YIG family, the His-Cysbox family and the HNH family. These families are characterized by structural motifs, which affect catalytic activity and recognition sequence. For instance, members of the LAGLIDADG family are characterized by having either one or two copies of the conserved LAGLIDADG motif. The four families of meganucleases are widely separated from one another with respect to conserved structural elements and, consequently, DNA recognition sequence specificity and catalytic activity. Meganucleases are found commonly in microbial species and have the unique property of having very long recognition sequences (>14 bp) thus making them naturally very specific for cutting at a desired location. This can be exploited to make site-specific double-stranded breaks in genome editing. One of skill in the art can use these naturally occurring meganucleases, however the number of such naturally occurring meganucleases is limited. To overcome this challenge, mutagenesis and high throughput screening methods have been used to create meganuclease variants that recognize unique sequences. For example, various meganucleases have been fused to create hybrid enzymes that recognize a new sequence. Alternatively, DNA interacting amino acids of the meganuclease can be altered to design sequence specific meganucleases (see e.g., U.S. Pat. No. 8,021,867). Meganucleases can be designed using the methods described in e.g., Certo, M T et al. Nature Methods (2012) 9:073-975; U.S. Pat. Nos. 8,304,222; 8,021,867; 8,119,381; 8,124,369; 8,129,134; 8,133,697; 8,143,015; 8,143,016; 8,148,098; or 8,163,514, the contents of each are incorporated herein by reference in their entirety. Alternatively, meganucleases with site specific cutting characteristics can be obtained using commercially available technologies e.g., Precision Biosciences' Directed Nuclease Editor™ genome editing technology.

ZFNs and TALENs—Two distinct classes of engineered nucleases, zinc-finger nucleases (ZFNs) and transcription activator-like effector nucleases (TALENs), have both proven to be effective at producing targeted double-stranded breaks (Christian et al., 2010; Kim et al., 1996; Li et al., 2011; Mahfouz et al., 2011; Miller et al., 2010).

Basically, ZFNs and TALENs restriction endonuclease technology utilizes a non-specific DNA cutting enzyme which is linked to a specific DNA binding domain (either a series of zinc finger domains or TALE repeats, respectively). Typically a restriction enzyme whose DNA recognition site and cleaving site are separate from each other is selected. The cleaving portion is separated and then linked to a DNA binding domain, thereby yielding an endonuclease with very high specificity for a desired sequence. An exemplary restriction enzyme with such properties is FokI. Additionally FokI has the advantage of requiring dimerization to have nuclease activity and this means the specificity increases dramatically as each nuclease partner recognizes a unique DNA sequence. To enhance this effect, FokI nucleases have been engineered that can only function as heterodimers and have increased catalytic activity. The heterodimer functioning nucleases avoid the possibility of unwanted homodimer activity and thus increase specificity of the double-stranded break.

Thus, for example to target a specific site, ZFNs and TALENs are constructed as nuclease pairs, with each member of the pair designed to bind adjacent sequences at the targeted site. Upon transient expression in cells, the nucleases bind to their target sites and the FokI domains heterodimerize to create a double-stranded break. Repair of these double-stranded breaks through the non-homologous endjoining (NHEJ) pathway most often results in small deletions or small sequence insertions. Since each repair made by NHEJ is unique, the use of a single nuclease pair can produce an allelic series with a range of different deletions at the target site. The deletions typically range anywhere from a few base pairs to a few hundred base pairs in length, but larger deletions have successfully been generated in cell culture by using two pairs of nucleases simultaneously (Carlson et al., 2012; Lee et al., 2010). In addition, when a fragment of DNA with homology to the targeted region is introduced in conjunction with the nuclease pair, the double-stranded break can be repaired via homology directed repair to generate specific modifications (Li et al., 2011; Miller et al., 2010; Urnov et al., 2005).

Although the nuclease portions of both ZFNs and TALENs have similar properties, the difference between these engineered nucleases is in their DNA recognition peptide. ZFNs rely on Cys2-His2 zinc fingers and TALENs on TALEs. Both of these DNA recognizing peptide domains have the characteristic that they are naturally found in combinations in their proteins. Cys2-His2 Zinc fingers typically found in repeats that are 3 bp apart and are found in diverse combinations in a variety of nucleic acid interacting proteins. TALEs on the other hand are found in repeats with a one-to-one recognition ratio between the amino acids and the recognized nucleotide pairs. Because both zinc fingers and TALEs happen in repeated patterns, different combinations can be tried to create a wide variety of sequence specificities. Approaches for making site-specific zinc finger endonucleases include, e.g., modular assembly (where Zinc fingers correlated with a triplet sequence are attached in a row to cover the required sequence), OPEN (low-stringency selection of peptide domains vs. triplet nucleotides followed by high-stringency selections of peptide combination vs. the final target in bacterial systems), and bacterial one-hybrid screening of zinc finger libraries, among others. ZFNs can also be designed and obtained commercially from e.g., Sangamo Biosciences™ (Richmond, CA).

Method for designing and obtaining TALENs are described in e.g. Reyon et al. Nature Biotechnology 2012 May; 30(5):460-5; Miller et al. Nat Biotechnol. (2011) 29: 143-148; Cermak et al. Nucleic Acids Research (2011) 39 (12): e82 and Zhang et al. Nature Biotechnology (2011) 29 (2): 149-53. A recently developed web-based program named Mojo Hand was introduced by Mayo Clinic for designing TAL and TALEN constructs for genome editing applications (can be accessed through www(dot)talendesign (dot)org). TALEN can also be designed and obtained commercially from e.g., Sangamo Biosciences™ (Richmond, CA).

CRISPR-Cas system—Many bacteria and archea contain endogenous RNA-based adaptive immune systems that can degrade nucleic acids of invading phages and plasmids. These systems consist of clustered regularly interspaced short palindromic repeat (CRISPR) genes that produce RNA components and CRISPR associated (Cas) genes that encode protein components. The CRISPR RNAs (crRNAs) contain short stretches of homology to specific viruses and plasmids and act as guides to direct Cas nucleases to degrade the complementary nucleic acids of the corresponding pathogen. Studies of the type II CRISPR/Cas system of *Streptococcus pyogenes* have shown that three components form an RNA/protein complex and together are sufficient for sequence-specific nuclease activity: the Cas9 nuclease, a crRNA containing 20 base pairs of homology to the target sequence, and a trans-activating crRNA (tracrRNA) (Jinek et al. Science (2012)337: 816-821). It was further demonstrated that a synthetic chimeric guide RNA (gRNA) composed of a fusion between crRNA and tracrRNA could direct Cas9 to cleave DNA targets that are complementary to the crRNA in vitro. It was also demonstrated that transient expression of Cas9 in conjunction with synthetic gRNAs can be used to produce targeted double-stranded brakes in a variety of different species (Cho et al., 2013; Cong et al., 2013; DiCarlo et al., 2013; Hwang et al., 2013a,b; Jinek et al., 2013; *Mali* et al., 2013).

The CRIPSR/Cas system for genome editing contains two distinct components: a gRNA and an endonuclease e.g. Cas9.

The gRNA is typically a 20 nucleotide sequence encoding a combination of the target homologous sequence (crRNA) and the endogenous bacterial RNA that links the crRNA to the Cas9 nuclease (tracrRNA) in a single chimeric transcript. The gRNA/Cas9 complex is recruited to the target sequence by the base-pairing between the gRNA sequence and the complement genomic DNA. For successful binding of Cas9, the genomic target sequence must also contain the correct Protospacer Adjacent Motif (PAM) sequence immediately following the target sequence. The binding of the gRNA/Cas9 complex localizes the Cas9 to the genomic target sequence so that the Cas9 can cut both strands of the DNA causing a double-strand break. Just as with ZFNs and TALENs, the double-stranded brakes produced by CRISPR/Cas can undergo homologous recombination or NHEJ.

The Cas9 nuclease has two functional domains: RuvC and HNH, each cutting a different DNA strand. When both of these domains are active, the Cas9 causes double strand breaks in the genomic DNA.

A significant advantage of CRISPR/Cas is that the high efficiency of this system coupled with the ability to easily create synthetic gRNAs enables multiple genes to be targeted simultaneously. In addition, the majority of cells carrying the mutation present biallelic mutations in the targeted genes.

However, apparent flexibility in the base-pairing interactions between the gRNA sequence and the genomic DNA target sequence allows imperfect matches to the target sequence to be cut by Cas9.

Modified versions of the Cas9 enzyme containing a single inactive catalytic domain, either RuvC- or HNH-, are called 'nickases'. With only one active nuclease domain, the Cas9 nickase cuts only one strand of the target DNA, creating a single-strand break or 'nick'. A single-strand break, or nick, is normally quickly repaired through the HDR pathway, using the intact complementary DNA strand as the template. However, two proximal, opposite strand nicks introduced by a Cas9 nickase are treated as a double-strand break, in what is often referred to as a 'double nick' CRISPR system. A double-nick can be repaired by either NHEJ or HDR depending on the desired effect on the gene target. Thus, if specificity and reduced off-target effects are crucial, using the Cas9 nickase to create a double-nick by designing two gRNAs with target sequences in close proximity and on opposite strands of the genomic DNA would decrease off-target effect as either gRNA alone will result in nicks that will not change the genomic DNA.

Modified versions of the Cas9 enzyme containing two inactive catalytic domains (dead Cas9, or dCas9) have no nuclease activity while still able to bind to DNA based on gRNA specificity. The dCas9 can be utilized as a platform for DNA transcriptional regulators to activate or repress gene expression by fusing the inactive enzyme to known regulatory domains. For example, the binding of dCas9 alone to a target sequence in genomic DNA can interfere with gene transcription.

There are a number of publically available tools available to help choose and/or design target sequences as well as lists of bioinformatically determined unique gRNAs for different genes in different species such as the Feng Zhang lab's Target Finder, the Michael Boutros lab's Target Finder (E-CRISP), the RGEN Tools: Cas-OFFinder, the CasFinder: Flexible algorithm for identifying specific Cas9 targets in genomes and the CRISPR Optimal Target Finder.

In order to use the CRISPR system, both gRNA and Cas9 should be expressed in a target cell. The insertion vector can contain both cassettes on a single plasmid or the cassettes are expressed from two separate plasmids. CRISPR plasmids are commercially available such as the px330 plasmid from Addgene.

"Hit and run" or "in-out"—involves a two-step recombination procedure. In the first step, an insertion-type vector containing a dual positive/negative selectable marker cassette is used to introduce the desired sequence alteration. The insertion vector contains a single continuous region of homology to the targeted locus and is modified to carry the mutation of interest. This targeting construct is linearized with a restriction enzyme at a one site within the region of homology, electroporated into the cells, and positive selection is performed to isolate homologous recombinants. These homologous recombinants contain a local duplication that is separated by intervening vector sequence, including the selection cassette. In the second step, targeted clones are subjected to negative selection to identify cells that have lost the selection cassette via intrachromosomal recombination between the duplicated sequences. The local recombination event removes the duplication and, depending on the site of recombination, the allele either retains the introduced mutation or reverts to wild type. The end result is the introduction of the desired modification without the retention of any exogenous sequences.

The "double-replacement" or "tag and exchange" strategy—involves a two-step selection procedure similar to the hit and run approach, but requires the use of two different targeting constructs. In the first step, a standard targeting vector with 3' and 5' homology arms is used to insert a dual positive/negative selectable cassette near the location where the mutation is to be introduced. After electroporation and positive selection, homologously-targeted clones are identified. Next, a second targeting vector that contains a region of homology with the desired mutation is electroporated into targeted clones, and negative selection is applied to remove the selection cassette and introduce the mutation. The final allele contains the desired mutation while eliminating unwanted exogenous sequences.

Site-Specific Recombinases—The Cre recombinase derived from the P1 bacteriophage and Flp recombinase derived from the yeast *Saccharomyces cerevisiae* are site-specific DNA recombinases each recognizing a unique 34 base pair DNA sequence (termed "Lox" and "FRT", respectively) and sequences that are flanked with either Lox sites or FRT sites can be readily removed via site-specific recombination upon expression of Cre or Flp recombinase, respectively. For example, the Lox sequence is composed of an asymmetric eight base pair spacer region flanked by 13 base pair inverted repeats. Cre recombines the 34 base pair lox DNA sequence by binding to the 13 base pair inverted repeats and catalyzing strand cleavage and religation within the spacer region. The staggered DNA cuts made by Cre in the spacer region are separated by 6 base pairs to give an overlap region that acts as a homology sensor to ensure that only recombination sites having the same overlap region recombine.

Basically, the site specific recombinase system offers means for the removal of selection cassettes after homologous recombination. This system also allows for the generation of conditional altered alleles that can be inactivated or activated in a temporal or tissue-specific manner. Of note, the Cre and Flp recombinases leave behind a Lox or FRT "scar" of 34 base pairs. The Lox or FRT sites that remain are typically left behind in an intron or 3' UTR of the modified locus, and current evidence suggests that these sites usually do not interfere significantly with gene function.

Thus, Cre/Lox and Flp/FRT recombination involves introduction of a targeting vector with 3' and 5' homology arms containing the mutation of interest, two Lox or FRT sequences and typically a selectable cassette placed between the two Lox or FRT sequences. Positive selection is applied and homologous recombinants that contain targeted mutation are identified. Transient expression of Cre or Flp in conjunction with negative selection results in the excision of the selection cassette and selects for cells where the cassette has been lost. The final targeted allele contains the Lox or FRT scar of exogenous sequences.

Transposases—As used herein, the term "transposase" refers to an enzyme that binds to the ends of a transposon and catalyzes the movement of the transposon to another part of the genome.

As used herein the term "transposon" refers to a mobile genetic element comprising a nucleotide sequence which can move around to different positions within the genome of a single cell. In the process the transposon can cause mutations and/or change the amount of a DNA in the genome of the cell.

A number of transposon systems that are able to also transpose in cells e.g. vertebrates have been isolated or designed, such as Sleeping Beauty [Izsvák and Ivics Molecular Therapy (2004) 9, 147-156], piggyBac [Wilson et al. Molecular Therapy (2007) 15, 139-145], Tol2 [Kawakami et al. PNAS (2000) 97 (21): 11403-11408] or Frog Prince [Miskey et al. Nucleic Acids Res. Dec. 1, (2003) 31(23): 6873-6881]. Generally, DNA transposons translocate from one DNA site to another in a simple, cut-and-paste manner. Each of these elements has their own advantages, for example, Sleeping Beauty is particularly useful in region-specific mutagenesis, whereas Tol2 has the highest tendency to integrate into expressed genes. Hyperactive systems are available for Sleeping Beauty and piggyBac. Most importantly, these transposons have distinct target site preferences, and can therefore introduce sequence alterations in overlapping, but distinct sets of genes. Therefore, to achieve the best possible coverage of genes, the use of more than one element is particularly preferred. The basic mechanism is shared between the different transposases, therefore piggyBac (PB) is described as an example.

PB is a 2.5 kb insect transposon originally isolated from the cabbage looper moth, Trichoplusiani. The PB transposon consists of asymmetric terminal repeat sequences that flank a transposase, PBase. PBase recognizes the terminal repeats and induces transposition via a "cut-and-paste" based mechanism, and preferentially transposes into the host genome at the tetranucleotide sequence TTAA. Upon insertion, the TTAA target site is duplicated such that the PB transposon is flanked by this tetranucleotide sequence. When mobilized, PB typically excises itself precisely to reestablish a single TTAA site, thereby restoring the host sequence to its pretransposon state. After excision, PB can transpose into a new location or be permanently lost from the genome.

Typically, the transposase system offers an alternative means for the removal of selection cassettes after homologous recombination quit similar to the use Cre/Lox or Flp/FRT. Thus, for example, the PB transposase system involves introduction of a targeting vector with 3' and 5' homology arms containing the mutation of interest, two PB terminal repeat sequences at the site of an endogenous TTAA sequence and a selection cassette placed between PB terminal repeat sequences. Positive selection is applied and homologous recombinants that contain targeted mutation are identified. Transient expression of PBase removes in conjunction with negative selection results in the excision of the selection cassette and selects for cells where the cassette has been lost. The final targeted allele contains the introduced mutation with no exogenous sequences.

For PB to be useful for the introduction of sequence alterations, there must be a native TTAA site in relatively close proximity to the location where a particular mutation is to be inserted.

Genome editing using recombinant adeno-associated virus (rAAV) platform—this genome-editing platform is based on rAAV vectors which enable insertion, deletion or substitution of DNA sequences in the genomes of live mammalian cells. The rAAV genome is a single-stranded deoxyribonucleic acid (ssDNA) molecule, either positive- or negative-sensed, which is about 4.7 kb long. These single-stranded DNA viral vectors have high transduction rates and have a unique property of stimulating endogenous homologous recombination in the absence of double-strand DNA breaks in the genome. One of skill in the art can design a rAAV vector to target a desired genomic locus and perform both gross and/or subtle endogenous gene alterations in a cell. rAAV genome editing has the advantage in that it targets a single allele and does not result in any off-target genomic alterations. rAAV genome editing technology is commercially available, for example, the rAAV GENESIS™ system from Horizon™ (Cambridge, UK).

It will be appreciated that the agent can be a mutagen that causes random mutations and the cells exhibiting downregulation of the expression level and/or activity of CD84 or SLAMF1 may be selected.

The mutagens may be, but are not limited to, genetic, chemical or radiation agents. For example, the mutagen may be ionizing radiation, such as, but not limited to, ultraviolet light, gamma rays or alpha particles. Other mutagens may include, but not be limited to, base analogs, which can cause copying errors; deaminating agents, such as nitrous acid; intercalating agents, such as ethidium bromide; alkylating agents, such as bromouracil; transposons; natural and synthetic alkaloids; bromine and derivatives thereof; sodium azide; psoralen (for example, combined with ultraviolet radiation). The mutagen may be a chemical mutagen such as, but not limited to, ICR191, 1,2,7,8-diepoxy-octane (DEO), 5-azaC, N-methyl-N-nitrosoguanidine (MNNG) or ethyl methane sulfonate (EMS).

Methods for qualifying efficacy and detecting sequence alteration are well known in the art and include, but not limited to, DNA sequencing, electrophoresis, an enzyme-based mismatch detection assay and a hybridization assay such as PCR, RT-PCR, RNase protection, in-situ hybridization, primer extension, Southern blot, Northern Blot and dot blot analysis.

Sequence alterations in a specific gene can also be determined at the protein level using e.g. chromatography, electrophoretic methods, immunodetection assays such as ELISA and western blot analysis and immunohistochemistry.

In addition, one ordinarily skilled in the art can readily design a knock-in/knock-out construct including positive and/or negative selection markers for efficiently selecting transformed cells that underwent a homologous recombination event with the construct. Positive selection provides a means to enrich the population of clones that have taken up foreign DNA. Non-limiting examples of such positive markers include glutamine synthetase, dihydrofolate reductase (DHFR), markers that confer antibiotic resistance, such as neomycin, hygromycin, puromycin, and blasticidin S resistance cassettes. Negative selection markers are necessary to select against random integrations and/or elimination of a marker sequence (e.g. positive marker). Non-limiting examples of such negative markers include the herpes simplex-thymidine kinase (HSV-TK) which converts ganciclovir (GCV) into a cytotoxic nucleoside analog, hypoxanthine phosphoribosyltransferase (HPRT) and adenine phosphoribosytransferase (ARPT). Another agent which can be used along with some embodiments of the invention to downregulate CD84 or SLAMF1 is a molecule which prevents CD84 or SLAMF1 activation or substrate binding.

According to one embodiment, when the agent used is an agent capable of decreasing an activity or expression of SLAMF1, the agent is not an agent capable of decreasing an activity or expression of CD84.

According to one embodiment, the subject is diagnosed with a malignant disease.

According to one embodiment, the subject is diagnosed with an autoimmune disease, an inflammatory disease or an infectious disease (e.g. viral disease).

As used herein, the term "diagnosed", "diagnosis" or "diagnosing" refers to classifying a pathology (e.g., malignancy).

According to one embodiment, the subject may be treated.

Thus, according to another aspect, there is provided a method of treating a malignant disease involving T cell exhaustion in a subject in need thereof, the method comprising administering to the subject a therapeutically effective amount of an agent capable of decreasing an activity or expression of SLAMF1.

According to another aspect, there is provided a use of a therapeutically effective amount of an agent capable of decreasing an activity or expression of SLAMF1, with the proviso that the agent is not an agent capable of decreasing an activity or expression of CD84, for treating a malignant disease involving T cell exhaustion in a subject in need thereof.

According to another aspect, there is provided a method of treating a malignant disease involving T cell exhaustion in a subject in need thereof, with the proviso that the malignant disease is not a B cell malignancy, the method comprising administering to the subject a therapeutically effective amount of an agent capable of decreasing an activity or expression of CD84.

According to another aspect, there is provided a use of a therapeutically effective amount of an agent capable of decreasing an activity or expression of CD84 for treating a malignant disease involving T cell exhaustion in a subject in need thereof, with the proviso that the malignant disease is not a B cell malignancy.

As used herein, the term "treating" includes abrogating, substantially inhibiting, slowing or reversing the progression of a condition, substantially ameliorating clinical or aesthetical symptoms of a condition or substantially preventing the appearance of clinical or aesthetical symptoms of a condition.

According to one embodiment, an individual is successfully "treated" if one or more symptoms associated with the disease are mitigated or eliminated, including but not limited to, reducing the proliferation of (or destroying) cancerous cells, decreasing symptoms resulting from the disease, increasing the quality of life of those suffering from the disease, decreasing the dose of other medications required to treat the disease, delaying the progression of the disease, and/or prolonging survival of individuals.

Treatment can be evaluated using any method known in the art for evaluation of the specific disease or condition (e.g. utilizing blood tests, ultrasound, CT scan, MRI, etc.) such a method can be determined by one of skill in the art.

As used herein, the term "malignant disease" or "cancer" refers to any cancerous disease. Cancer cells may be associated with phenotypes such uncontrolled proliferation, loss of specialized functions, immortality, significant metastatic potential, significant increase in anti-apoptotic activity, rapid growth and proliferation rate, and certain characteristic morphology and cellular markers. According to a specific embodiment the cancer involves exhaustion of T cells.

In some circumstances, cancer cells will be in the form of a tumor, such cells may exist locally within an animal (e.g. solid tumor), alternatively, cancer cells may circulate in the blood stream as independent cells, for example, leukemic cells (non-solid tumor), or may be dispersed throughout the body(e.g. metastasis). It will be appreciated that the term cancer as used herein encompasses all types of cancers, at any stage and in any form.

Types of malignant diseases amenable to diagnosis or treatment by the methods of some embodiments of the invention include benign tumors, warts, polyps, pre-cancers, and malignant tumors/cancers.

Specific examples of cancerous diseases which can be treated using the methods of the present invention include, but are not limited to, tumors of the gastrointestinal tract (colon carcinoma, rectal carcinoma, colorectal carcinoma, colorectal cancer, colorectal adenoma, hereditary nonpolyposis type 1, hereditary nonpolyposis type 2, hereditary nonpolyposis type 3, hereditary nonpolyposis type 6; colorectal cancer, hereditary nonpolyposis type 7, small and/or large bowel carcinoma, esophageal carcinoma, tylosis with esophageal cancer, stomach carcinoma, pancreatic carcinoma, pancreatic endocrine tumors), endometrial carcinoma, dermatofibrosarcoma protuberans, gallbladder carcinoma, Biliary tract tumors, prostate cancer, prostate adenocarcinoma, renal cancer (e.g., Wilms' tumor type 2 or type 1), liver cancer (e.g., hepatoblastoma, hepatocellular carcinoma, hepatocellular cancer), bladder cancer, embryonal rhabdomyosarcoma, germ cell tumor, trophoblastic tumor, testicular germ cells tumor, immature teratoma of ovary, uterine, epithelial ovarian, sacrococcygeal tumor, choriocarcinoma, placental site trophoblastic tumor, epithelial adult tumor, ovarian carcinoma, serous ovarian cancer, ovarian sex cord tumors, cervical carcinoma, uterine cervix carcinoma, small-cell and non-small cell lung carcinoma, nasopharyngeal, breast carcinoma (e.g., ductal breast cancer, invasive intraductal breast cancer, sporadic; breast cancer, susceptibility to breast cancer, type 4 breast cancer, breast cancer-1, breast cancer-3; breast-ovarian cancer), squamous cell carcinoma (e.g., in head and neck), neurogenic tumor, astrocytoma, ganglioblastoma, neuroblastoma, gliomas, adenocarcinoma, adrenal tumor, hereditary adrenocortical carcinoma, brain malignancy (tumor), various other carcinomas (e.g., bronchogenic large cell, ductal, Ehrlich-Lettre ascites, epidermoid, large cell, Lewis lung, medullary, mucoepidermoid, oat cell, small cell, spindle cell, spinocellular, transitional cell, undifferentiated, carcinosarcoma, choriocarcinoma, cystadenocarcinoma), ependimoblastoma, epithelioma, erythroleukemia (e.g., Friend, lymphoblast), fibrosarcoma, giant cell tumor, glial tumor, glioblastoma (e.g., multiforme, astrocytoma), glioma hepatoma, heterohybridoma, heteromyeloma, histiocytoma, hybridoma (e.g., B cell), hypernephroma, insulinoma, islet tumor, keratoma, leiomyoblastoma, leiomyosarcoma, leukemia (e.g., acute lymphatic, acute lymphoblastic, acute lymphoblastic pre-B cell, acute lymphoblastic T cell leukemia, acute—megakaryoblastic, monocytic, acute myelogenous, acute myeloid, acute myeloid with eosinophilia, B cell, basophilic, chronic myeloid, chronic, B cell, eosinophilic, Friend, granulocytic or myelocytic, hairy cell, lymphocytic, megakaryoblastic, monocytic, monocytic-macrophage, myeloblastic, myeloid, myelomonocytic, plasma cell, pre-B cell, promyelocytic, subacute, T cell, lymphoid neoplasm, predisposition to myeloid malignancy, acute nonlymphocytic leukemia), lymphosarcoma, lymphomas (e.g., Hodgkin's disease, non-Hodgkin's lymphoma, B cell, Burkitt, cutaneous T cell, histiocytic, lymphoblastic, T cell, thymic), melanoma, mammary tumor, mastocytoma, medulloblastoma, mesothelioma, metastatic tumor, monocyte tumor, multiple myeloma, myelodysplastic syndrome, myeloma, nephroblastoma, nervous tissue glial tumor, nervous tissue neuronal tumor, neurinoma, neuroblastoma, oligodendroglioma, osteochondroma, osteomyeloma, osteosarcoma (e.g., Ewing's), papilloma, transitional cell, pheochromocytoma, pituitary tumor (invasive), plasmacytoma, retinoblastoma, rhabdomyosarcoma, sarcoma (e.g., Ewing's, histiocytic cell, Jensen, osteogenic, reticulum cell), schwannoma, subcutaneous tumor, teratocarcinoma (e.g., pluripotent), teratoma, testicular tumor, thymoma and trichoepithelioma, gastric cancer, fibrosarcoma, glioblastoma multiforme; multiple *glomus* tumors, Li-Fraumeni syndrome, liposarcoma, lynch cancer family syndrome II, male germ cell tumor, mast cell leukemia, medullary thyroid, multiple meningioma, endocrine neoplasia myxosarcoma, paraganglioma, familial nonchromaffin, pilomatricoma, papillary, familial and sporadic, rhabdoid predisposition syndrome, familial, rhabdoid tumors, soft tissue sarcoma, and Turcot syndrome with glioblastoma.

Precancers are well characterized and known in the art (refer, for example, to Berman J J. and Henson D E., 2003. Classifying the precancers: a metadata approach.BMC Med Inform DecisMak. 3:8). Classes of precancers amenable to treatment via the method of the invention include acquired small or microscopic precancers, acquired large lesions with nuclear atypia, precursor lesions occurring with inherited hyperplastic syndromes that progress to cancer, and acquired diffuse hyperplasias and diffuse metaplasias. Examples of small or microscopic precancers include HGSIL (High grade squamous intraepithelial lesion of uterine cervix), AIN (anal intraepithelial neoplasia), dysplasia of vocal cord, aberrant crypts (of colon), PIN (prostatic intraepithelial neoplasia). Examples of acquired large lesions with nuclear atypia include tubular adenoma, AILD (angioimmunoblastic lymphadenopathy with dysproteinemia), atypical meningioma, gastric polyp, large plaque parapsoriasis, myelodysplasia, papillary transitional cell carcinoma in-situ, refractory anemia with excess blasts, and Schneiderian papilloma. Examples of precursor lesions occurring with inherited hyperplastic syndromes that progress to cancer include atypical mole syndrome, C cell adenomatosis and MEA. Examples of acquired diffuse hyperplasias and diffuse metaplasias include AIDS, atypical lymphoid hyperplasia, Paget's disease of bone, post-transplant lymphoproliferative disease and ulcerative colitis.

According to one embodiment, the cancer is a cancer that induces T cell exhaustion.

According to one embodiment, the cancer comprises a solid tumor.

For example, the solid tumor (cancer) may be an adrenocortical carcinoma, anal cancer, bladder cancer, brain tumor, glioma, breast carcinoma, cervical cancer, colon carcinoma, endometrial cancer, esophageal cancer, extrahepatic bile duct cancer, Ewings tumor, extracranial germ cell tumor, eye cancer, gall bladder cancer, gastric cancer, germ cell tumor, gestational trophoblastic tumor, head and neck cancer, hypopharyngeal cancer, islet cell carcinoma, kidney cancer, laryngeal cancer, lip and oral cavity cancer, liver cancer, lung cancer, melanoma, mesothelioma, merkel cell carcinoma, metastatic squamous head and neck cancer, myeloma, nasopharyngeal cancer, neuroblastoma, oral cancer, oropharyngeal cancer, osteosarcoma, ovarian cancer, pancreatic cancer, sinus and nasal cancer, parathyroid cancer, penile cancer, pituitary cancer, prostate cancer, rhabdomyosarcoma, rectal cancer, renal cell carcinoma, salivary gland cancer, skin cancer, soft tissue sarcoma, stomach cancer, testicular cancer, thyroid cancer, urethral cancer, uterine cancer, vaginal cancer, vulvar cancer, or Wilms' tumor.

According to further embodiments, the cancer is a solid tumor selected from the group consisting of liver cancer (e.g. hepatocellular carcinoma), lung cancer (e.g. lung carcinoma such as non-small cell lung carcinoma and lung adenocarcinoma), breast cancer (e.g. breast carcinoma such as breast adenocarcinoma), colon cancer (e.g. colorectal carcinoma, colon adenocarcinoma), renal cancer (e.g. renal cell carcinoma), prostate cancer, ovarian cancer, head and neck cancer, fibrosarcoma, uterine cervix cancer, esophagus cancer, rectum cancer, oral cavity cancer, and a pancreatic cancer.

According to a specific embodiment, the tumor is a metastasizing solid tumor (e.g., formed by metastatic cancer cells).

According to one embodiment, the malignant disease is a hematopoietic cancer.

According to one embodiment, the malignant disease is a T cell malignancy or a myeloid malignancy.

Exemplary T cell malignancies include, but are not limited to, Precursor T-lymphoblastic lymphoma/leukemia, Cutaneous T-cell lymphomas, Adult T-cell leukemia/lymphoma, Angioimmunoblastic T-cell lymphoma, Extranodal natural killer/T-cell lymphoma (nasal type), Enteropathy-associated intestinal T-cell lymphoma (EATL), Anaplastic large cell lymphoma (ALCL) and Peripheral T-cell lymphoma, unspecified.

Exemplary Myeloid malignancies include, but are not limited to, acute myelogenous leukemia (AML), chronic myeloid leukemia, acute myeloid leukemia, Myeloid leukemia adult acute, Myeloid leukemia childhood acute, Myelodysplastic syndrome (MDS), Myeloproliferative neoplasms (MPN) and Myeloid neoplasms associated with eosinophilia and abnormalities of PDGFR-A or -B, or FGFR1.

According to one embodiment, the malignant disease is not a B cell malignancy (e.g. when administering to the subject an agent capable of decreasing an activity or expression of CD84).

According to one embodiment, the malignant disease is a B cell malignancy (e.g. when administering to the subject an agent capable of decreasing an activity or expression of SLAMF1).

As used herein, the term "B cell malignancy" refers to a malignancy of hematopoietic or lymphoid tissues involving B lymphocytes of any subtype or stage of differentiation (e.g. early pre-B cells, pre-B cells, mature B cells, plasma cells).

According to one embodiment, the B cell malignancy comprises a lymphoma, a leukemia or a myeloma.

Such diseases include, but are not limited to, Hodgkin's Lymphoma, non-Hodgkin's Lymphoma, Diffuse large B-cell lymphoma (DLBCL), B-cell chronic lymphocytic leukemia (B-CLL)/chronic lymphoid leukemia (CLL), Chronic lymphocytic leukemia/small lymphocytic lymphoma, a chronic myelocytic leukemia (CML), an Extranodal marginal zone B-cell lymphoma—mucosa-associated lymphoid tissue lymphoma, a Follicular lymphoma, a Mantle cell lymphoma, a Nodal marginal zone B-cell lymphoma, a Burkitt's lymphoma, a Hairy cell leukemia, a Primary central nervous system lymphoma, a Splenic marginal zone B-cell lymphoma, a Lymphoplasmocytic lymphoma, a Primary mediastinal B-cell lymphoma, multiple myeloma, Acute lymphocytic leukemia (also known as acute lymphoblastic leukemia or ALL), acute lymphoblastic pre-B cell leukemia, plasma cell leukemia, pre-B cell leukemia (e.g. pre-B ALL), early pre-B cells ALL (e.g. early pre-B ALL) or pre-B acute lymphoblastoid leukemia.

According to one embodiment, the B cell malignancy is CLL.

As used herein the term "B-CLL" or "CLL" refers to an abnormal neoplastic proliferation of B-cells. CLL is considered to be identical to a disease called small lymphocytic lymphoma (SLL), a type of non-Hodgkin's lymphoma which presents primarily in the lymph nodes. The World Health Organization considers CLL and SLL to present different stages of the same disease [Chiorazzi N, Rai K R, Ferrarini M (2005). "Chronic lymphocytic leukemia" *N. Engl. J. Med.* 352 (8): 804-15].

The method of the present invention can be implemented for the treatment of other diseases involving exhaustion of T cells. Such diseases include, for example, immune related diseases including autoimmune, inflammatory, and infectious diseases (e.g. unresolved acute infections and chronic infections).

As mentioned above, the present inventors have further uncovered that CD84 plays a role in Bregs activity. Specifically, the present inventors uncovered that in the absence of CD84 expression, there is a marked increase in the activity and level of B regulatory cells, which are known as negative regulators of immune responses. Accordingly, in the presence of B regulatory cells, there is a marked decrease in autoimmunity and inflammation. Accordingly, the methods of the present invention can be further implemented for the treatment of diseases in which B regulatory cells are involved, including autoimmune, inflammatory, and infectious diseases.

According to another aspect of the invention, there is provided a method of treating an autoimmune or inflammatory disease in a subject in need thereof, the method comprising administering to a subject a therapeutically effective amount of an agent capable of decreasing an activity or expression of CD84, thereby treating the autoimmune or inflammatory disease in the subject.

According to another aspect of the invention, there is provided a use of a therapeutically effective amount of an agent capable of decreasing an activity or expression of CD84 for treating an autoimmune or inflammatory disease in a subject in need thereof.

According to another aspect of the invention, there is provided a method of elevating an activity or level of B regulatory cells in a subject in need thereof, the method comprising administering to a subject a therapeutically effective amount of an agent capable of decreasing an activity or expression of CD84, thereby elevating the activity or level of the B regulatory cells in the subject.

The term "B regulatory cells" or "Bregs" refers to B cells that suppress the immune response. Bregs can suppress T cell activation (directly or indirectly) and may also suppress antigen presenting cells (APCs), other innate immune cells, or other B cells. Bregs may express any B cell marker including, but not limited to, CD19, CD1d, CD5, CD24, CD27, CD38, CD40 or T cell immunoglobulin mucin-1 (TIM-1). Bregs can also secrete IL-10, TGFβ-1 and/or IL-35.

According to one embodiment, the activity or level of B regulatory cells is enhanced by at least about 10%, 20%, 30%, 40%, 50%, 60%, 70%, 80%, 90%, 100%, 120%, 150% or 200%. Measuring enhancement of B cell level is known to one of skill in the art and include, for example, flow cytometric assay (FACS). Likewise, measuring enhancement of B cell function is known to one of ordinary skill in the art and include, for example, flow cytometric assay (FACS), ELISA, ELISpot, intracellular cytokine staining (ICS), and Proliferation Assay.

According to some embodiments of the invention, elevating an activity or level of B regulatory cells is manifested by increased B regulatory cell levels in the spleen.

According to specific embodiments of the invention, elevating an activity or level of B regulatory cells is associated with an increase in B10 B regulatory cells.

According to some embodiments of the invention, elevating an activity or level of B regulatory cells is manifested by an increase in production of anti-inflammatory cytokines by the B regulatory cells. Exemplary anti-inflammatory cytokines include, but are not limited to, IL-10, TGFβ-1 and IL-35.

According to some embodiments of the invention, elevating an activity or level of B regulatory cells is associated with an increase in expression of a Breg marker. Exemplary Breg markers include, but are not limited to, CD19, CD1d, CD5, CD24, CD27, CD38, CD40 and/or TIM-1.

Examples of infectious diseases include, but are not limited to, chronic infectious diseases, subacute infectious diseases, acute infectious diseases, viral diseases, bacterial diseases, protozoan diseases, parasitic diseases, fungal diseases, *mycoplasma* diseases and prion diseases.

According to one embodiment, the disease involving exhaustion of T cells comprises a viral infection.

According to one embodiment, the disease involving exhaustion of T cells comprises a chronic viral infection.

Exemplary viral infections include, but are not limited to, infections resulting from lymphocytic choriomeningitis virus (LCMV), polyoma virus, adenovirus, Friend leukaemia virus, mouse hepatitis virus, human immunodeficiency virus (HIV), hepatitis B virus (HBV), hepatitis C virus (HCV), Ebola and Dengue.

Exemplary autoimmune diseases which may be treated by the present method include, but are not limited to, cardiovascular diseases, rheumatoid diseases, glandular diseases, gastrointestinal diseases, cutaneous diseases, hepatic diseases, neurological diseases, muscular diseases, nephric diseases, diseases related to reproduction, connective tissue diseases and systemic diseases.

Examples of autoimmune cardiovascular diseases include, but are not limited to atherosclerosis, myocardial infarction, thrombosis, Wegener's granulomatosis, Takayasu's arteritis, Kawasaki syndrome, anti-factor VIII autoimmune disease, necrotizing small vessel vasculitis, microscopic polyangiitis, Churg and Strauss syndrome, pauci-immune focal necrotizing and crescentic glomerulonephritis, antiphospholipid syndrome, antibody-induced heart failure, thrombocytopenic purpura, autoimmune hemolytic anemia, cardiac autoimmunity in Chagas' disease and anti-helper T lymphocyte autoimmunity.

Examples of autoimmune rheumatoid diseases include, but are not limited to rheumatoid arthritis and ankylosing spondylitis.

Examples of autoimmune glandular diseases include, but are not limited to, pancreatic disease, Type I diabetes, thyroid disease, Graves' disease, thyroiditis, spontaneous autoimmune thyroiditis, Hashimoto's thyroiditis, idiopathic myxedema, ovarian autoimmunity, autoimmune anti-sperm infertility, autoimmune prostatitis and Type I autoimmune polyglandular syndrome. diseases include, but are not limited to autoimmune diseases of the pancreas, Type 1 diabetes, autoimmune thyroid diseases, Graves' disease, spontaneous autoimmune thyroiditis, Hashimoto's thyroiditis, idiopathic myxedema, ovarian autoimmunity, autoimmune anti-sperm infertility, autoimmune prostatitis and Type I autoimmune polyglandular syndrome.

Examples of autoimmune gastrointestinal diseases include, but are not limited to, chronic inflammatory intestinal diseases, celiac disease, colitis, ileitis and Crohn's disease.

Examples of autoimmune cutaneous diseases include, but are not limited to, autoimmune bullous skin diseases, such as, but are not limited to, pemphigus vulgaris, bullous pemphigoid and pemphigus foliaceus.

Examples of autoimmune hepatic diseases include, but are not limited to, hepatitis, autoimmune chronic active hepatitis, primary biliary cirrhosis and autoimmune hepatitis.

Examples of autoimmune neurological diseases include, but are not limited to, multiple sclerosis, Alzheimer's disease, myasthenia gravis, neuropathies, motor neuropathies, Guillain-Barre syndrome and autoimmune neuropathies, myasthenia, Lambert-Eaton myasthenic syndrome, paraneoplastic neurological diseases, cerebellar atrophy, paraneoplastic cerebellar atrophy and stiff-man syndrome, non-paraneoplastic stiff man syndrome, progressive cerebellar atrophies, encephalitis, Rasmussen's encephalitis, amyotrophic lateral sclerosis, Sydeham chorea, Gilles de la Tourette syndrome and autoimmune polyendocrinopathies, dysimmune neuropathies, acquired neuromyotonia, arthrogryposis multiplex congenita, neuritis, optic neuritis and neurodegenerative diseases.

Examples of autoimmune muscular diseases include, but are not limited to, myositis, autoimmune myositis and primary Sjogren's syndrome and smooth muscle autoimmune disease.

Examples of autoimmune nephric diseases include, but are not limited to, nephritis and autoimmune interstitial nephritis.

Examples of autoimmune diseases related to reproduction include, but are not limited to, repeated fetal loss.

Examples of autoimmune connective tissue diseases include, but are not limited to, ear diseases, autoimmune ear diseases and autoimmune diseases of the inner ear.

Examples of autoimmune systemic diseases include, but are not limited to, systemic lupus erythematosus and systemic sclerosis.

Exemplary inflammatory diseases which may be treated by the present method include, but are not limited to, chronic inflammatory diseases and acute inflammatory diseases.

Inflammatory Diseases Associated with Hypersensitivity

Examples of hypersensitivity include, but are not limited to, Type I hypersensitivity, Type II hypersensitivity, Type III hypersensitivity, Type IV hypersensitivity, immediate hypersensitivity, antibody mediated hypersensitivity, immune complex mediated hypersensitivity, T lymphocyte mediated hypersensitivity and DTH.

Type I or immediate hypersensitivity, such as asthma.

Type II hypersensitivity include, but are not limited to, rheumatoid diseases, rheumatoid autoimmune diseases, rheumatoid arthritis (Krenn V. et al., Histol Histopathol 2000 July; 15 (3):791), spondylitis, ankylosing spondylitis (Jan Voswinkel et al., Arthritis Res 2001; 3 (3): 189), systemic diseases, systemic autoimmune diseases, systemic lupus erythematosus (Erikson J. et al., Immunol Res 1998; 17 (1-2):49), sclerosis, systemic sclerosis (Renaudineau Y. et al., Clin Diagn Lab Immunol. 1999 March; 6 (2):156); Chan O T. et al., Immunol Rev 1999 June; 169:107), glandular diseases, glandular autoimmune diseases, pancreatic autoimmune diseases, diabetes, Type I diabetes (Zimmet P. Diabetes Res Clin Pract 1996 October; 34 Suppl:S125), thyroid diseases, autoimmune thyroid diseases, Graves' disease (Orgiazzi J. Endocrinol Metab Clin North Am 2000 June; 29 (2):339), thyroiditis, spontaneous autoimmune thyroiditis (Braley-Mullen H. and Yu S, J Immunol 2000 Dec. 15; 165 (12):7262), Hashimoto's thyroiditis (Toyoda N. et al., Nippon Rinsho 1999 August; 57 (8):1810), myxedema, idiopathic myxedema (Mitsuma T. Nippon Rinsho. 1999 August; 57 (8):1759); autoimmune reproductive diseases, ovarian diseases, ovarian autoimmunity (Garza K M. et al., J Reprod Immunol 1998 February; 37 (2):87), autoimmune anti-sperm infertility (Diekman A B. et al., Am J Reprod Immunol. 2000 March; 43 (3):134), repeated fetal loss (Tincani A. et al., Lupus 1998; 7 Suppl 2:S107-9), neuro-degenerative diseases, neurological diseases, neurological autoimmune diseases, multiple sclerosis (Cross A H. et al., J Neuroimmunol 2001 Jan. 1; 112 (1-2):1), Alzheimer's disease (Oron L. et al., J Neural Transm Suppl. 1997; 49:77), myasthenia gravis (Infante A J. And Kraig E, Int Rev Immunol 1999; 18 (1-2):83), motor neuropathies (Kornberg A J. J Clin Neurosci. 2000 May; 7 (3):191), Guillain-Barre syndrome, neuropathies and autoimmune neuropathies (Kusunoki S. Am J Med Sci. 2000 April; 319 (4):234), myasthenic diseases, Lambert-Eaton myasthenic syndrome (Takamori M. Am J Med Sci. 2000 April; 319 (4):204), paraneoplastic neurological diseases, cerebellar atrophy, paraneoplastic cerebellar atrophy, non-paraneoplastic stiff man syndrome, cerebellar atrophies, progressive cerebellar atrophies, encephalitis, Rasmussen's encephalitis, amyotrophic lateral sclerosis, Sydeham chorea, Gilles de la Tourette syndrome, polyendocrinopathies, autoimmune polyendocrinopathies (Antoine J C. and Honnorat J. Rev Neurol (Paris) 2000 January; 156 (1):23); neuropathies, dysimmune neuropathies (Nobile-Orazio E. et al., Electroencephalogr Clin Neurophysiol Suppl 1999; 50:419); neuromyotonia, acquired neuromyotonia, arthrogryposis multiplex congenita (Vincent A. et al., Ann N Y Acad Sci. 1998 May 13; 841:482), cardiovascular diseases, cardiovascular autoimmune diseases, atherosclerosis (Matsuura E. et al., Lupus. 1998; 7 Suppl 2:S135), myocardial infarction (Vaarala O. Lupus. 1998; 7 Suppl 2:S132), thrombosis (Tincani A. et al., Lupus 1998; 7 Suppl 2:S107-9), granulomatosis, Wegener's granulomatosis, arteritis, Takayasu's arteritis and Kawasaki syndrome (Praprotnik S. et al., Wien Klin Wochenschr 2000 Aug. 25; 112 (15-16):660); anti-factor VIII autoimmune disease (Lacroix-Desmazes S. et al., Semin Thromb Hemost.2000; 26 (2):157); vasculitises, necrotizing small vessel vasculitises, microscopic polyangiitis, Churg and Strauss syndrome, glomerulonephritis, pauci-immune focal necrotizing glomerulonephritis, crescentic glomerulonephritis (Noel L H. Ann Med Interne (Paris). 2000 May; 151 (3):178); antiphospholipid syndrome (Flamholz R. et al., J Clin Apheresis 1999; 14 (4):171); heart failure, agonist-like β-adrenoceptor antibodies in heart failure (Wallukat G. et al., Am J Cardiol. 1999 Jun. 17; 83 (12A):75H), thrombocytopenic purpura (Moccia F. Ann Ital Med Int. 1999 Apr.-June; 14 (2):114); hemolytic anemia, autoimmune hemolytic anemia (Efremov D G. et al., Leuk Lymphoma 1998 January; 28 (3-4):285), gastrointestinal diseases, autoimmune diseases of the gastrointestinal tract, intestinal diseases, chronic inflammatory intestinal disease (Garcia Herola A. et al., Gastroenterol Hepatol. 2000 January; 23 (1):16), celiac disease (Landau Y E. and Shoenfeld Y. Harefuah 2000 Jan. 16; 138 (2):122), autoimmune diseases of the musculature, myositis, autoimmune myositis, Sjogren's syndrome (Feist E. et al., Int Arch Allergy Immunol 2000 September; 123 (1):92); smooth muscle autoimmune disease (Zauli D. et al., Biomed Pharmacother 1999 June; 53 (5-6):234), hepatic diseases, hepatic autoimmune diseases, autoimmune hepatitis (Manns M P. J Hepatol 2000 August; 33 (2):326) and primary biliary cirrhosis (Strassburg C P. et al., Eur J Gastroenterol Hepatol. 1999 June; 11 (6):595).

Type IV or T cell mediated hypersensitivity, include, but are not limited to, rheumatoid diseases, rheumatoid arthritis (Tisch R, McDevitt H O. Proc Natl Acad Sci USA 1994 Jan. 18; 91 (2):437), systemic diseases, systemic autoimmune diseases, systemic lupus erythematosus (Datta S K., Lupus 1998; 7 (9):591), glandular diseases, glandular autoimmune diseases, pancreatic diseases, pancreatic autoimmune diseases, Type 1 diabetes (Castano L. and Eisenbarth G S. Ann. Rev. Immunol. 8:647); thyroid diseases, autoimmune thyroid diseases, Graves' disease (Sakata S. et al., Mol Cell Endocrinol 1993 March; 92 (1):77); ovarian diseases (Garza K M. et al., J Reprod Immunol 1998 February; 37 (2):87), prostatitis, autoimmune prostatitis (Alexander R B. et al., Urology 1997 December; 50 (6):893), polyglandular syndrome, autoimmune polyglandular syndrome, Type I autoimmune polyglandular syndrome (Hara T. et al., Blood. 1991 Mar. 1; 77 (5):1127), neurological diseases, autoimmune neurological diseases, multiple sclerosis, neuritis, optic neuritis (Soderstrom M. et al., J Neurol Neurosurg Psychiatry 1994 May; 57 (5):544), myasthenia gravis (Oshima M. et al., Eur J Immunol 1990 December; 20 (12):2563), stiff-man syndrome (Hiemstra H S. et al., Proc Natl Acad Sci USA 2001 Mar. 27; 98 (7):3988), cardiovascular diseases, cardiac autoimmunity in Chagas' disease (Cunha-Neto E. et al., J Clin Invest 1996 Oct. 15; 98 (8):1709), autoimmune thrombocytopenic purpura (Semple J W. et al., Blood 1996 May 15; 87 (10):4245), anti-helper T lymphocyte autoimmunity (Caporossi A P. et al., Viral Immunol 1998; 11 (1):9), hemolytic anemia (Sallah S. et al., Ann Hematol 1997 March; 74 (3):139), hepatic diseases, hepatic autoimmune diseases, hepatitis, chronic active hepatitis (Franco A. et al., Clin Immunol Immunopathol 1990 March; 54 (3):382), biliary cirrhosis, primary biliary cirrhosis (Jones D E. Clin Sci (Colch) 1996 November; 91 (5):551), nephric diseases, nephric autoimmune diseases, nephritis, interstitial nephritis (Kelly C J. J Am Soc Nephrol 1990 August; 1 (2):140), connective tissue diseases, ear diseases, autoimmune connective tissue diseases, autoimmune ear disease (Yoo T J. et al., Cell Immunol 1994 August; 157 (1):249), disease of the inner ear (Gloddek B. et al., Ann N Y Acad Sci 1997 Dec. 29; 830:266), skin diseases, cutaneous diseases, dermal diseases, bullous skin diseases, pemphigus vulgaris, bullous pemphigoid and pemphigus foliaceus.

Examples of delayed type hypersensitivity include, but are not limited to, contact dermatitis and drug eruption.

Examples of types of T lymphocyte mediating hypersensitivity include, but are not limited to, helper T lymphocytes and cytotoxic T lymphocytes.

Examples of helper T lymphocyte-mediated hypersensitivity include, but are not limited to, $T_h1$ lymphocyte mediated hypersensitivity and $T_h2$ lymphocyte mediated hypersensitivity.

According to one embodiment, the inflammatory disease is not a B cell malignancy.

According to a specific embodiment, the inflammatory disease is not a B-CLL.

According to one embodiment, the autoimmune or inflammatory disease is a chronic condition.

According to one embodiment, the autoimmune or inflammatory disease is an acute condition.

According to one embodiment, the subject is diagnosed with an autoimmune or inflammatory disease (e.g. prior to the treatment).

According to a specific embodiment, the autoimmune or inflammatory disease is multiple sclerosis, ulcerative colitis (UC), Crohn's disease, Inflammatory Bowel Disease (IBD), arthritis or lupus.

The agents of some embodiments of the invention (capable of decreasing an activity or expression of CD84 or SLAMF1) can be administered to an organism per se, or in a pharmaceutical composition where it is mixed with suitable carriers or excipients.

As used herein a "pharmaceutical composition" refers to a preparation of one or more of the active ingredients described herein with other chemical components such as physiologically suitable carriers and excipients. The purpose of a pharmaceutical composition is to facilitate administration of a compound to an organism.

Herein the term "active ingredient" refers to the agent accountable for the biological effect. (i.e., down regulation in CD84 or SLAMF1 activity or expression)

Hereinafter, the phrases "physiologically acceptable carrier" and "pharmaceutically acceptable carrier" which may be interchangeably used refer to a carrier or a diluent that does not cause significant irritation to an organism and does not abrogate the biological activity and properties of the administered compound. An adjuvant is included under these phrases.

Herein the term "excipient" refers to an inert substance added to a pharmaceutical composition to further facilitate administration of an active ingredient. Examples, without limitation, of excipients include calcium carbonate, calcium phosphate, various sugars and types of starch, cellulose derivatives, gelatin, vegetable oils and polyethylene glycols.

Techniques for formulation and administration of drugs may be found in "Remington's Pharmaceutical Sciences," Mack Publishing Co., Easton, PA, latest edition, which is incorporated herein by reference.

Suitable routes of administration may, for example, include oral, rectal, transmucosal, especially transnasal, intestinal or parenteral delivery, including intramuscular, subcutaneous and intramedullary injections as well as intrathecal, direct intraventricular, intracardiac, e.g., into the right or left ventricular cavity, into the common coronary artery, intravenous, intraperitoneal, intranasal, or intraocular injections.

Alternately, one may administer the pharmaceutical composition in a local rather than systemic manner, for example, via injection of the pharmaceutical composition directly into a tissue region of a patient.

The term "tissue" refers to part of an organism consisting of cells designed to perform afunction or functions. Examples include, but are not limited to, brain tissue, retina, skin tissue, hepatic tissue, pancreatic tissue, bone, cartilage, connective tissue, blood tissue, muscle tissue, cardiac tissue brain tissue, vascular tissue, renal tissue, pulmonary tissue, gonadal tissue, hematopoietic tissue.

Pharmaceutical compositions of some embodiments of the invention may be manufactured by processes well known in the art, e.g., by means of conventional mixing, dissolving, granulating, dragee-making, levigating, emulsifying, encapsulating, entrapping or lyophilizing processes.

Pharmaceutical compositions for use in accordance with some embodiments of the invention thus may be formulated in conventional manner using one or more physiologically acceptable carriers comprising excipients and auxiliaries, which facilitate processing of the active ingredients into preparations which, can be used pharmaceutically. Proper formulation is dependent upon the route of administration chosen.

For injection, the active ingredients of the pharmaceutical composition may be formulated in aqueous solutions, preferably in physiologically compatible buffers such as Hank's solution, Ringer's solution, or physiological salt buffer. For transmucosal administration, penetrants appropriate to the barrier to be permeated are used in the formulation. Such penetrants are generally known in the art.

For oral administration, the pharmaceutical composition can be formulated readily by combining the active compounds with pharmaceutically acceptable carriers well known in the art. Such carriers enable the pharmaceutical composition to be formulated as tablets, pills, dragees, capsules, liquids, gels, syrups, slurries, suspensions, and the like, for oral ingestion by a patient. Pharmacological preparations for oral use can be made using a solid excipient, optionally grinding the resulting mixture, and processing the mixture of granules, after adding suitable auxiliaries if desired, to obtain tablets or dragee cores. Suitable excipients are, in particular, fillers such as sugars, including lactose, sucrose, mannitol, or sorbitol; cellulose preparations such as, for example, maize starch, wheat starch, rice starch, potato starch, gelatin, gum tragacanth, methyl cellulose, hydroxypropylmethyl-cellulose, sodium carbomethylcellulose; and/or physiologically acceptable polymers such as polyvinylpyrrolidone (PVP). If desired, disintegrating agents may be added, such as cross-linked polyvinyl pyrrolidone, agar, or alginic acid or a salt thereof such as sodium alginate.

Dragee cores are provided with suitable coatings. For this purpose, concentrated sugar solutions may be used which may optionally contain gum arabic, talc, polyvinyl pyrrolidone, carbopol gel, polyethylene glycol, titanium dioxide, lacquer solutions and suitable organic solvents or solvent mixtures. Dyestuffs or pigments may be added to the tablets or dragee coatings for identification or to characterize different combinations of active compound doses.

Pharmaceutical compositions which can be used orally, include push-fit capsules made of gelatin as well as soft, sealed capsules made of gelatin and a plasticizer, such as glycerol or sorbitol. The push-fit capsules may contain the active ingredients in admixture with filler such as lactose, binders such as starches, lubricants such as talc or magnesium stearate and, optionally, stabilizers. In soft capsules, the active ingredients may be dissolved or suspended in suitable liquids, such as fatty oils, liquid paraffin, or liquid polyethylene glycols. In addition, stabilizers may be added. All formulations for oral administration should be in dosages suitable for the chosen route of administration.

For buccal administration, the compositions may take the form of tablets or lozenges formulated in conventional manner.

For administration by nasal inhalation, the active ingredients for use according to some embodiments of the invention are conveniently delivered in the form of an aerosol spray presentation from a pressurized pack or a nebulizer with the use of a suitable propellant, e.g., dichlorodifluoromethane, trichlorofluoromethane, dichloro-tetrafluoroethane or carbon dioxide. In the case of a pressurized aerosol, the dosage unit may be determined by providing a valve to deliver a metered amount. Capsules and cartridges of, e.g., gelatin for use in a dispenser may be formulated containing a powder mix of the compound and a suitable powder base such as lactose or starch.

The pharmaceutical composition described herein may be formulated for parenteral administration, e.g., by bolus injection or continuous infusion. Formulations for injection may be presented in unit dosage form, e.g., in ampoules or in multidose containers with optionally, an added preservative. The compositions may be suspensions, solutions or emulsions in oily or aqueous vehicles, and may contain formulatory agents such as suspending, stabilizing and/or dispersing agents.

Pharmaceutical compositions for parenteral administration include aqueous solutions of the active preparation in water-soluble form. Additionally, suspensions of the active ingredients may be prepared as appropriate oily or water based injection suspensions. Suitable lipophilic solvents or vehicles include fatty oils such as sesame oil, or synthetic fatty acids esters such as ethyl oleate, triglycerides or liposomes. Aqueous injection suspensions may contain substances, which increase the viscosity of the suspension, such as sodium carboxymethyl cellulose, sorbitol or dextran. Optionally, the suspension may also contain suitable stabilizers or agents which increase the solubility of the active ingredients to allow for the preparation of highly concentrated solutions.

Alternatively, the active ingredient may be in powder form for constitution with a suitable vehicle, e.g., sterile, pyrogen-free water based solution, before use.

The pharmaceutical composition of some embodiments of the invention may also be formulated in rectal compositions such as suppositories or retention enemas, using, e.g., conventional suppository bases such as cocoa butter or other glycerides.

Pharmaceutical compositions suitable for use in context of some embodiments of the invention include compositions wherein the active ingredients are contained in an amount effective to achieve the intended purpose. More specifically, a therapeutically effective amount means an amount of active ingredients (e.g. agent capable of decreasing an activity or expression of CD84 or SLAMF1) effective to prevent, alleviate or ameliorate symptoms of a disorder (e.g., malignant disease) or prolong the survival of the subject being treated.

According to one embodiment, the therapeutically effective amount downregulates an activity or expression of at least one of programmed cell death ligand 1 (PD-L1), Programmed cell death 1 (PD-1), cytotoxic T lymphocyte antigen-4 (CTLA-4), lymphocyte-activation gene 3 (Lag-3), killer-cell lectin like receptor G1 (KLRG1) and/or 2B4 on exhausted T cell, i.e. markers of T cell exhaustion.

Downregulation of a T cell exhaustion marker (e.g. PD-L1, PD-1, CTLA-4, Lag-3, KLRG1 and/or 2B4) can be assessed using any method known in the art, e.g. using FACS analysis. According to one embodiment, downregulation of the T cell exhaustion marker is by at least about 10%, 20%, 30%, 40%, 50%, 60%, 70%, 80%, 90% or 100% as compared to exhausted T cells not treated with the agents of some embodiments of the invention.

According to one embodiment, the therapeutically effective amount leads to reversal of the T cell exhaustion which is associated with an increase in production of cytokines (e.g. IL-2, IL-4, IFNγ) and/or expression of CD107 by T cells.

Increase in cytokine production can be assessed using any method known in the art, e.g. using ELISA. According to one embodiment, increase in cytokine production is by at least about 10%, 20%, 30%, 40%, 50%, 60%, 70%, 80%, 90% or 100% as compared to exhausted T cells not treated with the agents of some embodiments of the invention.

Likewise, an increase in expression of a cellular marker associated with reactivation of T cell, e.g. CD107, can be assessed using any method known in the art, e.g. using FACS analysis. According to one embodiment, the increase in T cell marker is by at least about 10%, 20%, 30%, 40%, 50%, 60%, 70%, 80%, 90% or 100%, as compared to exhausted T cells not treated with the agents of some embodiments of the invention.

According to one embodiment, the therapeutically effective amount leads to reversal of the T cell exhaustion which results in killing of malignant cells (e.g. by effector T cells).

According to one embodiment, the therapeutically effective amount leads to apoptosis of malignant cells (i.e. due to an interruption of the CD84-induced survival pathway).

Assessing cell killing or apoptosis may be carried out using any method known in the art, e.g. cell proliferation assay, FACS analysis etc.

Determination of a therapeutically effective amount is well within the capability of those skilled in the art, especially in light of the detailed disclosure provided herein.

For any preparation used in the methods of the invention, the therapeutically effective amount or dose can be estimated initially from in vitro and cell culture assays. For example, a dose can be formulated in animal models to achieve a desired concentration or titer. Such information can be used to more accurately determine useful doses in humans.

A model for T cell exhaustion can be any animal model (e.g. mouse) with chronic viral disease or malignancy. Such models are described in McGary et al., "Animal models for viral infection and cell exhaustion", Curr Opin HIV AIDS (2014) 9(5): 492-499, incorporated herein by referenced. Additionally, Eμ-TCL1 (TCL-1) transgenic mice which develop a murine CLL that proceeds to a full blown clonal and lethal leukemia described previously [Bichi R. et al., Proc Natl Acad Sci USA (2002) 99(10): 6955-6960] and in the Examples section which follows. Additionally or alternatively, a B-CLL animal model such as the NOD-SCID mouse chimera as described previously [Shimoni A, Marcus H, Canaan A, et al. A model for human B-chronic lymphocytic leukemia in human/mouse radiation chimera: evidence for tumor-mediated suppression of antibody production in low-stage disease. Blood. 1997; 89:2210-2218], can be used to determine therapeutic efficacy of the agents of the present invention in vivo.

Toxicity and therapeutic efficacy of the active ingredients described herein can be determined by standard pharmaceutical procedures in vitro, in cell cultures or experimental animals. The data obtained from these in vitro and cell culture assays and animal studies can be used in formulating a range of dosage for use in human. The dosage may vary depending upon the dosage form employed and the route of administration utilized. The exact formulation, route of administration and dosage can be chosen by the individual physician in view of the patient's condition. (See e.g., Fingl, et al., 1975, in "The Pharmacological Basis of Therapeutics", Ch. 1 p. 1).

Dosage amount and interval may be adjusted individually to provide (tissue) levels of the active ingredient are sufficient to induce or suppress the biological effect (minimal effective concentration, MEC). The MEC will vary for each preparation, but can be estimated from in vitro data. Dosages necessary to achieve the MEC will depend on individual characteristics and route of administration. Detection assays can be used to determine plasma concentrations.

Depending on the severity and responsiveness of the condition to be treated, dosing can be of a single or a plurality of administrations, with course of treatment lasting from several days to several weeks or until cure is effected or diminution of the disease state is achieved.

The amount of a composition to be administered will, of course, be dependent on the subject being treated, the severity of the affliction, the manner of administration, the judgment of the prescribing physician, etc.

Compositions of some embodiments of the invention may, if desired, be presented in a pack or dispenser device, such as an FDA approved kit, which may contain one or more unit dosage forms containing the active ingredient. The pack may, for example, comprise metal or plastic foil, such as a blister pack. The pack or dispenser device may be accompanied by instructions for administration. The pack or dispenser may also be accommodated by a notice associated with the container in a form prescribed by a governmental agency regulating the manufacture, use or sale of pharmaceuticals, which notice is reflective of approval by the agency of the form of the compositions or human or veterinary administration. Such notice, for example, may be of labeling approved by the U.S. Food and Drug Administration for prescription drugs or of an approved product insert. Compositions comprising a preparation of the invention formulated in a compatible pharmaceutical carrier may also be prepared, placed in an appropriate container, and labeled for treatment of an indicated condition, as is further detailed above.

In order to enhance treatment of the malignant disease, the present invention further envisions administering to the subject an additional therapy such as radiotherapy, chemotherapy, biological therapy e.g., immunotherapy (e.g. antibody immunotherapy) or transplantation (e.g. bone marrow transplantation), phototherapy and photodynamic therapy, surgery, nutritional therapy, ablative therapy, combined radiotherapy and chemotherapy, brachiotherapy, proton beam therapy, cellular therapy and photon beam radiosurgical therapy, or combinations thereof. Analgesic agents and other treatment regimens are also contemplated. Examples of chemotherapeutic agents are described in detail below.

As used herein, the terms "chemotherapy" or "chemotherapeutic" refer to an agent that reduces, prevents, mitigates, limits, and/or delays the growth of neoplasms or metastases, or kills neoplastic cells directly by necrosis or apoptosis of neoplasms or any other mechanism, or that can be otherwise used, in a pharmaceutically-effective amount, to reduce, prevent, mitigate, limit, and/or delay the growth of neoplasms or metastases in a subject with neoplastic disease (e.g. cancer).

Chemotherapeutic agents include, but are not limited to, fluoropyrimidines; pyrimidine nucleosides; purine nucleosides; anti-folates, platinum agents; anthracyclines/anthracenediones; epipodophyllotoxins; camptothecins (e.g., Karenitecin); hormones; hormonal complexes; antihormonals; enzymes, proteins, peptides and polyclonal and/or monoclonal antibodies; immunological agents; vinca alkaloids; taxanes; epothilones; antimicrotubule agents; alkylating agents; antimetabolites; topoisomerase inhibitors; antivirals; and various other cytotoxic and cytostatic agents.

According to a specific embodiment, the chemotherapeutic agent includes, but is not limited to, abarelix, aldesleukin, aldesleukin, alemtuzumab, alitretinoin, allopurinol, altretamine, amifostine, anastrozole, arsenic trioxide, asparaginase, azacitidine, bevacuzimab, bexarotene, bleomycin, bortezomib, busulfan, calusterone, capecitabine, carboplatin, carmustine, celecoxib, cetuximab, cisplatin, cladribine, clofarabine, cyclophosphamide, cytarabine, dacarbazine, dactinomycin, actinomycin D, Darbepoetin alfa, Darbepoetin alfa, daunorubicin liposomal, daunorubicin, decitabine, Denileukindiftitox, dexrazoxane, dexrazoxane, docetaxel, doxorubicin, dromostanolone propionate, Elliott's B Solution, epirubicin, Epoetin alfa, erlotinib, estramustine, etoposide, exemestane, Filgrastim, floxuridine, fludarabine, fluorouracil 5-FU, fulvestrant, gefitinib, gemcitabine, gemtuzumabozogamicin, goserelin acetate, histrelin acetate, hydroxyurea, IbritumomabTiuxetan, idarubicin, ifosfamide, imatinibmesylate, interferon alfa 2a, Interferon alfa-2b, irinotecan, lenalidomide, letrozole, leucovorin, Leuprolide Acetate, levamisole, lomustine, CCNU, meclorethamine, nitrogen mustard, megestrol acetate, melphalan, L-PAM, mercaptopurine 6-MP, mesna, methotrexate, mitomycin C, mitotane, mitoxantrone, nandrolonephenpropionate, nelarabine, Nofetumomab, Oprelvekin, Oprelvekin, oxaliplatin, paclitaxel, palifermin, pamidronate, pegademase, pegaspargase, Pegfilgrastim, pemetrexed disodium, pentostatin, pipobroman, plicamycinmithramycin, porfimer sodium, procarbazine, quinacrine, Rasburicase, Rituximab, sargramostim, sorafenib, streptozocin, sunitinib maleate, tamoxifen, temozolomide, teniposide VM-26, testolactone, thioguanine 6-TG, thiotepa, thiotepa, topotecan, toremifene, Tositumomab, Trastuzumab, tretinoin ATRA, Uracil Mustard, valrubicin, vinblastine, vinorelbine, zoledronate and zoledronic acid.

According to another embodiment, in order to enhance treatment of the autoimmune disease or inflammatory disease, the present invention further envisions administering to the subject an additional therapy which may benefit treatment. One of skill in the art is capable of making such a determination.

Thus, for example, the anti-inflammatory therapy may include, without being limited to, NSAIDs (Non-Steroidal Anti-inflammatory Drugs), corticosteroids (such as prednisone) and anti-histamines.

As used herein the term "about" refers to ±10%.

The terms "comprises", "comprising", "includes", "including", "having" and their conjugates mean "including but not limited to".

The term "consisting of" means "including and limited to".

The term "consisting essentially of" means that the composition, method or structure may include additional ingredients, steps and/or parts, but only if the additional ingredients, steps and/or parts do not materially alter the basic and novel characteristics of the claimed composition, method or structure.

As used herein, the singular form "a", "an" and "the" include plural references unless the context clearly dictates otherwise. For example, the term "a compound" or "at least one compound" may include a plurality of compounds, including mixtures thereof.

Throughout this application, various embodiments of this invention may be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 3, 4, 5, and 6. This applies regardless of the breadth of the range.

Whenever a numerical range is indicated herein, it is meant to include any cited numeral (fractional or integral) within the indicated range. The phrases "ranging/ranges between" a first indicate number and a second indicate number and "ranging/ranges from" a first indicate number "to" a second indicate number are used herein interchangeably and are meant to include the first and second indicated numbers and all the fractional and integral numerals therebetween.

As used herein the term "method" refers to manners, means, techniques and procedures for accomplishing a given task including, but not limited to, those manners, means, techniques and procedures either known to, or readily developed from known manners, means, techniques and procedures by practitioners of the chemical, pharmacological, biological, biochemical and medical arts.

As used herein, the term "treating" includes abrogating, substantially inhibiting, slowing or reversing the progression of a condition, substantially ameliorating clinical or aesthetical symptoms of a condition or substantially preventing the appearance of clinical or aesthetical symptoms of a condition.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination or as suitable in any other described embodiment of the invention. Certain features described in the context of various embodiments are not to be considered essential features of those embodiments, unless the embodiment is inoperative without those elements.

Various embodiments and aspects of the present invention as delineated hereinabove and as claimed in the claims section below find experimental support in the following examples.

EXAMPLES

Reference is now made to the following examples, which together with the above descriptions, illustrate the invention in a non-limiting fashion.

Generally, the nomenclature used herein and the laboratory procedures utilized in the present invention include molecular, biochemical, microbiological and recombinant DNA techniques. Such techniques are thoroughly explained in the literature. See, for example, "Molecular Cloning: A laboratory Manual" Sambrook et al., (1989); "Current Protocols in Molecular Biology" Volumes I-III Ausubel, R. M., ed. (1994); Ausubel et al., "Current Protocols in Molecular Biology", John Wiley and Sons, Baltimore, Maryland (1989); Perbal, "A Practical Guide to Molecular Cloning", John Wiley & Sons, New York (1988); Watson et al., "Recombinant DNA", Scientific American Books, New York; Birren et al. (eds) "Genome Analysis: A Laboratory Manual Series", Vols. 1-4, Cold Spring Harbor Laboratory Press, New York (1998); methodologies as set forth in U.S. Pat. Nos. 4,666,828; 4,683,202; 4,801,531; 5,192,659 and 5,272,057; "Cell Biology: A Laboratory Handbook", Volumes I-III Cellis, J. E., ed. (1994); "Current Protocols in Immunology" Volumes I-III Coligan J. E., ed. (1994); Stites et al. (eds), "Basic and Clinical Immunology" (8th Edition), Appleton & Lange, Norwalk, CT (1994); Mishell and Shiigi (eds), "Selected Methods in Cellular Immunology", W. H. Freeman and Co., New York (1980); available immunoassays are extensively described in the patent and scientific literature, see, for example, U.S. Pat. Nos. 3,791,932; 3,839,153; 3,850,752; 3,850,578; 3,853,987; 3,867,517; 3,879,262; 3,901,654; 3,935,074; 3,984,533; 3,996,345; 4,034,074; 4,098,876; 4,879,219; 5,011,771 and 5,281,521; "Oligonucleotide Synthesis" Gait, M. J., ed. (1984); "Nucleic Acid Hybridization" Hames, B. D., and Higgins S. J., eds. (1985); "Transcription and Translation" Hames, B. D., and Higgins S. J., Eds. (1984); "Animal Cell Culture" Freshney, R. I., ed. (1986); "Immobilized Cells and Enzymes" IRL Press, (1986); "A Practical Guide to Molecular Cloning" Perbal, B., (1984) and "Methods in Enzymology" Vol. 1-317, Academic Press; "PCR Protocols: A Guide To Methods And Applications", Academic Press, San Diego, CA (1990); Marshak et al., "Strategies for Protein Purification and Characterization—A Laboratory Course Manual" CSHL Press (1996); all of which are incorporated by reference as if fully set forth herein. Other general references are provided throughout this document. The procedures therein are believed to be well known in the art and are provided for the convenience of the reader. All the information contained therein is incorporated herein by reference.

General Materials and Experimental Procedures

Stromal Cell Line

The murine BM cell line M210B4 (CRL-1972), was purchased from the ATCC (Manassas, VA, USA) and maintained in RPMI 1640 containing 10% (v/v) fetal calf serum. Cells were passaged every third day, with new passages seeded at $14.5 \times 10^3$ cells per $cm^2$.

Primary Human CLL Cells

B-CLL cells were obtained from the peripheral blood of CLL patients at varying stages of the disease (Hematology Institute of the Kaplan Medical Center, Rehovot, Israel; Tel-Aviv Sourasky Medical Center, Tel Aviv, Israel; and Asaf Harofeh Medical Center, Tzrifin, Israel).

Primary Human BM Cells

Primary human bone marrow (BM) stromal cells (BMSCs) cultures were established from BM aspirates obtained from both confirmed CLL patients and patients of healthy bone marrow characteristics (Asaf Harofeh Medical Center, Tzriffin, Israel). Mononuclear cells were isolated by layering on a Ficoll-Hypaque density gradient. $1 \times 10^6$ cells were thereafter plated in 24-well plates on fetal calf serum and incubated for 1 hour to let the cells adhere, then Chang medium was added thereto (Chang with gentamicin, L-glutamine, Irvine Scientific). The cultures were grown until confluent, approximately for 3 weeks, with weekly medium changes.

Additional cell lines used:

m210B4 (bone marrow mouse stromal cell line), REH (Acute Lymphoblastic Leukemia (ALL) cell line), 697 (ALL cell line), Daudi (Burkitt's lymphoma cell line) and Ramos (Burkitt's lymphoma cell line) were used. m210B4 cells were cultured with RPMI 1640 containing 10% (v/v) fetal calf serum. Cells were passaged every third day, with new passages seeded at $14.5 \times 10^3$ cells per $cm^2$. REH, 697, Daudi and Ramos cells were cultured with RPMI 1640 containing 10% (v/v) fetal calf serum. Cells were passaged every fourth day 1 to 3.

Co-Cultures

In co-cultures, a ratio of 1 to 16 for M210B4 to CLL was used, as at this ratio, M210B4 cells provided a survival advantage to CLL cells as previously described [Kurtova, A. V. et al., Blood (2009) 114(20): 4441-4450].

Isolation of Cells from Different Anatomical Sites

Murine splenocytes were isolated by smashing spleens between microscope slides or through 40-micrometer mesh. Bone marrow cells from tibia and femur were flushed out using syringes. Cells from the peritoneal cavity were collected by injection of PBS/BSA and collection of the fluid. Cells from the peripheral blood were collected from the orbital sinus/tail vein. Erythrocytes were removed using RBC lysis buffer (5 minutes), followed by a washing step to collect cells. Finally, cells were filtered through a 40-micrometer mesh and either prepared for injection or flow cytometry staining.

RNA Isolation and Reverse Transcription

Total RNA from CLL cells or M210B4 cells was isolated as previously described [Binsky, I. et al., Proc Natl Acad Sci USA (2007)104(33): 13408-13413; Binsky, I. et al., J Immunol (2010)184(9): 4761-4769].mRNA from primary human BM and T cell samples was isolated using Perfect Pure RNA Cultured Cell Kit (5 Prime, Hamburg, Germany) according to the manufacturer's manual.

Staining for Flow Cytometry

Isolated cells or cultured M210B4 cells were stained using specific antibodies (see Table 1, below) in staining buffer (0.5% BSA in PBS) for 30 minutes in the dark on ice. Cells were washed to remove unbound antibody and measured by flow cytometry (FACS Canto, BD Bioscience). Isotype controls were used according to the data sheets. Results were analyzed using FlowJo software (Version 10, Ashland, OR, USA).

TABLE 1

Antibodies used for FACS staining

| Target | Species | Fluorophore | Clone | Company |
|---|---|---|---|---|
| SLAMF1 | Human | APC | REA151 | Miltenyl |
| SLAMF1 | Mouse | PE | TC15-12F12.2 | Biolegend |
| CD5 | Mouse | BV421 | 53-7.3 | Biolegend |
| PDL-1 | Human | PE/CY7 | 29E.2A3 | Biolegend |
| PDL-1 | Mouse | BV711 | 10F.9G2 | Biolegend |
| B220/CD45R | human/mouse | FITC or APC | RA3-6B2 | Biolegend |
| CD19 | Mouse | FITC/PE | 6D5 | Biolegend |
| CD3 | Mouse | APC-CY7 | 17A2 | Biolegend |
| CD4 | Mouse | FITC/PERCP | RM4-5 | Biolegend |
| CD8 | Mouse | BV711 | 53-6.7 | Biolegend |
| PD1 | Mouse | PE/CY7 | RMP1-30 | Biolegend |
| PD1 | Human | BV711 | EH12.2H7 | Biolegend |
| Lag-3 | Mouse | PE | C9B7W | Biolegend |
| CTLA-4 | Mouse | APC | L3D10 | Biolegend |

RNA Expression of T Cells

Murine spleens were processed as writing above and thereafter incubated with B220 anti-mouse beads [25 µl beads/$10^7$ cells CD45R (B220) MicroBeads, mouse, Miltenyl] for 30 min. Then incubated with magnet for 20 minutes to remove B cells, the supernatant (majority T cells) were then incubated on CD3 and CD28 coated plates for 24 hours. After 24 hours the cells were harvested and RNA was purified.

Protein Expression of T Cells

Murine spleens were harvested and T cells were stimulated with anti-CD3 containing medium and thereafter stained for exhaustion markers or alternatively fixed and permeabilized (BD bioscience kit) and thereafter stained for cytokines and cytotoxicity factors.

CD84 Stimulation

M210B4 stroma cells were seeded in 24-well plates ($1 \times 10^5$ per well) the day before stimulation. Human CLL cells were thawed the day before the experiment in RPMI containing 20% FCS. For stimulation, medium was changed to medium containing the activating CD84 antibody (clone 152-1D5, Pierce/Thermo or SCBT) (M210B4 4 µg/ml, CLL $1 \times 10^7$ cells, 5 or 10 µg/ml) or isotype control (IgG1, clone MOPC-21, Biolegend) for 1 hour. Cells were washed and CD84 cross-linked with 1 µg of the F(ab')$_2$ antibody (Jackson Immuno Research), followed by incubation for indicated time periods as previously described [Binsky-Ehrenreich, I. et al., Oncogene (2014)33(8): 1006-1016].

SLAMF1 Stimulation

M210B4 stroma cells were seeded in 24-well plates ($1 \times 10^5$ per well) the day before stimulation. For stimulation, medium was changed to medium containing the activating anti-SLAMF1 antibody (10 µg/ml, Clone: 9D1, Ebioscience) or isotype control Rat IgG1 (Clone: eBRG1, Ebioscience) for 72 hours. Cells were washed and SLAMF1 cross-linked with 1 µg of the F(ab')$_2$ antibody (Jackson Immuno Research), followed by incubation for 24 hours.

CD84 Blocking

M210B4 stroma cells were seeded in 24-well plates ($1 \times 10^5$ cells per well) and CLL cells thawed the day before the experiment. In all experiments, 5 µg/ml of CD84-B4 antibody was used for blocking CD84 homophilic interactions in cultures. The same amount IgG2a (MOPC-173, Biolegend or eBM2a, eBioscience) was used as an isotype control. To block CD84 specifically on the stroma, B4 antibody was incubated on the stroma for 1 hour, unbound antibody was removed by three washes with medium, and then the CLL ($1.6 \times 10^6$) cells were added.

SLAMF1 Blocking $2 \times 10^6$ CLL cells were thawed and seeded in 24-well plates the day before the experiment. In all experiments, 10 µg/ml of anti-SLAMF1 antibody was used (Clone: A12, Biolegend) for blocking CD84 homophilic interactions in cultures. The same amount IgG1, kappa (MOPC-21, Biolegend) was used as an isotype control and incubated for 24 hours.

SLAMF1 Downregulation by siRNA

Downregulation of SLAMF1 was done by siRNA introduced by electroporation using a Nepagene Super Electroporator NEPA21 Type II. Adherent M201B4 cells ($0.625 \times 10^5$) were electroporated in with 120 nM siRNA using the Adherent Cell Electrode with 125V, 3 msec. SiRNA was purchased from GE Lifescience: mouse SLAMF1: Dharmacon ON-TARGET plus SMART pool mouse SLAMF1 (Cat #L-056021-01-0005), non-specific control siRNA: Dharmacon ON-TARGET plus Non-targeting Pool (D-001810-10).

Cell Viability

CLL cell viability was determined using Annexin-V-FITC/7-AAD staining according to the manufacturers (BD Bioscience) protocol, and evaluated by flow cytometry.

TCL-1 Adoptive Transfer

Eµ-TCL1 (TCL-1) transgenic mice develop a murine CLL that proceeds to a full blown clonal and lethal leukemia [Bichi R. et al., Proc Natl Acad Sci USA (2002) 99(10): 6955-6960]. To date, it is the most extensively validated and widely used murine CLL model. Eµ-TCL1 mice accumulate B220$^{int}$IgM$^+$CD5$^+$ B lymphocytes in the peritoneal cavity, peripheral blood, bone marrow and lymphoid organs. The TCL1 transgenic mice have been shown to display features of unmutated CLL disease, with B-cell receptor characteristics akin to human disease and also show epigenetic changes similar to human CLL.

Accordingly, TCL-1 transgenic mice were analyzed for their malignant population (CD5+B220+ cells) in the peripheral blood starting at 9 months of age. Mice whose malignant population in the peripheral blood (PB) was above 30% were sacrificed and their splenocytes prepared for injection. TCL-1 splenocytes ($4 \times 10^7$) were injected into the tail vein of 6-8 week old, female recipient wild type (wt) mice. Progression of the engraftment was monitored in the peripheral blood using flow cytometry for the B220/CD5 population.

In Vivo CD84 Blocking

Blocking of CD84 in vivo was performed using the B4 antibody and the IgG2a isotype control (eBioscience). In the 4 hour experiments, 20 µg antibody was injected i.v. into the tail vein 1 hour after CLL injection. In adoptive transfer experiments, treatment with B4 or IgG2a isotype control antibody started the second day after TCL-1 splenocyte injection and continued every second day at 1 mg/kg body weight injected into the tail vein.

Mice

SLAMF5 (CD84) deficient mice were used as previously described [see Cannons J. L. et al. Immunity (2010)32: 253-65]. All animals were used at 6-10 weeks of age. All animal procedures were approved by the Animal Research Committee at the Weizmann Institute of Science.

EAE Model 10 weeks old wild type (wt) or CD84 knock-out (CD84$^{-/-}$ ko or CD84 ko) mice were injected subcutaneously (S.C.) with 200 µg MOG 35-55 peptide/100 µl/mouse. The MOG 35-55 peptide preparation further comprised complete Freund's adjuvant (CFA) containing 4 mg/ml heat-killed *Mycobacterium tuberculosis*. The dose was split into two administrations at two sites near the mouse tail (50 µl emulsion/ site). Mice were then intraperitoneally (I.P.) injected with 200 ng pertussis toxin (PT) (in 200 μl PBS). PT injection was repeated after 48 hours (i.e. PT was administered on days 0 and 2).

Mice were scored and weight daily or every two days (as indicated) for clinical symptoms of EAE. Scoring was as follows: 0=no disease, 1=limp tail and/or unsteady gait, 2=hind limb paresis, 2.5=partial hind limb paralysis, 3=hind limb paralysis, 4=hind limb and fore limb paralysis, 5=moribund/death.

Colitis Model

Acute disease: Mice at 6-8 weeks, wt or CD84 ko, received 2% DSS via their drinking water for 5 days. At day 5, the drinking water was replaced with normal water for 4-7 days, or until the end of the experiment. Mice were weighted daily for monitoring of disease progression.

Chronic disease: Mice at 6-8 weeks, wt or CD84 ko, received two cycles of 5 days 2% DSS with 10 days recovery between the two cycles. Specifically, the first cycle was from day 0 to day 5 followed by 10 days with water for recovery. The second cycle of DSS was given at day 15 for 5 more days followed with regular drinking water. Mice were weighted daily for monitoring of disease progression.

Isolation and Activation of B Regulatory Cells

Spleen or mesenteric lymph nodes were obtained from wt or CD84 ko mice at the end of treatment. B cells were enriched by using B220$^+$ beads and activated with LPS for 5 or 24 hours. PIM (PMA, Ionomycin and Monensin) were added in the last 5 hours of activation. The cells were then stained for extracellular and intracellular markers in order to evaluate the regulatory B cell populations by Flow cytometry.

Statistics

Data analysis was performed using Graphpad Prism (Version 6.0f, GraphPad Software, Inc., La Jolla, CA, USA). Generally, the mean with the SEM is provided. To determine significance of differences, Student's t-test was used, either one- or two-sided depending on the experiment. For normalized data, a ratio t-test was performed to correct for non-normal distributed data points. Results were deemed significant with a p value≤0.05.

Example 1

Target Genes of CD84

To follow the role of CD84 in regulation of the microenvironment control of CLL survival, the inventors searched for target genes of CD84 in microenvironmental cells. CD84 expressed on human patient-derived Nurse like cells or M210B4 stromal cells was stimulated with anti-CD84 (4 μg/ml) or with control IgG antibodies for 24 hours. In addition, CD84 expressed on primary patient bone marrow (BM) samples from aspirates of both CLL patients and healthy BM was blocked for 24 hours in a co-culture setting with CLL using the anti-CD84 B4 antibody, a blocking antibody developed in inventor's lab [Binsky-Ehrenreich I. et al., Oncogene(2014) 33: 1006-1016]. RNA was purified and genes which expression is modulated by CD84 were analyzed by AffymetrixGeneChip® expression analysis system. One of the genes that was upregulated following CD84 activation and was downregulated when it was blocked was SLAMF1 (data not shown).

Example 2

SLAMF1 Expression is a CD84 Target Gene in Stroma Cells

Figure 3A:
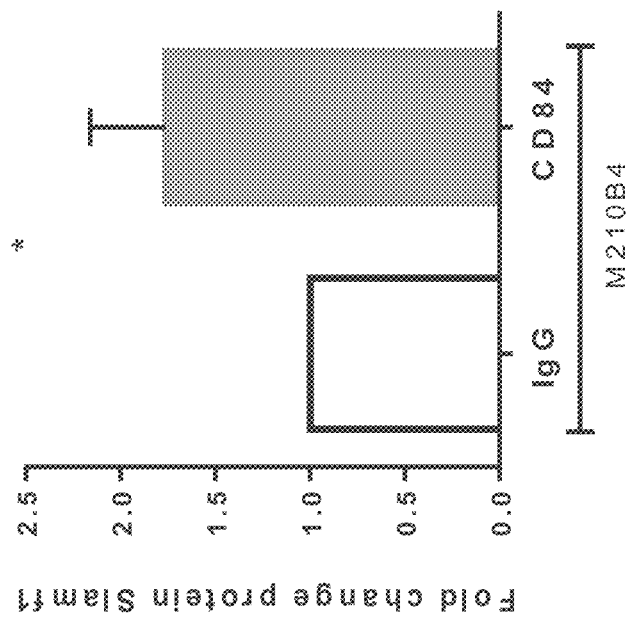
FIGS. 3A-3H are graphs illustrating that SLAMF1 expression is elevated on microenvironmental and CLL cells following CD84 activation.
Figure 3B:
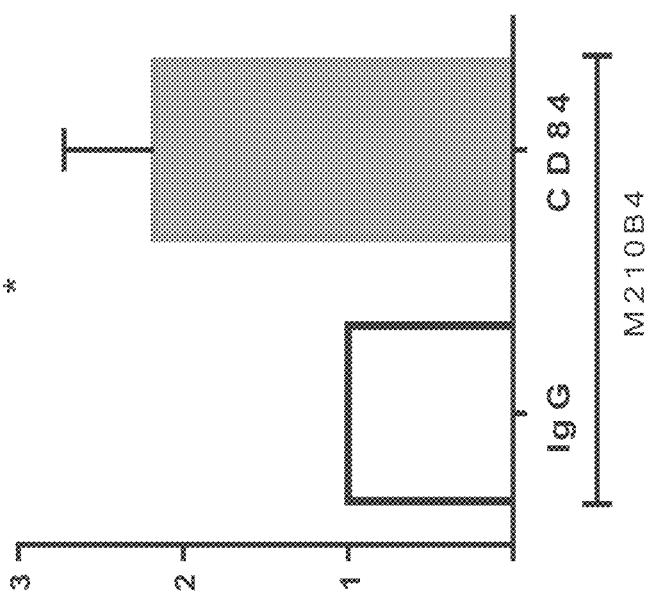
Figure 3D:
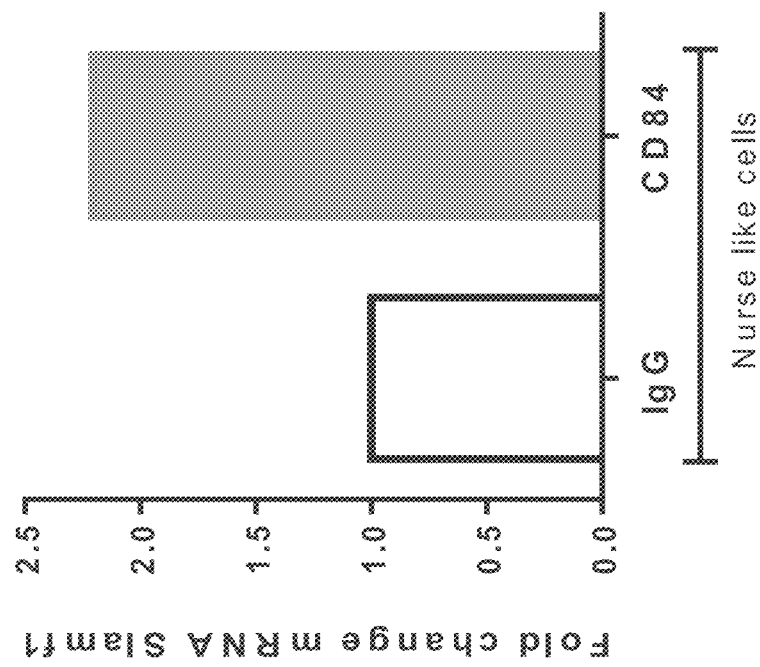
Figure 3C:
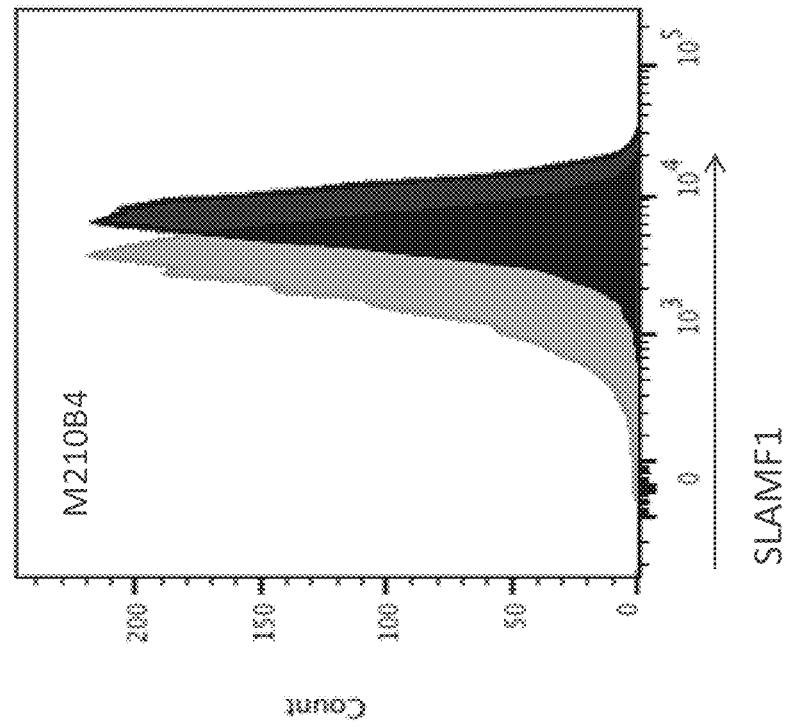
Figure 3E:
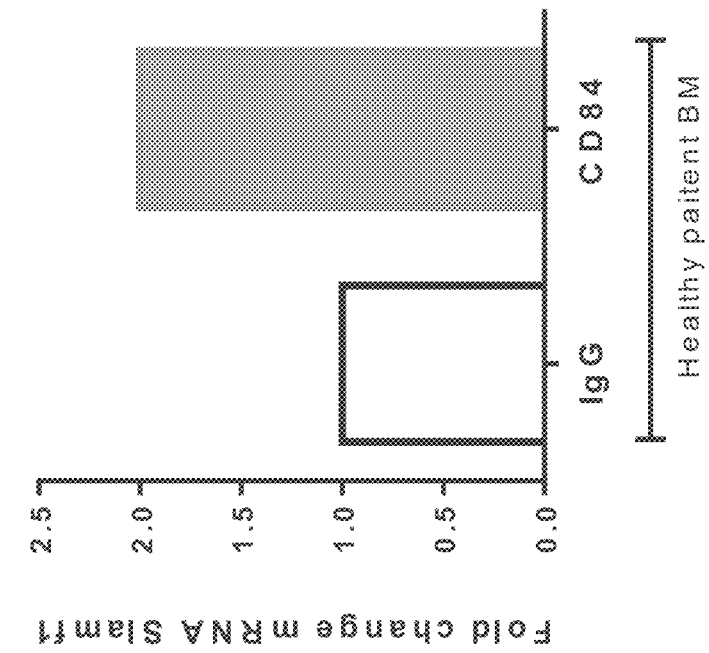
Figure 3F:
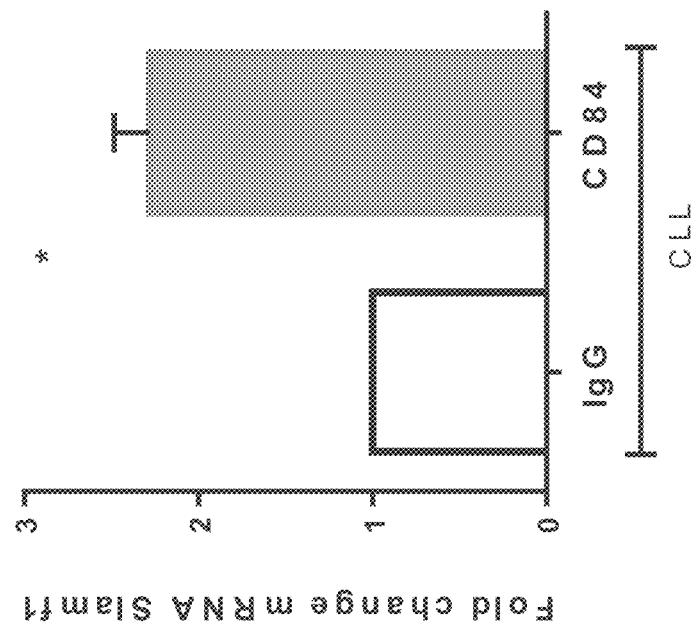
Figure 3H:
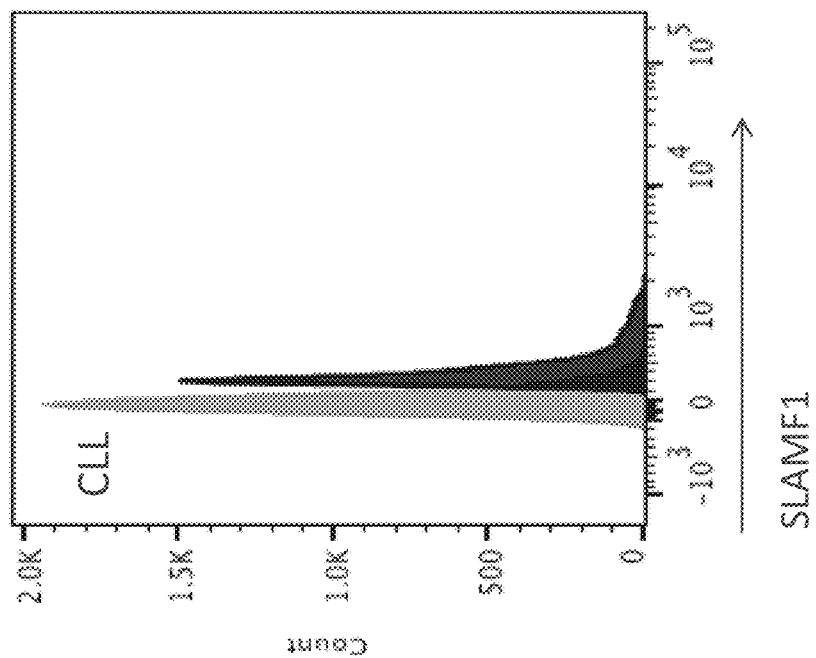
Figure 3G:
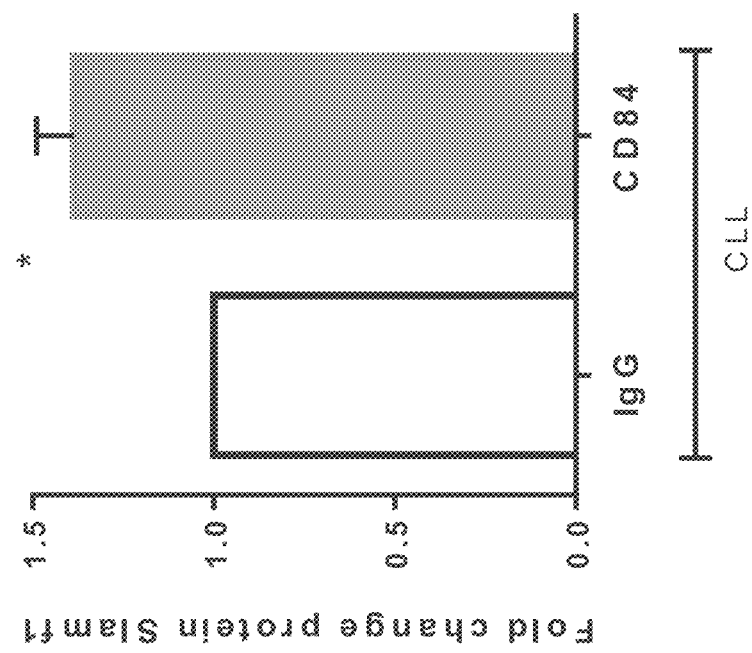

SLAMF1 is an additional member of the SLAM family of receptors, which is known to mediate cell-cell interactions [Cannons J. L. et al., Annu Rev Immunol (2011) 29: 665-705]. First, the DNA chip results were confirmed. Accordingly, M210B4 stromal cells were stimulated with anti-CD84 stimulating antibody (4 μg/ml) and SLAMF1 mRNA (FIG. 3A) and protein (FIGS. 3B-C) levels were analyzed. CD84 stimulation significantly elevated SLAMF1 expression levels in M210B4 stromal cells. Furthermore, SLAMF1 mRNA was upregulated following activation of monocyte-derived nurse like cells (NLC) (FIG. 3D) and on primary human bone marrow stromal cells from a healthy patient (FIG. 3E). Interestingly, stimulation of CD84 expressed on CLL resulted in elevation of SLAMF1 mRNA (FIG. 3F) and protein level (FIGS. 3G-H). These results suggest that CD84 induces expression of SLAMF1 in both CLL and cells in their microenvironment.

Figure 4B:
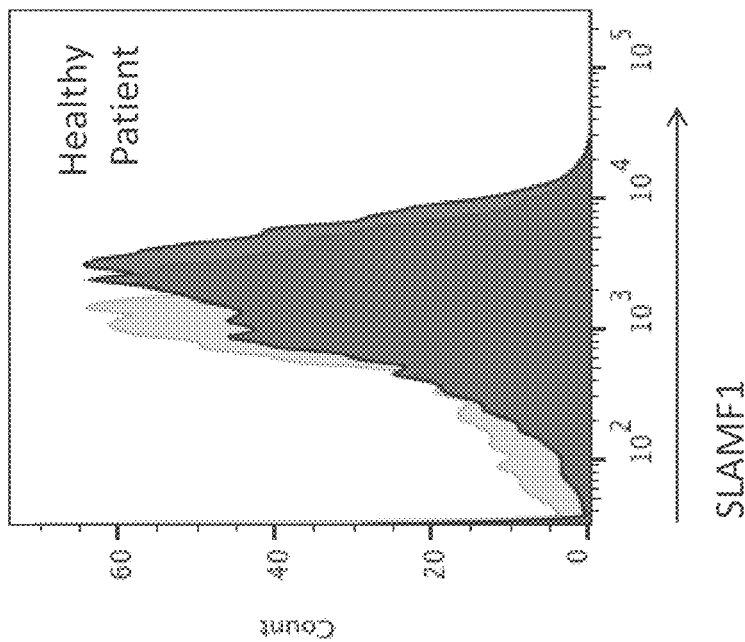
FIGS. 4A-4E are graphs illustrating that SLAMF1 is overexpressed in BM derived from CLL patients and on TCL cells from the Eμ-TCL1 transgenic mouse.
Figure 4A:
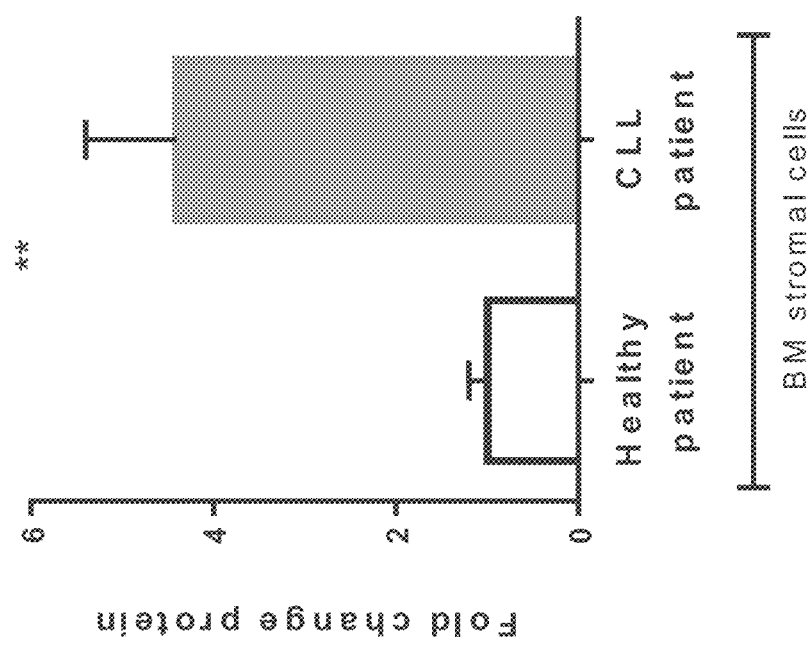
Figure 4D:
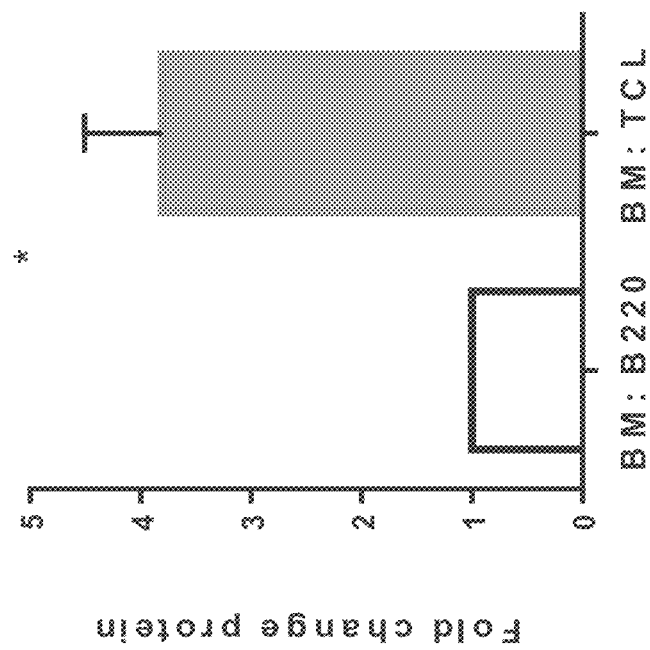
Figure 4C:
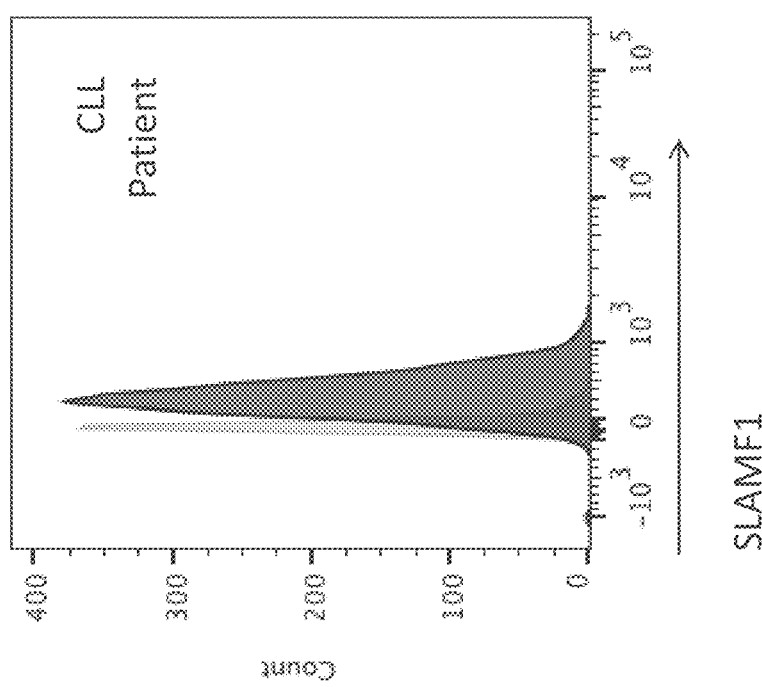

Next, SLAMF1 expression on cells derived from bone aspirates that grew out in vitro to become stromal cells was analyzed. Interestingly, the bone marrow stromal cells from these patients showed about a five-fold increase in SLAMF1 expression compared to cells derived from a confirmed healthy bone marrow, displaying that the receptor could play a role in the pathogenesis of the disease (FIGS. 4A-C).

Figure 4E:
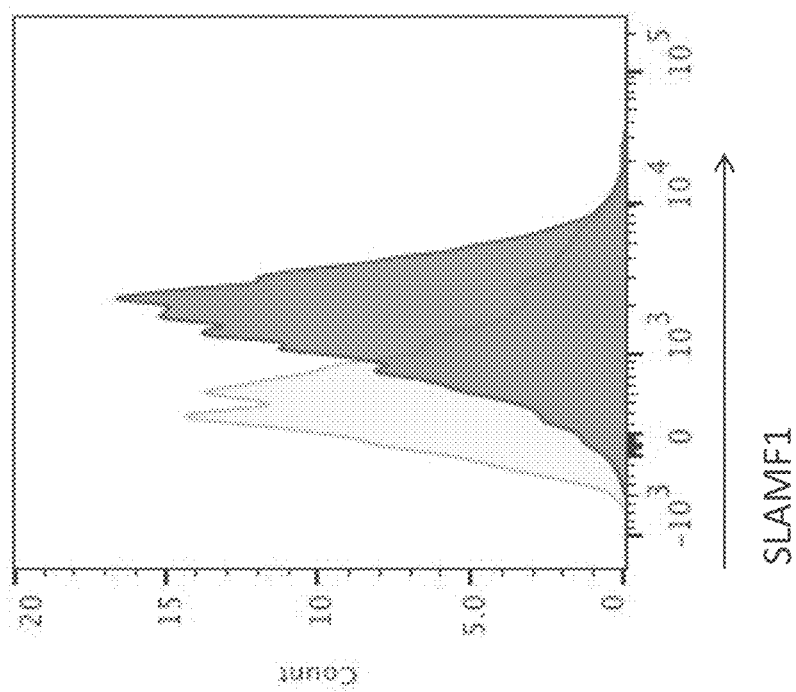

Next, the expression of SLAMF1 on BM derived Eμ-TCL1 transgenic mouse cells, which are the murine model for CLL, was determined. A significant increase in SLAMF1 expression was detected on the murine TCL-1 derived BM cells compared to the expression on non-malignant B cells from the same mice (FIGS. 4D-E).

Example 3

Figure 5:
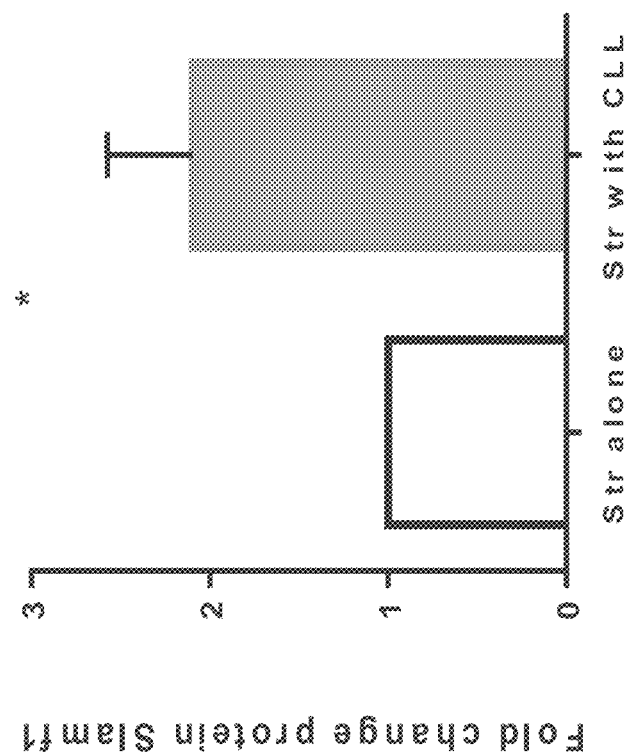
FIG. 5 is a graph illustrating that stromal cells increase their expression of SLAMF1 when in contact with CLL cells. $1\times10^5$ M210B4 cells were plated in 24 well plates, 24 hrs later $1.6\times10^6$ CLL cells were seeded on top of the adherent layer. 48 hrs later the CLL were washed off and the stromal cells were harvested and stained in flow cytometry for SLAMF1 expression (n=4, *p<0.05).

SLAMF1 Expression is Upregulated Following CLL and their Microenvironment Contact in a CD84 Dependent Manner Previous results showed that CD84 is an important player in the CLL-microenvironments interaction both in vitro and in vivo (Marom et al., 2016 submitted). To determine whether this interaction induces SLAMF1 expression, human CLL cells from patient peripheral blood samples were co-cultured with the M210B4 stromal cells line and SLAMF1 expression on the M210B4 stromal cells was compared. As shown in FIG. 5, SLAMF1 levels were significantly increased when the cells were grown with the CLL cells. This suggests that SLAMF1 is involved in the interaction between these two cells.

Figure 6B:
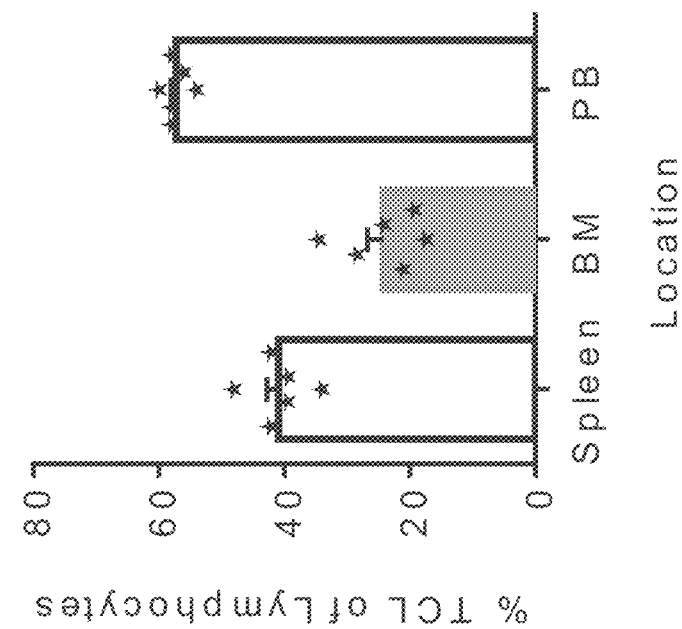
FIGS. 6A-6B are graphs illustrating development of TCL populations in the adoptive transfer model. C57BL/6 mice were injected with $4\times10^7$ TCL-1 splenocytes.
Figure 6A:
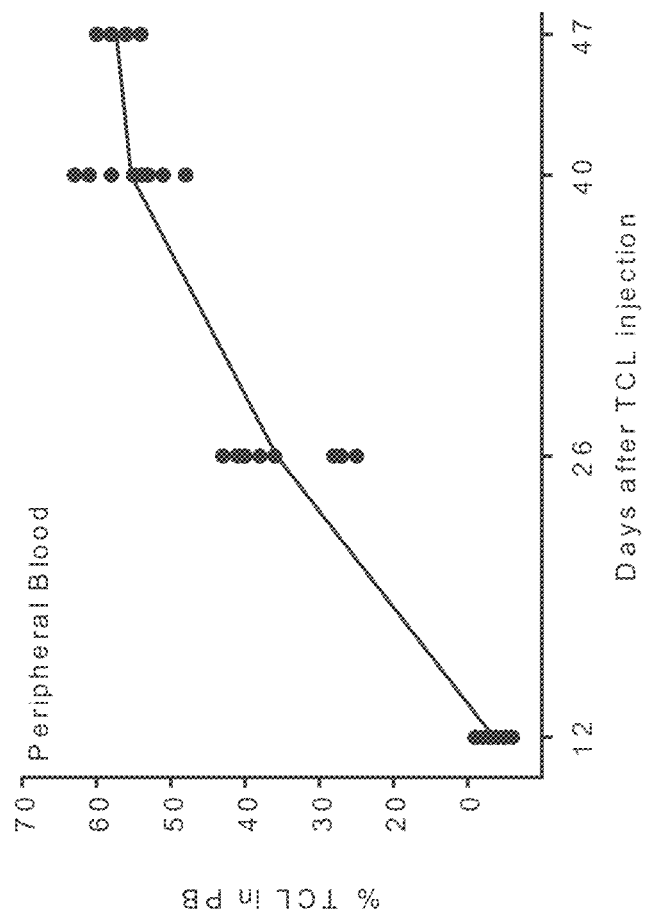
Figure 7A:
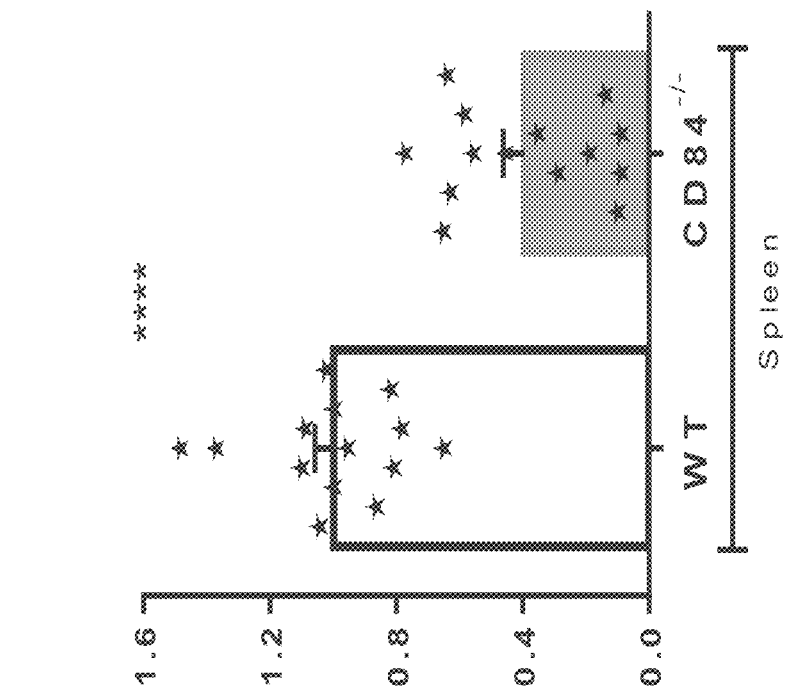
FIGS. 7A-7D are graphs illustrating that CD84 supports the maintenance of TCL-1 cells in vivo. TCL-1 splenocytes ($4\times10^7$) were injected i.v.C57BL/6 wt or CD84$^{-/-}$ mice.
Figure 7B:
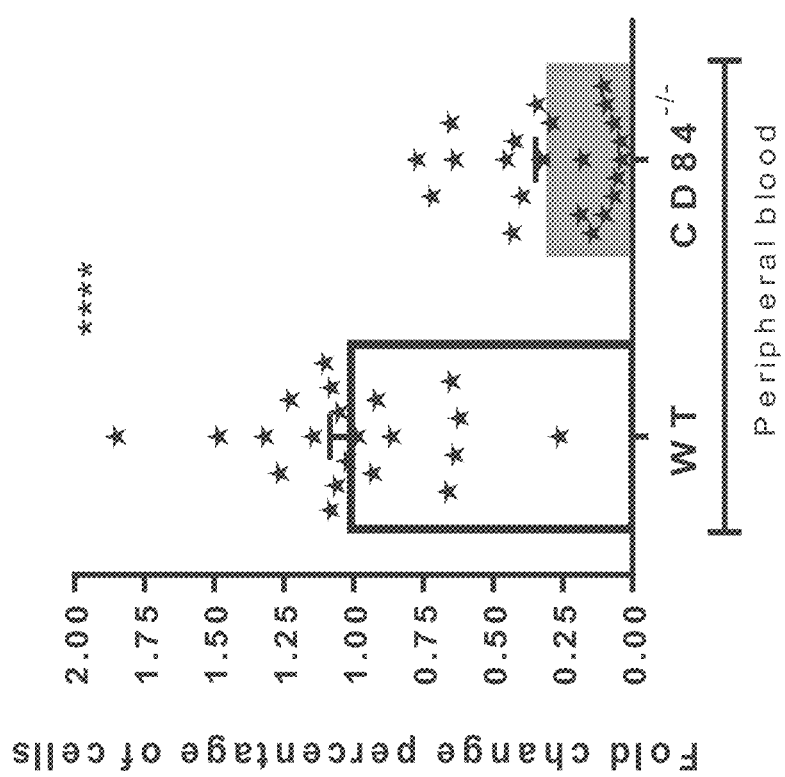
Figure 7C:
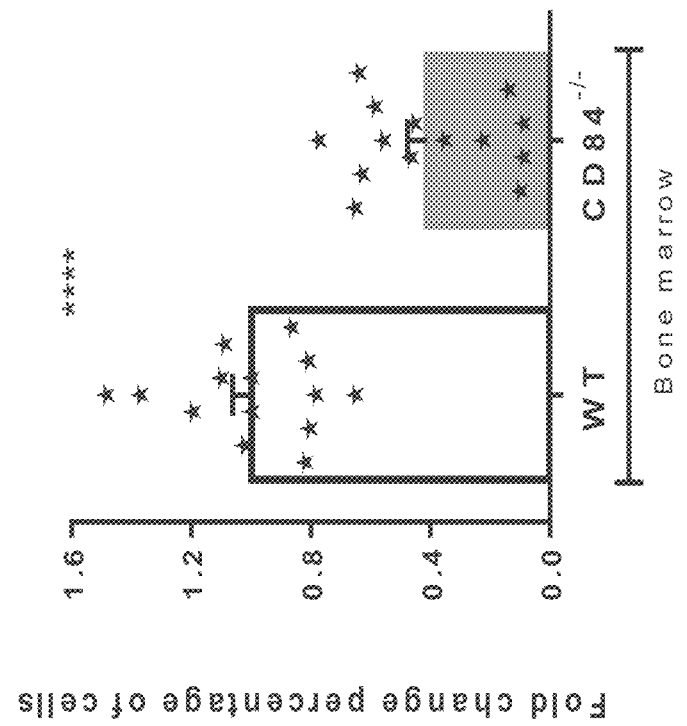
Figure 7D:
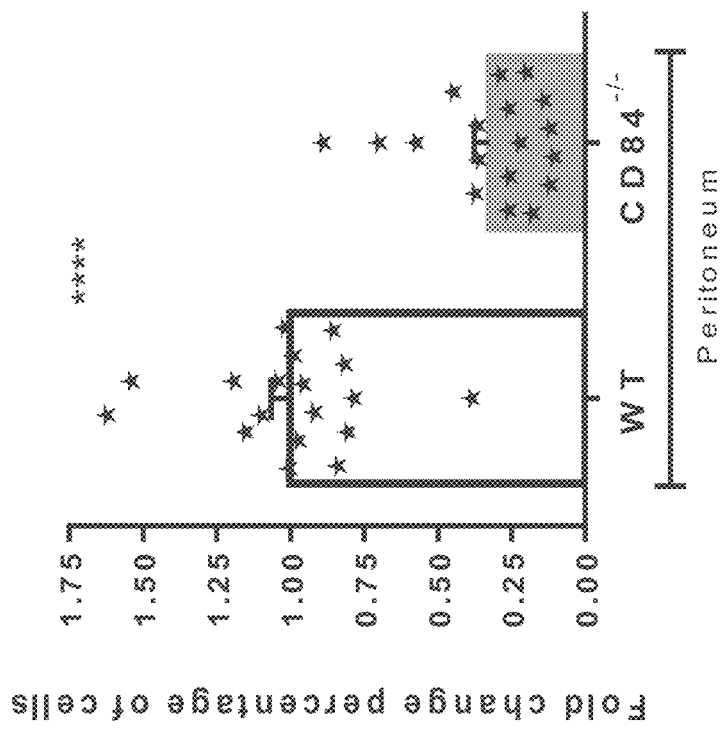

The present inventors hypothesized that since CD84 stimulation up-regulates SLAMF1 expression in vitro, it will have an effect on its expression in vivo. Therefore the in vivo effect of CD84 on SLAMF1 expression was analyzed in an adoptive transfer model [i.e. the model previously described by Hofbauer J. P. et al., Leukemia (2011) 25(9): 1452-1458], in which the mice develop a disease resembling a progressive CLL disease. Splenic cells from tumor-bearing TCL-1 mice were injected to coisogenic wild-type or CD84 deficient mice and the development of a CLL like disease was monitored. TCL-1 cells were detected in the peripheral blood in the wild type microenvironment 12 days after cell transfer and their numbers increased over time (FIG. 6A). After 7 weeks, the TCL-1 cells comprised about 40% of the splenic lymphocytes, 25% of the BM, and 58% of the peripheral blood (FIG. 6B).

Importantly, after 14 days, a significant reduction in the malignant population was detected in the CD84 deficient microenvironment in all compartments, the BM, spleen, peritoneum and peripheral blood (FIGS. 7A-D). While the difference was smaller for the BM (about a 40% reduction), the differences in spleen and peritoneum (each about 55% reduction) and peripheral blood (about a 65% reduction) were more pronounced. Results were normalized to the wild type group since the percentages of the TCL populations varied between different experiments (FIGS. 7A-D).

Figure 8D:
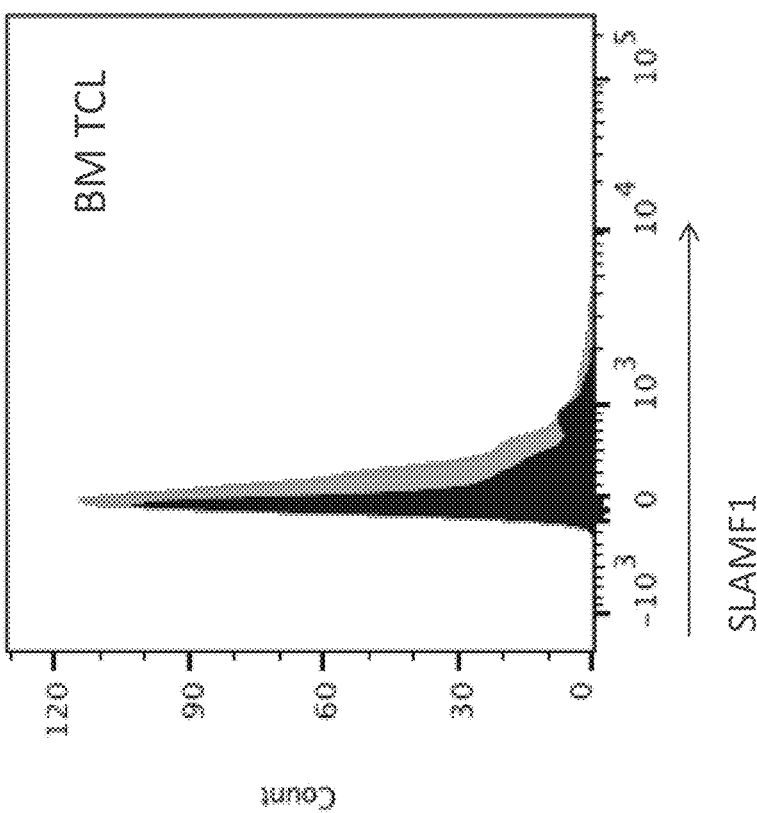
Figure 8C:
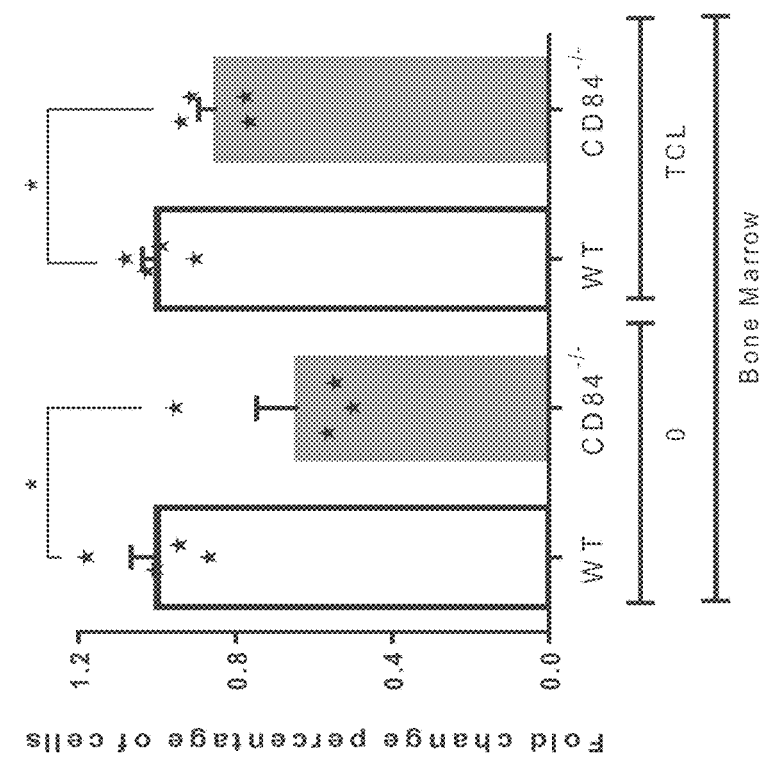
Figure 8H:
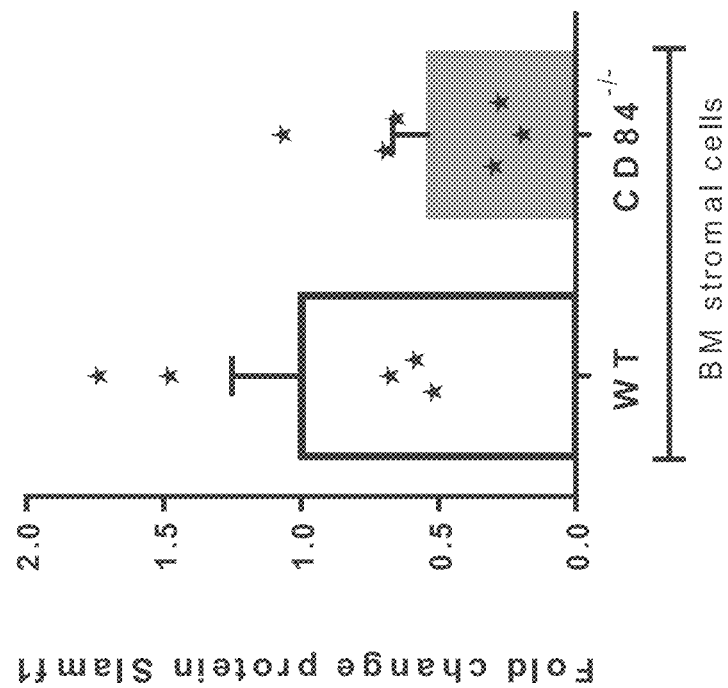
Figure 8G:
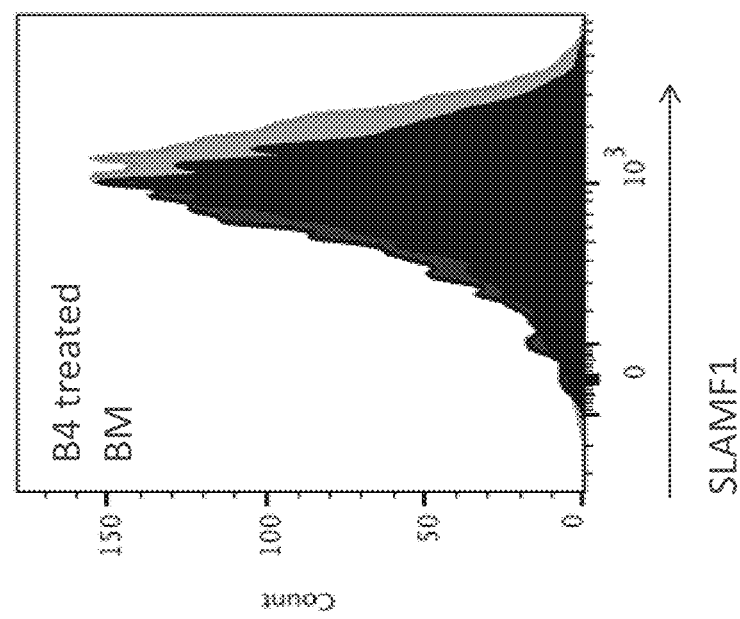

Next, SLAMF1 expression was analyzed on the TCL-1 cells. As shown in FIGS. 8A and 8C, the levels of SLAMF1 on TCL-1 cells were significantly decreased at 14 days post adoptive transfer in the CD84$^{-/-}$ environment compared to their wild type controls. This reduction was detected in the peritoneum (FIGS. 8A-B) and in the BM (FIGS. 8C-D), the two organs that have been previously found to be important in Eμ-TCL1 mouse model [Bichi R. et al., (2002), supra]. However, no change in SLAMF1 expression was observed in the spleen and peripheral blood (data not shown). The regulation was not limited to the malignant population, as the decrease in SLAMF1 was also detected on the normal B cells (FIGS. 8A, 8C), however, it is important to note that the microenvironment of these cells is still malignant. Furthermore, treating the TCL-1 transferred wild type mice with the anti-CD84 B4 hybridoma decreased the amount of SLAMF1 expressed on the TCL1 cells in peritoneum and bone marrow (FIGS. 8E-G).

Figure 8I:
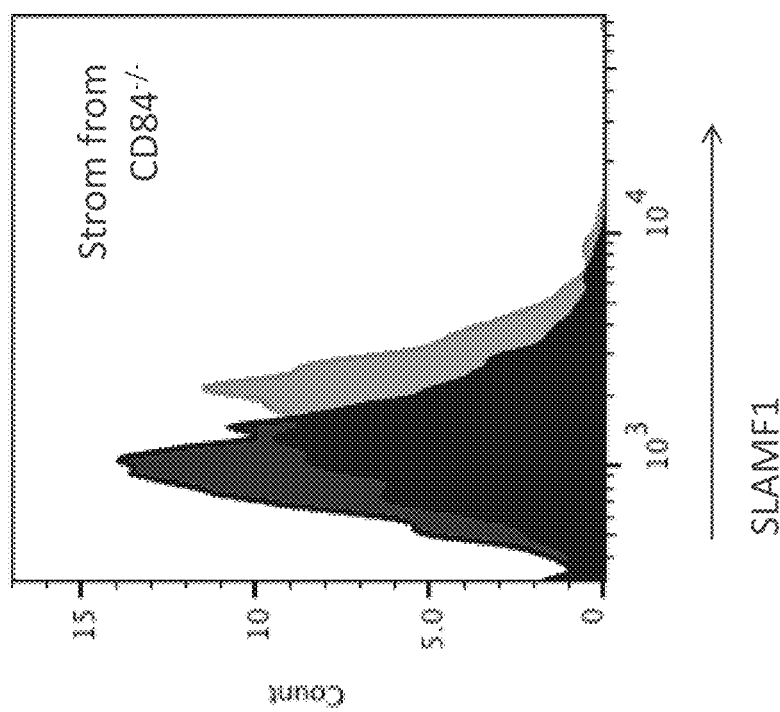

To determine the effect of the tumor environment on SLAMF1 expression on BM stromal cells, bone marrow stromal cells were harvested and analyzed for SLAMF1 expression. After three weeks of culture these cells still showed a decrease in the amount of SLAMF1 expression (FIGS. 8H-I).

Example 4

Down-Regulation of SLAMF1 Induces CLL Cell Death

Figure 9C:
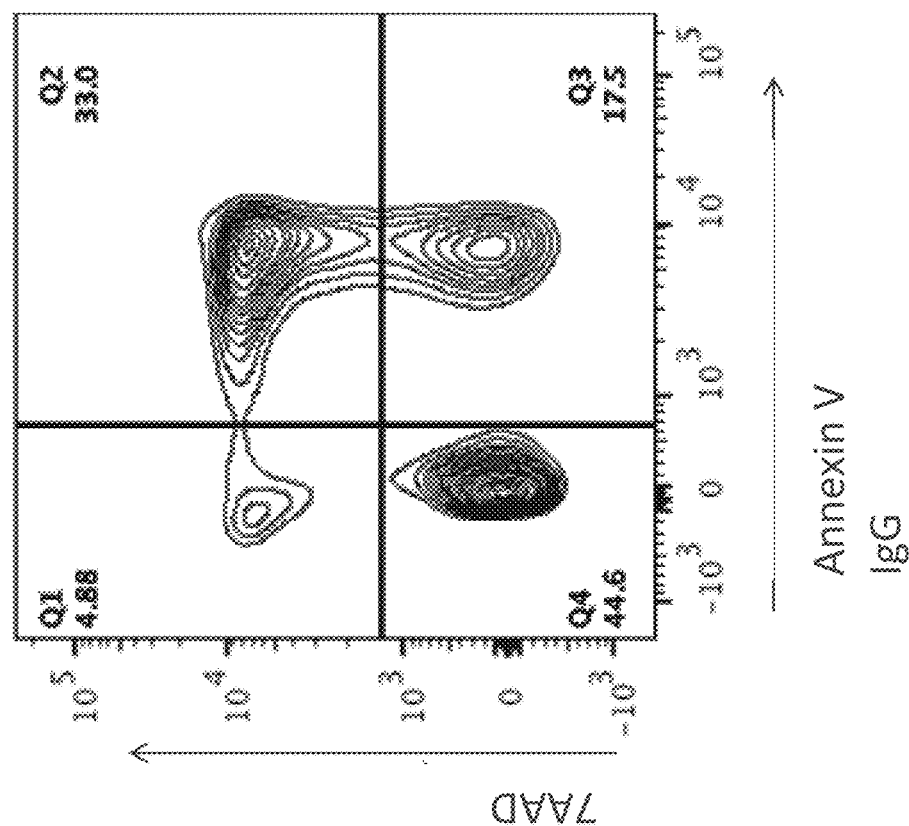
Figure 9B:
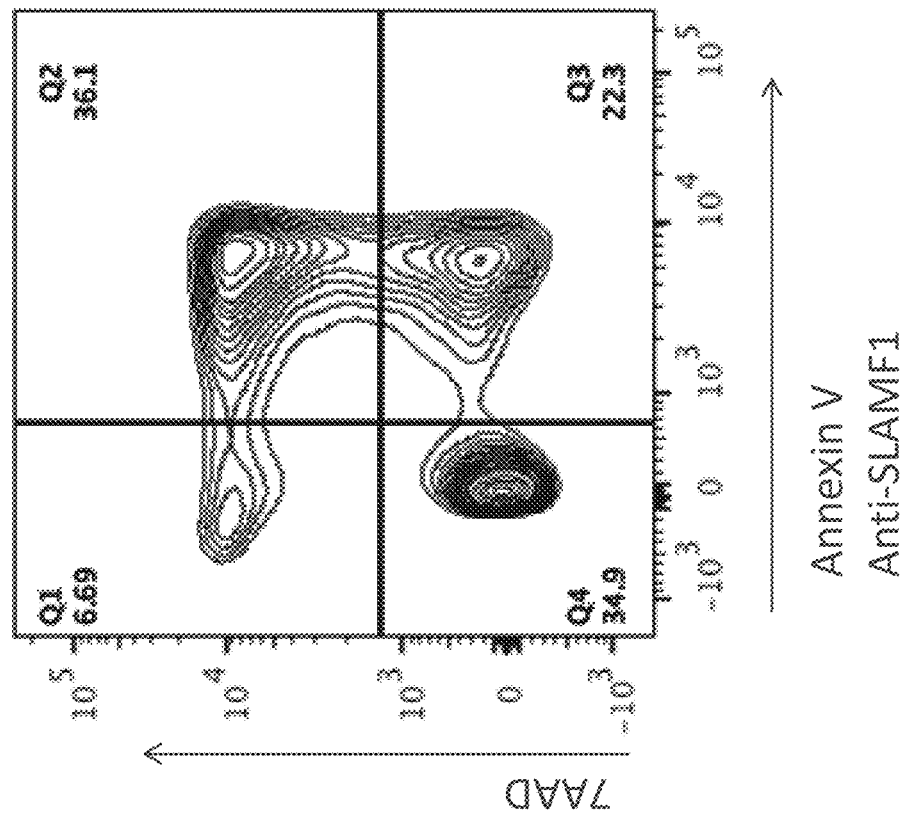

To determine whether SLAMF1 is involved in the regulation of CLL survival, primary CLL cells were incubated with or without an antagonistic SLAMF1 antibody (Clone: A12, Biolegend) for 48 hours and the differences in survival were determined. As illustrated in FIGS. 9A-C, a decrease of 25% in surviving CLL cells was found with the CLL cells.

Figure 9E:
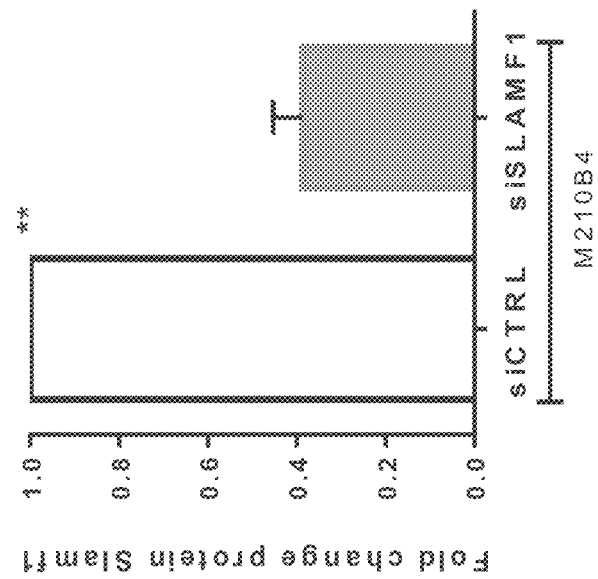
Figure 9D:
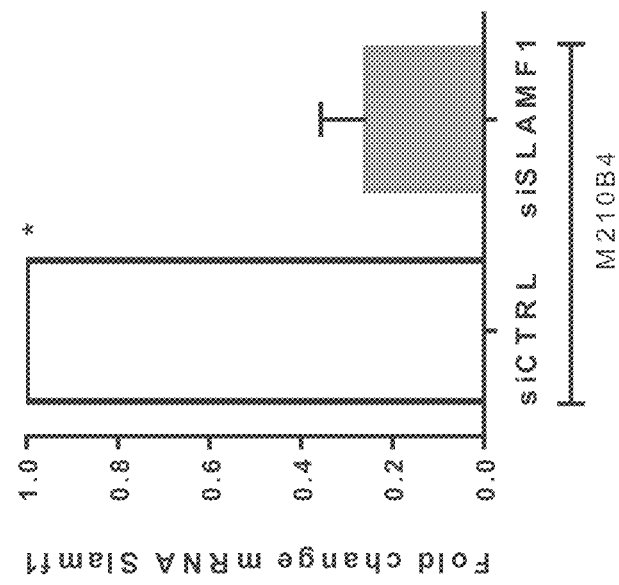
Figure 9G:
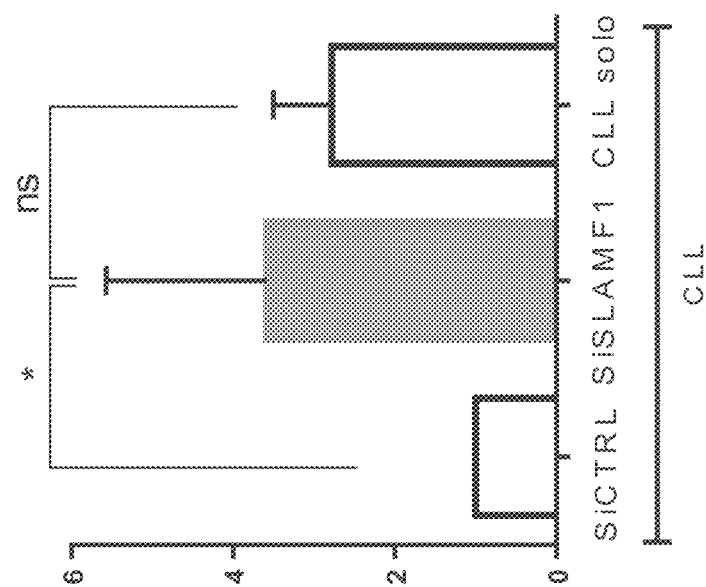
Figure 9F:
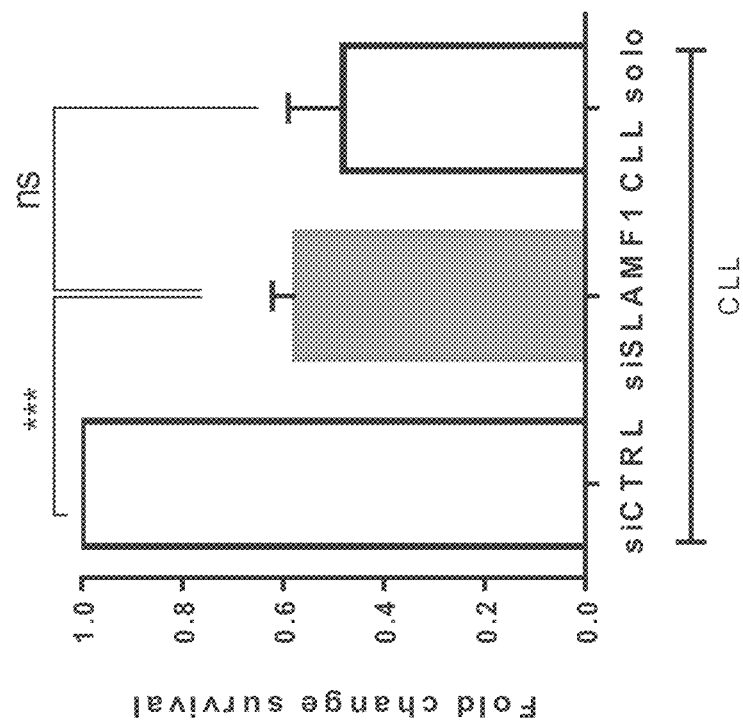

Next, the role of SLAMF1 expressed on stroma on the survival of the CLL cells was examined. Accordingly, SLAMF1 expression in M210B4 stromal cells was down-regulated by siRNA and the effect on CLL survival was monitored. A decrease of 70% in SLAMF1 mRNA (FIG. 9D) and 60% in protein (FIG. 9E) levels were detected in M210B4 stroma cells treated with SLAMF1 siRNA. Next, CLL cells were added to the siSLAMF1 treated M210B4 stroma cells for a 48 hour co-culture. Knockdown of SLAMF1 expression in the microenvironment led to a 43% reduction in live CLL cells (FIGS. 9F, 9H) and reached survival and apoptotic levels of CLL cells grown in solo-cultures (FIGS. 9F-J). This result suggests that SLAMF1 expressed on stroma regulates CLL survival.

Example 5

Stimulation of SLAMF1 Increases Bcl-2 and PD-L1

Figure 10A:
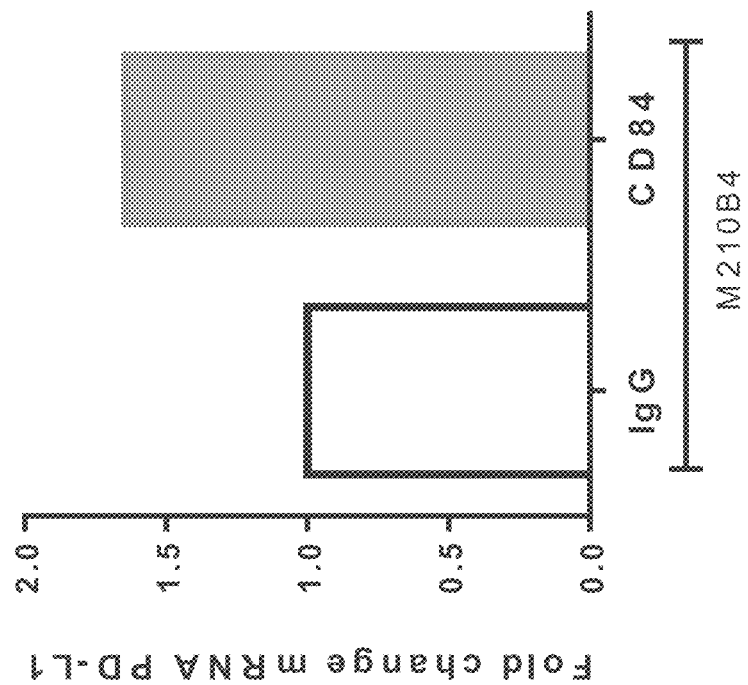
FIGS. 10A-10B are graphs illustrating that stimulation of M210B4 with SLAMF1 increases Bcl-2 and PD-L1.1×10$^5$ M210B4 cells were incubated with an agonistic anti-SLAMF1 antibody (10 μg/ml) or isotype control Rat IgG1 for 72 hrs. RNA was purified and the mRNA expression of Bcl-2 (FIG. 10A) or PD-L1 (FIG. 10B) was measured by qRT-PCR (n=1).
Figure 10B:
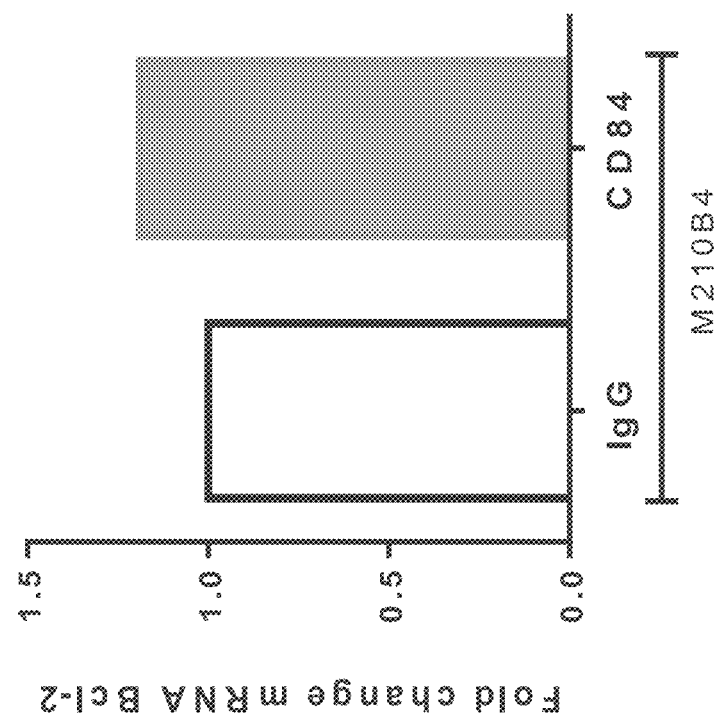

To further elucidate the role of SLAMF1 expressed in the microenvironment, its downstream induced cascade was followed. Therefore, SLAMF1 expressed on M210B4 stroma cells was activated by anti-SLAMF1 antibody (10 μg/ml, Clone: 9D1, Ebioscience) and genes which expression were upregulated following this stimulation were followed. As shown in FIGS. 10A-B, an increase in Bcl2 (FIG. 10A) and programmed cell death ligand 1 (PD-L1) (FIG. 10B) mRNA levels were detected.

Example 6

CD84 Regulates SLAMF1 Expression on Multiple Myeloma, Acute Lymphocytic Leukemia and Burkitt's Lymphoma Cells The present inventors were interested to determine whether the regulation of SLAMF1 expression is specific for CLL or if it would also be found in other malignancies. Therefore, CD84 was activated on primary multiple myeloma (MM) cells derived from patients (FIG. 11A). Stimulation of CD84 elevated SLAMF1 expression in about 2-fold (FIG. 11A). Furthermore, SLAMF1 expression on primary multiple myeloma patient cells were more than ten-fold higher as compared to its levels on healthy control cells (FIG. 11B).

Figure 12A:
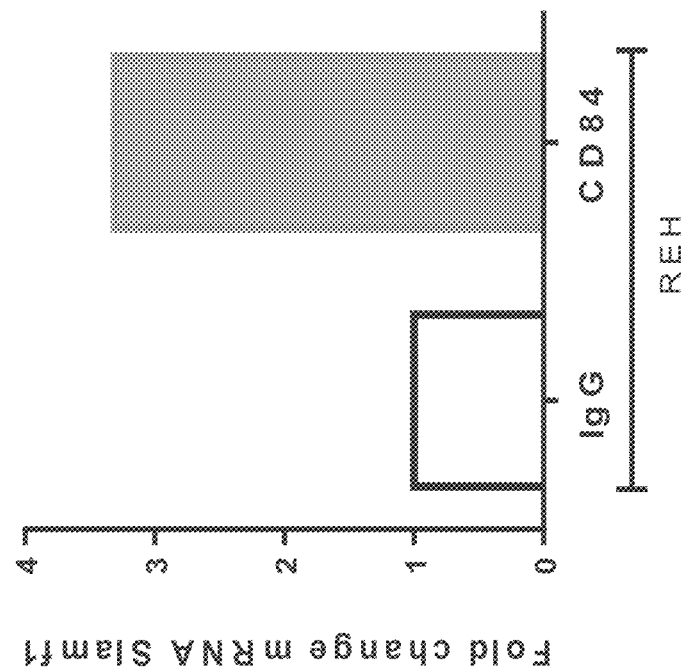
FIGS. 12A-12D are graphs illustrating that CD84 might regulate SLAMF1 in other B cell malignancies.
Figure 12B:
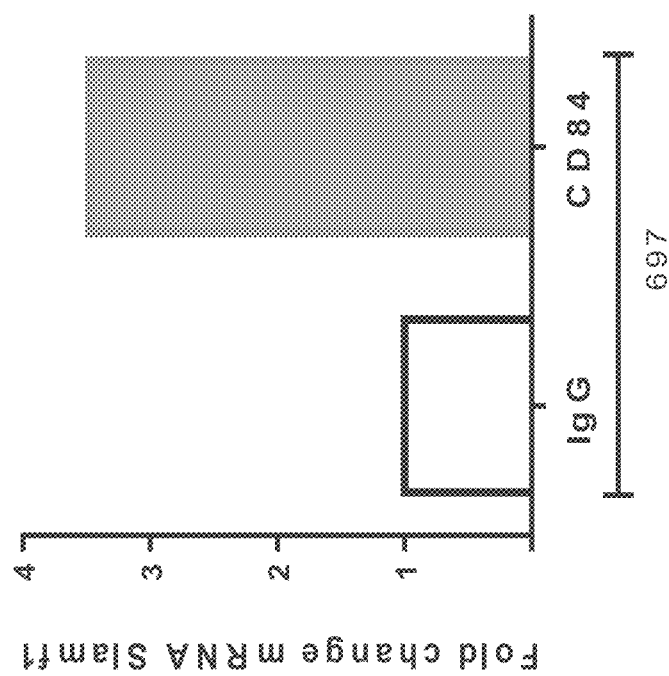
Figure 12D:
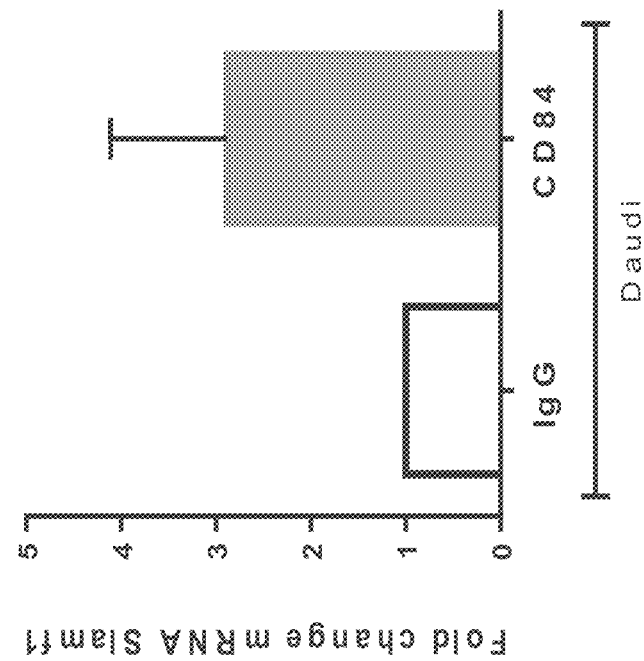
Figure 12C:
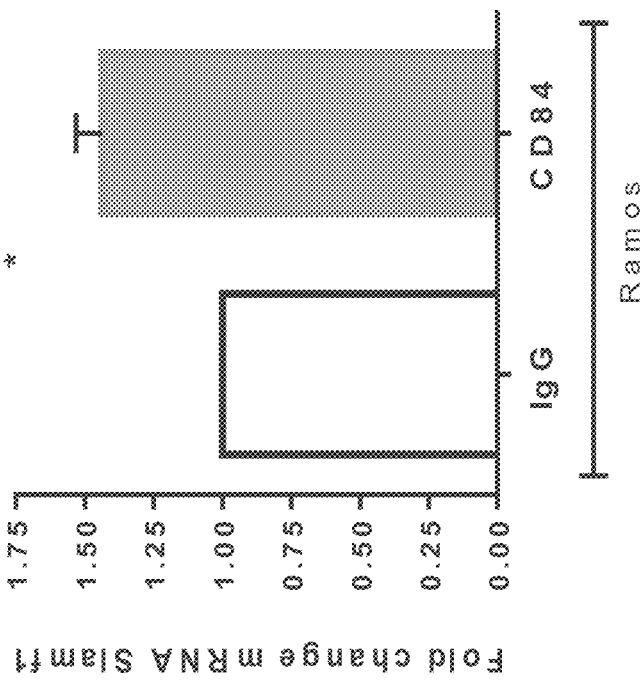
Figure 13A:
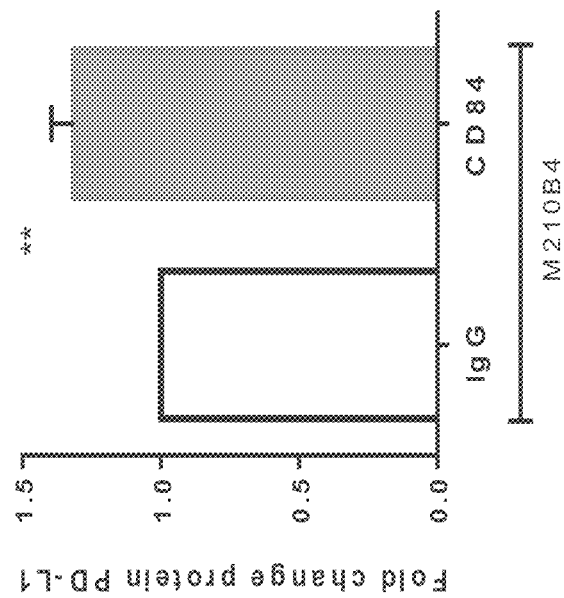
Figure 13B:
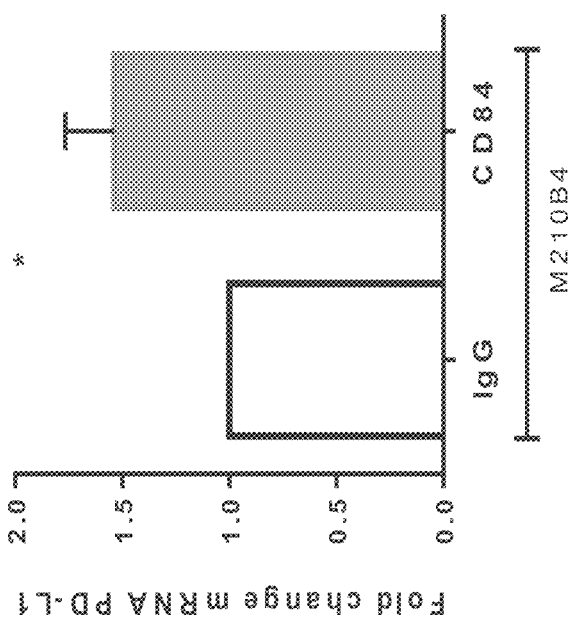
Figure 13D:
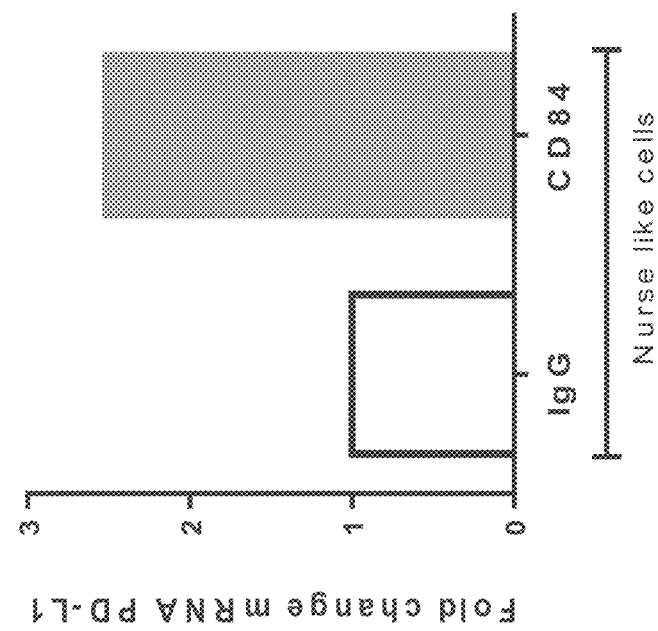
Figure 13C:
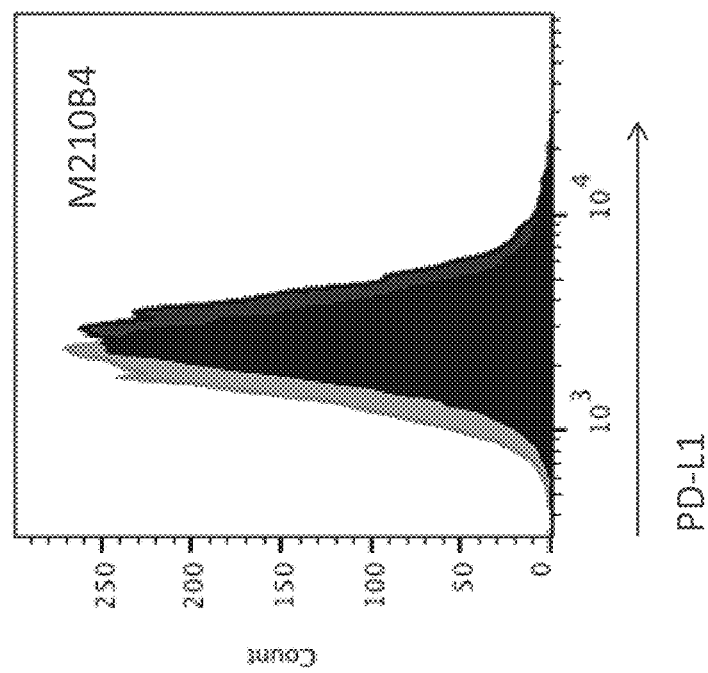

Next, SLAMF1 expression was analyzed in Acute Lymphoblastic Leukemia (ALL) and Burkitt's lymphoma cell lines following CD84 stimulation. Again, a 24 hour stimulation elevated SLAMF1 expression levels on ALL cell lines 697 and REH (FIGS. 12A-B), and on Burkitt's lymphoma cell lines Ramos and Daudi (FIGS. 12C-D), illustrating that this regulatory role is more general to B cell malignancies and not relevant solely to CLL.

Example 7A

PD-L1 is Up-Regulated Following CD84 Stimulation

Figure 23E:
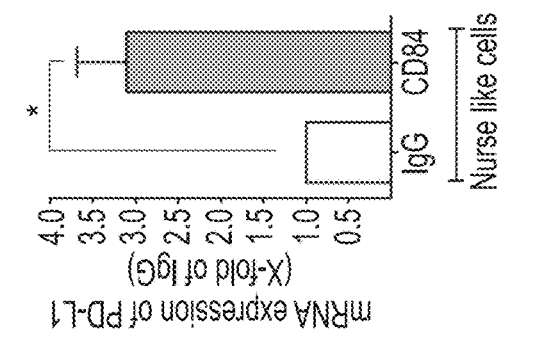
Figure 23F:
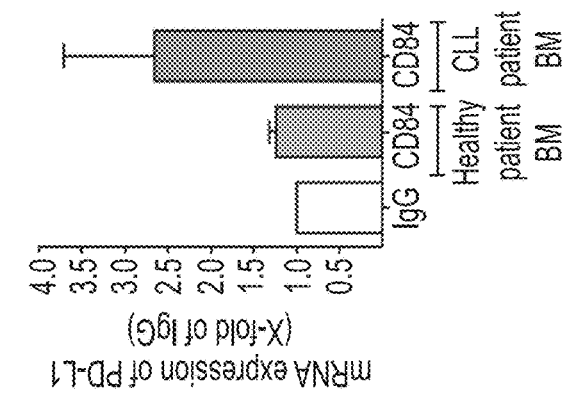
Figure 23G:
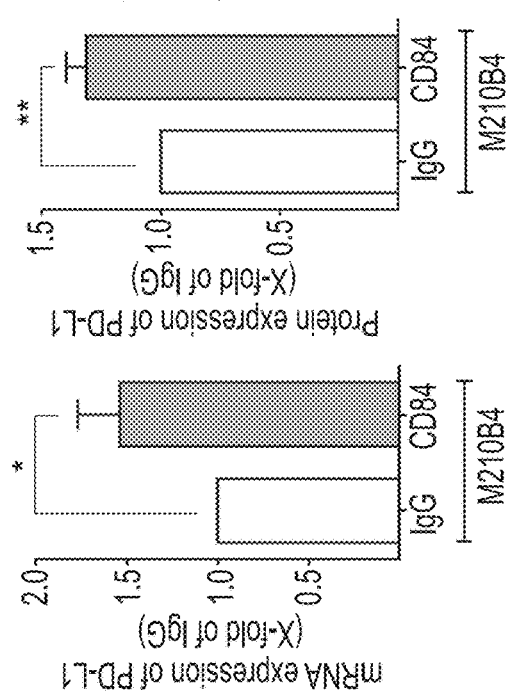
Figure 27G:
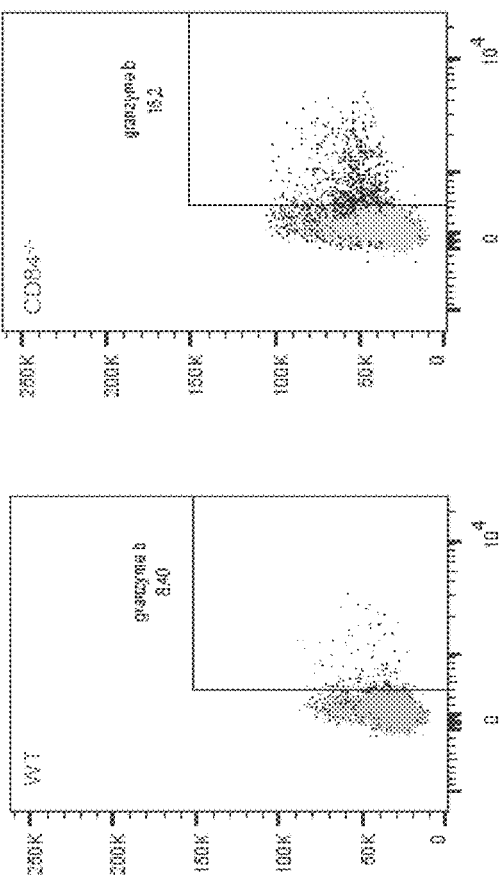
Figure 27H:
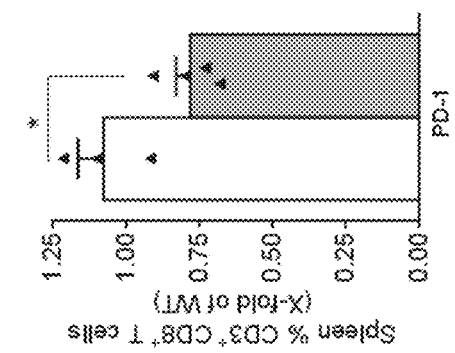
Figure 27F:
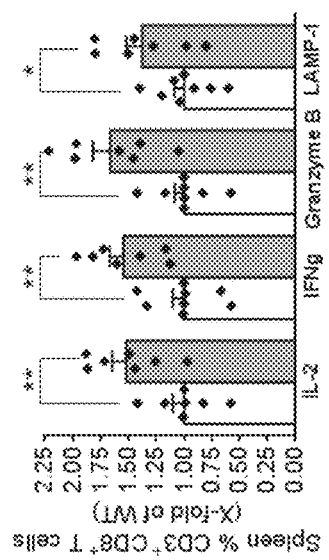
Figure 28A:
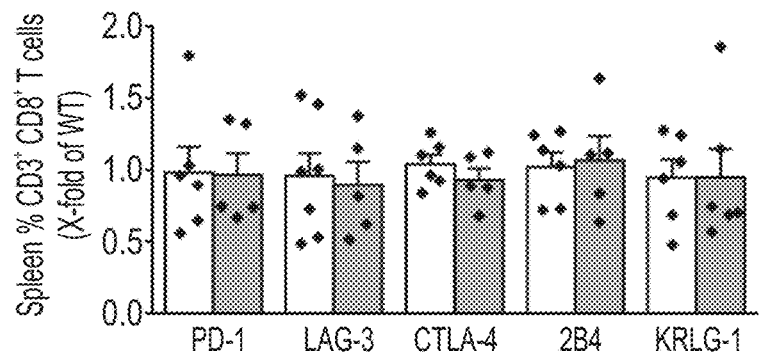
FIGS. 28A-28C are graphs illustrating that $CD84^{-/-}$ mice without murine CLLs do not have differences on CD8 T cell functionality. Cells were harvested from the spleen and cultured for 24 hours with anti-CD3 (Biolegend) and the last two hours of culture with brefeldin-A. The CD8 T cells were stained for the exhaustive markers: PD-1, Lag-3, CTLA-4, 2B4, KLRG-1 (n=5-7, ns p=0.9508, ns p=0.7836, ns p=0.3026, ns p=0.8253, ns p=0.9909) (FIGS. 28A, 28C) and cytokines/cytotoxic markers: IFNγ, IL-2, Granzyme B and LAMP-1 (n=5-7, ns p=0.6461, ns p=0.7897, ns p=0.8740, ns p=0.8495) (FIG. 28B).
Figure 28B:
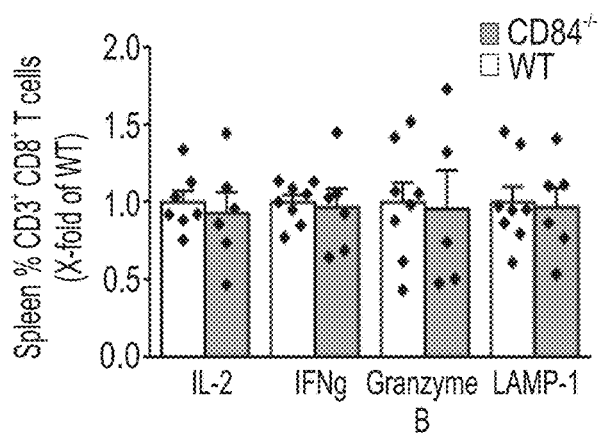
Figure 28C:
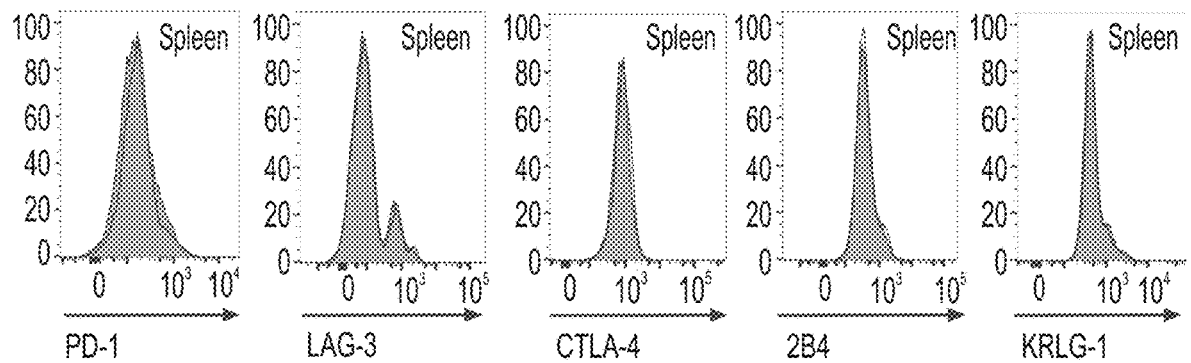
Figure 32A:
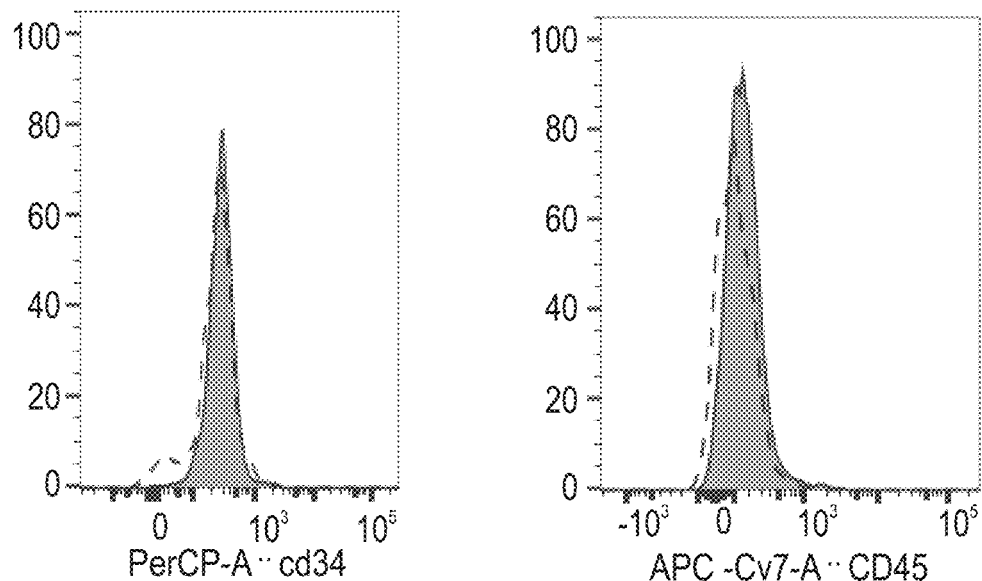
FIGS. 32A-32B are graphs illustrating primary stromal cells grown out from human bone marrow aspirates (FIG. 32A) and flushed out mouse tibia femur bones (FIG. 32B) stained for CD34 and CD45, displaying that they are of non-hematopoietic origin.
Figure 32B:
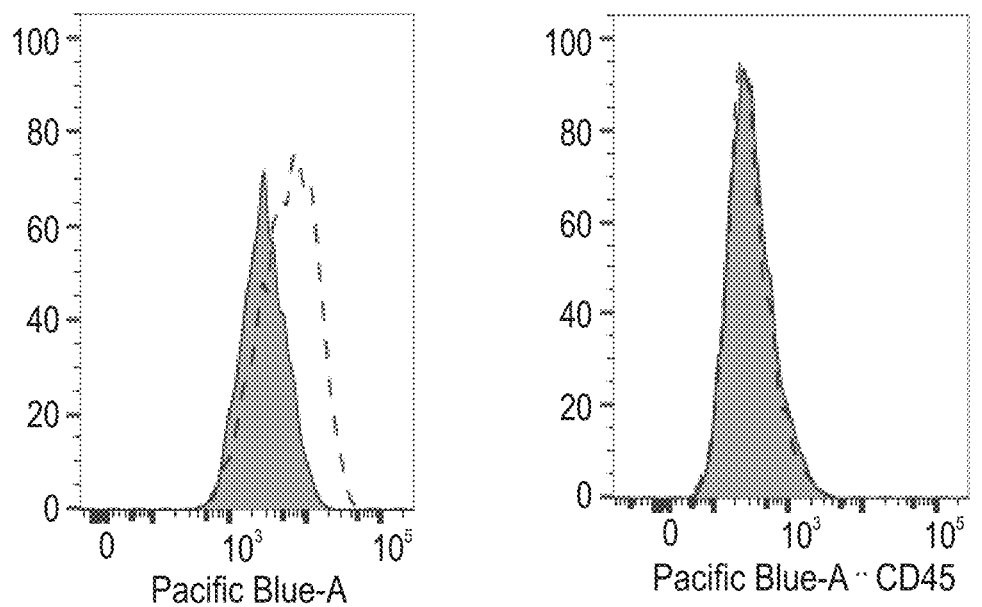

Another CD84 target gene which was chosen to follow was PD-L1. To verify the ability of CD84 to regulate its expression, CD84 expressed on M210B4 mouse stromal cell line (FIGS. 13A-C and 23E), human patient derived nurse like cells (FIGS. 13D and 23G), CLL cells both human and murine (FIGS. 13F-H and 23A-B) and human primary bone marrow healthy and CLL stromal cells (FIGS. 13E and 23F) were stimulated with an anti-CD84 or a control IgG antibody for 24 hours. As shown in FIGS. 13A, 13D, 13E, 13F, 23A-B, 23E and 23F, PD-L1 mRNA levels were elevated in all the stimulated cells. Furthermore, decreased levels of PD-L1 mRNA were observed in the AffymetrixGeneChip® analysis performed on antagonist anti-CD84 treatment in primary CLL patient bone marrow samples compared it its levels in healthy BM in a co-culture with CLL (data not shown). Further the expression levels of PD-L1 on murine and human stromal cells derived from CLL patients/CLL mouse model was significantly elevated compared to healthy controls (FIGS. 23C-D). These cells were determined to be stromal cells and therefore of none hematopoietic origin by CD34 and CD45 staining (FIGS. 32A-B).

Figure 14A:
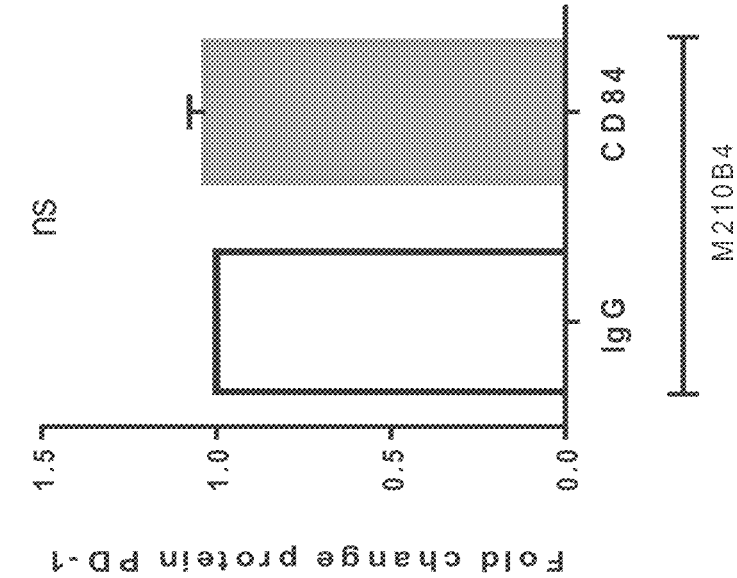
FIGS. 14A-14E are graphs illustrating that CD84 negatively regulates PD-1 in CLL, but not in bone marrow stromal cells.
Figure 14B:
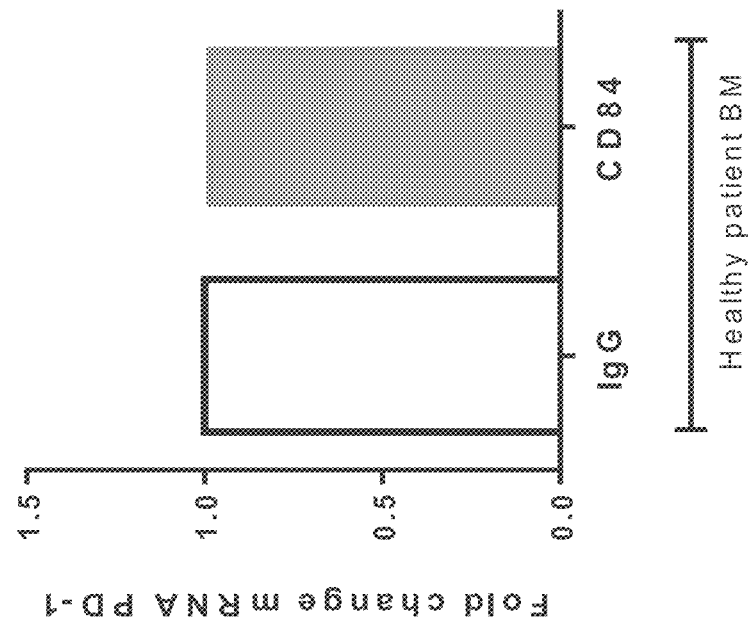

Next, the expression of PD-L1 receptor, programmed cell death 1 (PD-1), was analyzed before and after anti-CD84 antibody stimulation. Stimulation of CD84 on BM cells of healthy patient (FIG. 14A) or M210B4 stroma cells (FIG. 14B) had no effect on PD-1 protein expression levels. Interestingly, stimulation of CD84 expressed on CLL cells resulted in a significant decrease in PD-1 mRNA (FIG. 14C) and protein (FIGS. 14D-E) expression levels.

Example 7B

CD84 Activation Up-Regulates PD-L1 Through the AKT-mTOR Pathway

The present inventors next followed the CD84 induced cascade that results in PD-L1 expression. Expression of PD-L1 has been previously shown to be under the control of the AKT-mTOR and the MAPK pathways. Therefore, these pathways were analyzed in CD84 stimulated M210B4 cells. While almost no change was detected in the MAPK pathway (FIG. 24A), CD84 stimulation elevated levels of pAKT in activated compared to non-activated M210B4 cells (FIG. 24A-B). In addition, CD84 stimulation induced phosphorylation of S6, a known regulator of PD-L1 in lung cancer. This was further confirmed by flow cytometry (FIGS. 24B-C). Thus, CD84 elevated PD-L1 protein expression through activation of AKT/mTOR and phospho-S6.

Example 8

PD-1/PD-L1 Levels are Regulated by CD84 In Vivo

Figure 15A:
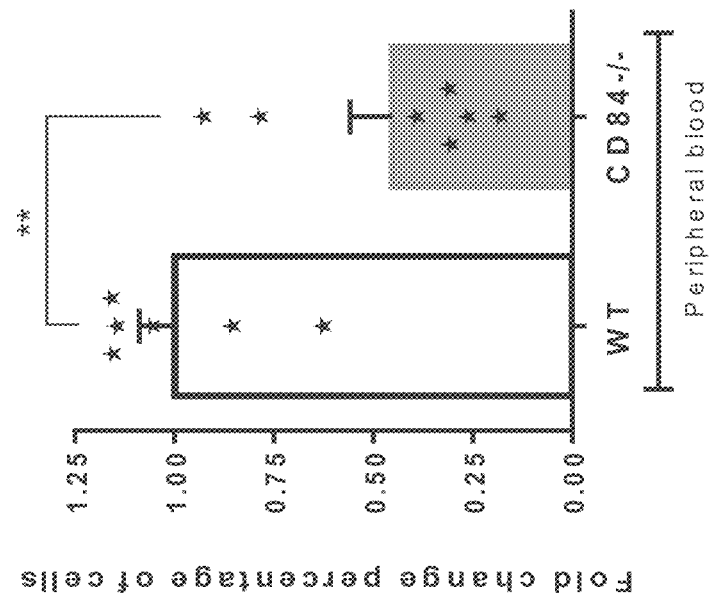
Figure 15B:
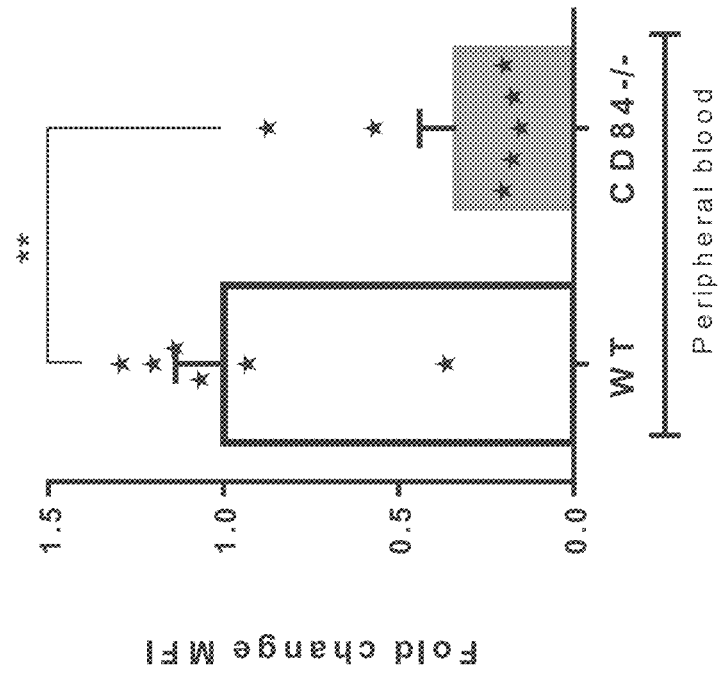
Figure 15C:
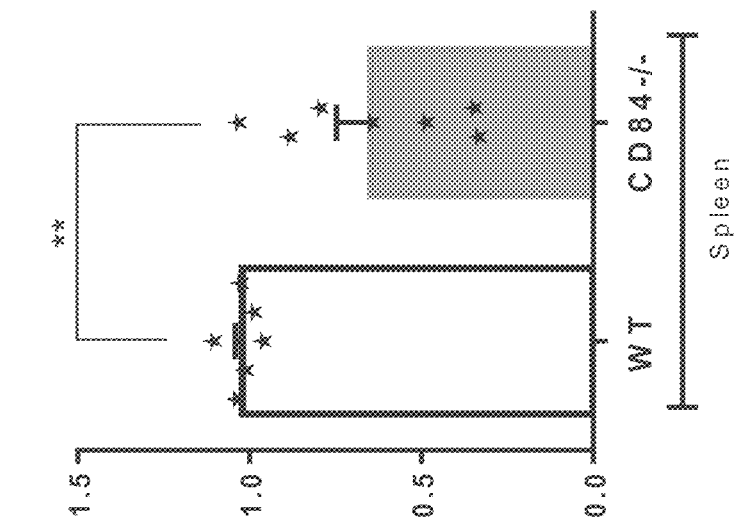
Figure 15D:
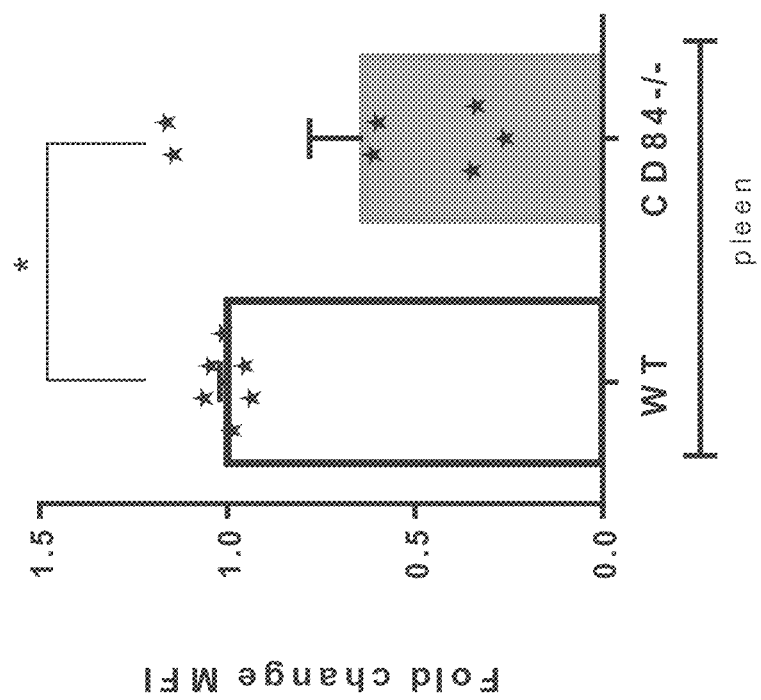
Figure 15E:
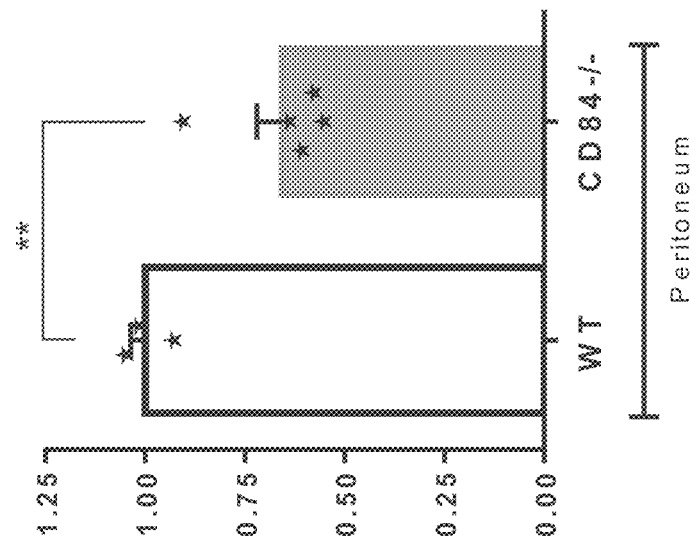
Figure 15F:
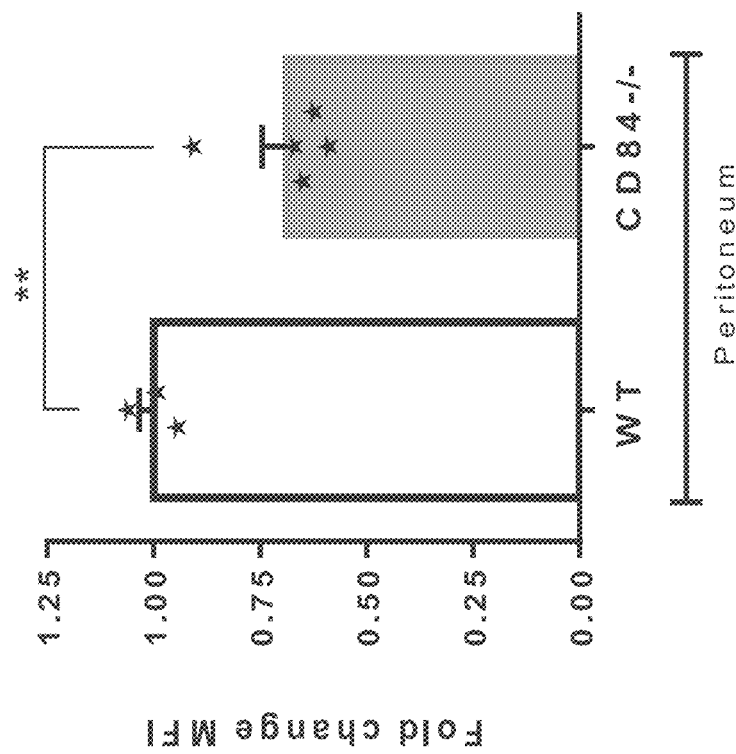

Previous studies have described PD-L1 as an immune co-inhibitor used by leukemic progenitors to escape the immune system [Norde, W. J. et al., Cancer Res (2011)71 (15): 5111-5122]. Moreover, others have shown that blocking the PD-L1/PD-1 pathway in the Eµ-TCL1 CLL model mouse resolved CLL induced chronic inflammation [McClanahan, F. et al, Blood (2015)126(2): 203-211]. Consequently, the regulatory role of CD84 on the PD-L1/PD-1 pathway in CLL disease progression was followed in vivo. Spleens from TCL-1 mice were harvested and injected into a coisogenic wild type or $CD84^{-/-}$ mice and BM, lymph node (LN), spleen, peripheral blood and peritoneum were harvested. As shown in FIGS. 15A-G and 25A-E, a significant reduction in PD-L1 levels was detected on TCL-1 cells derived from all organs harvested from a CD84 lacking microenvironment, except for lymph nodes (FIG. 25F). Thus, CD84 expressed on the microenvironment regulates PD-L1 expression. In its absence lower levels of PD-L1 are detected on TCL cells. Furthermore, mice treated with the antagonistic anti-CD84 B4 hybridoma, shown in FIG. 15H, had significantly reduced levels of PD-L1 expression in the peritoneal cavity (FIGS. 15I and 25G). This, again, displays the regulatory role of CD84 on PD-L1 in vivo. Furthermore, bone marrow stromal cells derived from these mice were grown for approximately 3 weeks and their PD-L1 levels were analyzed (FIGS. 15J and 26A), these results illustrate a significant decrease in PD-L1 expression on microenvironmental BM cells lacking CD84. In addition, BM macrophages (FIG. 26C), BM DCs (FIG. 26D), splenic macrophages (FIG. 26E), splenic DCs (FIG. 26F) and PB monocytes (FIG. 26G) in the CD84 deficient environment displayed reduced PD-L1 expression, as compared to control derived cells. These results suggest a global regulation of PD-L1 expression in the tumor microenvironment mediated by CD84.

Figure 14C:
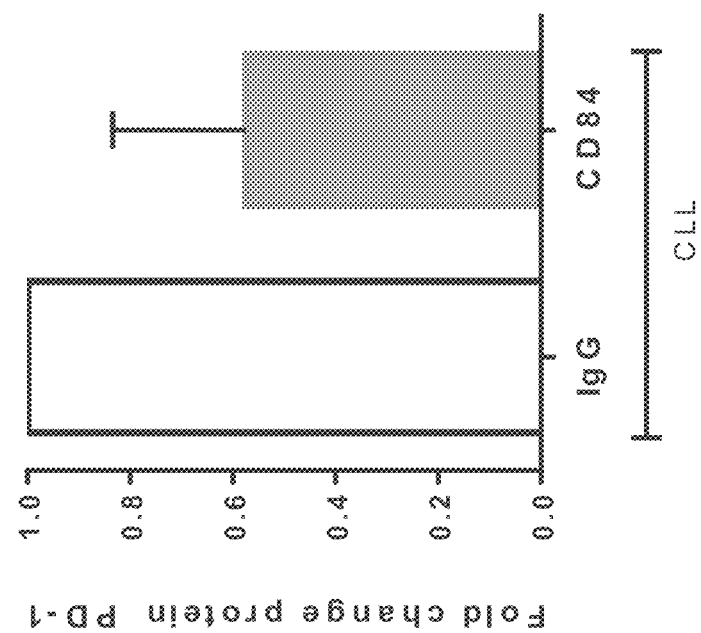
Figure 14D:
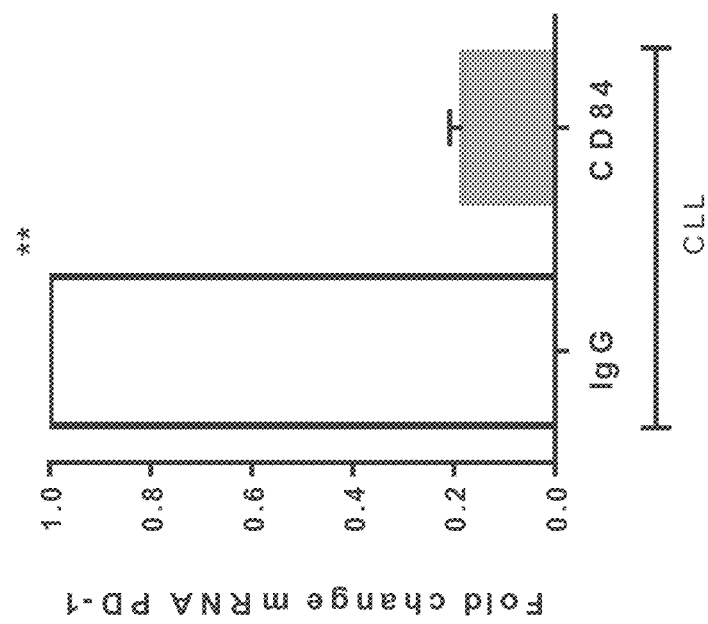
Figure 14E:
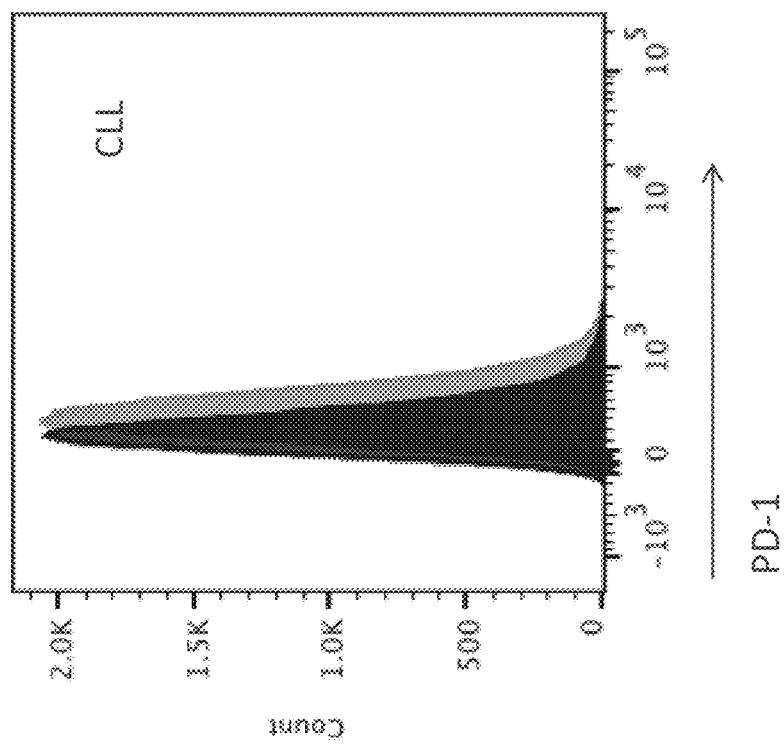

As the expression of PD-L1 was decreased in the $CD84^{-/-}$ mice, the amount of the receptor, PD-1, on TCL cells was also analyzed. 28 days post injection a significant increase of about 2 fold in mean fluorescent (MFI) was observed in the $CD84^{-/-}$ mice as compared to control mice (FIGS. 16A-B), which agrees with the previous in vitro results of CLL cells, where CD84 stimulation leads to a decrease in PD-1 (FIGS. 14C-E).

Example 9

Expression of PD-1, Lag3, 2b4, KLRG-1 and CTLA-4 are Decreased in the $CD84^{-/-}$ CLL Adoptive Transfer Mouse, Solely in the Organs where PD-L1 was Reduced PD-1 was shown to be co-expressed with Lag-3 and CTLA-4 on exhaustive and dysfunctional tumor infiltrating T cells [Baitsch, L. et al., PLoS One (2012) 7(2): e30852; Duraiswamy, J. et al., Cancer Res (2013) 73(12): 3591-3603]. The present inventors therefore suggested that decreased PD-L1 expression in the $CD84^{-/-}$ mice would induce more functional T cells and consequently a less exhaustive phenotype. Therefore, T cell exhaustive phenotype in the $CD84^{-/-}$ adoptive transferred mice was analyzed.

Figure 17A:
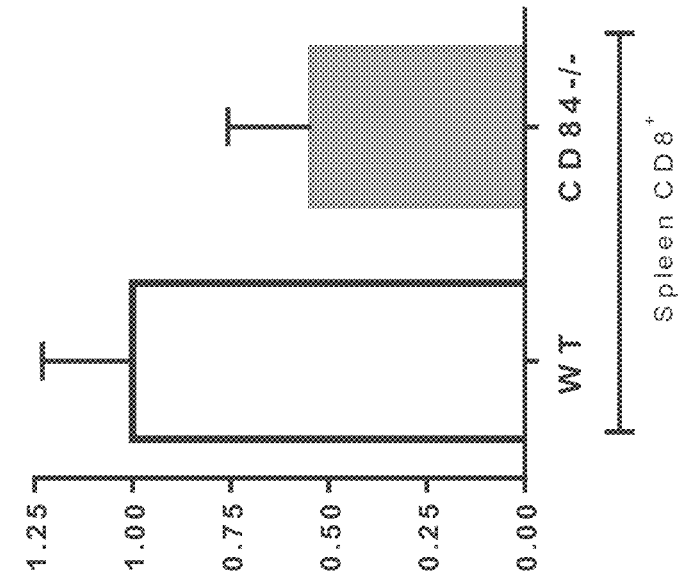
Figure 17B:
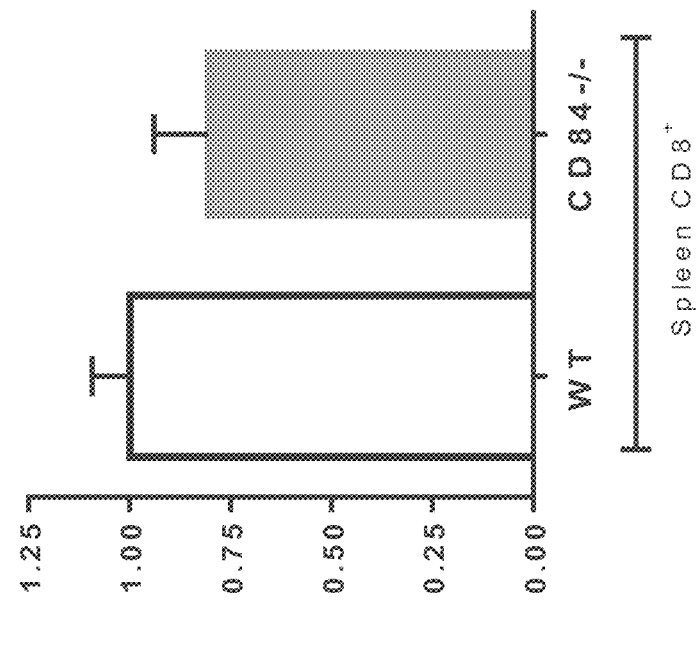
Figure 17C:
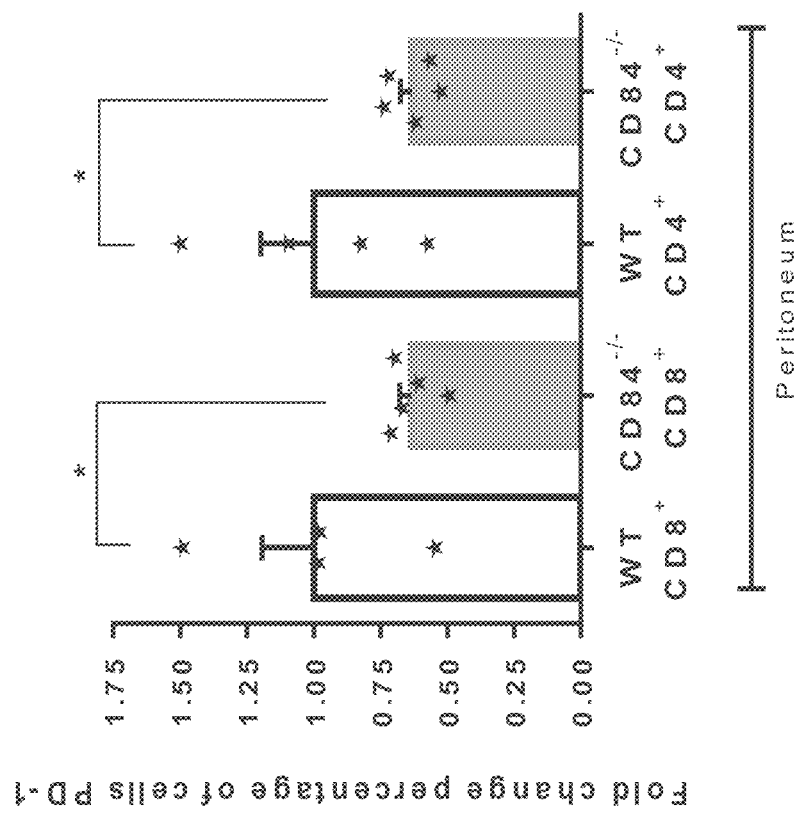
Figure 17D:
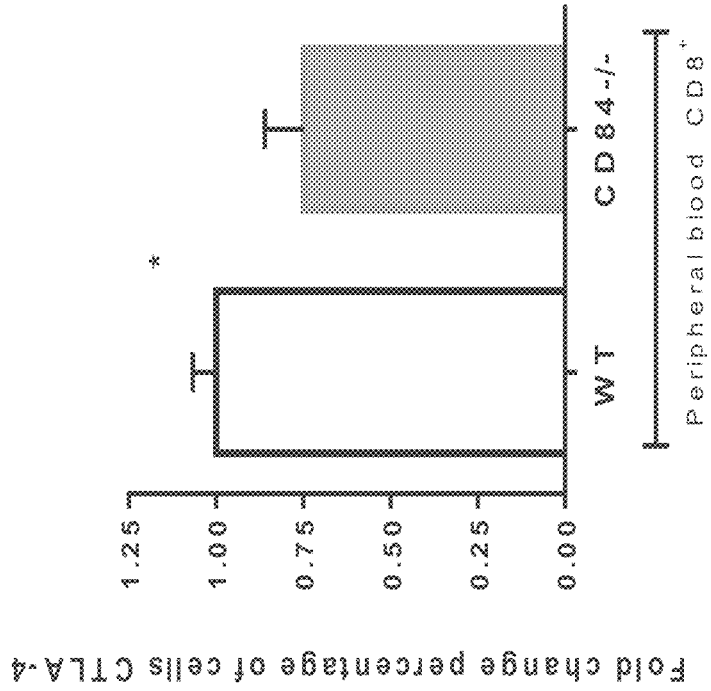
Figure 17H:
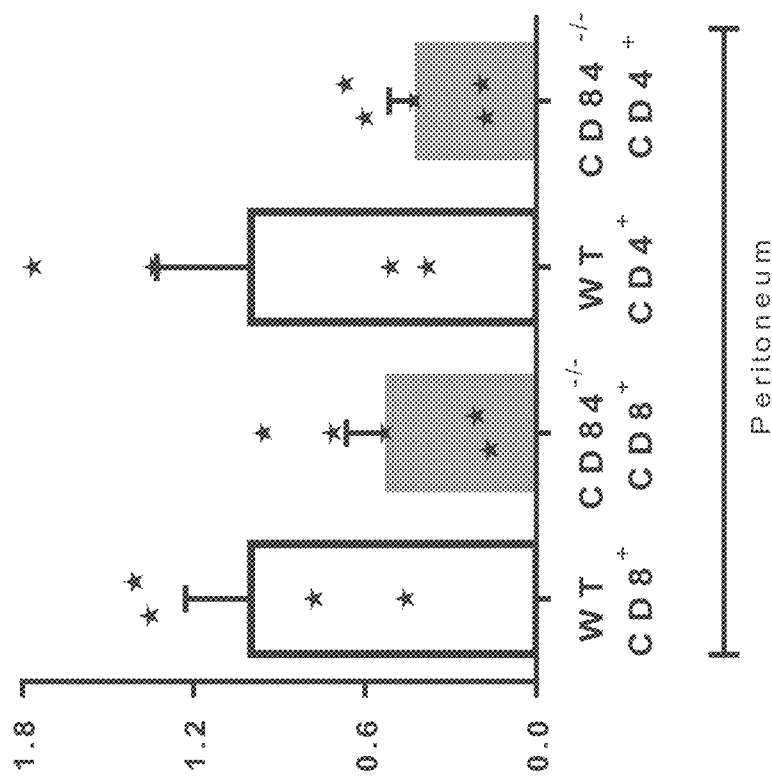
Figure 17G:
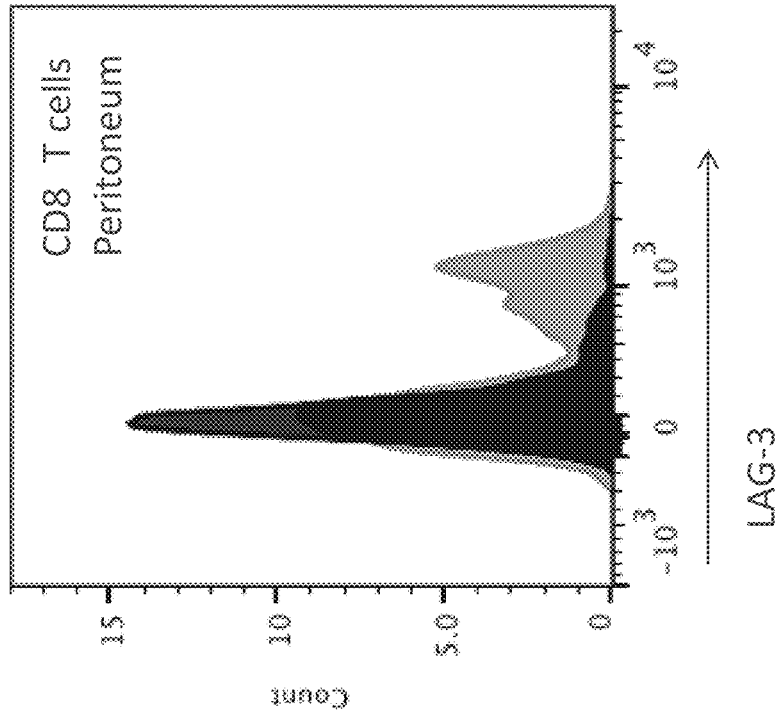
Figure 17J:
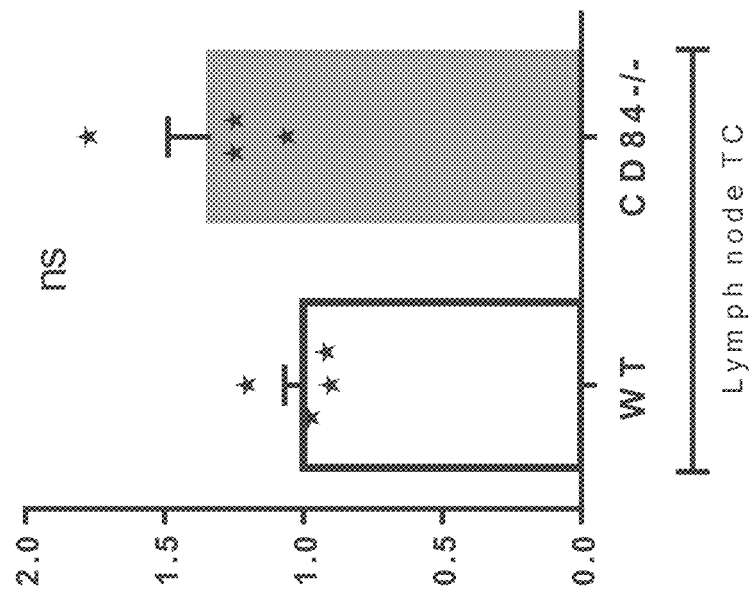
Figure 17I:
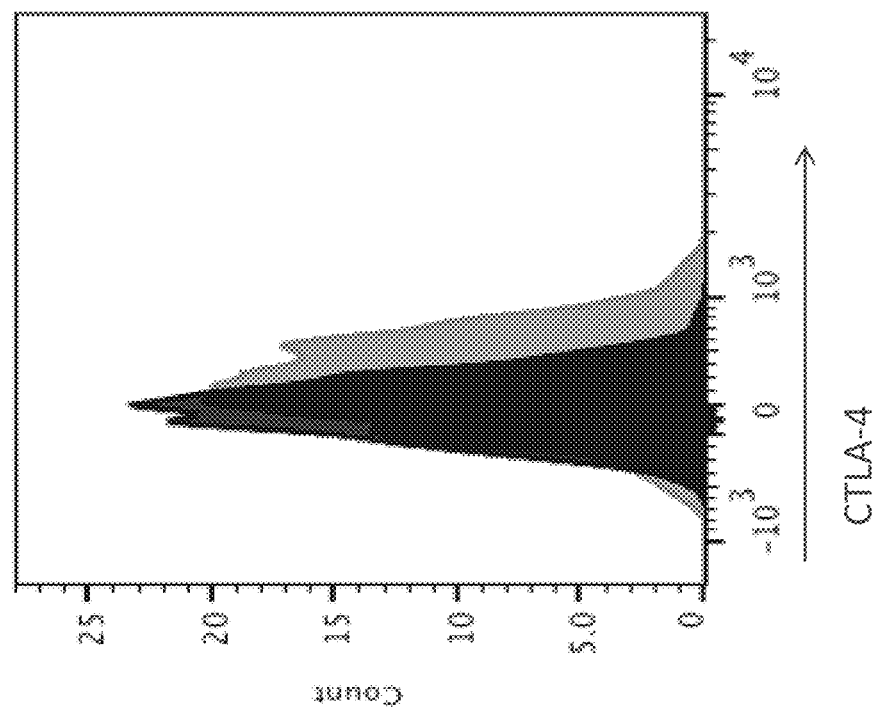
Figure 17K:
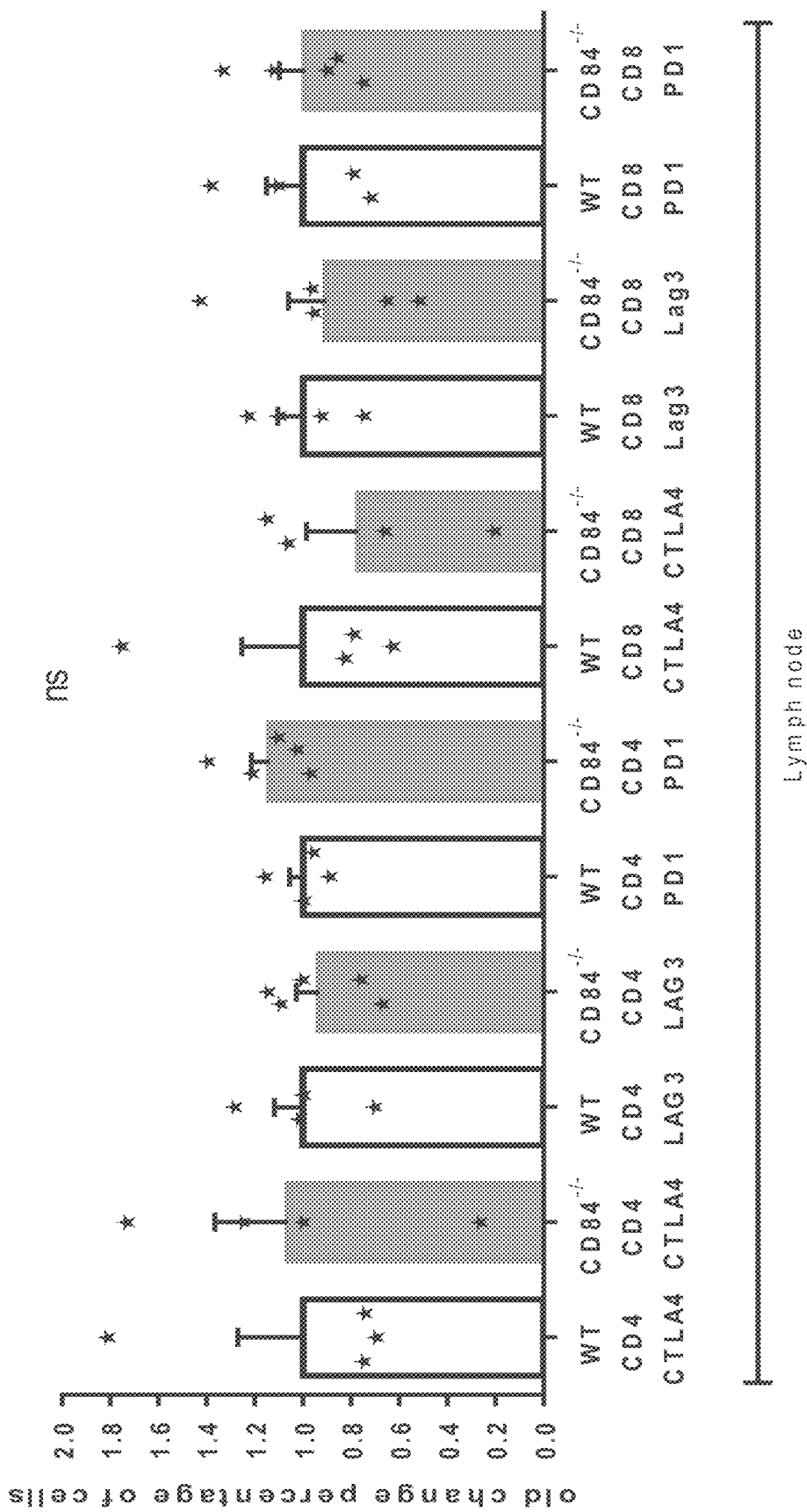
Figure 18B:
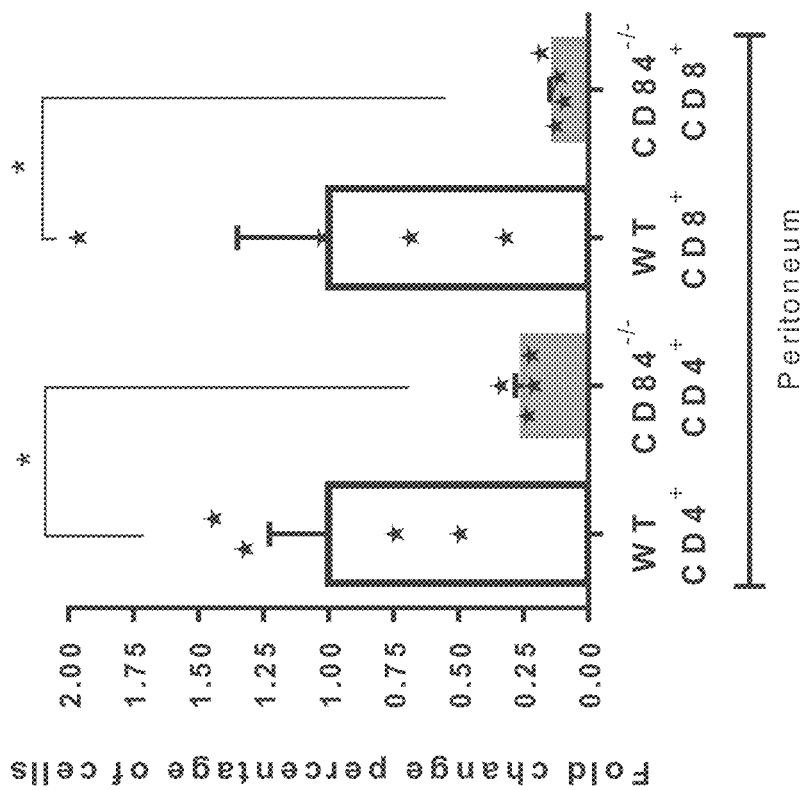
FIGS. 18A-18F are graphs illustrating that six months old chimeric TCL-CD84$^{-/-}$ mice display reduced levels of PD-L1 on TCLs and, conversely, reduced PD-1 on T cells.
Figure 18A:
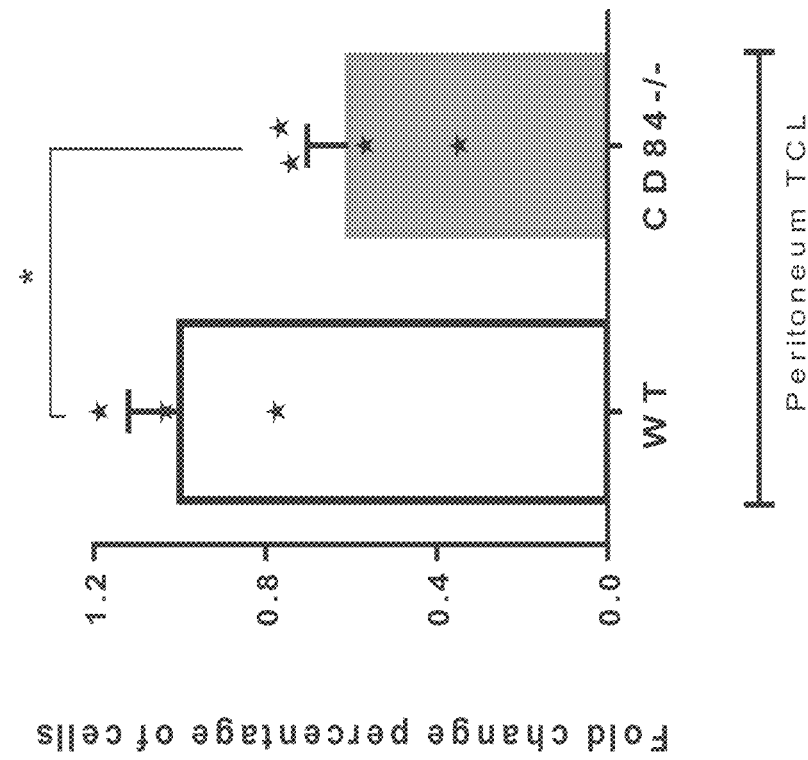
Figure 18D:
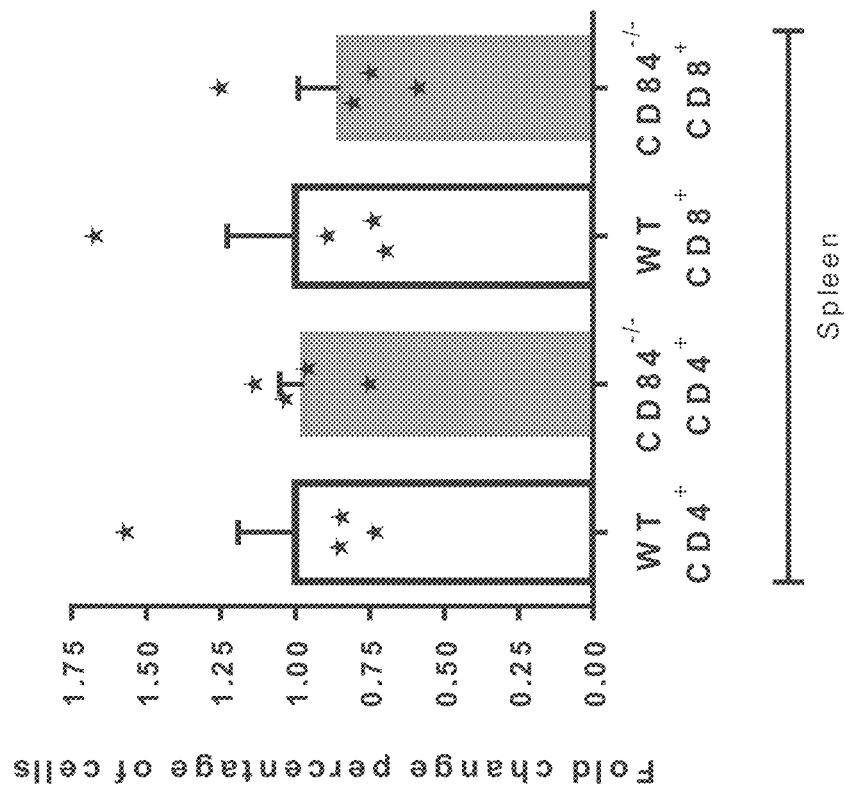
Figure 18C:
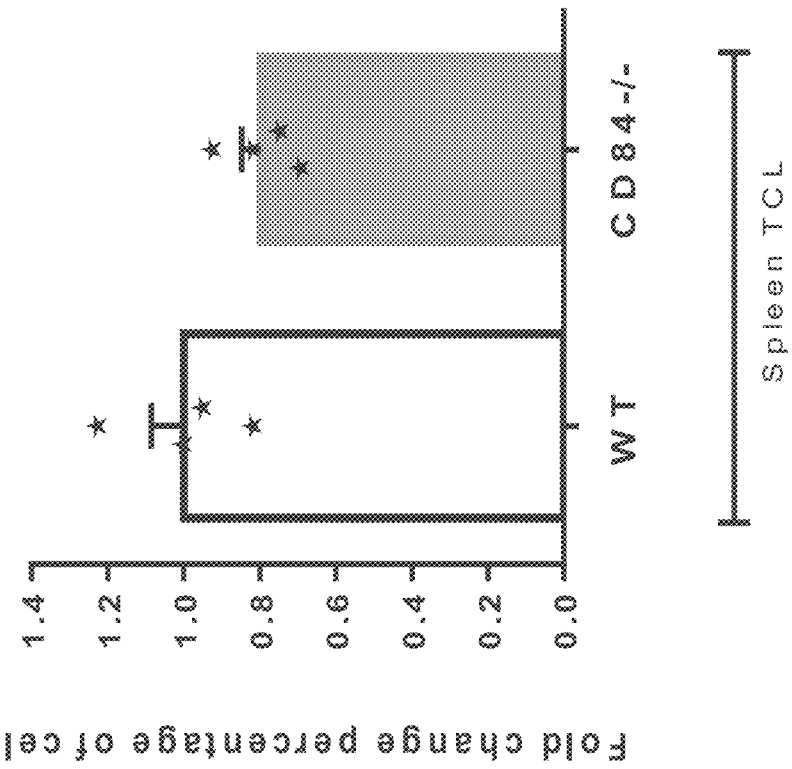
Figure 18E:
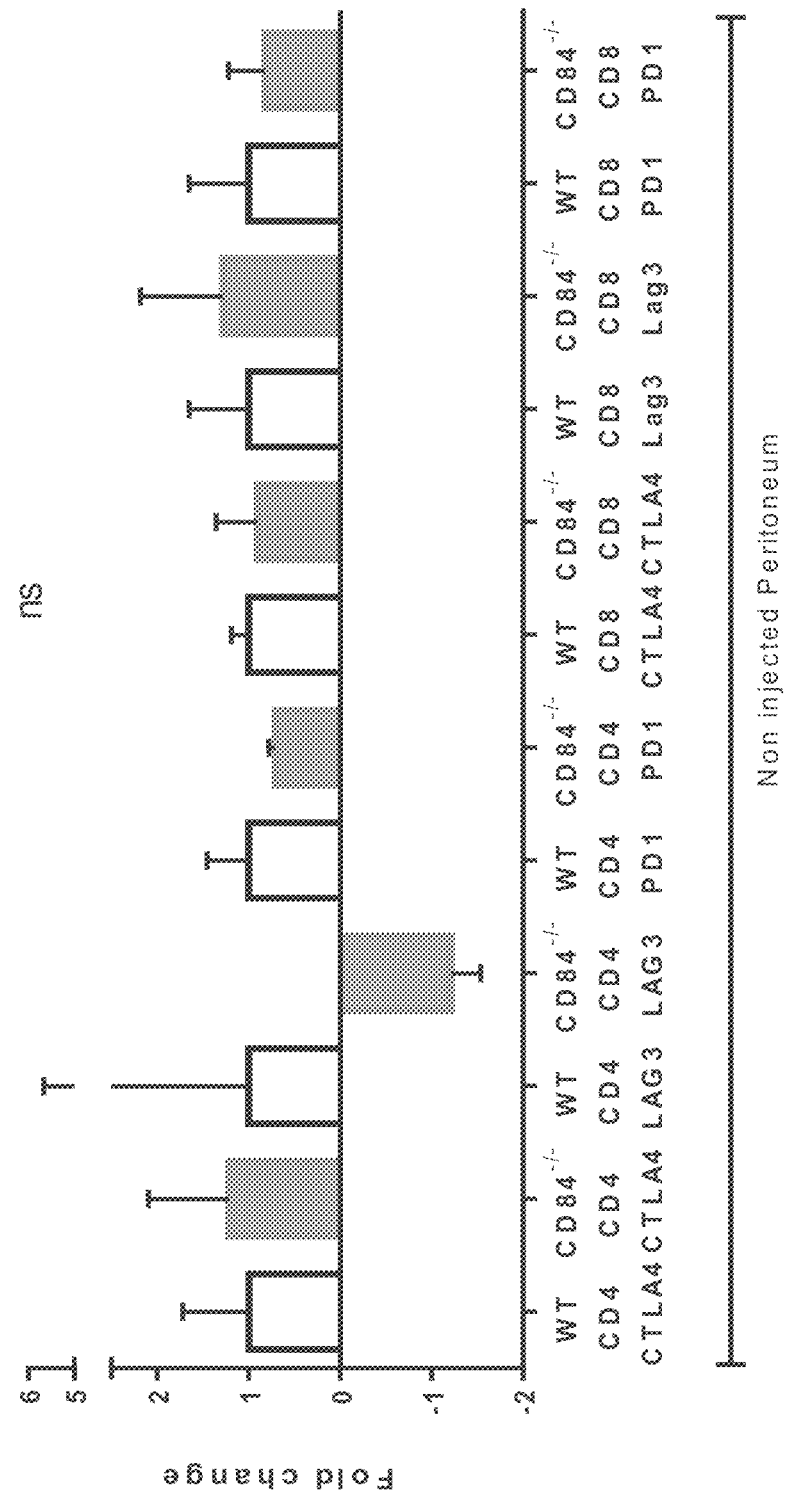
Figure 18F:
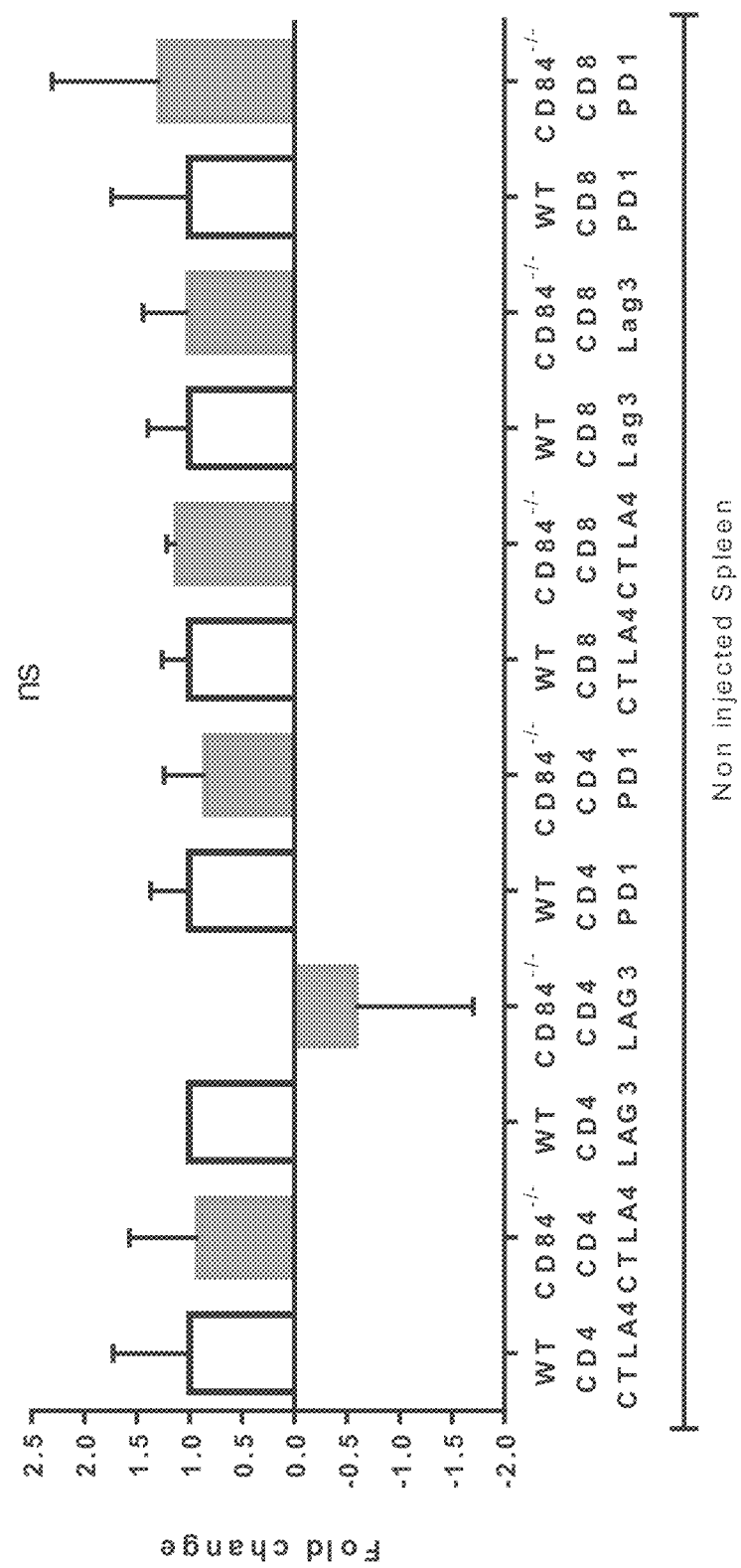
Figure 33:
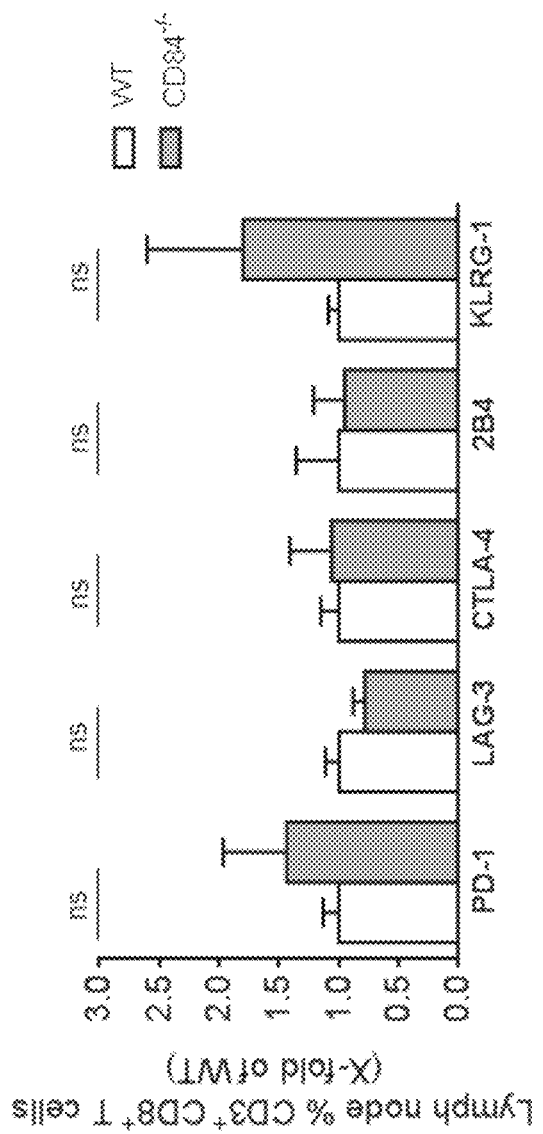
FIG. 33 is a graph illustrating CD8 T cell exhaustion markers in lymph nodes (n=3-8, ns p=0.1738, ns p=0.4895, ns p=0.8798, ns p=0.9190, ns p=0.4381).
Figure 35A:
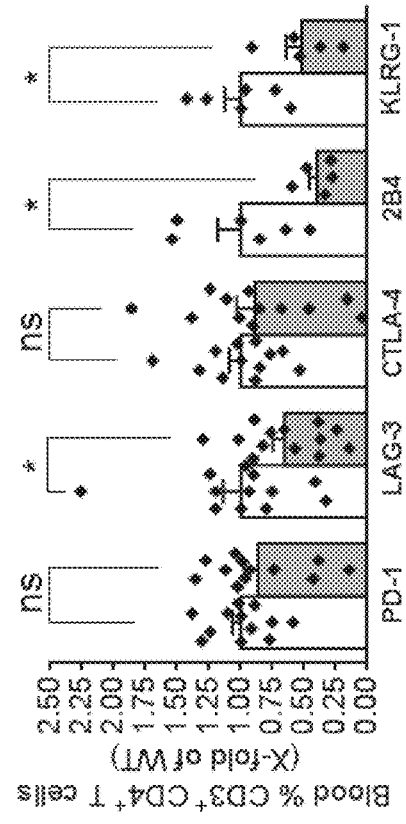
FIGS. 35A-35F are graphs illustrating that CD84$^{-/-}$ mice injected with murine CLLs exhibit less exhausted CD4 T cells. TCL-1 splenocytes (4×10$^7$) were injected i.v. into the tail vein of C57BL/6 wt or CD84$^{-/-}$ mice. After 14-21 days, the mice were sacrificed and expression of the exhaustive marker PD-1, Lag-3, CTLA-4, 2B4 and KLRG1 was determined on CD4 on spleen (n=6-11, ns p=0.1664, *p<0.05, *p<0.05, **p<0.01) (FIG. 35A); peripheral blood (n=5-11, ns p=0.3124, *p<0.05, ns p=0.5285, *p<0.05, *p<0.05) (FIG. 35B); peritoneal cavity (n=6-10, **p<0.01, *p<0.05, *p<0.05, *p<0.05, **p<0.01) (FIG. 35C); and bone marrow (n=4-7, ns p=0.0900, *p<0.05, ns p=0.6569, *p<0.05, **p<0.01) (FIG. 35D). From the spleen, cells were collected and cultured for 24 hours with anti-CD3 (Biolegend) and the last two hours of culture with brefeldin-A. These cells were then harvested and CD4 T cells were examined for expression of IFNγ and IL-2 (n=7-8, *p<0.05, ns p=0.3172) (FIG. 35E). BM cells (5×10$^6$) derived from 8-week-old TCL-1 mice or negative control littermates (wt) were injected into lethally irradiated C57BL/6 (wt) or CD84$^-$ deficient (CD84$^{-/-}$) mice. After 6 months, mice were killed and the expression of PD-1 was determined on CD4 (FIG. 35F) (n=3-4, *p<0.05).
Figure 35B:
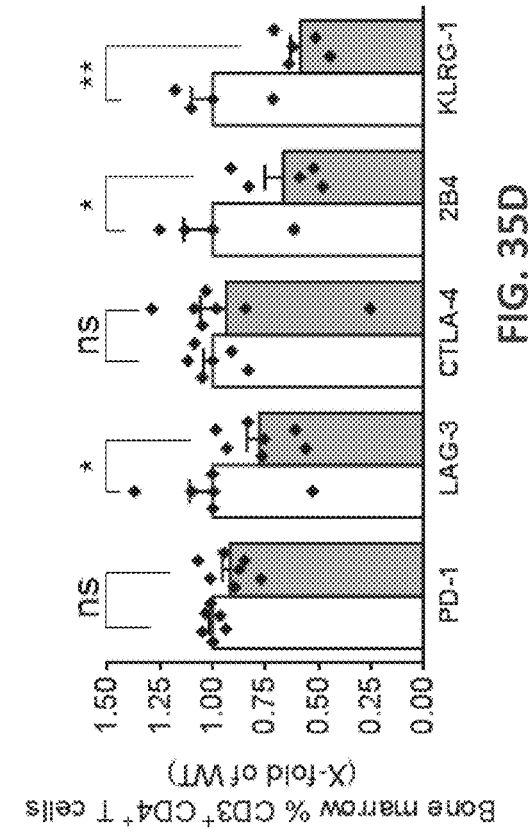
Figure 35C:
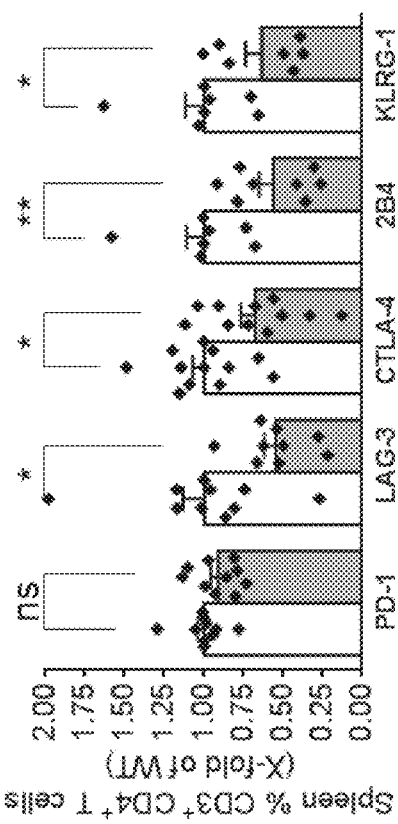
Figure 35D:
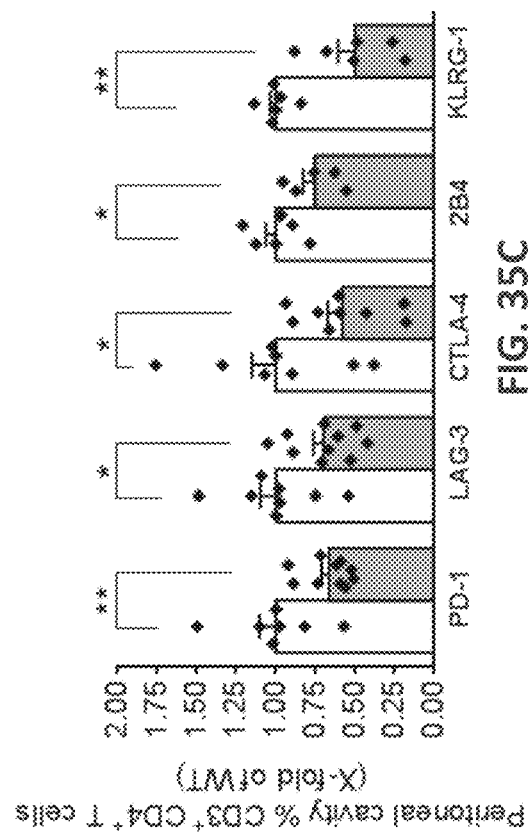
Figure 35F:
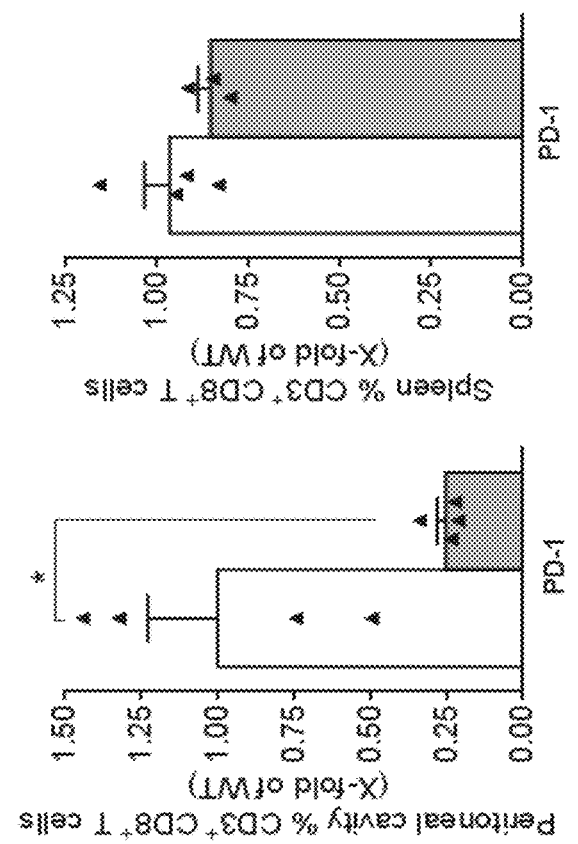
Figure 35E:
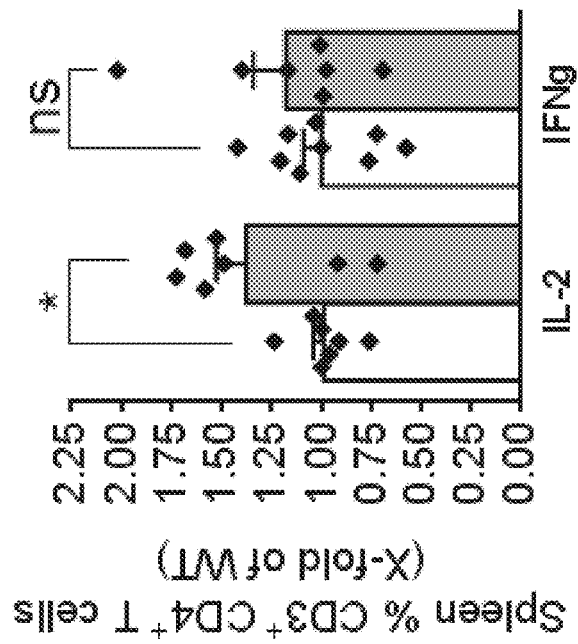

As shown in FIGS. 17A-I and 27A-E, PD-1, Lag-3, 2B4, KLRG-1 and CTLA4 cell surface expression levels were reduced on CD8 T cells when PD-L1 levels on TCL cells were low in the spleen, peritoneum and peripheral blood. In the lymph node, where no decrease in PD-L1 was observed, no significant decrease in Lag-3, CTLA-4 and PD-1 was detected (FIGS. 17J-K and 33).

To further prove that the effect on PD-1, LAG3 and CTLA-4 were due to the decrease in PD-L1 expression on the malignant cells and not due to an intrinsic lack of CD84 in T cells, chimeric mice were generated by irradiating $CD84^{-/-}$ mice and injecting them with wild type TCL BM. This generated mice with immune cells expressing CD84, while the microenvironment did not express this protein. As shown in FIGS. 18A-D, 25H-I and 27H, a significant decrease in PD-L1 staining was detected on TCL cells derived from the $CD84^{-/-}$ environment and conversely a decrease in PD-1 on T cells, suggesting that the reduced expression in not a T cell intrinsic effect.

Furthermore, comparison of non-injected CD3 activated cells derived from the peritoneum and spleen of wild type and $CD84^{-/-}$ mice did not illustrate a significant effect on the exhaustive phenotype as in the injected mice, strengthening the notion that the regulation is TCL-1 dependent (FIGS. 18E-F and 28A-C).

Figure 19B:
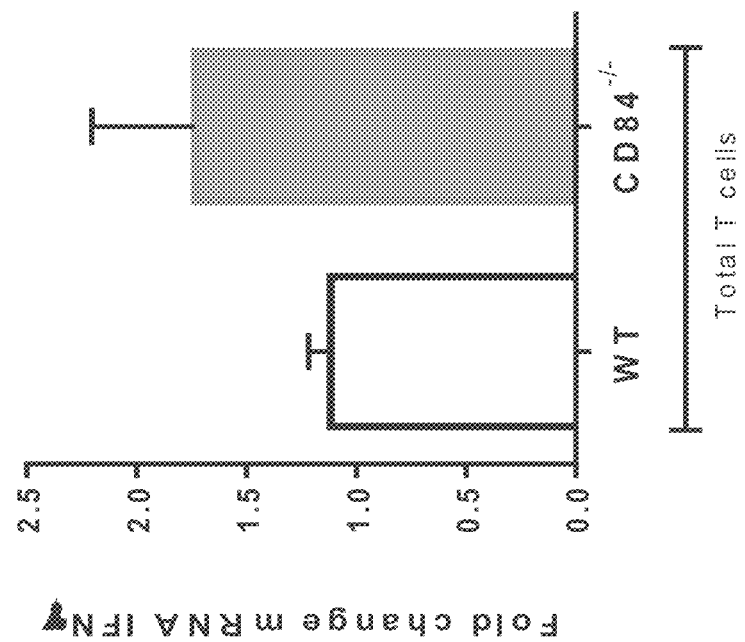
FIGS. 19A-19B are graphs illustrating increased functionality of T cells from CD84$^{-/-}$ TCL injected mice.
Figure 19A:
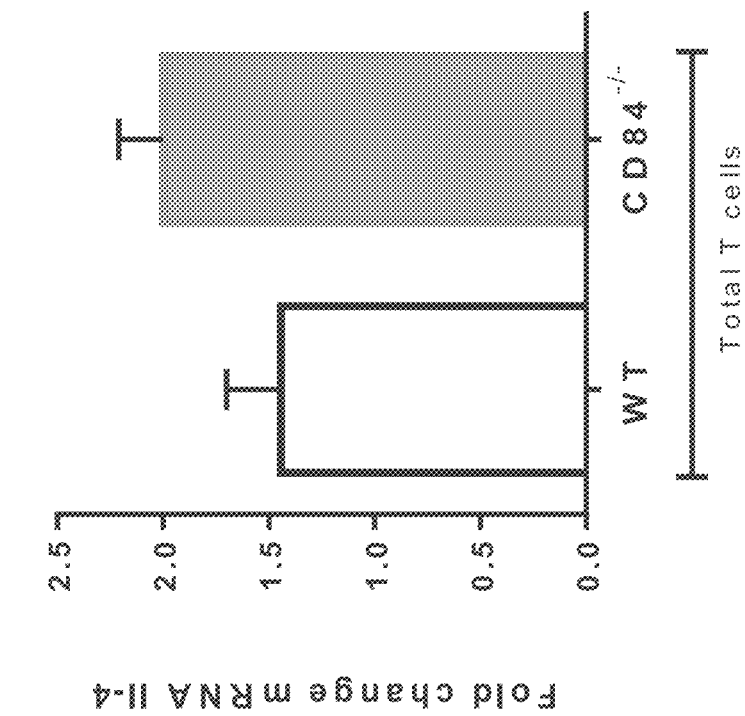
Figure 20B:
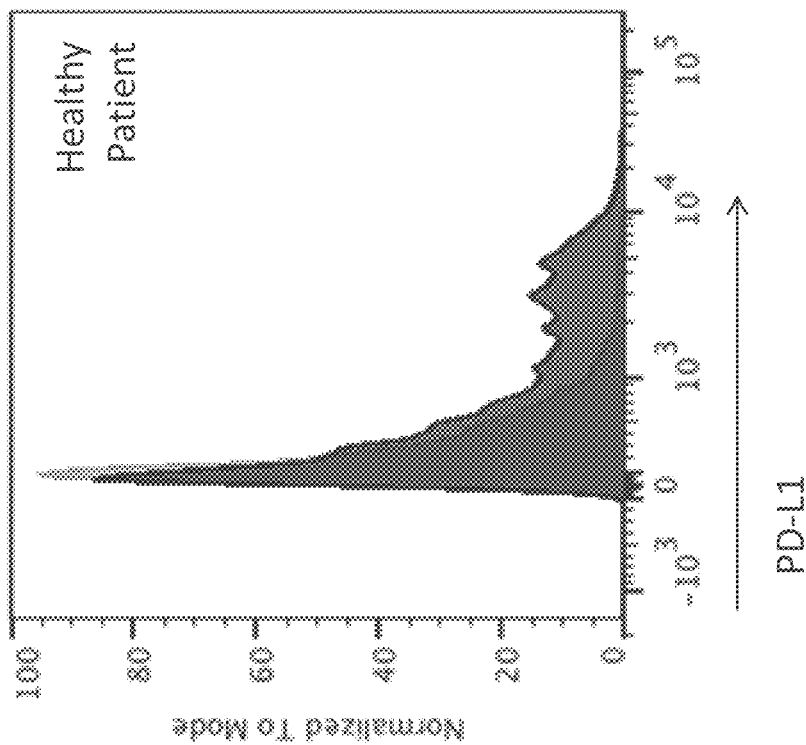
FIGS. 20A-20F are graphs illustrating increased PD-L1, as well as CD84 expression, on bone marrow stromal cells in CLL patients.
Figure 20A:
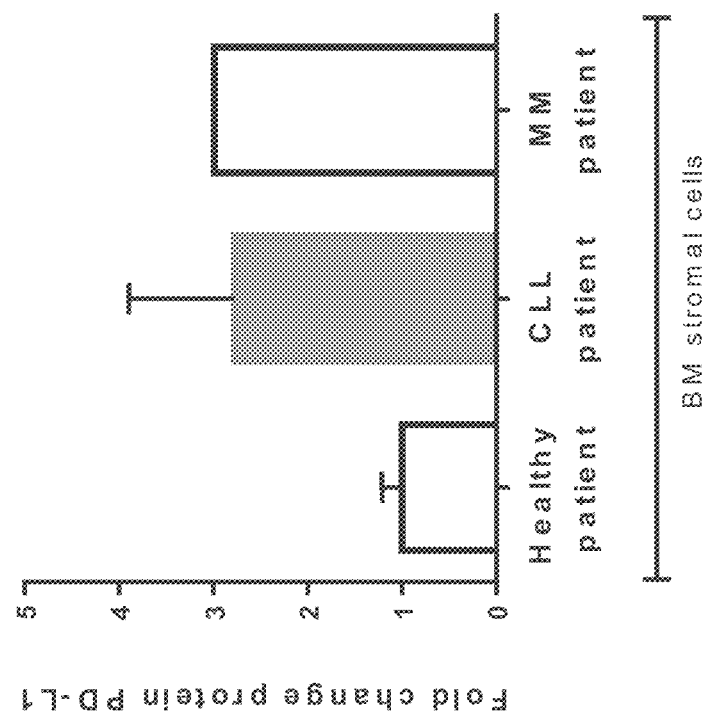
Figure 20D:
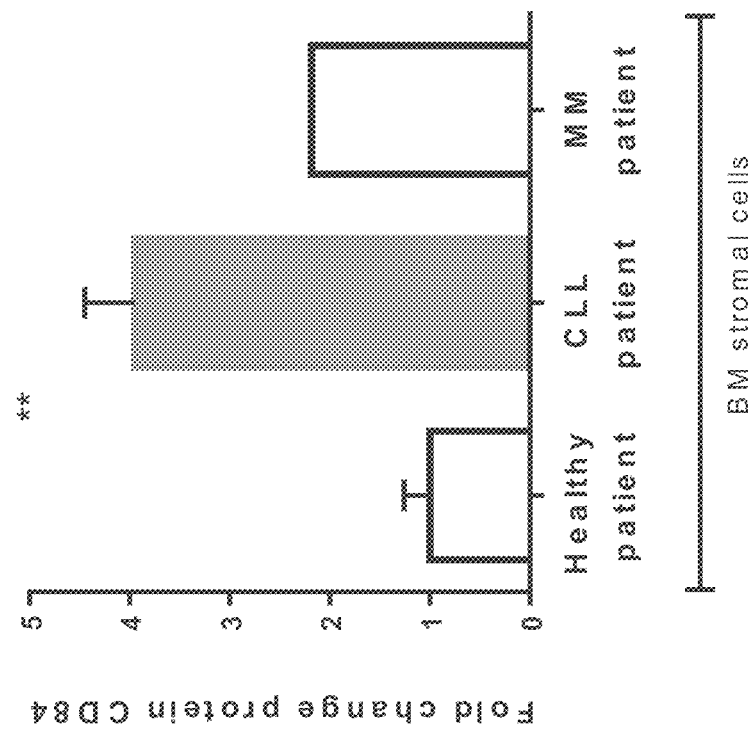
Figure 20C:
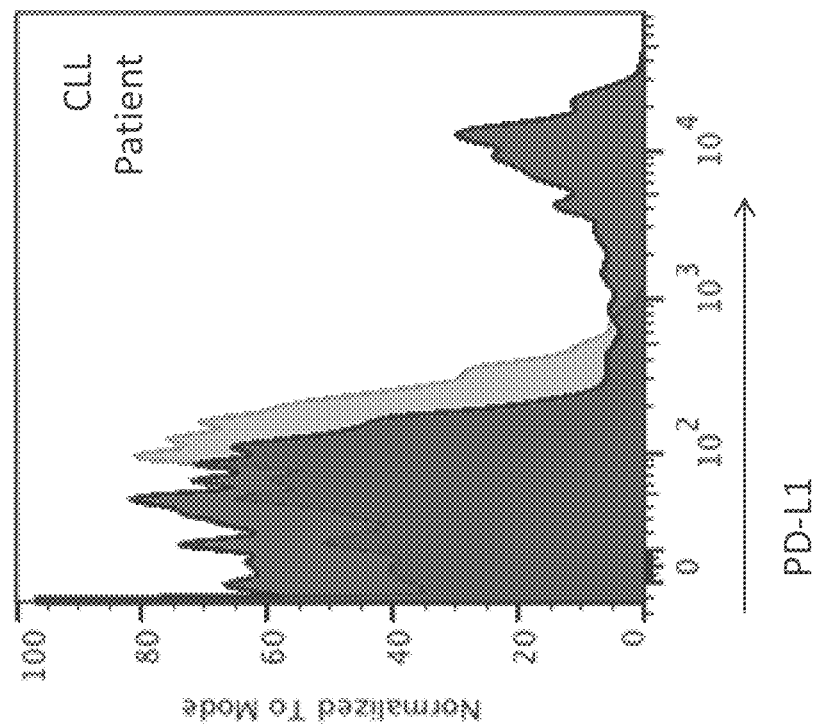
Figure 20F:
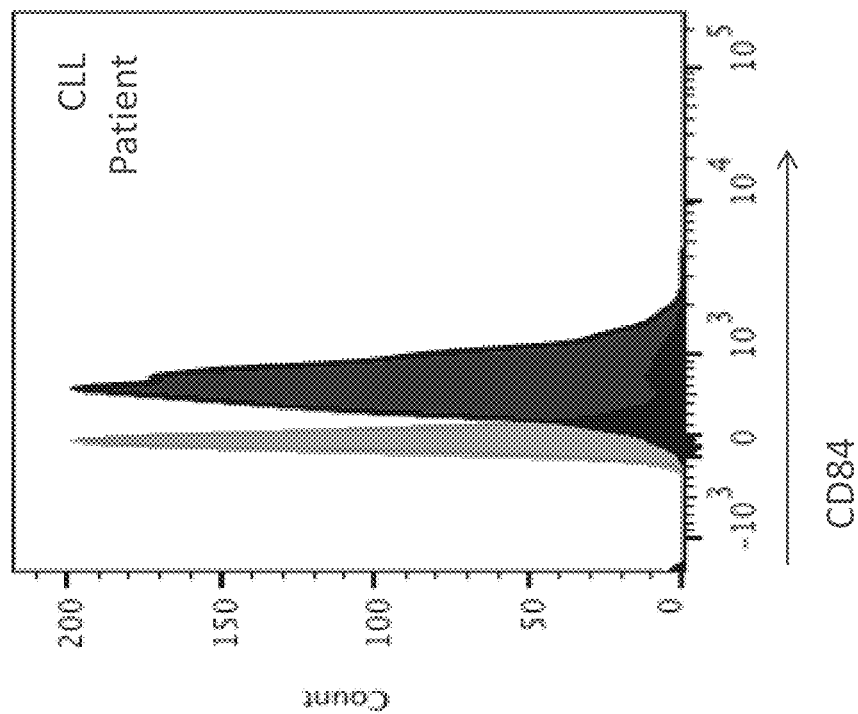
Figure 20E:
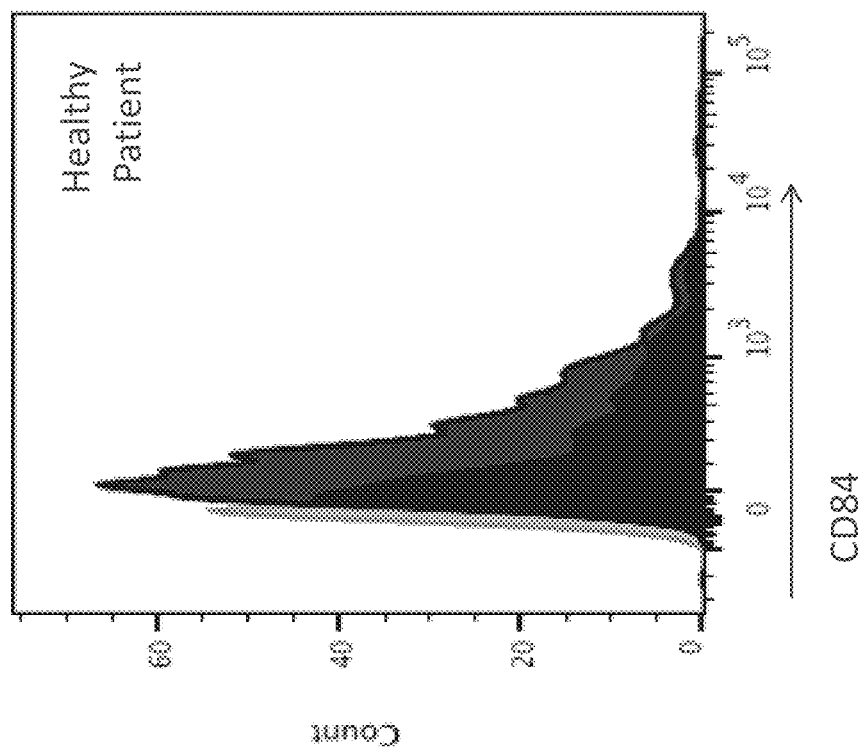

The present inventors then wished to determine the CD84 dependent effect on the TCL-1 derived T cells. To this end, spleens from the $CD84^{-/-}$ or wild type CLL adoptive transfer model mouse were harvested, and the B220 negative population was harvested. The cells were then grown on CD3-CD28 coated plates for 24 hours. mRNA was purified from the T cells and cytokine levels were than analyzed by qRT-PCR. As shown in FIGS. 19A-B, T cells harvested from $CD84^{-/-}$ mice showed an increase in the mRNA of IL-4 (FIG. 19A) and IFNγ (FIG. 19B) as compared to the levels in the wild type environment. This suggests that CD84 expressed on the microenvironment upregulates PD-L1 levels that reduces T cell activity. In its absence, PD-L1 levels are reduced resulting in more functional T cells, which display reduced exhaustive markers and are producing higher levels of IL-4 and IFNγ.

Example 10

CLL and Multiple Myeloma Patients have Increased PD-L1 Expression on their Bone Marrow Stroma To substantiate these results, the expression of PD-L1 and CD84 was analyzed on stroma cells derived from bone marrow aspirates derived from both confirmed healthy patient and CLL patients, as well as multiple myeloma patients. A marked increase in PD-L1 (FIGS. 20A-C and 30B) and CD84 (FIGS. 20D-F and 30A) expression levels were detected on cells derived from CLL and MM patients compared to the levels on healthy controls.

Example 11A

PD-L1 is Regulated by CD84 in Additional B Cell Malignances

The present inventors next wanted to explore the regulation of PD-L1 expression by CD84 in additional B cell malignancies.

Figure 21B:
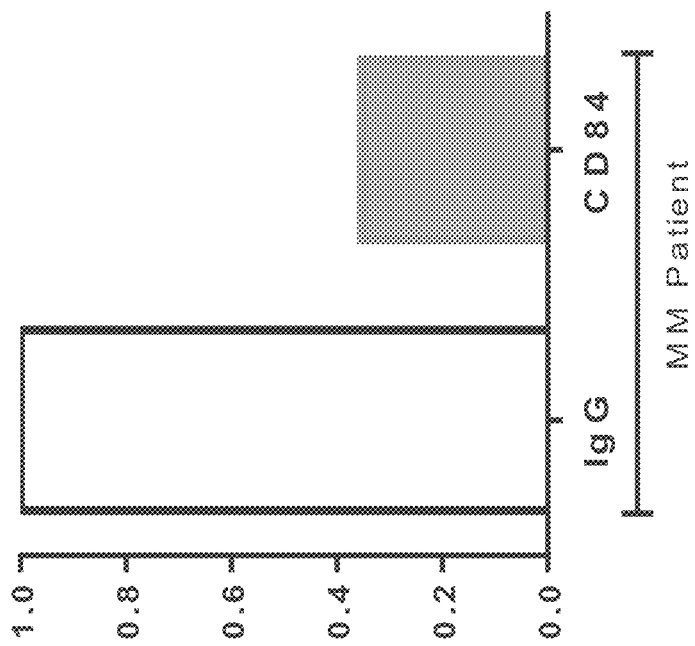
FIG. 21A-21B are graphs illustrating regulation of PD-L1 by CD84, in Multiple myeloma.
Figure 21A:
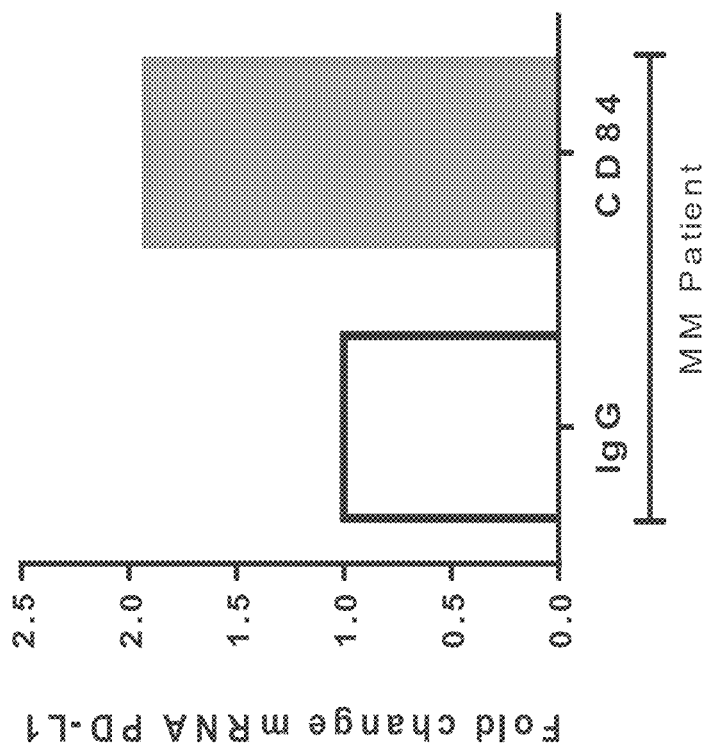

As illustrated in FIGS. 21A and 30D, an increase in PD-L1 was detected following activation of CD84, in which cells were sorted for mRNA levels and stained for CD38 and CD138 for protein levels. Furthermore, in this sample, the expression of the receptor PD-1 was decreased (FIG. 21B) similarly to what was observed in CLL cells (FIGS. 14C-D). To further determine if CD84 regulates PD-L1 in the microenvironment of MM, bone marrow stromal cells derived from patient bone marrow aspirates were stimulated with CD84. A significant increase in PD-L1 was observed on both RNA and protein levels (FIG. 30C).

Figure 22A:
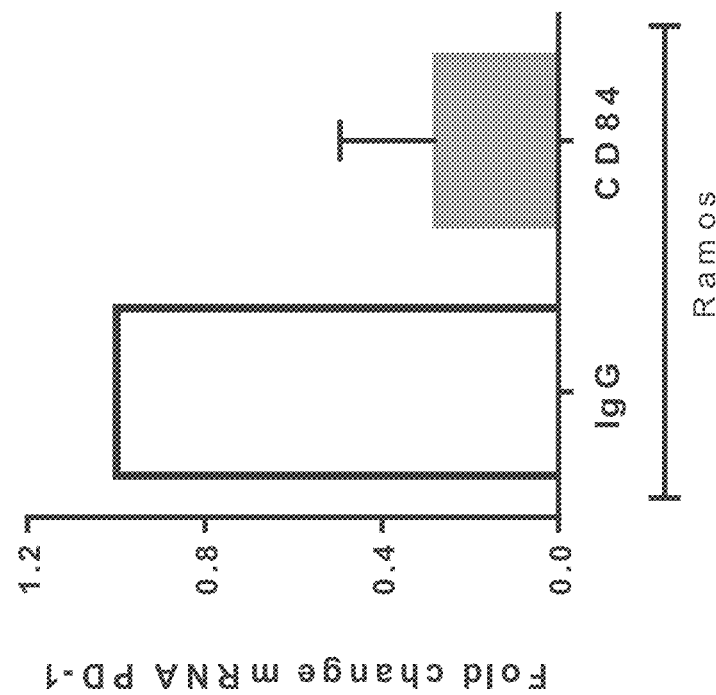
FIGS. 22A-22F are graphs illustrating that CD84 might regulate PD-L1/PD-1 in other B cell malignancies.
Figure 22B:
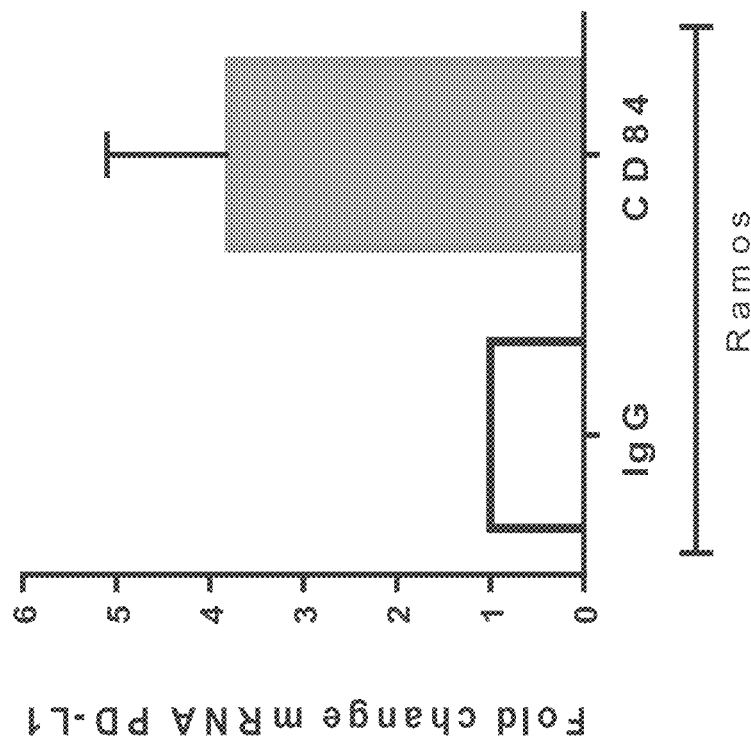
Figure 22D:
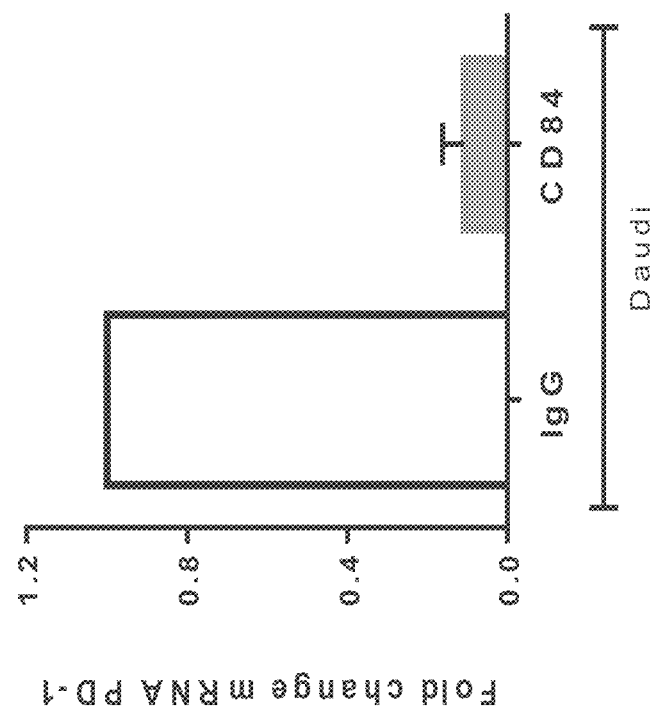
Figure 22C:
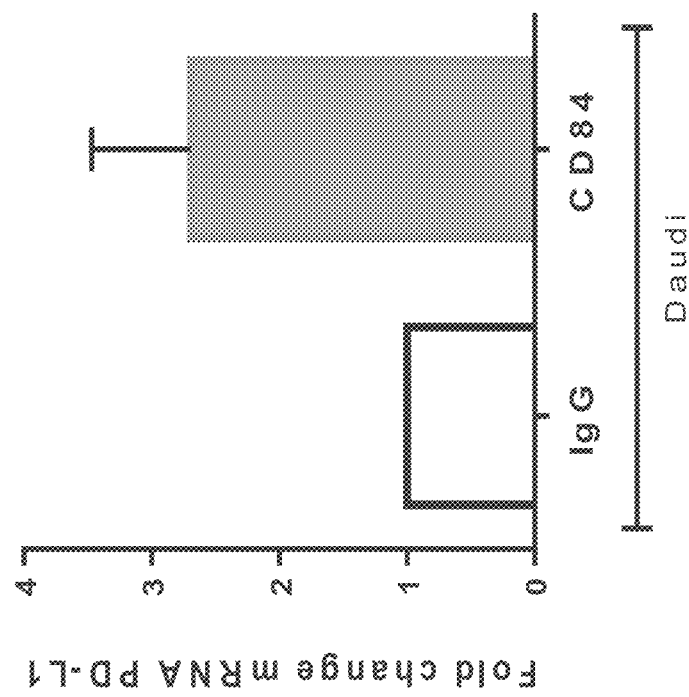
Figure 22F:
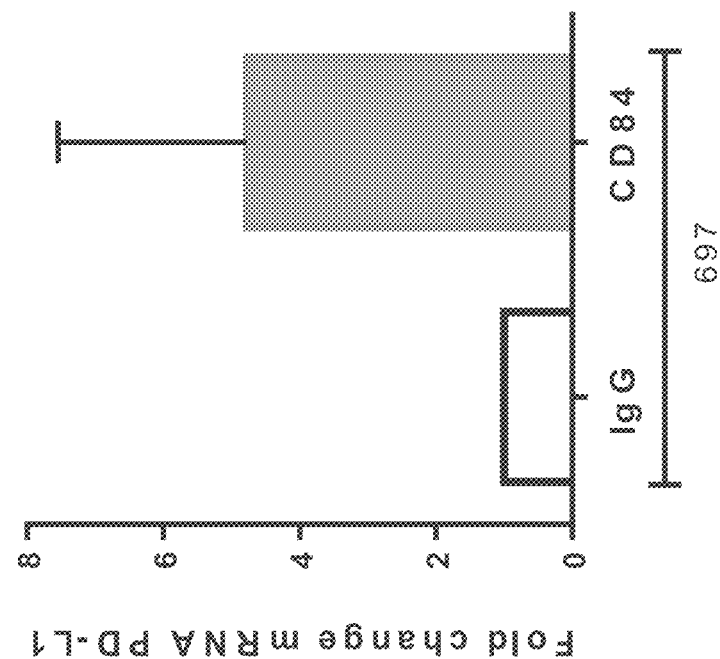
Figure 22E:
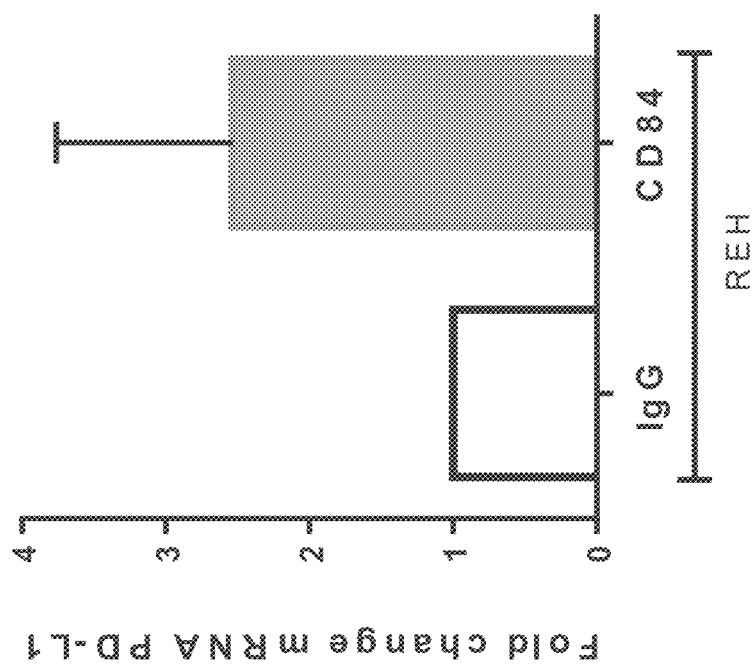

Moreover, stimulation of CD84 expressed on the Burkitt's lymphoma cell lines, Ramos and Daudi, with anti-CD84 antibody (4 µg/ml) elevated the amount of PD-L1 mRNA by 4- and 2.5-fold, respectively (FIGS. 22A and 22C, respectively). This stimulation decreased the amount of the PD-1 receptor, as seen for CLL and MM, by about 0.9 fold for the Daudi cell line and about 0.7 fold for the Ramos cell line (FIGS. 22B and 22D, respectively). The stimulation was also analyzed on the Acute Lymphoblastic Leukemia (ALL) cell lines REH and 697 where the increase of PD-L1 mRNA was about 2- and 4-fold, respectively (FIGS. 22E-D, respectively).

Taken together, this shows that CD84 regulates PD-L1/PD-1 expression in various B cell malignancies.

Example 11B

CD84 Activation Might Also Up Regulate PD-L1 in Multiple Myeloma Cells In Vivo

Figures 37A, 37B:
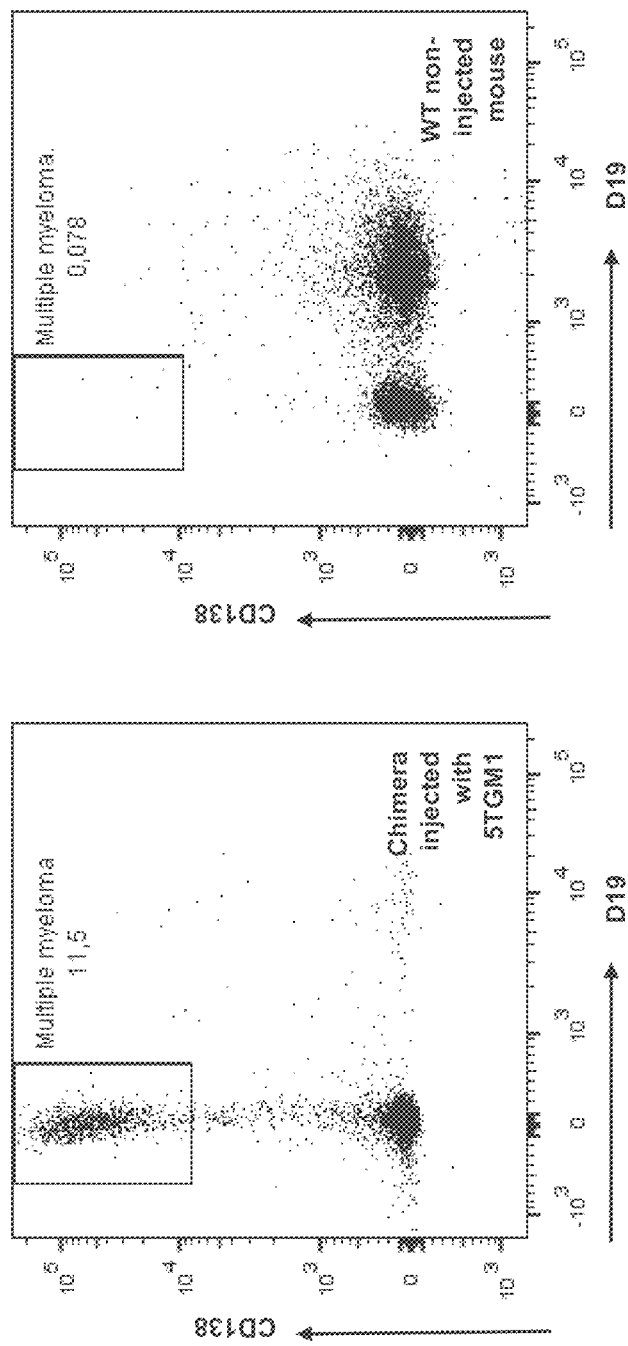
FIGS. 37A-37B are graphs illustrating the MM chimeric mice. CD84$^{-/-}$ or wt mice were lethally irradiated and their bone marrow was reconstituted with C57BL/Kalwrij bone marrow and thereafter injected with the 5TGM1 MM cell line. Displayed is a comparison between an injected mouse and a WT, clearly displaying the MM cells.

To address the question whether CD84 deficiency could affect T cells, as in CLL, the present inventors used the 5TGM1 and the C57BL/KaLwRijHsd model. This model cannot engraft and create myeloma in C57BL/6 mice, therefore C57BL/6 CD84$^{-/-}$ and WT mice were irradiated and reconstituted with bone marrow of C57BL/KaLwRijHsd mice. The mice were then I.V. injected with the 5TGM1 cells, which resulted in the development of the multiple myeloma disease (FIGS. 37A-B).

As shown in FIG. 31A, PD-L1 expression on 5TGM1 cells in the BM was reduced. Further CD8 and CD4 T cells displayed reduced exhaustion markers (FIGS. 31B, 31D) as well as increased cytokines and cytotoxic factors (FIGS. 31C, 31E).

Taken together, these results suggest a similar regulatory mechanism for CD84 in MM.

Example 11C

Regulation of Activity of CLL Derived Human T Cells

Figure 36A:
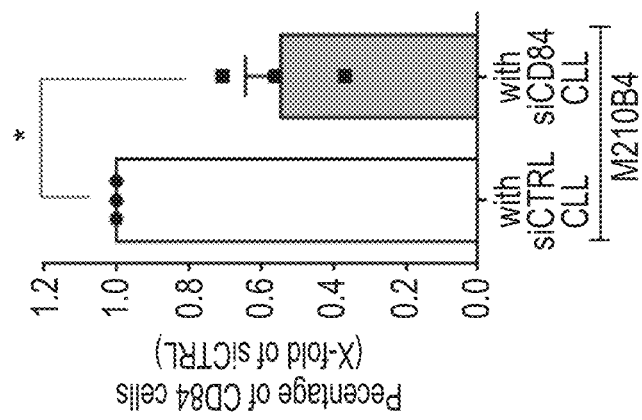
FIGS. 36A-36B are graphs illustrating that M210B4 cells co-cultured with siCD84 treated CLL display reduced levels of CD84 (n=3, *p<0.05) (FIG. 36A). Prior to co-culture, CLL cells were purified with beads (anti-CD19 beads, Miltenyl) and determined to contain solely CLL cells (FIG. 36B), and thereafter treated with siRNA against CD84.
Figure 36B:
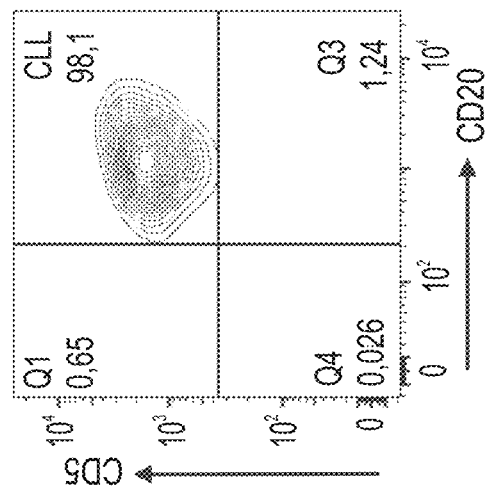

The presently described murine models displayed a regulation of PD-L1 expression by CD84 that could be utilized as a regulation of functionality of T cells. The present inventors next wished to determine whether CD84 regulates PD-L1 expression and T cell function in cells derived from CLL patients. For this aim, peripheral blood (PB) CLL cells were purified (purity after CD19 beads is shown in FIG. 36B) and treated with siCD84 or siCTRL (100 nm, Dharmacon). 24 hours later the rest of the peripheral blood cells were added back to a 48 hour co-culture.

Reduced expression of CD84 in CLL cells resulted in downregulation of PD-L1 expression on these cells (FIGS. 29A-B). Strikingly, T cells incubated with the CD84 deficient CLL cells, showed reduced expression levels of the exhaustion markers PD-1, Lag-3 and CTLA-4 (FIGS. 29D-E). Interestingly, in a very similar fashion to the phenotype in the murine TCL-1 model, the effect on CD8+ T cells was more significant compared to the effect on the CD4+ population (FIG. 29F).

Finally, the present inventors wanted to determine whether disruption of CD84 could abolish the increased PD-L1 observed in the microenvironment. To this end, CD84 expression levels in CLL cells were downregulated with siCD84. After 24 hours, these cells were co-cultured with M210B4 cells for an additional 48 hours. A significant decrease in PD-L1 to expression levels detected in M210B4 cultured alone were detected when CD84 levels were lowered on CLL (FIG. 29C), in addition the M210B4 also displayed decreased CD84 (FIG. 36A).

Together, these results suggest that reduced expression of CD84 in CLL downregulated PD-L1 expression levels on itself and in the microenvironment, resulting in induced activity of the T cells.

Example 12

A Role for CD84 in Acute DSS Induced Colitis

Figure 38:
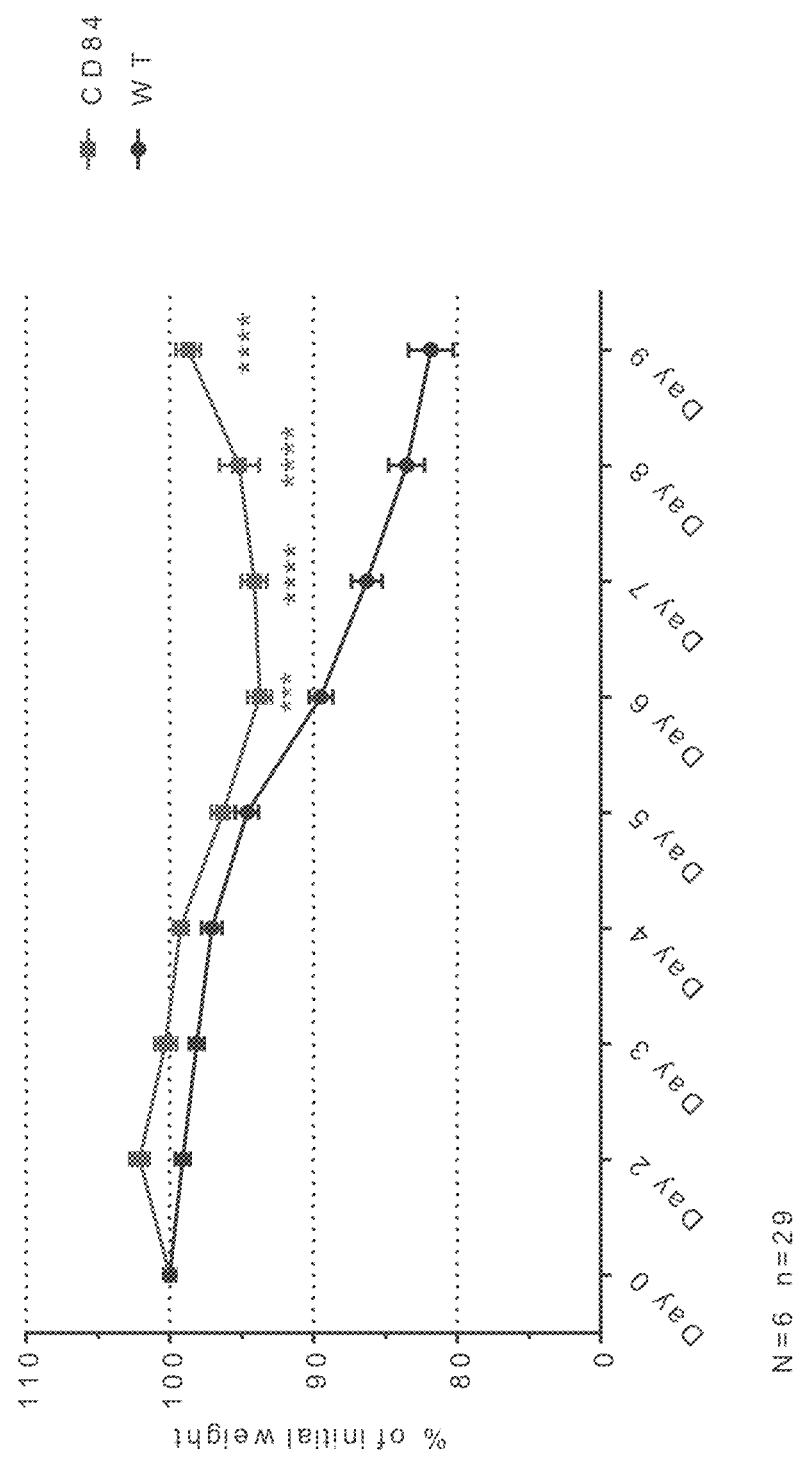
FIG. 38 is a graph illustrating the role of CD84 in acute DSS induced colitis. Mice were treated with 2% DSS via their drinking water for 5 days and then received normal water for 4-7 days, or until the end of the experiment. Mice were weighted daily for monitoring of disease progression. The graph shows the percent of weight change in wt mice compared to CD84 ko mice. Bars show SEM.

One of the models to study Bregs in mice is the Dextran sulfate sodium (DSS)-induced colitis model. In order to understand if CD84 plays a role in colitis, it was first assessed whether CD84 plays a role in the development and severity of colitis. In the acute DSS model, mice received 2% DSS in their drinking water for 5 days, and then normal water for 4-7 days until the end of the experiment. The weight of the treated mice was determined every day in order to follow the clinical sign of the disease. As illustrated in FIG. 38, CD84$^{-/-}$ (CD84 ko) mice lost less weight as compared to wild type (wt) mice. These results suggest that the CD84 plays a role in colitis induction, and in its absence the inflammatory response is reduced.

Example 13

A Role for CD84 in Chronic DSS Induced Colitis

Figure 39:
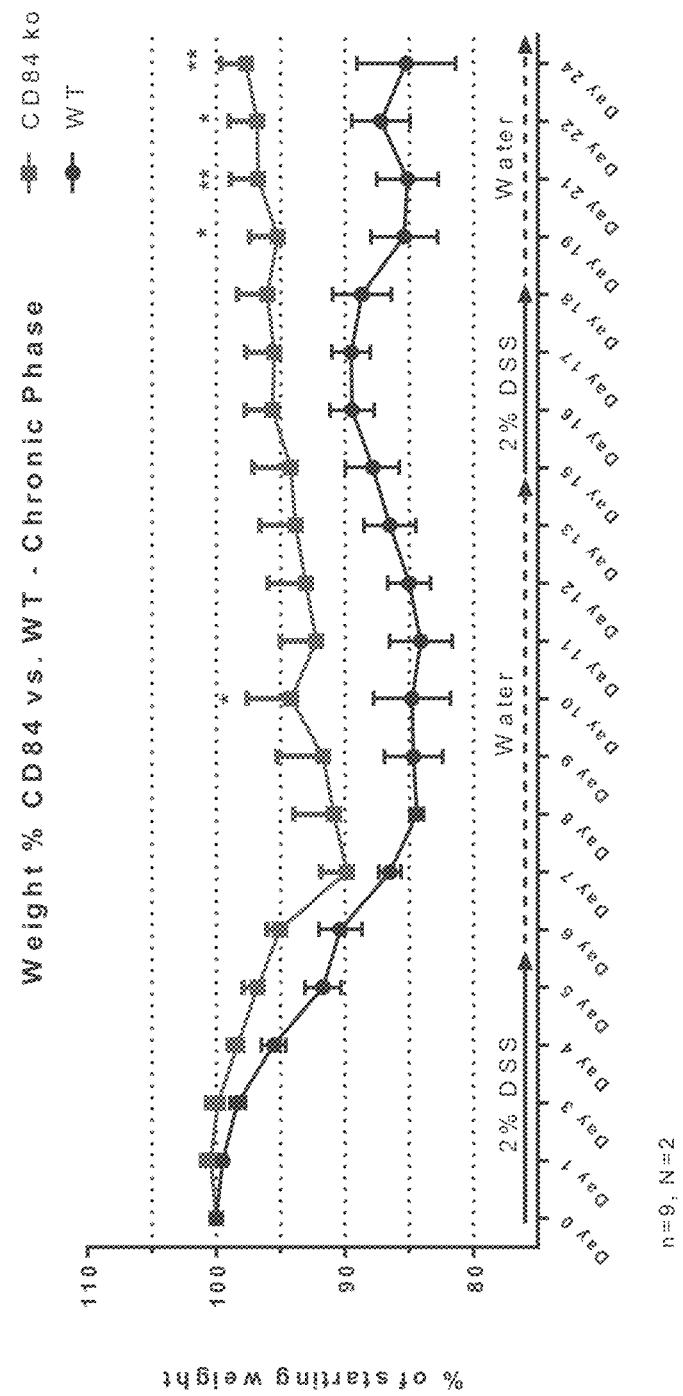
FIG. 39 is a graph illustrating the role of CD84 in chronic DSS induced colitis. Wt and CD84$^{-/-}$ mice were treated with two cycles of 2% DSS. The first cycle was from day 0 to day 5 followed by 10 days with water for recovery. The second cycle of DSS was given at day 15 for 5 more days followed with regular drinking water. Weight was monitored daily for monitoring of disease progression. Graphs show weight change in wt mice compared to CD84 ko mice. Bars show SEM.

Inflammatory bowel diseases (IBD) are typically known as chronic pathologies. Chronic models of colitis in mice exhibit different immune responses and different cytokines when compared to acute disease. Therefore, the present inventors next analyzed a chronic model of colitis, in which DSS was administered in repetitive cycles leading to chronic intestinal inflammation. Mice received two cycles of 5 days 2% DSS with 10 days recovery between the two cycles. As illustrated in FIG. 39, CD84$^{-/-}$ (ko) mice were completely resistant to the second cycle of DSS and continued their healing process. These results imply a role for CD84 in regulation of the immune response during inflammation.

Example 14

CD84 Affects Regulatory B Cell Populations in Colitis

Since it was shown that CD84 deficient mice are more resistant to DSS induced colitis, the present inventors examined next whether CD84 plays a role in regulating Breg subsets. For this aim, different subsets of regulatory B cells (i.e. B10: $CD19^+$, $IL-10^+$, $CD1d^{hi}$, $CD5^+$; Mz: $CD19^+$, $IL-10^+$, $CD24^+$, $CD21^+$, $CD23^-$; T2-MzP: $CD19^+$, $il-10^+$, $CD24^+$, $CD21^+$, $CD23^+$) were analyzed in spleen and mesenteric lymph nodes (MLN).

Spleen and MLN were harvested from wt and $CD84^{-/-}$ mice on day 10 from the start of DSS induced colitis. B cells were enriched by using $B220^+$ beads and activated with LPS for 5 or 24 hours. PIM (PMA, Ionomycin and Monensin) were added for the last 5 hours of activation. As seen in FIGS. 40A and 40C, CD84 deficiency led to a significant increase in almost all the regulatory B cell populations in the spleen, both in 5 and 24 hours of activation. In the mesenteric lymph nodes, however, a reduction in the regulatory B cell populations in CD84 deficiency was observed (FIGS. 40B and 40D). These results may indicate that CD84 has an effect on regulatory B cells generation both in spleen and MLNs. The significant increase of Bregs in the spleen correlated with the milder disease seen in the $CD84^{-/-}$ mice.

Example 15

CD84 Role in EAE

In order to evaluate the involvement of CD84 in regulation of Bregs differentiation and function, another animal model was used, namely the murine experimental autoimmune encephalomyelitis (EAE) model for multiple sclerosis (MS). EAE was induced in wt and $CD84^{-/-}$ ko mice by treating these mice with MOG 35-55 peptide and pertussis toxin (PT). Mice were followed for 27 days to observe the clinical EAE phenotype. The results illustrated that $CD84^{-/-}$ ko mice exhibited a significant milder disease compared to wt mice, as seen by the lower clinical score (FIG. 41A) and lower weight loss (FIG. 41B). At day 27 of the disease, the regulatory B cell population in the spleen was analyzed 5 hours (FIG. 41C) or 24 hours (FIG. 41D) hours following activation. As illustrated in FIGS. 41C-D, a significant increase in Breg populations, namely B10, Mz and T2-MzP, was detected in the two time points. In addition, the T cell response in this model was analyzed. No significant differences were detected in the CD4 T cell population (FIGS. 41E-F). These results suggest that CD84 deficiency protected the mice from induced EAE, which likely results via elevation of the regulatory B cell population.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims.

It is the intent of the applicant(s) that all publications, patents and patent applications referred to in this specification are to be incorporated in their entirety by reference into the specification, as if each individual publication, patent or patent application was specifically and individually noted when referenced that it is to be incorporated herein by reference. In addition, citation or identification of any reference in this application shall not be construed as an admission that such reference is available as prior art to the present invention. To the extent that section headings are used, they should not be construed as necessarily limiting. In addition, any priority document(s) of this application is/are hereby incorporated herein by reference in its/their entirety.

What is claimed is:

1. A method of treating an autoimmune or inflammatory disease in a subject in need thereof, the method comprising administering to the subject a therapeutically effective amount of a polynucleotide agent capable of hybridizing to a gene or mRNA encoding CD84 and decreasing expression of a CD84 polypeptide or an antibody capable of decreasing an activity of a CD84 polypeptide, thereby treating the autoimmune or inflammatory disease in the subject, with the proviso that said disease is not a B cell malignancy.

2. The method of claim 1, wherein said autoimmune or inflammatory disease is selected from the group consisting of a multiple sclerosis, ulcerative colitis, Crohn's disease, arthritis and lupus.

3. The method of claim 1, wherein said autoimmune or inflammatory disease is a chronic condition.

4. The method of claim 1, wherein said autoimmune or inflammatory disease is an acute condition.

5. The method of claim 1, wherein said polynucleotide agent is selected from the group consisting of an antisense, a siRNA, a microRNA, a Ribozyme and a DNAzyme.

6. The method of claim 1, wherein said antibody binds at least one epitope of an extracellular portion of said CD84.

7. The method of claim 1, wherein said antibody is a CD84 neutralizing antibody.

8. The method of claim 1, further comprising administering to said subject an antibody immunotherapy.

9. The method of claim 1, wherein the subject is a human subject.

* * * * *